United States Patent
Davis et al.

(10) Patent No.: US 6,825,008 B2
(45) Date of Patent: Nov. 30, 2004

(54) EXPRESSED LIGAND—VASCULAR INTERCELLULAR SIGNALLING MOLECULE

(75) Inventors: Samuel Davis, New York, NY (US); George D. Yancopoulos, Yorktown Heights, NY (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 136 days.

(21) Appl. No.: 10/225,060

(22) Filed: Aug. 21, 2002

(65) Prior Publication Data

US 2003/0092891 A1 May 15, 2003

Related U.S. Application Data

(62) Division of application No. 09/709,188, filed on Nov. 9, 2000, now Pat. No. 6,441,137, which is a continuation of application No. 08/740,223, filed on Oct. 25, 1996, now Pat. No. 6,265,564.
(60) Provisional application No. 60/022,999, filed on Aug. 2, 1996.

(51) Int. Cl.$^7$ .......................... G12P 21/06; C12N 15/00; C12N 5/02; C12N 1/20; C07H 21/04
(52) U.S. Cl. .................. 435/69.1; 536/23.4; 435/320.1; 435/252.3; 435/325; 435/455
(58) Field of Search .................. 536/23.4; 435/69.1, 435/455, 325, 252.3, 320.1

(56) References Cited

U.S. PATENT DOCUMENTS 6,265,564 B1 * 7/2001 Davis et al.
6,441,137 B1 * 8/2002 Davis et al.

FOREIGN PATENT DOCUMENTS

| WO | WO96/11269 | * | 4/1996 |
| WO | WO96/31598 | * | 10/1996 |

OTHER PUBLICATIONS

Maisonpierre et al,. Angiopoietin-2, a natural antagonist for Tie2 that disrupts in vivo angiogenesis. Science. 277(5322):55–60 1997.*

* cited by examiner

Primary Examiner—Christina Chan
Assistant Examiner—Maher Haddad
(74) Attorney, Agent, or Firm—Valeta Gregg, Esq.

(57) ABSTRACT

The present invention provides for a modified TIE-2 ligand which has been altered by addition, deletion or substitution of one or more amino acids, or by way of tagging, with for example, the Fc portion of human IgG-1, but which retains its ability to bind the TIE-2 receptor. The invention further provides for a modified TIE-2 ligand which is a chimeric TIE-2 ligand comprising at least a portion of a first TIE-2 ligand and a portion of a second TIE-2 ligand which is different from the first. In a specific embodiment, the invention further provides for a chimeric TIE ligand comprising at least a portion of TIE-2 Ligand-1 and a portion of TIE-2 Ligand-2. In addition the present invention provides for isolated nucleic acid molecule encoding the modified TIE-2 ligands described. The invention also provides for therapeutic compositions as well as a method of blocking blood vessel growth, a method of promoting neovascularization, a method of promoting the growth or differentiation of a cell expressing the TIE receptor, a method of blocking the growth or differentiation of a cell expressing the TIE receptor and a method of attenuating or preventing tumor growth in a human.

7 Claims, 47 Drawing Sheets r EHK-1 ecto/h IgG1 Fc
Gelfoam (6ug)

r TIE-2 ecto/h IgG1 Fc
Gelfoam (6ug)

Fig. 4A

```
        10         20         30         40         50         60         70         80
         .          .          .          .          .          .          .          .
CAGCTGACTCAGGCAGGCTCCATGCTGAACGGTCACACAGAGAGGAAACATAAATCTCAGTCTATGCAATAAATATC 90        100        110        120        130        140        150        160
         .          .          .          .          .          .          .          .
TCAAGTTTTAAGAAGAAAAACATCATTGCAGTGAAATAAAAATTTTAAATTTTAGAACAAAGCTAACAAATGGCTAG 170        180        190        200        210        220        230        240
         .          .          .          .          .          .          .          .
TTTTCTATGATTCTTCTTCAAACGCTTTCTTTTGACGGGGAAAGAGTCAAACAAACAGTTTTACCTGAAATAAAGAA 250        260        270        280        290        300        310
         .          .          .          .          .          .          .
CTAGTTTTAGAGGTCAGAAGAAGGAGCAAGTTTTGCAGGAGGCACGGAAGGAGTGTGCTGGCAGTACA ATG ACA
                                                                         H   T>

320        330        340        350        360        370
         .          .          .          .          .          .
GTT TTC CTT TCC TTT GCT TTC CTC GCT GCC ATT CTG ACT CAC ATA GGG TGC AGC AAT CAG
 V   F   L   S   F   A   F   L   A   A   I   L   T   H   I   G   C   S   N   Q>

380        390        400        410        420        430
         .          .          .          .          .          .
CGC CGA AGT CCA GAA AAC AGT GGG AGA AGA TAT AAC CGG ATT CAA CAT GGG CAA TGT GCC
 R   R   S   P   E   N   S   G   R   R   Y   N   R   I   Q   H   G   Q   C   A>

440        450        460        470        480        490
         .          .          .          .          .          .
TAC ACT TTC ATT CTT CCA GAA CAC GAT GGC AAC TGT CGT GAG AGT ACG ACA GAC CAG TAC
 Y   T   F   I   L   P   E   H   D   G   N   C   R   E   S   T   T   D   Q   Y>

500        510        520        530        540        550
         .          .          .          .          .          .
AAC ACA AAC GCT CTG CAG AGA GAT GCT CCA CAC GTG GAA CCG GAT TTC TCT TCC CAG AAA
 N   T   N   A   L   Q   R   D   A   P   H   V   E   P   D   F   S   S   Q   K>
```

Fig. 4B

```
 560.          570.         580.         590.         606.         610.
CTT CAA CAT CTG GAA CAT GTG ATG GAA AAT TAT ACT CAG TGG CTG CAA AAA CTT GAG AAT
 L   Q   H   L   E   H   V   M   E   N   Y   T   Q   W   L   Q   K   L   E   N 620.          630.         640.         650.         660.         670.
TAC ATT GTC GAA AAC ATG AAG TCG GAG ATG GCC CAG ATA CAG CAG AAT GCA GTT CAG AAC
 Y   I   V   E   N   M   K   S   E   M   A   Q   I   Q   Q   N   A   V   Q   N 680.          690.         700.         710.         720.         730.
CAC ACG GCT ACC ATG CTG GAG ATA GGA ACC AGC CTC TCT CAG ACT GCA GAG CAG ACC
 H   T   A   T   M   L   E   I   G   T   S   L   S   Q   T   A   E   Q   T 740.          750.         760.         770.         780.         790.
AGA AAG CTG ACA GAT GTT GAG ACC CAG GTA CTA CAT CAA ACT TCT CGA CTT GAG ATA CAG
 R   K   L   T   D   V   E   T   Q   V   L   H   Q   T   S   R   L   E   I   Q 800.          810.         820.         830.         840.         850.
CTG CTG GAG AAT TCA TTA TCC ACC TAC AAG CTA GAG AAG CAA CTT CTT CAA CAG ACA AAT
 L   L   E   N   S   L   S   T   Y   K   L   E   K   Q   L   L   Q   Q   T   N 860.          870.         880.         890.         900.         910.
GAA ATC TTG AAG ATC CAT CAT GAG AAG AAC AGT CTT TTA GAA CAT AAA ATC TTA GAA ATG GAA
 E   I   L   K   I   H   H   E   K   N   S   L   L   E   H   K   I   L   E   M   E 920.          930.         940.         950.         960.         970.
GGA AAA CAC AAG GAA GAG TTG GAC ACC TTA AAG GAA GAG AAA GAG AAC CTT CAA GGC TTG
 G   K   H   K   E   E   L   D   T   L   K   E   E   K   E   N   L   Q   G   L 980.          990.        1000.        1010.        1020.        1030.
GTT ACT CGT CAA ACA TAT ATA CAG GAG CTG GAA AAG CAG TTA AAC AGA GCT ACC ACC
 V   T   R   Q   T   Y   I   Q   E   L   E   K   Q   L   N   R   A   T   T 1040.         1050.        1060.        1070.        1080.        1090.
AAC AAC AGT GTC CTT CAG AAG CAG CAA CTG GAG CTG ATG GAC ACA GTC CAC AAC CTT GTC
 N   N   S   V   L   Q   K   Q   Q   L   E   L   M   D   T   V   H   N   L   V
```

Fig. 4C

```
     1100        1110        1120        1130        1140        1150
       .           .           .           .           .           .
AAT CTT TGC ACT AAA GAA GGT GTT TTA CTA AAG GGA GGA AAA AGA GAG GAA AAA CCA
 N   L   C   T   K   E   G   V   L   L   K   G   G   K   R   E   E   K   P 1160        1170        1180        1190        1200        1210
       .           .           .           .           .           .
TTT AGA GAC TGT GCA GAT GTA TAT CAA GCT GGT TTT AAT AAA AGT GGA ATC TAC ACT ATT
 F   R   D   C   A   D   V   Y   Q   A   G   F   N   K   S   G   I   Y   T   I 1220        1230        1240        1250        1260        1270
       .           .           .           .           .           .
TAT ATT AAT AAT ATG CCA GAA CCC AAA AAG GTC TTT TGC AAT CAT GAT GTC AAT GGG GGA
 Y   I   N   N   M   P   E   P   K   K   V   F   C   N   H   D   V   N   G   G 1280        1290        1300        1310        1320        1330
       .           .           .           .           .           .
GGT TGG ACT GTA ATA CAA CAT CGT GAA GAT GGA AGT CTA GAT TTC CAA AGA GGC TGG AAG
 G   W   T   V   I   Q   H   R   E   D   G   S   L   D   F   Q   R   G   W   K 1340        1350        1360        1370        1380        1390
       .           .           .           .           .           .
GAA TAT AAA ATG GGT TTT GGA AAT CCC TCC GGT GAA TAT TGG CTG GGG AAT GAG TTT ATT
 E   Y   K   M   G   F   G   N   P   S   G   E   Y   W   L   G   N   E   F   I 1400        1410        1420        1430        1440        1450
       .           .           .           .           .           .
TTT GCC ATT ACC AGT CAG AGG CAG TAC ATG CTA AGA ATT GAG TTA ATG GAC TGG GAA GGG
 F   A   I   T   S   Q   R   Q   Y   M   L   R   I   E   L   M   D   W   E   G 1460        1470        1480        1490        1500        1510
       .           .           .           .           .           .
AAC CGA GCC TAT TCA CAG TAT GAC AGA TTC CAC ATA GGA AAT GAA AAG CAA AAC TAT AGG
 N   R   A   Y   S   Q   Y   D   R   F   H   I   G   N   E   K   Q   N   Y   R
```

Fig. 4D

```
     1580          1590          1600          1610          1620          1630
      .             .             .             .             .             .
GCT GAT TTC AGC ACT AAA GAT GCT GAT AAT GAC AAC TGT ATG TGC AAA TGT GCC CTC ATG
 A   D   F   S   T   K   D   A   D   N   D   N   C   M   C   K   C   A   L   M 1640          1650          1660          1670          1680          1690
      .             .             .             .             .             .
TTA ACA GGA GGA TGG TTT GAT GCT TGT GGC CCC TCC AAT CTA AAT GGA ATG TTC TAT
 L   T   G   G   W   F   D   A   C   G   P   S   N   L   N   G   M   F   Y 1700          1710          1720          1730          1740          1750
      .             .             .             .             .             .
ACT GCG GGA CAA AAC CAT GGA AAA CTG AAT GGG ATA AAG TGG CAC TAC TTC AAA GGG CCC
 T   A   G   Q   N   H   G   K   L   N   G   I   K   W   H   Y   F   K   G   P 1760          1770          1780          1790          1800          1810
      .             .             .             .             .             .
AGT TAC TCC TTA CGT TCC ACA ACT ATG ATT CGA CCT TTA GAT TTT TGA AAG CGCAATGT
 S   Y   S   L   R   S   T   T   M   I   R   P   L   D   F   *

1820          1830          1840          1850          1860          1870          1880          1890
      .             .             .             .             .             .             .             .
CAGAAGGGATTATGAAGCAACAAGAAATCCGGAGAGCTGCCAGGTGAGAAACTGTTTGAAAACTTCAGAGCAAACA 1900          1910          1920          1930          1940          1950          1960          1970
      .             .             .             .             .             .             .             .
ATATTGCTCCCTTCCAGCAATAAGTGGTAGTTATGTGAAGTTCACCAAGGTTCTGACGGTGAATCTGAGCCGTTTGAG 1980          1990          2000          2010          2020          2030          2040          2050
      .             .             .             .             .             .             .             .
TTCCAAGAGTCTCTACTTGGGTGACAGTGCTCAGTGCTCTGACTATAGAAAACTCCACTGACTGTCGGCTTTAAAA 2060          2070          2080          2090          2100          2110          2120          2130
      .             .             .             .             .             .             .             .
AGGGAAGAAACTGCTAGCTTGCTCTGTCTTCAAACTACTACTGGACCTTATTTTGGAACTATGGTAGCCAGATGATAAAT

2140
      .
ATGGTTAATTTC
```

Fig. 5A

```
          10         20         30         40         50         60         70         80
           .          .          .          .          .          .          .          .
CAGCTGACTCAGGCAGCTTCCATGCTGAACTGAACGGTCACACAGAGAGGAAACAATAAATCTCAGCTACTATCAATAAATATC 90        100        110        120        130        140        150        160
           .          .          .          .          .          .          .          .
TCAAGTTTAACGAAGAAAAACATCATTGCAGTGAATAAAAATTTTAAATTTTAGAACAAAGCTAACAAATGGCTAG 170        180        190        200        210        220        230        240
           .          .          .          .          .          .          .          .
TTTTCTATGATTCTTCTTCAAGGCTTTCTTTGAGGGGAAAGAGTCAAACAACAGCAGTTTTAACTGAAATAAAGAA 250        260        270        280        290        300        310
           .          .          .          .          .          .          .
CTAGTTTTAGAGTCAGAAGAAAGGAGCAAGTTTTGCGGAGGCAAGGAGAGTGTCCTGGCAGTACA ATG ACA
                                                                    M   T>

320        330        340        350        360        370
           .          .          .          .          .          .
GTT TTC CTT TCC TTT GCT TTC CTC GCT GCC ATT CTG ACT CAC ATA GGG TGC AGC AAT CAG
 V   F   L   S   F   A   F   L   A   A   I   L   T   H   I   G   C   S   N   Q>

380        390        400        410        420        430
           .          .          .          .          .          .
CGC CGA AGT CCA GAA AAC AGT GGG AGA AGA TAT AAC CGG ATT CAA CAT GGG CAA TGT GCC
 R   R   S   P   E   N   S   G   R   R   Y   N   R   I   Q   H   G   Q   C   A>

440        450        460        470        480        490
           .          .          .          .          .          .
TAC ACT TTC ATT CTT CCA GAA CAC GAT GGC AAC TGT GAG AGT ACG ACA GAC CAG TAC
 Y   T   F   I   L   P   E   H   D   G   N   C   R   E   S   T   T   D   Q   Y>

500        510        520        530        540        550
           .          .          .          .          .          .
AAC ACA AAC GCT CTG CAG AGA GAT GCT CCA CAC GTG GAA CCG GAT TTC TCT TCC CAG AAA
 N   T   N   A   L   Q   R   D   A   P   H   V   E   P   D   F   S   S   Q   K>
```

Fig. 5B

```
560    570           580            590            600            610
 .      .             .              .              .              .
CTT CAA CAT CTG GAA CAT GTG GAA AAT TAT ACT CAC TGG CTG CAA AAA CTT GAG AAT
 L   Q   H   L   E   H   V   E   N   Y   T   H   W   L   Q   K   L   E   N 620    630           640            650            660            670
 .      .             .              .              .              .
TAC ATT GTG GAA AAC ATC AAG ATG TCG GAG ATG GCC CAG ATA CAG CAG AAT GCA GTT CAG AAC
 Y   I   V   E   N   I   K   M   S   E   M   A   Q   I   Q   Q   N   A   V   Q   N 680    690           700            710            720            730
 .      .             .              .              .              .
CAC ACG GCT ACC ATG CTG GAG ATA GGA ACC AGC CTC CTC TCT CAG ACT GCA GAG CAG ACC
 H   T   A   T   M   L   E   I   G   T   S   L   L   S   Q   T   A   E   Q   T 740    750           760            770            780            790
 .      .             .              .              .              .
AGA AAG CTG ACA GAT GTT GAG ACC CAG GTA CTA AAT CAA ACT TCT CGA CTT GAG ATA CAG
 R   K   L   T   D   V   E   T   Q   V   L   N   Q   T   S   R   L   E   I   Q 800    810           820            830            840            850
 .      .             .              .              .              .
CTG CTG GAG AAT TCA TTA TCC TAC AAG CTA GAG AAG CTT CAA CAG ACA ACT
 L   L   E   N   S   L   S   Y   K   L   E   K   L   Q   Q   T   T 860    870           880            890            900            910
 .      .             .              .              .              .
GAA ATC TTG AAG ATC CAT GAA AAC AGT TTA TTA AAA ATC TTA AAG GAA ATG GAA
 E   I   L   K   I   H   E   N   S   L   L   K   I   L   K   E   H   E 920    930           940            950            960            970
 .      .             .              .              .              .
GGA AAA CAC AAG GAA GAA TTG GAC ACC TTA AAG GAA GAG AAG GAA AAC TTA AAC AGA GCT ACC ACC
 G   K   H   K   E   E   L   D   T   L   K   E   E   K   E   N   L   N   R   A   T   T 980    990           1000           1010           1020           1030
 .      .             .              .              .              .
GTT ACT CGT CAA ACA TAT ATA ATT CAG CTG CAA GAG CTG CAA AAG CAA TTA CAA GGC TTG
 V   T   R   Q   T   Y   I   I   Q   L   Q   E   L   Q   K   Q   L   Q   G   L 1040   1050          1060           1070           1080           1090
 .      .             .              .              .              .
AAC AAC AGT GTC CTT CAG AAG CAG CAA CTG GAG CTG ATG GAC ACA GTC AAC AAC CTT GTC
 N   N   S   V   L   Q   K   Q   Q   L   E   L   M   D   T   V   N   N   L   V
```

Fig. 5C

```
1100        1110        1120        1130        1140        1150
  .           .           .           .           .           .
AAT CTT TGC ACT AAA GAA GTT TTA CTA AAG GGA GGA AAA AGA GAG GAG GAG AAA CCA TTT
 N   L   C   T   K   E   V   L   L   K   G   G   K   R   E   E   E   K   P   F 1160        1170        1180        1190        1200        1210
  .           .           .           .           .           .
AGA GAC TGT GCA GAT GTA TAT CAA GCT GGT TTT AAT AGT GGA ATC TAC ACT ATT TAT
 R   D   C   A   D   V   Y   Q   A   G   F   N   S   G   I   Y   T   I   Y 1220        1230        1240        1250        1260        1270
  .           .           .           .           .           .
ATT AAT AAT ATG CCA GAA CCC AAA AAG GTG TTT TGC AAT ATG GAT GTC AAT GGG GGA GGT
 I   N   N   M   P   E   P   K   K   V   F   C   N   M   D   V   N   G   G   G 1280        1290        1300        1310        1320        1330
  .           .           .           .           .           .
TGG ACT GTA ATA CAA CAT CGT GAA GAT GGA AGT TCC GGT CAA AGA GCC TGG AAG GAA
 W   T   V   I   Q   H   R   E   D   G   S   L   D   F   Q   R   G   W   K   E 1340        1350        1360        1370        1380        1390
  .           .           .           .           .           .
TAT AAA ATG GGT TTT GGA AAT CCC TCC GGT GAA TAT TGG CTC GGG AAT GAG TTT ATT TTT
 Y   K   M   G   F   G   N   P   S   G   E   Y   W   L   G   N   E   F   I   F 1400        1410        1420        1430        1440        1450
  .           .           .           .           .           .
GCC ATT ACC AGT CAG AGG CAG TAC ATG CTA AGA ATT GAG TTA CAC GAC TGG GAA GGG AAC
 A   I   T   S   Q   R   Q   Y   M   L   R   I   E   L   H   D   W   E   G   N 1460        1470        1480        1490        1500        1510
  .           .           .           .           .           .
CGA GCC TAT TCA CAG TAT GAC AGA TTC CAC ATA GGA AAT GAA AAG CAA AAC TAT AGG TTG
 R   A   Y   S   Q   Y   D   R   F   H   I   G   N   E   K   Q   N   Y   R   L 1520        1530        1540        1550        1560        1570
  .           .           .           .           .           .
TAT TTA AAA GGT CAC ACT GGG ACA GGA AAA CAG AGC AGC ATC TTA CAC GGT GCT
 Y   L   K   G   H   T   G   T   G   K   Q   S   S   I   L   H   G   A
```

Fig. 5D

```
     1580        1590       1600        1610        1620       1630
      .           .           .           .           .          .
GAT TTC AGC ACT AAA GAT GCT GAT AAT GAC AAC TGT ATG TGC AAA TGT GCC CTC ATG TTA
 D   F   S   T   K   D   A   D   N   D   N   C   M   C   K   C   A   L   H   L >

1640        1650       1660        1670        1680       1690
      .           .           .           .           .          .
ACA GGA GGA TGG TGG TTT GAT GCT TGT GGC CCC AAT CTA AAT GGA ATG TTC TAT ACT
 T   G   G   W   W   F   D   A   C   G   P   N   L   N   G   M   F   Y   T >

1700        1710       1720        1730        1740       1750
      .           .           .           .           .          .
GCG GGA CAA AAC CAT GGA AAA CTG AAT GGG ATA AAG TGG CAC TAC TTC AAA GGG CCC AGT
 A   G   Q   N   H   G   K   L   N   G   I   K   W   H   Y   F   K   G   P   S >

1760        1770       1780        1790        1800       1810
      .           .           .           .           .          .
TAC TCC TTA CGT TCC ACA ACT ATG ATG ATT CGA CCT TTA GAT TTT TGA AAGCCAATGTCAGAA
 Y   S   L   R   S   T   T   M   M   I   R   P   L   D   F   * >

1820    1830    1840    1850    1860    1870    1880    1890
       .       .       .       .       .       .       .       .
CCGATTATGAAGCAACAAGAAATCCCGAGAAGCTGCCAGTGAGAAACTGTTTGAAACTTCAGAAGCAAACAATATT 1900    1910    1920    1930    1940    1950    1960    1970
       .       .       .       .       .       .       .       .
GTCTCCCTTCCAGCAATAGTAGTTATGTGAAGTCACCAAGGTTCTTGACCTGAATCTGAGCCGTTTGAGTTCAC 1980    1990    2000    2010    2020    2030    2040    2050
       .       .       .       .       .       .       .       .
AAGAGTCTTACTTGGGGTGACAGTTGCTCACGTGGCTCGACTATAGAAAACTCCACTGACTGTCGGGCTTTAAAAGGGA 2060    2070    2080    2090    2100    2110    2120    2130
       .       .       .       .       .       .       .       .
AGAAACTGCTGAGCTTGCTTCGTGTCTTCAAACTACTACTGACCTTATTTGGAACTATGGTAGCCAGATGATAAATATCGT

2140
       .
TAATTTC
```

Fig. 6A

```
                10          20          30          40          50          60          70          80
                 .           .           .           .           .           .           .           .
GAATTCCTGGGTTGTGTTTATCTCCCCAGCCTTGAGGAGGAACAACACTGTAGGATCTGGGAGAGAGGAACAAA 90         100         110         120         130         140         150         160
                 .           .           .           .           .           .           .           .
GGACCGTGAAAGCTGCTCTGTAAAAGCTGAGACACAGCCCTCCCAAGTGAGCAGACTGTTCTTCCCACTGCAATCTGACAG 170         180         190         200         210         220         230         240
                 .           .           .           .           .           .           .           .
TTTTACTGCATGCCTGGAGAGAACACAGCAGTAAAACCAGGTTTGCTACTGGAAAAAGAGAAAGAGAAGACTTTCATTG 250         260         270         280         290         300         310         320
                 .           .           .           .           .           .           .           .
ACGGACCCAGCAGCCATGGCAGCGTAGCAGGCCCTGCGGTTCAGACGGCCAGCTCGGACTCTGGACGTGTGTTTGCCCTCA 330         340         350         360         370         380
                 .           .           .           .           .           .
AGTTTGCTAAGCTGCCTGGTTGTTTATTACTGAAGAAAGA ATG TGG CAG ATT GTT TTC TTT ACT CTG AGC TGT C>
                                          M   W   Q   I   V   F   F   T   L   S   C 390         400         410         420         430         440
                 .           .           .           .           .           .
GAT CTT GTC TTG GCC GCA TAT AAC AAC TTT CGG AAG AGC ATG GAC AGC ATA GGA AAG
 D   L   V   L   A   A   Y   N   N   F   R   K   S   M   D   S   I   G   K>

450         460         470         480         490         500
                 .           .           .           .           .           .
AAG CAA TAT CAG GTC CAG CAT GGG TCC TGC AGC TAC ACT TTC CTC CTG CCA GAG ATG GAC
 K   Q   Y   Q   V   Q   H   G   S   C   S   Y   T   F   L   L   P   E   M   D>

510         520         530         540         550         560
                 .           .           .           .           .           .
AAC TGC CGC TCT TCC TCC AGC CCC TAC GTG TCC AAT GCT GTG CAG AGG GAC GCG CCG CTC
 N   C   R   S   S   S   S   P   Y   V   S   N   A   V   Q   R   D   A   P   L>
```

Fig. 6B

```
570                 580                 590                 600                 610                 620
GAA TAC GAT GAC TCG GTG CAG AGG CTG CAA GTG CTG GAG AAC ATC ATG GAA AAC ACT
 E   Y   D   D   S   V   Q   R   L   Q   V   L   E   N   I   M   E   N   T 630                 640                 650                 660                 670                 680
CAG TGG CTA ATG AAG CTT GAG AAT TAT ATC CAG GAC AAC ATG AAG AAA GAA ATG GTA GAG
 Q   W   L   M   K   L   E   N   Y   I   Q   D   N   M   K   K   E   M   V   E 690                 700                 710                 720                 730                 740
ATA CAG CAG AAT GCA GTA CAG AAC ACG GCT GTG ATG ATA GAA ATA GGG ACA AAC CTG
 I   Q   Q   N   A   V   Q   N   T   A   V   M   I   E   I   G   T   N   L 750                 760                 770                 780                 790                 800
TTG AAC ACA GCT GAG CAA ACG CGG AAG TTA ACT GAT GTG GAA GCC CAA GTA TTA AAT
 L   N   T   A   E   Q   T   R   K   L   T   D   V   E   A   Q   V   L   N 810                 820                 830                 840                 850                 860
CAG ACC ACG AGA CTT GAA CTT CAG CTC CTC TCG ACA AAC AAA TTG GAA
 Q   T   T   R   L   E   L   Q   L   E   H   S   L   S   T   N   K   L   E 870                 880                 890                 900                 910                 920
AAA CAG ATT TTG GAC CAG ACC AGT GAA ATA AAC ATC CAA GAT AAG AAC AGT TTC CTA
 K   Q   I   L   D   Q   T   S   E   I   N   K   L   Q   D   K   N   S   F   L 930                 940                 950                 960                 970                 980
GAA AAG AAG GTG CTA GCT ATG GAA GAC AAG CAC ATC CAA CTA CAG TCA ATA AAA GAA
 E   K   K   V   L   A   M   E   D   K   H   I   Q   L   Q   S   I   K   E 990                 1000                1010                1020                1030                1040
GAG AAA GAT CAG CTA CAG GTG TTA GTA TCC AAG CAA AAT TCC ATC ATT GAA CTA GAA
 E   K   D   Q   L   Q   V   L   V   S   K   Q   N   S   I   I   E   E   E 1050                1060                1070                1080                1090                1100
AAA AAA ATA GTG ACT GCC ACG GTG AAT AAT TCA GTT CTT CAA AAG CAG CAA CAT GAT CTC
 K   K   I   V   T   A   T   V   N   N   S   V   L   Q   K   Q   Q   H   D   L
```

Fig. 6C

```
1110                 1120              1130              1140              1150              1160
  .                    .                 .                 .                 .                 .
ATG GAG ACA GTT AAT AAC TTA CTG ACT ATG TCC ACA AAC TCA AAC GCT CCT AAG GAC CCC
 M   E   T   V   N   N   L   L   T   M   S   T   N   S   N   A   P   K   D   P 1170                 1180              1190              1200              1210              1220
  .                    .                 .                 .                 .                 .
ACT GTT GCT AAA GAA GAA ATC AGC TTC AGA GAC TGT GCT GAA GTA TTC AAA TCA GGA
 T   V   A   K   E   E   I   S   F   R   D   C   A   E   V   F   K   S   G 1230                 1240              1250              1260              1270              1280
  .                    .                 .                 .                 .                 .
CAC ACC ACA AAT GGC ATC TAC ACG TTA ACA TTC CCT AAT TCT ACA GAA GAG ATC AAG GCC
 H   T   T   N   G   I   Y   T   L   T   F   P   N   S   T   E   E   I   K   A 1290                 1300              1310              1320              1330              1340
  .                    .                 .                 .                 .                 .
TAC TGT GAC ATG GAA GCT GGA GGC GGG ACA ATT ATT CAG CGA CGT GAG GAT GGC
 Y   C   D   M   E   A   G   G   G   T   I   I   Q   R   R   E   D   G 1350                 1360              1370              1380              1390              1400
  .                    .                 .                 .                 .                 .
AGC GTT GAT TTT CAG AGG ACT TGG AAA GAA TAT AAA GTG GGA TTT GGT AAC CCT TCA GGA
 S   V   D   F   Q   R   T   W   K   E   Y   K   V   G   F   G   N   P   S   G 1410                 1420              1430              1440              1450              1460
  .                    .                 .                 .                 .                 .
GAA TAT TGG CTG GGA AAT GAG TTT GTT TCG CAA CTG ACT AAT CAG CAA CGC TAT GTG CTT
 E   Y   W   L   G   N   E   F   V   S   Q   L   T   N   Q   Q   R   Y   V   L 1470                 1480              1490              1500              1510              1520
  .                    .                 .                 .                 .                 .
AAA ATA CAC CTT AAA GAC TGG GAA GGG AAT GAG GCT TAC TCA TTG TAT GAA CAT TTC TAT
 K   I   H   L   K   D   W   E   G   N   E   A   Y   S   L   Y   E   H   F   Y 1530                 1540              1550              1560              1570              1580
  .                    .                 .                 .                 .                 .
CTC TCA AGT GAA GAA CTC AAT TAT AGG ATT CAC CTT AAA GGA CTT ACA GGG ACA GCC GGC
 L   S   S   E   E   L   N   Y   R   I   H   L   K   G   L   T   G   T   A   G
```

Fig. 6D

```
     1590.     1600.     1610.     1620.     1630.     1640.
AAA ATA AGC AGC ATC AGC CAA CCA GGA AAT GAT TTT AGC ACA AAG GAT GGA GAC AAC GAC
 K   I   S   S   I   S   Q   P   G   N   D   F   S   T   K   D   G   D   N   D>

1650.     1660.     1670.     1680.     1690.     1700.
AAA TGT ATT TGC AAA TGT TCA CAA ATG CTA ACA GGA GGC TGG TGG TTT GAT GCA TGT GGT
 K   C   I   C   K   C   S   Q   M   L   T   G   G   W   W   F   D   A   C   G>

1710.     1720.     1730.     1740.     1750.     1760.
CCT TCC AAC TTG AAC GGA ATG TAC TAT CCA CAG AGG CAG AAC ACA AAT AAG TTC AAC GGC
 P   S   N   L   N   G   M   Y   Y   P   Q   R   Q   N   T   N   K   F   N   G>

1770.     1780.     1790.     1800.     1810.     1820.
ATT AAA TGG TAC TAC TGG AAA GGC TCA GGC TAT TCG CTC AAG GCC ACA ACC ATG ATG ATC
 I   K   W   Y   Y   W   K   G   S   G   Y   S   L   K   A   T   T   M   M   I>

1830.     1840.     1850.     1860.     1870.     1880.     1890.     1900.
CGA CCA GCA GAT TTC TAAACATCCAGTCCACTGAGGAACTGTCTCGAACTATTTCAAAGACTTAAGCCCAGT
 R   P   A   D   F>

1910.     1920.     1930.     1940.     1950.     1960.     1970.     1980.
GCACTGAAAGTCACGGCTGGGCACTGTGTCTCTTCCACCACAGAGGGGCGTGTGCTCGGTGTGACGCGGACCCACATGCT 1990.     2000.     2010.     2020.     2030.     2040.     2050.     2060.
CCAGATTAGAGACCCTGTAAACTTTATCACTTAAACTGCATCACTTAACGGACCAAAGCAAGACCCTAAACATCCATAATT 2070.     2080.     2090.     2100.     2110.     2120.     2130.     2140.
GTGATTAGACAGAACACCTATGCAAAGATGAACCCGAGGCTGAGAATCAGACTGACAGTTTACAGCGCTGCTGTCACAA 2150.     2160.     2170.     2180.     2190.     2200.     2210.     2220.
CCAAGAAATGTTATGTGCAAGTTTATCAGTAAATAACTGAAAACAGAACACTTATGTTATACAATACAGATCATCTTGGA 2230.     2240.     2250.     2260.     2270.     2280.
ACTGCATTCTTCTTGAGCACTGTTTATACACTGTGTAAATACCCATATGTCCTGAATTC
```

Fig. 21A

```
         10         20         30         40         50         60         70         80         90
          *          *          *          *          *          *          *          *          *
CTGTCCTGGT ACCTGACAAG ACCACCTCAC CACCACTTGG TCTTCAG ATG CTC TGC CAG CCA GCT ATG CTA CTA GAT GGC CTC CTG CTG
                                                    M   L   C   Q   P   A   M   L   L   D   G   L   L   L 100            110            120            130            140            150            160            170
     *              *              *              *              *              *              *              *
GCC ACC ATG GCT GCA GCC CAG AGA GGG CCA GAA GCC GGT GGG CAC CGC CAG ATT CAC CAG GTC CGG CGG GGC CAG TGC AGC
 A   T   M   A   A   A   Q   R   G   P   E   A   G   G   H   R   Q   I   H   Q   V   R   R   G   Q   C   S 180            190            200            210            220            230            240            250
     *              *              *              *              *              *              *              *
TAC ACC TTT GTG GTG CCG GAG CCT GAT ATC TGC CAG CTA CCG ACA GCG GCG CCT CAG GCT TTG GGG GGC TCC AAT AGC CTC
 Y   T   F   V   V   P   E   P   D   I   C   Q   L   P   T   A   A   P   Q   A   L   G   G   S   N   S   L 260            270            280            290            300            310            320            330            340
     *              *              *              *              *              *              *              *              *
CAG AGG GAC TTG CCT GCC TCG AGG CTG CAC CTA CAC CTG ACA CAC TGG CGA GCC CAG AGG GCC CAG CGT GTG AGC CAG CTG
 Q   R   D   L   P   A   S   R   L   H   L   H   L   T   D   W   R   A   Q   R   A   Q   R   V   S   Q   L 350            360            370            380            390            400            410            420
     *              *              *              *              *              *              *              *
GAG AAG ATA CTA GAG AAT AAC ACT CAG CTG CTG AAG CTG GAG CAG TCC ATC AAG GTG CAC CTG AGG TCA CAC CTG GTG CAG
 E   K   I   L   E   N   N   T   Q   L   L   K   L   E   Q   S   I   K   V   H   L   R   S   H   L   V   Q 430            440            450            460            470            480            490            500            510
     *              *              *              *              *              *              *              *              *
GCC CAG CAG GAC ACA ATC CAG ACA CAG ACT ATG CTG GCA CTG ACC ATG CTA ATG CAT CAT AAG ACC CAA ATG CTG GAG ACC
 A   Q   Q   D   T   I   Q   T   Q   T   M   L   A   L   T   M   L   M   H   H   K   T   Q   M   L   E   T 520            530            540            550            560            570            580            590
     *              *              *              *              *              *              *              *
CAG CAG CTG ACT GTT GAG GCA CAG GTC CTA ACC CTG CAG GCC CAG CGG CTG CAG GGT CGC AAC CAG ATG CTG AAA GCT CAG
 Q   Q   L   T   V   E   A   Q   V   L   T   L   Q   A   Q   R   L   Q   G   R   N   Q   M   L   K   A   Q 600            610            620            630            640            650            660            670
     *              *              *              *              *              *              *              *
CAC AAG CTG GAG GCA CAA CAT CAG GCC CTT AAC AGC TTG CAC CAG GCA GAG CTG CAG GGT CGC ATG AGG GCC CTG GAG AGG
 H   K   L   E   A   Q   H   Q   A   L   N   S   L   H   Q   A   E   L   Q   G   R   M   R   A   L   E   R 680            690            700            710            720            730            740            750            760
     *              *              *              *              *              *              *              *              *
CAG GCA CTG GAA GCA CAA CAA CAT CAT AAC AGC CGT GAG CTT CAA CTC AGC CTC CAA GAG AAG AGG GAA CAG CTG CAC AGT CTG CTG GGC CAT CAG
 Q   A   L   E   A   Q   Q   H   H   N   S   R   E   L   Q   L   S   L   Q   E   K   R   E   Q   L   H   S   L   L   G   H   Q
```

Fig. 21B

```
       770       780       790       800       810       820       830       840
        *         *         *         *         *         *         *         *
ACC GGG ACC CTG GCT AAC CTG AAG CAC AAT CTG AGC AGC AAT TCC AGC CTG CAG CAG CAA CTG
 T   G   T   L   A   N   L   K   H   N   L   S   S   N   S   S   L   Q   Q   Q   L 850       860       870       880       890       900       910       920       930
        *         *         *         *         *         *         *         *         *
ACG GAG TTT GTA CAG CGC CTG GTA GCC ATT GTA CGG CAT CCG GTT TCC TTA AAG ACA CCT AAG GTG TTC CAG
 T   E   F   V   Q   R   L   V   A   I   V   R   H   P   V   S   L   K   T   P   K   V   F   Q 940       950       960       970       980       990      1000      1010
        *         *         *         *         *         *         *         *
GAC TGT GCA GAG ATC AAG CGC TCC GGG GTT AAT ACC AGC AGC GGT GTT TAT ACC ATC TAT TAC CCT CTC AAG
 D   C   A   E   I   K   R   S   G   V   N   T   S   S   G   V   Y   T   I   Y   Y   P   L   K 1020      1030      1040      1050      1060      1070      1080      1090
        *         *         *         *         *         *         *         *
GTG TTC TGT GAC ATG GAG ACT GAT GGA GGT GGC TGG ACC GTT GGC GAT AGC ATG ACA AAG ACC ATG TTC CAG
 V   F   C   D   M   E   T   D   G   G   G   W   T   V   G   D   S   M   T   K   T   M   F   Q 1100      1110      1120      1130      1140      1150      1160      1170      1180
        *         *         *         *         *         *         *         *         *
AAT TTC CAG AGG ACC
 N   F   Q   R   T

TGG GAA GAA TAC AAA GAG GGT TTT GGT AAT GTG AGA GAG CAC TGG CTG GGC AAT GAG GTG CAC CGC CTC ACC AGC AGA
 W   E   E   Y   K   E   G   F   G   N   V   R   E   H   W   L   G   N   E   V   H   R   L   T   S   R 1190      1200      1210      1220      1230      1240      1250      1260
        *         *         *         *         *         *         *         *
ACG GCC TAC TTG CTA CGC GTG GAG CTG CAT GAC TGG GAA GGC CGC CAG ACC TCC ATC CAG TAT GAG AAC TTC CAG CTG GGC AGC
 T   A   Y   L   L   R   V   E   L   H   D   W   E   G   R   Q   T   S   I   Q   Y   E   N   F   Q   L   G   S 1270      1280      1290      1300      1310      1320      1330      1340      1350
        *         *         *         *         *         *         *         *         *
GAG AGG CAG CGG TAC AGC CTC TCT GTG AAT GAC TAC AGT GGT ACA GCA GGG GAT GCC CTG GCT GCC CGG ATC CGG TTC CAG
 E   R   Q   R   Y   S   L   S   V   N   D   Y   S   G   T   A   G   D   A   L   A   A   R   I   R   F   Q 1360      1370      1380      1390      1400      1410      1420      1430
        *         *         *         *         *         *         *         *
TTC AGC ACC AAA GAC ATG GAT AAC GAT AAC TGC ATG TGT AAA TGT GCT CAG ATG CTG TCT GGA GGG TGG TGG TTT GAT GCC TGT
 F   S   T   K   D   M   D   N   D   N   C   M   C   K   C   A   Q   M   L   S   G   G   W   W   F   D   A   C
```

Fig. 21C

```
      1440        1450        1460        1470        1480        1490        1500        1510
        *           *           *           *           *           *           *           *
GGC CTC TCC AAC CTC AAT GGC ATC TAC TAT TCA GTT CAT CAG CAC TTG CAC AAG ATC CGC ATC TGG CAC TAC TTC CGA
 G   L   S   N   L   N   G   I   Y   Y   S   V   H   Q   H   L   H   K   I   R   I   W   H   Y   F   R→

1520        1530        1540        1550        1560        1570        1580        1590        1600
        *           *           *           *           *           *           *           *           *
GGC CCC AGC TAC TCA CTG CAC GGC ACA CGC ATG ATG CTG AGG CCA ATG CTG TGA CACA CAGCCCTGCA GAGACTGATG
 G   P   S   Y   S   L   H   G   T   R   M   M   L   R   P   M   L   *→

1610        1620        1630        1640        1650        1660        1670        1680        1690        1700
          *           *           *           *           *           *           *           *           *           *
CCGTAGGAGG ATTCTCAACC CAGGTGACTC TGTGCACGCT GGGCCCTGCC CAGAAATCAG TGCCCCAGGGC TCATCTTGAC ATTCTGAAC ATCGGAACCA 1710        1720        1730        1740        1750        1760        1770        1780        1790        1800
          *           *           *           *           *           *           *           *           *           *
CCTTACCTTG CCCCTGAATT ACAAGAATTC ACCTGCCTCC CTGTTGCCCT CTGTTGCCCT CTAATTGTGA AATTGCTGGG TGCTTGAAGG CACCTGCCTC TGTTGAACC 1810        1820        1830        1840
          *           *           *           *
ATACTCTTTC CCCCTCCTGC TGCATGCCCG GGAATCCCTG CCATGAACT
```

Fig. 22 A

```
              10         20         30         40         50         60         70         80
mTL3    MLLDGLILLA THARAQHRGP EAGGHRQIHQ VRRGQCSYTF VVPEDICQL APTAAPEALG GSNSLQRDLP ASRLHIADWR
hTL1.   af.aai.thi -gcsn.r.s. .ns.r-rynr iqh....a.. il..h-dg-n cresttdq-y nt.a.....a- ---p.-v-e->
chTL1.  af.aa..ahi -gctt.r... ..s.r-rfnr iqh...t... il..q-dg-n cresttdq-y nt.a.....a- ---p.-v-e->
mTL1.   mtvflsfaffaailthigcsn.r.n. .n..r.-ynr iqh....a.. il..h.-gn- cres.t.qy- nt.a.....a. ----.v-e-->
mTL2.   mwqiifltfgwd.v.. saysnfrksv dst.r...y. .qn.p..... ll..t.s.r- -ssss-ym-- -.av...a. ---.dy---->
hTL2    mwqivfftlscd.v.. aaynnfrksm dsi.kk.-y. .qh.s..... ll..m.n.r- -ssss.-yv- -..av...a. ----.ey---->

90        100        110        120        130        140        150        160
mTL3    AQRAQRAQRV SQLEKIIENN TQWLLKLEQS IKVNLRSHLV QAQQDTIQNQ TTTMLALGAN LMNTKAQTH KLTAVEAQVL
hTL1.   pdf--ss.kl qh..hvm..y .....q...ny .ve.mk.ema .i..nav..h a...ei.ts .ls..ae..r ...d.t....>
chTL1.  qdf--sf.kl qh..hvm..y .....q...sy .ve.mk.em. .l..nav..h a...ei.ts .ls..ae..r ...d.t....>
mTL1.   pdfs--s.kl qh..hvm..y .....q...ny .ve.mk.ema .i..nav..h a...ei.ts .l...ae..r ...d......>
mTL2.   -dsv..l.-. --..n..... .....m....ny .qd.mkkem. ei..nvv... av.iei.ts .l...a...r ...d......>
hTL2    -dsv..l.-. --..n.m... .....m....ny .qd.mkkem. ei..nav... av.iei.t. .l...ae..r ...d......>

170        180        190        200        210        220        230        240
mTL3    NQTLHMKTQM LENSLSTNKL ERQMLMQSRE LQRLQGRNRA LETRLQALEA QHQAQLNSLQ EKREQEHSLL GHQTGTLANL
hTL1.   ...srlei.l .......y.. .k.l.q.tn. ilkihek.sl ..hkilem.g k.kee.dt.k .ek.n.qg.v tr.yiiqe.>
chTL1.  ...srlei.l .......y.. .k.l.q.tn. ilkihek.sl ..hkilem.e r.keemdt.k .ek.n.q..v tr.syiiqe.>
mTL1.   ...srlei.l .......y.. .k.l.q.tn. ilkihek.sl ..hkilem.g k.kee.dt.k .ek.n.qg.v sr..fiiqe.>
mTL2.   ...trlel.l .qh.i..... .k.i.d.ts. ink..nk.sf ..qkvldm.g k.se..q.mk .qkde.qv.v sk.ssvide.>
hTL2.   ...trlel.l .h....... .k.i.d.ts. ink..nk.sf ..kkvl.m.d k.ii..q.ik .ekd..qv.v sk.nsiiee.>

250        260        270        280        290        300        310        320
mTL3    KHNLMLSSN SSSLQQQQQQ LTEFVQRLVR IV---AQ-DQHP--v--S L-KTPKPVFQD CAEIKRSGVN TSGVYTYET NMTKPLXVFC
hTL1.   ekq.nratt. n.v..k..le .mdt.hn..n lc----tkevllk-g--g k-reeekp.r. ..dvyqa.f. k.i....in ..pe.k....>
chTL1.  ekq.nkatt. n.v..k..le .mdt.ht.it lc----sk-egvlkn--a k-.eeekp.r. ..dvyq..f. k......in .vsd.k....>
mTL1.   ekq.sratn. n.i..k..le .mdt.hn..s lc---tk-egvl--lkgg k-reeekp.r. ..dvyqa.f. k......fn ..pe.k....>
mTL2.   ekk.vtatv. n.l..k..hd .m.t.ns.lt mmss-pn-skss---..a ir.eeqtt.r. ....fk..lt ...i.i.ltfp .s.eei.ay.>
hTL2.   ekkivtatv. n.v..k..hd .m.t.nn.lt mmstsns-akd.---t--v a-.eeqis.r. ...vfk.ht ...n.i.ltfp .s.eei.ay.>
```

Fig. 22 B

```
              330        340        350        360        370        380        390        400
         DMETDGGWT LIQHREDGSV NFQRTWEEYK EGFGNWAREH WLGNEAVHRL TSRTAYLLRV ELHDWEGRQT SIQYENFQLG
mTL3
hTL1.    n.dvn..... v......... d...g.k... m....psg.y ......fifai ..qrq.m..i ..m....nra ys..dr.hi.>
chTL1.   n..vn..... v......... d..kg.k... m....spsg.. ......fifai ..qrq.s..i ..m....nra ys..dr.hi.>
mTL1.    n.dvn..... v......... d...g.k... m....psg.y ......fifai ..qrq.m..i ..m....nra ys..dr.hi.>
mTL1.    ..dvg..... v......... d......... ......plg.y ......f.sq. .gqhr.v.ki q.k....nea hsl.dh.y.a>
mTL2.    ...ag..... i..r....... ......... v.......... ......f.sq. .nqqr.v.ki h.k....nea ysl..h.y.s>
hTL2.

410        420        430        440        450        460        470        480
         SERQRYSLSV NDSSSSAGRK NSLAPQGTKF STKDMDNDNC MCKCAQMLSG GWWFDACGLS NLNGIYYSVH QHLHKTNGIR
mTL3
hTL1.    n.k.n.r.yl kghtgt..kq s..ilh.ad. ......a... ......... ......p. ......mf.tag .nhg.l...k>
chTL1.   n.k.n.r.yl kgh.gt..kg s..ilh.ae. ......a... ......l..t. ......p. ......mf..ag .nhg.l...k>
mTL1.    n.k.n.r.yl kghtgt..kg s..ilh.ad. ......a... ......l..t. ......p. ......mf.tag .nhg.l...k>
mTL1.    n.k.n.r.yl kghtgt..kg s..isqp.sd. ......s...k. i........ ......s...t. ......p. ......q..pqk .ntn.f...k>
mTL2.    g.esn.rihl tgltgt.aki s.isqp.sd. ......s...k. i........ ......s...t. ......p. ......q..pqk .ntn.f...k>
hTL2.    ..eln.rihl kgltgt..ki s.isqp.nd. ......g...k. i........ ......s...t. ......p. ......m..pqr .ntn.f...k>

490        500
         WHYFERGPSYS IHGTRMHLRP MGA*
mTL3
hTL1.    ....k..... .rs.t..i.. ldf
chTL1.   ....k..r.. .rs.t..i.. ldf>
mTL1.    ....k..... .rs.t..i.. ldf>
mTL1.    .y.wk.sg.. .ka.t..i.. adf>
mTL2.    .v.wk.sg.. .ka.t..i.. adf>
hTL2.
```

Fig. 23A

```
      10              20              30              40              50              60
ATG CTC TCC CAG CTA GCC ATG CTG CAG GGC AGC CTC CTC CTT GTG GCC ACC ATG TCT GTG GCT
 M   L   S   Q   L   A   M   L   Q   G   S   L   L   L   V   A   T   M   S   V   A
      70              80              90             100             110             120             130
CAA CAG ACA AGG CAG GAG GCG GAT AGG GGC TGC GAG ACA CTT GTA GTC CAG CAC GGC CAC TGT AGC
 Q   Q   T   R   Q   E   A   D   R   G   C   E   T   L   V   V   Q   H   G   H   C   S
     140             150             160             170             180             190
TAC ACC TTC TTG CTG CCC AAG TCT GAG CCC TGC CCT CCG GGG CCT GAG GTC TCC AGG GAC TCC AAC
 Y   T   F   L   L   P   K   S   E   P   C   P   P   G   P   E   V   S   R   D   S   N
     200             210             220             230             240             250             260
ACC CTC CAG AGA GAA TCA CTG GCC AAC CCA AAC ACG CAG CTG CAC CTG GGG AAG TTG CCC ACC CAG CAG AAA
 T   L   Q   R   E   S   L   A   N   P   N   T   Q   L   H   L   G   K   L   P   T   Q   Q   K
     270             280             290             300             310             320             330
CAG CTG GAG CAG GCA CTG AAC CAG AAC ACG CAG TGG CTG AAG AAG TTG GAG CTA AGG AGG GCC ATC AAG ACG
 Q   L   E   Q   A   L   N   Q   N   T   Q   W   L   K   K   L   E   L   R   R   A   I   K   T
     340             350             360             370             380             390
ATC TTG AGG TCG AAG CTG GAG CAG GTC CAG CAG CAA ATG GCC CAG AAT CAG ACG GCC CCC ATG CTA
 I   L   R   S   K   L   E   Q   V   Q   Q   Q   M   A   Q   N   Q   T   A   P   M   L
     400             410             420             430             440             450             460
GAG CTG GGC ACC AGC CTC CTG AAC CAG ACA TCA AGA ACT GCC CAG ATC CGC AAG CTG ACC TTT CTG TCC ACC AAG GAC ATG GAG GCT
 E   L   G   T   S   L   L   N   Q   T   S   R   T   A   Q   I   R   K   L   T   F   L   S   T   K   D   M   E   A
     470             480             490             500             510             520
CAG CTC CTG AAC CAG ACA TCA AGA ATG GAT GCC CAG ATG CCA GAG ACC TTT CTG TCC ACC AAC AAG
 Q   L   L   N   Q   T   S   R   M   D   A   Q   M   P   E   T   F   L   S   T   N   K
     530             540             550             560             570             580             590
CTG GAG AAC CAG CAG CTG CTA CAG CAG AGG CAG AAG CTC CAG CTT CAG GGC CAA AAC AGC GCG CTC
 L   E   N   Q   Q   L   L   Q   Q   R   Q   K   L   Q   L   Q   G   Q   N   S   A   L
```

```
     600         610         620         630         640         650         660
GAG AAG CGG TTG CAG GCC CTG GAG ACC AAG CAG GAG GAG CTG GCC AGC ATC CTC AGC AAG AAG
 E   K   R   L   Q   A   L   E   T   K   Q   E   E   L   A   S   I   L   S   K   K
             670         680         690         700         710         720
GCG AAG CTG CTG AAC ACG CTG AGC CGC CAG CGC GCC CTC ACC AAC ATC GAG CGC GGC CTG CGC
 A   K   L   L   N   T   L   S   R   Q   R   A   L   T   N   I   E   R   G   L   R
     730         740         750         760         770         780         790
GGT GTC AGG CAC AAC TCC AGC CTG CAG GAC CAG CAG CAC AGC CTG CGC CAG CTG CTG GTG TTG
 G   V   R   H   N   S   S   L   Q   D   Q   Q   H   S   L   R   Q   L   L   V   L
             800         810         820         830         840         850
TTG CGG CAC CTG GTG CAA GAA AGG GCT AAC GCC TCG GCC TTC ATA ATG GCA GGT GAG CAG
 L   R   H   L   V   Q   E   R   A   N   A   S   A   F   I   M   A   G   E   Q
     860         870         880         890         900         910         920
GTG TTC CAG GAC TGT GCA GAG ATC CAG CGC TCT GGG GCC AGT GCC AGT GTC TAC ACC ATC CAG
 V   F   Q   D   C   A   E   I   Q   R   S   G   A   S   A   S   V   Y   T   I   Q
             930         940         950         960         970         980
GTG TCC AAT GCA ACG AAG CCC AGG AAG GTG TTC TGT GAC CTG CAG AGC AGT GGA AGG TGG ACC
 V   S   N   A   T   K   P   R   K   V   F   C   D   L   Q   S   S   G   R   W   T
     990        1000        1010        1020        1030        1040        1050
CTC ATC CAG CGC CGT GAG AAT GGC ACC GTG AAT TTT CAG CGG AAC TGG AAG GAT TAC AAA CAG GGC
 L   I   Q   R   R   E   N   G   T   V   N   F   Q   R   N   W   K   D   Y   K   Q   G
            1060        1070        1080        1090        1100        1110        1120
TTC GGA GAC CCA GCT GGG GAG CAC TGG CTG GGC AAT GAA GTG GTG CAC CAG CTC ACC AGA AGG GCA
 F   G   D   P   A   G   E   H   W   L   G   N   E   V   V   H   Q   L   T   R   R   A
            1130        1140        1150        1160        1170        1180
GCC TAC TCT CTG CGT GTG GAG CTG CAA GAC TGG GAA GGC CAC GAG GCC TAT GCC CAG TAC GAA CAT
 A   Y   S   L   R   V   E   L   Q   D   W   E   G   H   E   A   Y   A   Q   Y   E   H
```

Fig. 23C

```
1190            1200            1210            1220            1230            1240            1250
TTC CAC CTG GGC AGT GAG AAC CAG CTA TAC AGG CTT TCT GTG GGG TAC AGC GGC TCA GCA GGG
 F   H   L   G   S   E   N   Q   L   Y   R   L   S   V   G   Y   S   G   S   A   G 1260            1270            1280            1290            1300            1310            1320
CGC CAG AGC AGC CTG GTC CTG CAG AAC ACC AGC TTT AGC ACC CTT GAC TCA GAC AAC GAC CAC TGT
 R   Q   S   S   L   V   L   Q   N   T   S   F   S   T   L   D   S   D   N   D   H   C 1330            1340            1350            1360            1370            1380
CTC TGC AAG TGT GCC CAG GTG ATG TCT GGA GGG TGG TTT GAC GCC TGT GGC CTG TCA AAC CTC
 L   C   K   C   A   Q   V   M   S   G   G   W   F   D   A   C   G   L   S   N   L 1390            1400            1410            1420            1430            1440            1450
AAC GGC GTC TAC TAC CAC GCT CCC GAC AAC AAG TAC AAG ATG GAC GGC ATC CGC TGG CAC TAC TTC
 N   G   V   Y   Y   H   A   P   D   N   K   Y   K   M   D   G   I   R   W   H   Y   F 1460            1470            1480            1490            1500            1510
AAG GGC CCC AGC TAC TCA CTG CGT GCC TCT CGC ATG ATG ATA CGG CCT TTG GAC ATC TAA
 K   G   P   S   Y   S   L   R   A   S   R   M   M   I   R   P   L   D   I   *
```

Fig. 24B

```
       550         560         570         580         590         600         610         620         630
        *           *           *           *           *           *           *           *           *
ACA AAT GAA ATC TTG AAG ATC CAT GAA AAA AAC AGT TTA GAA CAT GTA ATC TTA GAA ATG GAA CTT AAA CAC AAG GAA GAG TTG GAC
TGT TTA CTT TAG AAC TTC TAG GTA CTT TTG TCA AAT CTT GTA TAT TAG AAT TAC CTT TTT GTG CTT CTC AAC CTG
 T   N   E   I   L   K   I   H   E   K   N   S   L   E   H   V   I   L   E   M   E   L   K   H   K   E   E   L   D>

640         650         660         670         680         690         700         710         720
        *           *           *           *           *           *           *           *           *
ACC TTA AAG GAA GAG AAC CTT CAG AAG GTC CTT CAA GGC TTG CAA GTT ACT CGT CAA GTA ACA TAT ATA TAT CAG GAG CTG GAA AAG CAA TTA AAC AGA GCT
TGG AAT TTC CTC TTG GAA GTT CCG AAC GTT CAA TGA TGC GCA AGT TAT ATA TAT GTC CTC GAC CTT TTC GTT AAT TTG TCT CGA
 T   L   K   E   E   N   L   Q   K   V   L   Q   G   L   Q   V   T   R   Q   V   T   Y   I   Y   Q   E   L   E   K   Q   L   N   R   A>

730         740         750         760         770         780         790         800         810
        *           *           *           *           *           *           *           *           *
ACC ACC AAC AGT GTC CTT CAG AAG CAG CTG GAG CTG ATG GAC CTG ATG GAC CTT GTC AAT CTT GTC AAC CTT GAA ACG TGA ACT TTT AAA GAA GGT GTT
TGG TTG TCA CAG GTT CTC GTC TTC GTC GAC CTC GAC CTA CTG GAC TAC TTG GAA CAG TTG GAA ACG TGA CTT CCA CAA
 T   T   N   S   V   L   Q   K   Q   L   E   L   M   D   L   M   D   L   V   N   L   V   N   L   E   T   *   L   F   K   E   G   V>

820         830         840         850         860         870         880         890         900
        *           *           *           *           *           *           *           *           *
TTA CTA AAG GGA GAA AGA GAG CTT CTC GAG GAG TGT GCT GAA AAA CCA GTA TCA AAA TCA GAC CAC GTG ACA AAT GGC ATC TAC
AAT GAT TTC CCT AAT GGA TTA AGA TGT CTT GCT AGT CGA CGA TTT GGT ATA AGT TTT AGT CTG TGT CAC TGT TTA CCG TAG ATG
 L   L   K   G   E   R   E   L   L   E   E   C   A   E   K   P   V   S   K   S   D   H   V   T   N   G   I   Y>

910         920         930         940         950         960         970         980         990
        *           *           *           *           *           *           *           *           *
TGC AAT TGT AAG GGA TTA AGA TGT CTT GCT AGA GAG CTT CTC TAG GAT GAG GAG TAC TGT GAC ATG GAC ATG GAC CTG ATG GAA GGA GCT CCG GGG CCC CCG ACC TGT TAA TAA CTG GCT GCA
ACG TTA ACA TTC CCT AAT TCT ACA GAA GAG ATC TCT CAG CGA TAG TCC GAA TTG CAG GTC TAC ATA GTC TAC CTG ACA TTG AGT CGA CCT CCC CGG GGC TGG ACA ATT ATT CAG CGA GCT GCA
 C   N   C   K   G   L   R   C   L   A   E   E   L   L   E   I   R   T   E   K   E   L   L   E   I   *   *   A   Y   C   D   M   D   C   D   L   M   E   G   A   P   G   P   P   T   C   *   *   L   A>

1000        1010        1020        1030        1040        1050        1060        1070        1080
        *           *           *           *           *           *           *           *           *
ACG TTA CAA TTC CCT AAT TCT ACA GAA GAG ATC AAA GAA GAT TTT CAG AGG ACT TGG AAA GTG CAC CTT AAA CCT TCA GGA TAT TGG CTG GGA AAT GAC
TGC AAT GTT AAG GGA TTA AGA TGT CTT CTA CTA AAA GTC TCC TGA ACC TTT CAC GTG GAA TTT GGA AGT CCT ATA ACC GAC CCT TTA CTC
 T   L   Q   F   P   N   S   T   E   E   I   K   E   D   F   Q   R   T   W   K   V   H   L   K   P   S   G   Y   W   L   G   N   D>

1090        1100        1110        1120        1130        1140        1150        1160        1170
        *           *           *           *           *           *           *           *           *
GAG GAT GGC AGC GTT CAA CTA AAA GTC TCC TGA ACC TTT CAC GTG GAA TTT GGA AGT CCT ATA ACC GAC CCT TTA CTC
CTC CTA CCG TCG CAA GTT GAT TTT CAG CAG AAG TAT ATA TAT GTC CTA ATA ACG GCT TTA CTC GAA CTA CAC GAT GTG GAC GAG GGG CCC TTA CTC GAA GCT GTT AAC AGT ATG ATA TTG TAA
 E   D   G   S   V   Q   L   K   V   S   *   T   F   H   V   E   F   G   S   P   I   T   D   P   L   L>

1090        1100        1110        1120        1130        1140        1150        1160        1170
        *           *           *           *           *           *           *           *           *
TTT GTT TCG CAA CTG CAA ACT AAT CAG CAA GTA ATA CAC GTG CTT AAA ATA TAT GTC CTA ATA ACG GCT TTA CTC GAA GCT GTT AAC AGT ATG ATA TTG TAA
AAA CAA AGC GTT GAC GTT TGA TTA GTC GTT CAT TAT GTG CAC GAA TTT TAT ATA CAG GAT TAT TGC CGA AAT GAG CTT CGA CAA TTG TCA TAC TAT AAC ATT
 F   V   S   Q   L   Q   T   N   Q   Q   V   L   K   I   H   L   K   D   W   E   G   N   E   A   Y   S   L   Y   E>
```

Fig. 24C

```
           1180            1190            1200            1210            1220            1230            1240            1250            1260
             *               *               *               *               *               *               *               *               *
CAT TTC TAT CTC TCA AGT GAA GAA CTC AAT TAT AGG ATT CAC CTT AAA GGA CTT ACA GCC AAA ATA AGC AGC ATC AGC CAA
GTA AAG ATA GAG AGT TCA CTT CTT GAG TTA ATA TCC TAA GTG GAA TTT CCT GAA TGT CGG CCG TTT TAT TCG TCG TAG TCG GTT
 H   F   Y   L   S   S   E   E   L   N   Y   R   I   H   L   K   G   L   T   A   K   I   S   S   I   S   Q>

1270            1280            1290            1300            1310            1320            1330            1340            1350
             *               *               *               *               *               *               *               *               *
CCA GGA AAT GAT TTT AGC ACA AAG GAT GGA GAC AAC TTG CTG TTT ATT TGC AAA GAC TGT TCA ATG TGT CAA GTT CTA ACA GGA GGC TGG TGG TTT GAT
GGT CCT TTA CTA AAA TCG TGT TTC CTA CCT CTG TTG AAC GAC AAA TAA ACG TTT CTG ACA AGT GTA CAC AGT TAC AGT GAT TGT CCT ACC GCG ACC AAA CTA
 P   G   N   D   F   S   T   K   D   G   D   N   L   L   F   I   C   K   D   C   S   M   C   Q   V   L   T   G   G   W   W   F   D>

1360            1370            1380            1390            1400            1410            1420            1430            1440
             *               *               *               *               *               *               *               *               *
GCA TGT GGT CCT TCC AAC TTG AAC GGA ATG TAC TAT CCA CAG AGG CAG AAC ACA AAT AAG TTC AAC GGC ATT AAA TGG TAC TAC ATG ACC TGG AAA
CGT ACA CCA'GGA AGG TTG AAC TTG CCT TAC ATG TAC ATG GGT GTC TCC GTC TTG TGT TTA TTC AAG TTG CCG TAA TTT ACC ATG ATG TAC TGG ACC TTT
 A   C   G   P   S   N   L   N   G   M   Y   Y   P   Q   R   Q   N   T   N   K   F   N   G   I   K   W   Y   Y   M   T   W   K>

1450            1460            1470            1480            1490
             *               *               *               *               *
GGC TCA GGC TAT TCG CTC AAG GCC ACA ACC ATG ATC CGA CCA GCA GAT TTC TAA
CCG AGT CCG ATA AGC GAG TTC CGG TGT TGG TAC TAC TAG GCT GGT CGT CTA AAG ATT
 G   S   G   Y   S   L   K   A   T   T   M   I   R   P   A   D   F   *>
```

```
        550            560            570            580            590            600            610            620            630
          *              *              *              *              *              *              *              *              *
ATA AAC AAA TTG CAA GAT AAG AAC AGT TTC CTA GAA AAG GTG CTA GCT ATG GAA GAC ATC AAC ATC CAA CTA CAG TCA CAG ATA AAA
TAT TTG AAC GTT CTA TTC TTG TCA AAG GAT CTT TTC CAC CGA TAG CTT CTG GTG TAG TTG TAT GTT GAT GTC AGT TAT TTT
 I   N   K   L   Q   D   K   N   S   F   L   E   K   V   L   A   M   E   D   I   N   I   Q   L   Q   S   I   K>

640            650            660            670            680            690            700            710            720
          *              *              *              *              *              *              *              *              *
GAA GAG AAA GAT CAG GTG TTA GTA CAG GTG TTA TCC AAG CAA AAT CCC ATT GAA CTA GAA CTA GAA AAA ATA GTG ACT GCC ACG GTG AAT
CTT CTC TTT CTA GTC GAT GTC CAC AAT CAT AGG TTC GTT TTA AGG TAA CTT GAT CTT GAT CTT TTT TAT CAC TGA TGC CAC TTA
 E   E   K   D   Q   V   L   V   Q   V   L   S   K   Q   N   P   I   E   L   E   L   E   K   K   I   V   T   A   T   V   N>

730            740            750            760            770            780            790            800            810
          *              *              *              *              *              *              *              *              *
AAT TCA GTT CTT CAA AAG CAG CAA CAT GAT CTC ATG GAG ACA GTT AAT AAC TTA CTG ACT ATG ATG TCC ACA TCA AAC TCA GCT AAG GAC
TTA AGT CAA GAA GTT TTC GTC GTT GTA CTA GAG TAC CTC TGT CAA TTA AAT GAC TGA CAC TAC TAC AGG TGT AGT TTG AGT TCG CTG
 N   S   V   L   Q   K   Q   Q   H   D   L   M   E   T   V   N   N   L   L   T   M   M   S   T   S   N   S   A   K   D>

820            830            840            850            860            870            880            890            900
          *              *              *              *              *              *              *              *              *
CCC ACT GTT GCT AAA GAA GAA CAA ATC TTC AGA GAC TGT GCA GAT TAT CAA GGT TTT AAT AAA AGT GGA ATC TAC ACT ATT
GGG TGA CAA CGA CTT CTT GTT TAG AAG TCT CTG ACA CGT CTA CAT AGT CCA AAA TTA TTT TCA CCT TAG ATG TGA TAA
 P   T   V   A   K   E   E   Q   I   F   R   D   C   A   D   Y   Q   G   F   N   K   S   G   I   Y   T   I>

910            920            930            940            950            960            970            980            990
          *              *              *              *              *              *              *              *              *
TAT ATT AAT AAT ATG CCA GAA CCC AAA AAG GTG TTC AAT ATG GAT GTC AAT GGA GGA CCT CCT GTA ATA CAA CAT CGT GAA GAT
ATA TAA TTA TTA TAC GGT CTT GGG TTT TTC CAC CTT TAC CTA CAG TTA CCT CCT GGA GGA CAT TAT GTT GTA GCA GCT CTA
 Y   I   N   N   M   P   E   P   K   K   V   F   N   M   D   V   N   G   G   P   P   V   I   Q   H   R   E   D>

1000           1010           1020           1030           1040           1050           1060           1070           1080
          *              *              *              *              *              *              *              *              *
GGA AGT CTA GAT TTC CAA AGA GGC TGG ACC TTC GGA GAA TAT AAA ATG GGT TTT CCA AAC ATG TAC CCC TCC GGT GAA TAT TGG CTG GGG CCC AAT GAG TTT ATT
CCT TCA GAT CTA AAG GTT TCT CCG ACC TGG AAG CCT CTT ATA TTT TAC CCA AAT GGT TAC ATG GGG AGG CCA CTT ATA ACC GAC CCA CTT AAA TAA
 G   S   L   D   F   Q   R   G   W   T   F   G   E   Y   K   M   G   F   P   N   M   Y   P   S   G   E   Y   W   L   G   N   E   F   I>

1090           1100           1110           1120           1130           1140           1150           1160           1170
          *              *              *              *              *              *              *              *              *
TTT GCC ATT ACC AGT CAG AGG CAG AGG TAC ATG CTA AGA ATT GAG TTA ATG GAC TGG ACC CTG TTT CCC GAA GGG AAC CGA GCC TAT TCA CAG TAT GAC AGA TTC
AAA CGG TAA TGG TCA GTC TCC GTC TCC ATG TAC GAT TCT TAA CTC AAT TAC CTG ACC TGG GAC AAA GGG CTT CCC TTG GCT CGG ATA AGT GTC ATA CTG TCT AAG
 F   A   I   T   S   Q   R   Q   R   Y   M   L   R   I   E   L   M   D   W   E   G   N   R   A   Y   S   Q   Y   D   R   F   P>
```

Fig. 25C

```
          1180        1190        1200        1210        1220        1230        1240        1250        1260
           *           *           *           *           *           *           *           *           *
CAC ATA GGA AAT GAA AAG CAA AAC TAT ATA AGG TTG TAT TTA AAA GGT CAC ACT GGG ACA GCA GGA AAA CAG AGC AGC CTG ATC TTA CAC GGT
GTG TAT CCT TTA CTT TTC GTT CTA TAT TCC AAC ATA TTG TTT CCA GTG TGA CCC TGT CGT TAC CTT TTT GTC GAC TAG AAT GTG CCA
 H   I   G   N   E   K   Q   N   Y   I   R   L   Y   L   K   G   H   T   G   T   A   G   K   Q   S   S   L   I   L   H   G 1270        1280        1290        1300        1310        1320        1330        1340        1350
           *           *           *           *           *           *           *           *           *
GCT GAT TTC AGC ACT AAA GAT GCT AAT GAT GAC AAC TGT ATG TGC CTC ATG TTA ACA GGA GGA TGG TGG TTT GAT GCT TGT
CGA CTA AAG TCG TGA TTT CTA CGA TTA CTG CTG TTG ACA TAC ACG GAG TAC AAT TGT CCT CCT ACC AAA CTA CGA ACA
 A   D   F   S   T   K   D   A   N   D   D   N   C   M   C   L   M   L   T   G   G   W   W   F   D   A   C 1360        1370        1380        1390        1400        1410        1420        1430        1440
           *           *           *           *           *           *           *           *           *
GGC CCC TCC AAT CTA AAT GGA TTC TAT ACT GCG GGA CAA CTG GAT TTT GAC AAA CTG AAT GGG ATA AAG TGG CAC TAC TTC AAA GGG CCC
CCG GGG AGG TTA GAT TTA CCT AAG ATA TGA CGC CTG TTG GTA CTA AAA CTG TTT GAC CTT TAT TTC ACC GTG ATG AAG TTT CCC GGG
 G   P   S   N   L   N   G   F   Y   T   A   G   Q   L   D   F   D   K   L   N   G   I   K   W   H   Y   F   K   G   P 1450        1460        1470        1480        1490
           *           *           *           *           *
AGT TAC TCC TTA CGT TCC ACA ACT ATG ATT CGA CCT TTA GAT TTT TGA
TCA ATG AGG AAT GCA AGG TGT TGA TAC TAA GCT GGA AAT CTA AAA ACT
 S   Y   S   L   R   S   T   T   M   I   R   P   L   D   F   *
```

```
        550              560              570              580              590              600              610              620              630
         *                *                *                *                *                *                *                *                *
ACC AGT GAA ATA AAC AAA TTG CAA GAT AAG AAC AGT TTC CTA GAA AAG GTG CTA GCT ATG GAA GAC AAG CAC ATC CAA CTA CAG
TGG TCA CTT TAT TTG TTT AAC GTT CTA TTC CTT CTT TTG TCA AAG GAT CTT TTC CAC GAT CGA CTA CTT CTG TTC GTT GAT GTC
 T   S   E   I   N   K   L   Q   D   K   N   S   F   L   E   K   V   L   A   M   E   D   K   H   I   Q   L   Q>

640              650              660              670              680              690              700              710              720
         *                *                *                *                *                *                *                *                *
TCA ATA TTT CTC GAG AAA GAG AAA GAT CAG CTA CAG CTA GTG TTA TCC AAG CAA AAT TCC ATC ATT GAA GAA CTA GAA AAA ATA GTC ACT GCC
AGT TAT AAA GAG CTC TTT CTC TTT CTA GTC GAT CAC AAT AGG TTC GTT TTA AGG TAG TAA CTT GAT CTT GAT CTT TAT CAC TGA CGG
 S   I   F   L   E   K   E   K   D   Q   L   Q   L   V   L   S   K   Q   N   S   I   I   E   E   L   E   K   I   V   T   A>

730              740              750              760              770              780              790              800              810
         *                *                *                *                *                *                *                *                *
ACG GTG AAT AAT TCA GTT CTT CTT CAA AAG CAG CAA CAT GAT CTC ATG GAG ACA GTT AAT AAC TTA CTG ACT ATG TCC ACA AAC TCA
TGC CAC TTA AGT CAA GTT TTC CAA GRA GTT GTC GTT GTA CTA GAG TAC CTC TGT CAA TTA ATG GAC TGA TAC TAC AGG TGT AGT TTG AGT
 T   V   N   N   S   V   L   L   Q   K   Q   Q   H   D   L   M   E   T   V   N   N   L   L   T   M   S   T   N   S>

820              830              840              850              860              870              880              890              900
         *                *                *                *                *                *                *                *                *
GCT AAG GAC CCC ACT GTT GCT AAA GAA CAA GAA ATC AGC TTC AGA GAC TGT GCT GAA GTA TTC AAA TTT AGT CCT GTG CAC ACC ACA AAT GGC ATC
CGA TTC CTG GGG TGA CAA CGA TTT CTT GTT CTT TAG TCG AAG TCT CTG ACA CGA CTT CAT AAG TTT AAA TCA GGA CAC GTG TGG TGT TTA CCG TAG
 A   K   D   P   T   V   A   K   E   Q   E   I   S   F   R   D   C   A   E   V   F   K   S   G   H   T   T   N   G   I>

910              920              930              940              950              960              970              980              990
         *                *                *                *                *                *                *                *                *
TAC ACG TTA ACA TTC CCT AAT TCT ACA GAA GAG ATC CTC TAG CTT AAG GCC TAC TGT GAC ATG GAA GCT GGA GGC GGG CCC ACC TGT TAA TAA GTC GCT
ATG TGC AAT TGT AAG GGA TTA AGA TGT CTT CTC TAG GAG ATC GAA TTC CGG ATG ACA CTG TAC CTT CGA CCT CCG CCC GGG TGG ACA ATT ATT CAG CGA
 Y   T   L   T   F   P   N   S   T   E   E   I   L   E   K   A   Y   C   D   M   E   A   G   G   G   P   T   W   T   I   I   Q   R>

1000             1010             1020             1030             1040             1050             1060             1070             1080
         *                *                *                *                *                *                *                *                *
CGT GAG GAT GGC AGC GTT GAT CAA GTT TTT CAG GAT GTA CTA AAA GAA TAT AAA GTG GGA TTT GGT AAC CCT CTT GGA TAT TGG CTG GGA AAT
GCA CTC CTA CCG TCG CAA CTA GTT CAA AAA GTC CTA CAT GAT TTT CTT ATA TTT CAC CCT AAA CCA TTG GGA GAA CCT ATA ACC GAC CCT TTA
 R   E   D   G   S   V   D   Q   V   F   Q   D   V   L   K   E   Y   K   V   G   F   G   N   P   S   G   Y   W   L   G   N>
```

```
        1090              1100              1110              1120              1130              1140              1150              1160              1170
          *                 *                 *                 *                 *                 *                 *                 *                 *
GCC ATT ACC AGT CAG AGG CAG TAC ATG CTA AGA ATT GAG TTA CTC AAT CGA GCC TAT TCA CAG TAT GAC AGA TTC CAC
CGG TAA TGG TCA GTC TCC GTC ATG GAT TCT TAA CTC AAT GAG TTA CTT GCT CGG ATA AGT GTC ATA CTG TCT AAG GTG
 A   I   T   S   Q   R   Q   Y   M   L   R   I   E   L   L   N   R   A   Y   S   Q   Y   D   R   F   H>

1180              1190              1200              1210              1220              1230              1240              1250              1260
          *                 *                 *                 *                 *                 *                 *                 *                 *
ATA GGA AAT GAA AAG CAA AAC TAT AGG TTG TAT TTA AAA GGT CAC GTG ACA GCA GGA AAA CAG AGC AGC CTG ATC TTA CAC GGT GCT
TAT CCT TTA CTT TTC GTT TTG ATA TCC AAC ATA AAT TTT CCA GTG CAC TGT CGT CCT TTT GTC TCG TCG GAC TAG AAT GTG CCA CGA
 I   G   N   E   K   Q   N   Y   R   L   Y   L   K   G   H   V   T   A   G   K   Q   S   S   L   I   L   H   G   A>

1270              1280              1290              1300              1310              1320              1330              1340              1350
          *                 *                 *                 *                 *                 *                 *                 *                 *
GAT TTC AGC ACT AAA GAT GCT GAT AAT GAC AAC TGT ATG TGC AAA TGT ACA CGG TTA ACA GGA TGG TTT GAT GCT TGT GGC
CTA AAG TCG TGA TTT CTA CGA CTA TTA CTG TTG ACA TAC ACG TTT ACA TGT GCC AAT TGT CCT ACC AAA CTA CGA CA CCG
 D   F   S   T   K   D   A   D   N   D   N   C   M   C   K   C   T   R   L   T   G   W   F   D   A   C   G>

1360              1370              1380              1390              1400              1410              1420              1430              1440
          *                 *                 *                 *                 *                 *                 *                 *                 *
CCC TCC AAT CTA AAT GGA ATG TTC TAT ACT GCG GGA CAA AAC CAT GGA CTG AAT GGG ATA AAG TTC CAC TAC TTC AAA GGG CCC AGT
GGG AGG TTA GAT TTA CCT TAC AAG ATA TGA CGC CCT GTT TTG GTA GAC TTA CCC TAT TTC AAG GTG ATG AAG TTT CCC GGG TCA
 P   S   N   L   N   G   M   F   Y   T   A   G   Q   N   H   G   L   N   G   I   K   F   H   Y   F   K   G   P   S>

1450              1460              1470              1480
          *                 *                 *                 *
TAC TCC TTA CGT TCC ACA ACT ATG ATG ATT CGA CCT TTA GAT TTT TGA
ATG AGG AAT GCA TGT TGT TGA TAC TAC TAA GCT GGA AAT CTA AAA ACT
 Y   S   L   R   S   T   T   M   M   I   R   P   L   D   F   *>
```

EXPRESSED LIGAND— VASCULAR INTERCELLULAR SIGNALLING MOLECULE

This application is a divisional application of U.S. Ser. No. 09/709,188 filed 9 Nov. 2000, now U.S. Pat. No. 6,441,137, which is a continuation application of U.S. Ser. No. 08/740,223, filed on Oct. 25, 1996, now U.S. Pat. No. 6,265,564, which claims the priority of U.S. Provisional application No. 60/022,999 filed Aug. 2, 1996, now abandoned.

INTRODUCTION

The present invention relates generally to the field of genetic engineering and more particularly to genes for receptor tyrosine kinases and their cognate ligands, their insertion into recombinant DNA vectors, and the production of the encoded proteins in recipient strains of microorganisms and recipient eukaryotic cells. More specifically, the present invention is directed to a novel modified TIE-2 ligand that binds the TIE-2 receptor, as well as to methods of making and using the modified ligand. The invention further provides a nucleic acid sequence encoding the modified ligand, and methods for the generation of nucleic acid encoding the modified ligand and the gene product. The modified TIE-2 ligand, as well as nucleic acid encoding it, may be useful in the diagnosis and treatment of certain diseases involving endothelial cells and associated TIE receptors, such as neoplastic diseases involving tumor angiogenesis, wound healing, thromboembolic diseases, atherosclerosis and inflammatory diseases. In addition, the modified ligand may be used to promote the proliferation and/or differentiation of hematopoietic stem cells.

More generally, the receptor activating modified TIE-2 ligands described herein may be used to promote the growth, survival, migration, and/or differentiation and/or stabilization or destabilization of cells expressing TIE receptor. Biologically active modified TIE-2 ligand may be used for the in vitro maintenance of TIE receptor expressing cells in culture. Cells and tissues expressing TIE receptor include, for example, cardiac and vascular endothelial cells, lens epithelium and heart epicardium and early hematopoietic cells. Alternatively, such human ligand may be used to support cells which are engineered to express TIE receptor. Further, modified TIE-2 ligand and its cognate receptor may be used in assay systems to identify further agonists or antagonists of the receptor.

BACKGROUND OF THE INVENTION

The cellular behavior responsible for the development, maintenance, and repair of differentiated cells and tissues is regulated, in large part, by intercellular signals conveyed via growth factors and similar ligands and their receptors. The receptors are located on the cell surface of responding cells and they bind peptides or polypeptides known as growth factors as well as other hormone-like ligands. The results of this interaction are rapid biochemical changes in the responding cells, as well as a rapid and a long-term readjustment of cellular gene expression. Several receptors associated with various cell surfaces may bind specific growth factors.

The phosphorylation of tyrosine residues in proteins by tyrosine kinases is one of the key modes by which signals are transduced across the plasma membrane. Several currently known protein tyrosine kinase genes encode transmembrane receptors for polypeptide growth factors and hormones such as epidermal growth factor (EGF), insulin, insulin-like growth factor-I (IGF-I), platelet derived growth factors (PDGF-A and -B), and fibroblast growth factors (FGFs). (Heldin et al., Cell Regulation, 1: 555–566 (1990); Ullrich, et al., Cell, 61: 243–54 (1990)). In each instance, these growth factors exert their action by binding to the extracellular portion of their cognate receptors, which leads to activation of the intrinsic tyrosine kinase present on the cytoplasmic portion of the receptor. Growth factor receptors of endothelial cells are of particular interest due to the possible involvement of growth factors in several important physiological and pathological processes, such as vasculogenesis, angiogenesis, atherosclerosis, and inflammatory diseases. (Folkman, et al. Science, 235: 442–447 (1987)). Also, the receptors of several hematopoietic growth factors are tyrosine kinases; these include c-fms, which is the colony stimulating factor 1 receptor, Sherr, et al., Cell, 41: 665–676 (1985), and c-kit, a primitive hematopoietic growth factor receptor reported in Huang, et al., Cell, 63: 225–33 (1990).

The receptor tyrosine kinases have been divided into evolutionary subfamilies based on the characteristic structure of their ectodomains. (Ullrich, et al. Cell, 61: 243–54 (1990)). Such subfamilies include, EGF receptor-like kinase (subclass I) and insulin receptor-like kinase (subclass II), each of which contains repeated homologous cysteine-rich sequences in their extracellular domains. A single cysteine-rich region is also found in the extracellular domains of the eph-like kinases. Hirai, et al., Science, 238: 1717–1720 (1987); Lindberg, et al. Mol. Cell. Biol., 10: 6316–24 (1990); Lhotak, et al., Mol. Cell. Biol. 11: 2496–2502 (1991). PDGF receptors as well as c-fms and c-kit receptor tyrosine kinases may be grouped into subclass III; while the FGF receptors form subclass IV. Typical for the members of both of these subclasses are extracellular folding units stabilized by intrachain disulfide bonds. These so-called immunoglobulin (Ig)-like folds are found in the proteins of the immunoglobulin superfamily which contains a wide variety of other cell surface receptors having either cell-bound or soluble ligands. Williams, et al., Ann. Rev. Immunol., 6: 381–405 (1988).

Receptor tyrosine kinases differ in their specificity and affinity. In general, receptor tyrosine kinases are glycoproteins which consist of (1) an extracellular domain capable of binding the specific growth factor(s); (2) a transmembrane domain which usually is an alpha-helical portion of the protein; (3) a juxtamembrane domain where the receptor may be regulated by, e.g., protein phosphorylation; (4) a tyrosine kinase domain which is the enzymatic component of the receptor; and (5) a carboxyterminal tail which in many receptors is involved in recognition and binding of the substrates for the tyrosine kinase.

Processes such as alternative exon splicing and alternative choice of gene promoter or polyadenylation sites have been reported to be capable of producing several distinct polypeptides from the same gene. These polypeptides may or may not contain the various domains listed above. As a consequence, some extracellular domains may be expressed as separate, secreted proteins and some forms of the receptors may lack the tyrosine kinase domain and contain only the extracellular domain inserted in the plasma membrane via the transmembrane domain plus a short carboxyl terminal tail.

A gene encoding an endothelial cell transmembrane tyrosine kinase, originally identified by RT-PCR as an unknown tyrosine kinase-homologous cDNA fragment from human leukemia cells, was described by Partanen, et al., Proc. Natl. Acad. Sci. USA, 87: 8913–8917 (1990). This gene and its encoded protein are called "TIE" which is an abbreviation for "tyrosine kinase with Ig and EGF homology domains." Partanen, et al. Mol. Cell. Biol. 12: 1698–1707 (1992).

It has been reported that tie mRNA is present in all human fetal and mouse embryonic tissues. Upon inspection, tie message has been localized to the cardiac and vascular endothelial cells. Specifically, tie mRNA has been localized to the endothelia of blood vessels and endocardium of 9.5 to 18.5 day old mouse embryos. Enhanced tie expression was shown during neovascularization associated with developing ovarian follicles and granulation tissue in skin wounds. Korhonen, et al. Blood 80: 2548–2555 (1992). Thus the TIEs have been suggested to play a role in angiogenesis, which is important for developing treatments for solid tumors and several other angiogenesis-dependent diseases such as diabetic retinopathy, psoriasis, atherosclerosis and arthritis.

Two structurally related rat TIE receptor proteins have been reported to be encoded by distinct genes with related profiles of expression. One gene, termed tie-1, is the rat homolog of human tie. Maisonpierre, et al., Oncogene 8: 1631–1637 (1993). The other gene, tie-2, may be the rat homolog of the murine tek gene, which, like tie, has been reported to be expressed in the mouse exclusively in endothelial cells and their presumptive progenitors. Dumont, et al. Oncogene 8: 1293–1301 (1993). The human homolog of tie-2 is described in Ziegler, U.S. Pat. No. 5,447,860 which issued on Sep. 5, 1995 (wherein it is referred to as "ork"), which is incorporated in its entirety herein.

Both genes were found to be widely expressed in endothelial cells of embryonic and postnatal tissues. Significant levels of tie-2 transcripts were also present in other embryonic cell populations, including lens epithelium, heart epicardium and regions of mesenchyme. Maisonpierre, et al., Oncogene 8: 1631–1637 (1993).

The predominant expression of the TIE receptor in vascular endothelia suggests that TIE plays a role in the development and maintenance of the vascular system. This could include roles in endothelial cell determination, proliferation, differentiation and cell migration and patterning into vascular elements. Analyses of mouse embryos deficient in TIE-2 illustrate its importance in angiogenesis, particularly for vascular network formation in endothelial cells. Sato, T. N., et al., Nature 376:70–74 (1995). In the mature vascular system, the TIEs could function in endothelial cell survival, maintenance and response to pathogenic influences.

The TIE receptors are also expressed in primitive hematopoietic stem cells, B cells and a subset of megakaryocytic cells, thus suggesting the role of ligands which bind these receptors in early hematopoiesis, in the differentiation and/or proliferation of B cells, and in the megakaryocytic differentiation pathway. Iwama, et al. Biochem. Biophys. Research Communications 195:301–309 (1993); Hashiyama, et al. Blood 87:93–101 (1996), Batard, et al. Blood 87:2212–2220 (1996).

SUMMARY OF THE INVENTION

The present invention provides for a composition comprising a modified TIE-2 ligand substantially free of other proteins. As used herein, modified TIE-2 ligand refers to a ligand of the TIE family of ligands, whose representatives comprise ligands TL1, TL2, TL3 and TL4 as described herein, which has been altered by addition, deletion or substitution of one or more amino acids, or by way of tagging, with for example, the Fc portion of human IgG-1, but which retains its ability to bind the TIE-2 receptor. Modified TIE-2 ligand also includes a chimeric TIE-2 ligand comprising at least a portion of a first TIE-2 ligand and a portion of a second TIE-2 ligand which is different from the first. By way of non-limiting example, the first TIE-2 ligand is TL1 and the second TIE-2 ligand is TL2. The invention envisions other combinations using additional TIE-2 ligand family members. For example, other combinations for creating a chimeric TIE-2 ligand are possible, including but not limited to those combinations wherein the first ligand is selected from the group consisting of TL1, TL2, TL3 and TL4, and the second ligand, different from the first ligand, is selected from the group consisting of TL1, TL2, TL3 and TL4.

The invention also provides for an isolated nucleic acid molecule encoding a modified TIE-2 ligand. In one embodiment, the isolated nucleic acid molecule encodes a TIE-2 ligand of the TIE family of ligands, whose representatives comprise ligands TL1, TL2, TL3 and TL4 as described herein, which has been altered by addition, deletion or substitution of one or more amino acids, or by way of tagging, with for example, the Fc portion of human IgG-1, but which retains its ability to bind the TIE-2 receptor. In another embodiment, the isolated nucleic acid molecule encodes a modified TIE-2 ligand which is a chimeric TIE-2 ligand comprising at least a portion of a first TIE-2 ligand and a portion of a second TIE-2 ligand which is different from the first. By way of non-limiting example, the first TIE-2 ligand is TL1 and the second TIE-2 ligand is TL2. The invention envisions other combinations using additional TIE-2 ligand family members. For example, other combinations are possible, including but not limited to those combinations wherein the isolated nucleic acid molecule encodes a modified TIE-2 ligand which is a chimeric TIE-2 ligand comprising a portion of a first ligand selected from the group consisting of TL1, TL2, TL3 and TL4, and a portion of a second ligand, different from the first ligand, selected from the group consisting of TL1, TL2, TL3 and TL4.

The isolated nucleic acid may be DNA, cDNA or RNA. The invention also provides for a vector comprising an isolated nucleic acid molecule encoding a modified TIE-2 ligand. The invention further provides for a host-vector system for the production in a suitable host cell of a polypeptide having the biological activity of a modified TIE-2 ligand. The suitable host cell may be bacterial, yeast, insect or mammalian. The invention also provides for a method of producing a polypeptide having the biological activity of a modified TIE-2 ligand which comprises growing cells of the host-vector system under conditions permitting production of the polypeptide and recovering the polypeptide so produced.

The invention herein described of an isolated nucleic acid molecule encoding a modified TIE-2 ligand further provides for the development of the ligand as a therapeutic for the treatment of patients suffering from disorders involving cells, tissues or organs which express the TIE-2 receptor. The present invention also provides for an antibody which specifically binds such a therapeutic molecule. The antibody may be monoclonal or polyclonal. The invention also provides for a method of using such a monoclonal or polyclonal antibody to measure the amount of the therapeutic molecule in a sample taken from a patient for purposes of monitoring the course of therapy.

The present invention also provides for an antibody which specifically binds a modified TIE-2 ligand as described herein. The antibody may be monoclonal or polyclonal. Thus the invention further provides for therapeutic compositions comprising an antibody which specifically binds a modified TIE-2 ligand, in a pharmaceutically acceptable vehicle. The invention also provides for a method of blocking blood vessel growth in a mammal by administering an effective amount of a therapeutic composition comprising an antibody which specifically binds a receptor activating modified TIE-2 ligand as described herein, in a pharmaceutically acceptable vehicle.

The invention further provides for therapeutic compositions comprising a modified TIE-2 ligand as described herein, in a pharmaceutically acceptable vehicle. The invention also provides for a method of promoting neovascularization in a patient by administering an effective amount of a therapeutic composition comprising a receptor activating modified TIE-2 ligand as described herein, in a pharmaceutically acceptable vehicle. In one embodiment, the method may be used to promote wound healing. In another embodiment, the method may be used to treat ischemia. In yet another embodiment, a receptor activating modified TIE-2 ligand as described herein is used, alone or in combination with other hematopoietic factors, to promote the proliferation or differentiation of hematopoietic stem cells, B cells or megakaryocytic cells.

Alternatively, the invention provides that a modified TIE-2 ligand may be conjugated to a cytotoxic agent and a therapeutic composition prepared therefrom. The invention further provides for a receptorbody which specifically binds a modified TIE-2 ligand. The invention further provides for therapeutic compositions comprising a receptorbody which specifically binds a modified TIE-2 ligand in a pharmaceutically acceptable vehicle. The invention also provides for a method of blocking blood vessel growth in a mammal by administering an effective amount of a therapeutic composition comprising a receptorbody which specifically binds a modified TIE-2 ligand in a pharmaceutically acceptable vehicle.

The invention also provides for a TIE-2 receptor antagonist as well as a method of inhibiting TIE-2 biological activity in a mammal comprising administering to the mammal an effective amount of a TIE-2 antagonist. According to the invention, the antagonist may be a modified TIE-2 ligand as described herein which binds to, but does not activate, the TIE-2 receptor.

BRIEF DESCRIPTION OF THE FIGURES

FIG. 1A: embryos treated with EHK-1 RB (rEHK-1 ecto/hIgG1 Fc) were viable and possessed normally developed blood vessels in their surrounding CAM. FIG. 1B: all embryos treated with TIE-2 RB (r TIE-2 ecto/hIgG1 Fc) were dead, diminished in size and were almost completely devoid of surrounding blood vessels.

FIGS. 4A–4D—Nucleic acid (SEQ ID NO: 1) and deduced amino acid (SEQ ID NO: 2) (single letter code) sequences of human TIE-2 ligand 1 from clone λgt10 encoding htie-2 ligand 1.

FIGS. 5A–5D—Nucleic acid (SEQ ID NO: 3) and deduced amino acid (SEQ ID NO: 4) (single letter code) sequences of human TIE-2 ligand 1 from T98G clone.

FIGS. 6A–6D—Nucleic acid and deduced amino acid (single letter code) sequences of human TIE-2 ligand 2 from clone pBluescript KS encoding human TIE 2 ligand 2.

FIGS. 21A–21C—Nucleotide (SEQ ID NO: 9) and deduced amino acid (SEQ ID NO: 10) (single letter code) sequences of TIE ligand-3. The coding sequence starts at position 47. The fibrinogen-like domain starts at position 929.

FIGS. 22A–22B—Comparison of Amino Acid Sequences of TIE Ligand Family Members. mTL3=mouse TIE ligand-3 (SEQ ID NO: 11); hTL1=human TIE-2 ligand1 (SEQ ID NO: 12); chTL1=chicken TIE-2 ligand1 (SEQ ID NO; 13); mTL1=mouse TIE-2 ligand 1 (SEQ ID NO: 14); mTL2= mouse TIE-2 ligand 2 (SEQ ID NO: 15); hTL2=human TIE-2 ligand 2 (SEQ ID NO: 16). The boxed regions indicate conserved regions of homology among the family members.

FIGS. 23A–23C—Nucleotide (SEQ ID NO: 17) and deduced amino acid (SEQ ID NO: 18) (single letter code) sequences of TIE ligand-4. Arrow indicates nucleotide position 569.

FIGS. 25A–25C—Nucleotide (SEQ ID NO: 21) and deduced amino acid (SEQ ID NO: 22) (single letter code) sequences of chimeric TIE ligand designated 2N2C1F (chimera 2). The putative leader sequence is encoded by nucleotides 1–48.

FIGS. 26A–26C—Nucleotide (SEQ ID NO: 23) and deduced amino acid (SEQ ID NO: 24) (single letter code) sequences of chimeric TIE ligand designated 1N2C2F (chimera 3). The putative leader sequence is encoded by nucleotides 1–60.

FIGS. 27A–27C—Nucleotide (SEQ ID NO: 25) and deduced amino acid (SEQ ID NO: 26) (single letter code) sequences of chimeric TIE ligand designated 2N1C1F (chimera 4). The putative leader sequence is encoded by nucleotides 1–48.

DETAILED DESCRIPTION OF THE INVENTION

Figure 1:
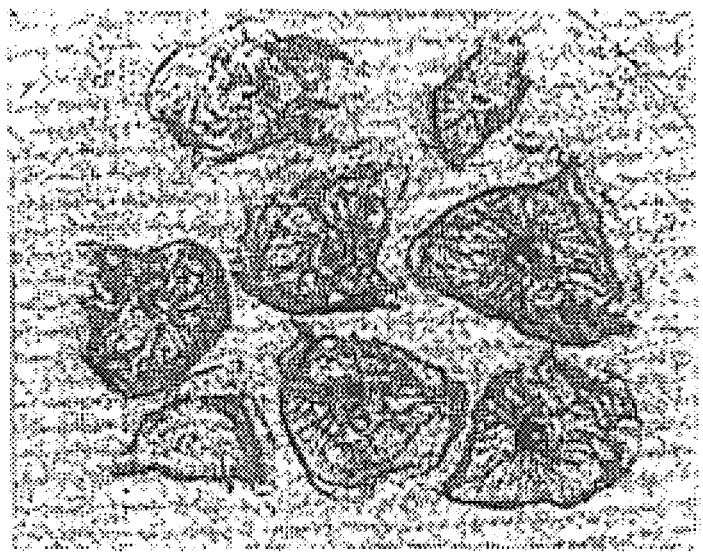
FIGS. 1A and 1B—TIE-2 receptorbody (TIE-2 RB) inhibits the development of blood vessels in the embryonic chicken chorioallantoic membrane (CAM). A single piece of resorbable gelatin foam (Gelfoam) soaked with 6 μg of RB was inserted immediately under the CAM of 1-day chick embryos. After 3 further days of incubation, 4 day old embryos and surrounding CAM were removed and examined.
Figure 1:
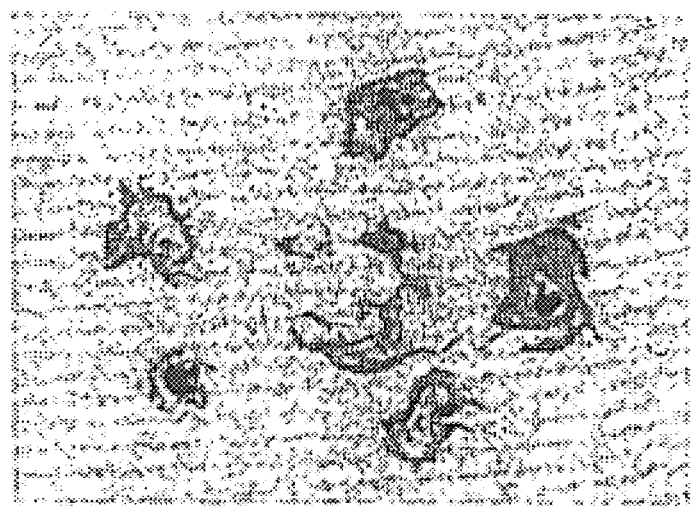

As described in greater detail below, applicants have created novel modified TIE-2 ligands that bind the TIE-2 receptor. The present invention provides for a composition comprising a modified TIE-2 ligand substantially free of other proteins. As used herein, modified TIE-2 ligand refers to a ligand of the TIE family of ligands, whose representatives comprise ligands TL1, TL2, TL3 and TL4 as described herein, which has been altered by addition, deletion or substitution of one or more amino acids, or by way of tagging, with for example, the Fc portion of human IgG-1, but which retains its ability to bind the TIE-2 receptor. Modified TIE-2 ligand also includes a chimeric TIE-2 ligand comprising at least a portion of a first TIE-2 ligand and a portion of a second TIE-2 ligand which is different from the first. By way of non-limiting example, the first TIE-2 ligand is TL1 and the second TIE-2 ligand is TL2. The invention envisions other combinations using additional TIE-2 ligand family members. For example, other combinations for creating a chimeric TIE-2 ligand are possible,)including but not limited to those combinations wherein the first ligand is selected from the group consisting of TL1, TL2, TL3 and TL4, and the second ligand, different from the first ligand, is selected from the group consisting of TL1, TL2, TL3 and TL4.

The invention also provides for an isolated nucleic acid molecule encoding a modified TIE-2 ligand. In one embodiment, the isolated nucleic acid molecule encodes a TIE-2 ligand of the TIE family of ligands, whose representatives comprise ligands TL1, TL2, TL3 and TL4 as described herein, which has been altered by addition, deletion or substitution of one or more amino acids, or by way of tagging, with for example, the Fc portion of human IgG-1, but which retains its ability to bind the TIE-2 receptor. In another embodiment, the isolated nucleic acid molecule encodes a modified TIE-2 ligand which is a chimeric TIE-2 ligand comprising at least a portion of a first TIE-2 ligand and a portion of a second TIE-2 ligand which is different from the first. By way of non-limiting example, the first TIE-2 ligand is TL1 and the second TIE-2 ligand is TL2. The invention envisions other combinations using additional TIE-2 ligand family members. For example, other combinations are possible, including but not limited to those combinations wherein the isolated nucleic acid molecule encodes a modified TIE-2 ligand which is a chimeric TIE-2 ligand comprising a portion of a first ligand selected from the group consisting of TL1, TL2, TL3 and TL4, and a portion of a second ligand, different from the first ligand, selected from the group consisting of TL1, TL2, TL3 and TL4.

The present invention comprises the modified TIE-2 ligands and their amino acid sequences, as well as functionally equivalent variants thereof, as well as proteins or peptides comprising substitutions, deletions or insertional mutants of the described sequences, which bind TIE-2 receptor and act as agonists or antagonists thereof. Such variants include those in which amino acid residues are substituted for residues within the sequence resulting in a silent change. For example, one or more amino acid residues within the sequence can be substituted by another amino acid(s) of a similar polarity which acts as a functional equivalent, resulting in a silent alteration. Substitutes for an amino acid within the sequence may be selected from other members of the class to which the amino acid belongs. For example, the class of nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Also included within the scope of the invention are proteins or fragments or derivatives thereof which exhibit the same or similar biological activity as the modified TIE-2 ligands described herein, and derivatives which are differentially modified during or after translation, e.g., by glycosylation, proteolytic cleavage, linkage to an antibody molecule or other cellular ligand, etc. Functionally equivalent molecules also include molecules that contain modifications, including N-terminal modifications, which result from expression in a particular recombinant host, such as, for example, N-terminal methylation which occurs in certain bacterial (e.g. *E. coli*) expression systems.

The present invention also encompasses the nucleotide sequences that encode the proteins described herein as modified TIE-2 ligands, as well as host cells, including yeast, bacteria, viruses, and mammalian cells, which are genetically engineered to produce the proteins, by e.g. transfection, transduction, infection, electroporation, or microinjection of nucleic acid encoding the modified TIE-2 ligands described herein in a suitable expression vector. The present invention also encompasses introduction of the nucleic acid encoding modified TIE-2 ligands through gene therapy techniques such as is described, for example, in Finkel and Epstein FASEB J. 9:843–851 (1995); Guzman, et al. PNAS (USA) 91:10732–10736 (1994).

One skilled in the art will also recognize that the present invention encompasses DNA and RNA sequences that hybridize to a modified TIE-2 ligand encoding nucleotide sequence, under conditions of moderate stringency, as defined in, for example, Sambrook, et al. Molecular Cloning: A Laboratory Manual, 2 ed. Vol. 1, pp. 101–104, Cold Spring Harbor Laboratory Press (1989). Thus, a nucleic acid molecule contemplated by the invention includes one having a nucleotide sequence deduced from an amino acid sequence of a modified TIE-2 ligand prepared as described herein, as well as a molecule having a sequence of nucleotides that hybridizes to such a nucleotide sequence, and also a nucleotide sequence which is degenerate of the above sequences as a result of the genetic code, but which encodes a ligand that binds TIE-2 receptor and which has an amino acid sequence and other primary, secondary and tertiary characteristics that are sufficiently duplicative of a modified TIE-2 ligand described herein so as to confer on the molecule the same biological activity as the modified TIE-2 ligand described herein.

The present invention provides for an isolated nucleic acid molecule encoding a modified TIE-2 ligand that binds and activates TIE-2 receptor comprising a nucleotide sequence encoding TIE-2 ligand 1 wherein the portion of the nucleotide sequence that encodes the N-terminal domain of TIE-2 ligand 1 is replaced by a nucleotide sequence that encodes the N-terminal domain of TIE-2 ligand 2. The invention also provides for such a nucleic acid molecule, with a further modification such that the portion of the nucleotide sequence that encodes the coiled-coil domain of TIE-2 ligand 1 is replaced by a nucleotide sequence that encodes the coiled-coil domain of TIE-2 ligand 2.

Figure 27A:
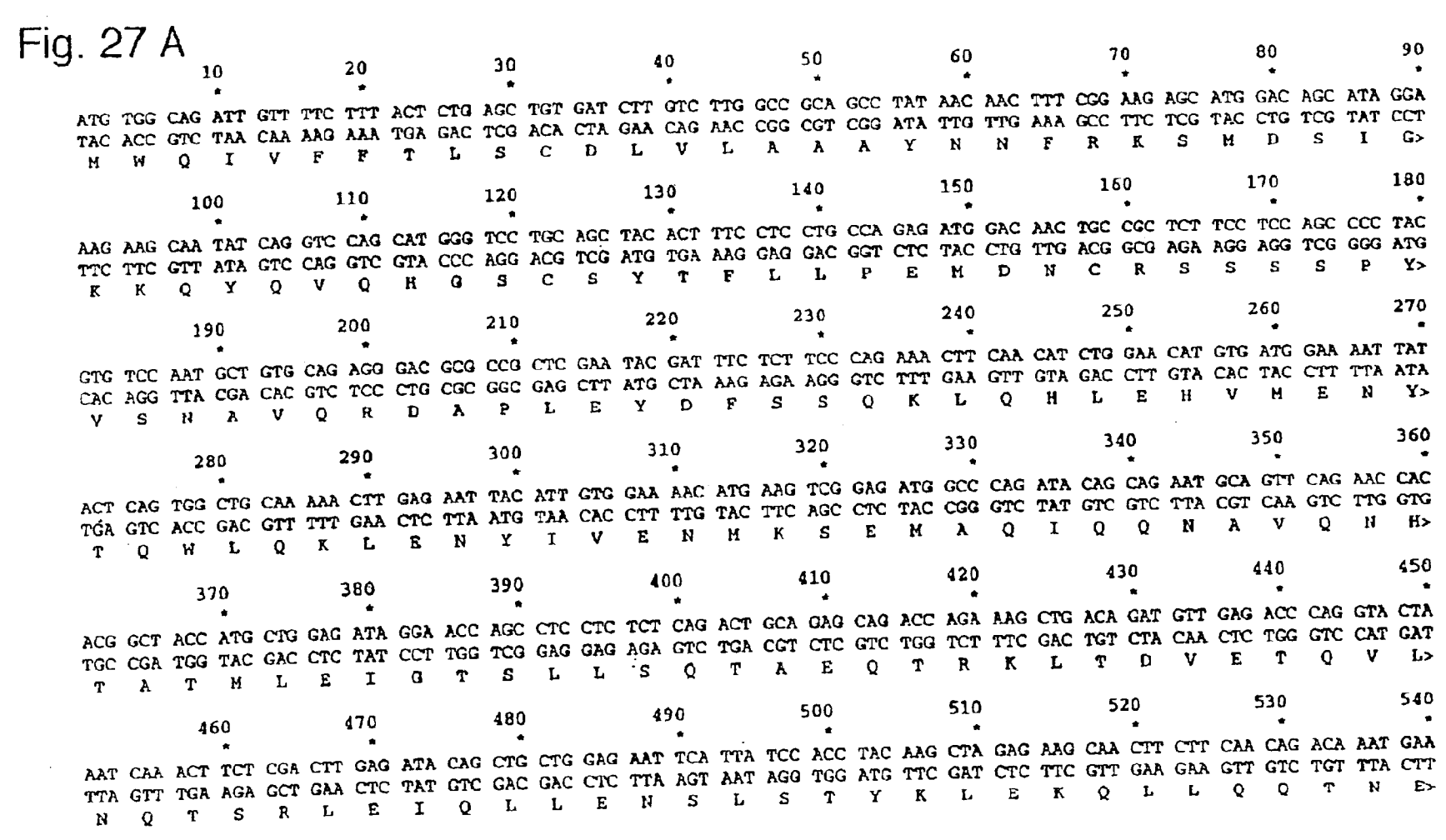
Figure 27B:
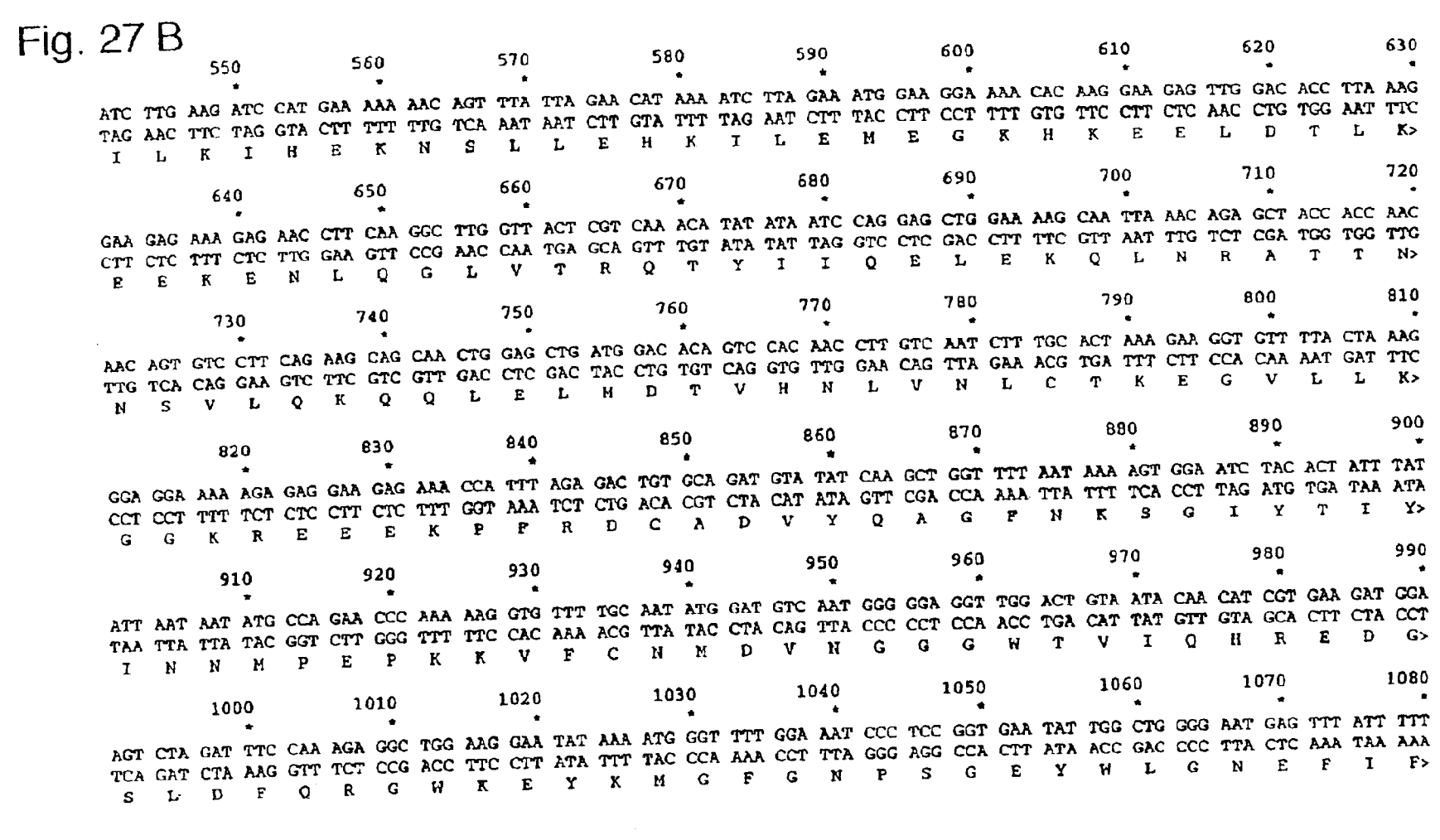

The present invention also provides for an isolated nucleic acid molecule encoding a modified TIE-2 ligand that binds and activates TIE-2 receptor comprising a nucleotide sequence encoding TIE-2 ligand 1 wherein the portion of the nucleotide sequence that encodes the N-terminal domain of TIE-2 ligand 1 is replaced by a nucleotide sequence that encodes the N-terminal domain of TIE-2 ligand 2 and which is further modified to encode a different amino acid instead of the cysteine residue encoded by nucleotides 784–786 as set forth in FIGS. 27A–27C (SEQ ID NO: 25 and SEQ ID NO: 26). A serine residue is preferably substituted for the cysteine residue. In another embodiment, the nucleic acid molecule is further modified to encode a different amino acid instead of the arginine residue encoded by nucleotides 199–201 as set forth in FIGS. 27A–27C (SEQ ID NO: 25 and SEQ ID NO: 26). A serine residue is preferably substituted for the arginine residue.

The present invention also provides for an isolated nucleic acid molecule encoding a modified TIE-2 ligand that binds and activates TIE-2 receptor comprising a nucleotide sequence encoding TIE-2 ligand 1 which is modified to encode a different amino acid instead of the cysteine residue at amino acid position 245. A serine residue is preferably substituted for the cysteine residue.

The invention further provides for an isolated nucleic acid molecule encoding a modified TIE-2 ligand that binds but does not activate TIE-2 receptor comprising a nucleotide sequence encoding TIE-2 ligand 1 wherein the portion of the nucleotide sequence that encodes the N-terminal domain of TIE-2 ligand 1 is deleted. The invention also provides for such a nucleic acid molecule further modified so that the portion of the nucleotide sequence that encodes the coiled-coil domain of TIE-2 ligand 1 is deleted and the portion encoding the fibrinogen-like domain is fused in-frame to a nucleotide sequence encoding a human immunoglobulin gamma-1 constant region (IgG1 Fc).

The invention further provides for an isolated nucleic acid molecule encoding a modified TIE-2 ligand that binds but does not activate TIE-2 receptor comprising a nucleotide sequence encoding TIE-2 ligand 2 wherein the portion of the nucleotide sequence that encodes the N-terminal domain of TIE-2 ligand 2 is deleted. The invention also provides for such a nucleic acid molecule further modified so that the portion of the nucleotide sequence that encodes the coiled-coil domain of TIE-2 ligand 2 is deleted and the portion encoding the fibrinogen-like domain is fused in-frame to a nucleotide sequence encoding a human immunoglobulin gamma-1 constant region (IgG1 Fc).

The invention further provides for an isolated nucleic acid molecule encoding a modified TIE-2 ligand that binds but does not activate TIE-2 receptor comprising a nucleotide sequence encoding TIE-2 ligand 1 wherein the portion of the nucleotide sequence that encodes the fibrinogen-like domain of TIE-2 ligand 1 is replaced by a nucleotide sequence that encodes the fibrinogen-like domain of TIE-2 ligand 2. The invention also provides for such a nucleic acid molecule further modified so that the portion of the nucleotide sequence that encodes the coiled-coil domain of TIE-2 ligand 1 is replaced by a nucleotide sequence that encodes the coiled-coil domain of TIE-2 ligand 2.

The invention further provides for a modified TIE-2 ligand encoded by any of nucleic acid molecules of the invention.

The present invention also provides for a chimeric TIE-2 ligand comprising at least a portion of a first TIE-2 ligand and a portion of a second TIE-2 ligand which is different from the first, wherein the first and second TIE-2 ligands are selected from the group consisting of TIE-2 Ligand-1, TIE-2 Ligand-2, TIE Ligand-3 and TIE Ligand-4. Preferably, the chimeric TIE ligand comprises at least a portion of TIE-2 Ligand-1 and a portion of TIE-2 Ligand-2.

Figure 24:
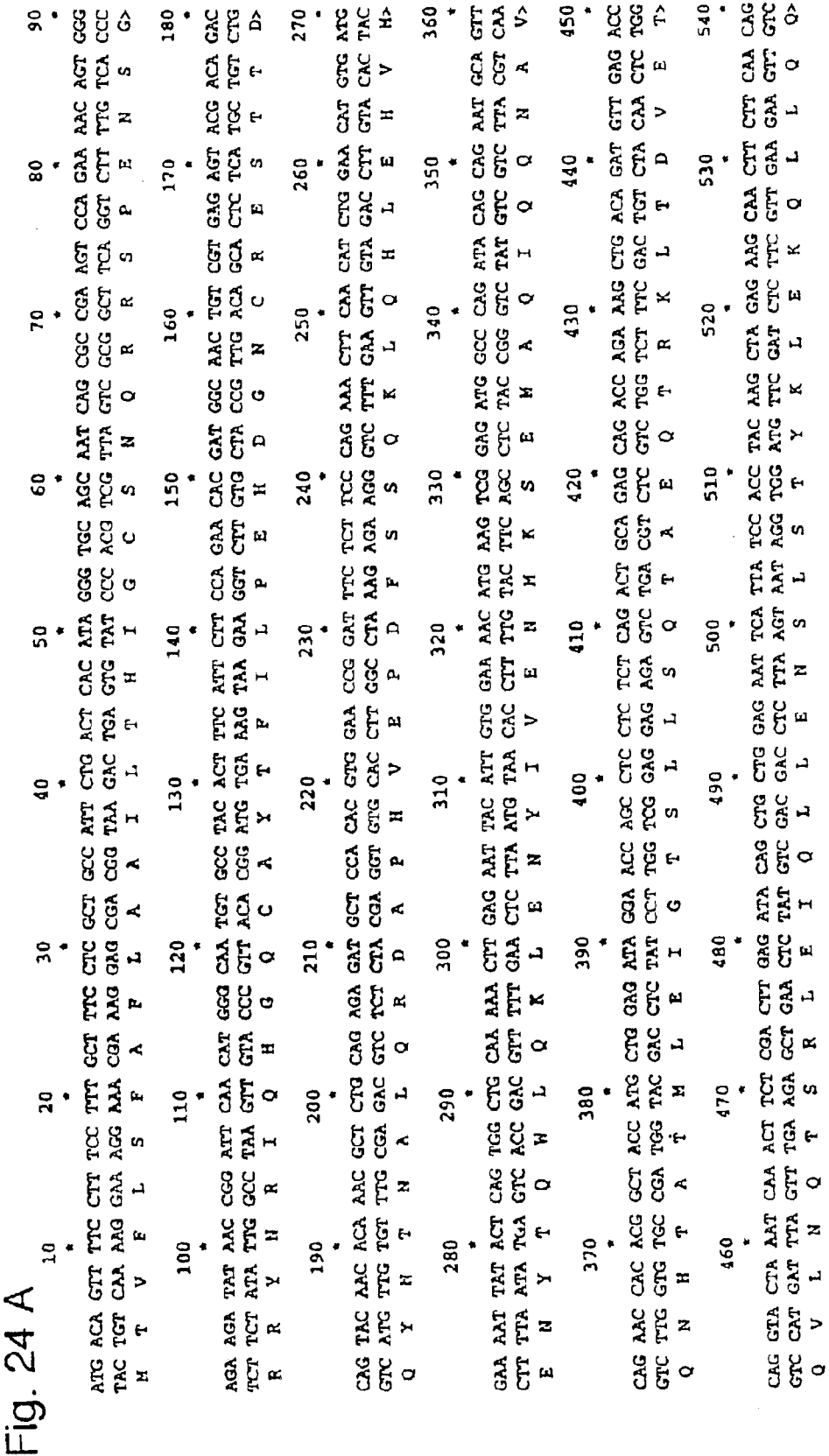
FIGS. 24A–24C—Nucleotide (SEQ ID NO: 19) and deduced amino acid (SEQ ID NO: 20) (single letter code) sequences of chimeric TIE ligand designated 1N1C2F (chimera 1). The putative leader sequence is encoded by nucleotides 1–60.

The invention also provides a nucleic acid molecule that encodes a chimeric TIE ligand as set forth in FIGS. 24A–24C (SEQ ID NO: 19 and SEQ ID NO: 20), 25A–25C (SEQ ID NO: 21 and SEQ ID NO: 22), 26A–26C (SEQ ID NO: 23 and SEQ ID NO: 24), or 27A–27C (SEQ ID NO: 25 and (SEQ ID NO: 26). The invention also provides a chimeric TIE ligand as set forth in FIGS. 24A–24C (SEQ ID NO: 19 and SEQ ID NO: 20), 25A–25C (SEQ ID NO: 21 and SEQ ID NO: 22), 26A–26C (SEQ ID NO: 23 and SEQ ID NO: 24), or 27A–27C (SEQ ID NO: 25 and SEQ ID NO: 26). The invention further provides a chimeric TIE ligand as set forth in FIGS. 27A–27C (SEQ ID NO: 25 and SEQ ID NO: 26), modified to have a different amino acid instead of the cysteine residue encoded by nucleotides 784–786.

Any of the methods known to one skilled in the art for the insertion of DNA fragments into a vector may be used to construct expression vectors encoding a modified TIE-2 ligand using appropriate transcriptional/translational control signals and the protein coding sequences. These methods may include in vitro recombinant DNA and synthetic techniques and in vivo recombinations (genetic recombination). Expression of a nucleic acid sequence encoding a modified TIE-2 ligand or peptide fragments thereof may be regulated by a second nucleic acid sequence which is operably linked to the a modified TIE-2 ligand encoding sequence such that the modified TIE-2 ligand protein or peptide is expressed in a host transformed with the recombinant DNA molecule. For example, expression of a modified TIE-2 ligand described herein may be controlled by any promoter/enhancer element known in the art. Promoters which may be used to control expression of the ligand include, but are not limited to the long terminal repeat as described in Squinto et al., (Cell 65:1–20 (1991)); the SV40 early promoter region (Bernoist and Chambon, Nature 290:304–310), the CMV promoter, the M-MuLV 5' terminal repeat, the promoter contained in the 3' long terminal repeat of Rous sarcoma virus (Yamamoto, et al., Cell 22:787–797 (1980)), the herpes thymidine kinase promoter (Wagner et al., Proc. Natl. Acad. Sci. U.S.A. 78:144–1445 (1981)), the adenovirus promoter, the regulatory sequences of the metallothionein gene (Brinster et al., Nature 296:39–42 (1982)); prokaryotic expression vectors such as the β-lactamase promoter (Villa-Kamaroff, et al., Proc. Natl. Acad. Sci. U.S.A. 75:3727–3731 (1978)), or the tac promoter (DeBoer, et al., Proc. Natl. Acad. Sci. U.S.A. 80:21–25 (1983)), see also "Useful proteins from recombinant bacteria" in Scientific American, 242:74–94 (1980); promoter elements from yeast or other fungi such as the Gal 4 promoter, the ADH (alcohol dehydrogenase) promoter, PGK (phosphoglycerol kinase) promoter, alkaline phosphatase promoter, and the following animal transcriptional control regions, which exhibit tissue specificity and have been utilized in transgenic animals; elastase I gene control region which is active in pancreatic acinar cells (Swift et al., Cell 38:639–646 (1984); Ornitz et al., Cold Spring Harbor Symp. Quant. Biol. 50:399–409 (1986); MacDonald, Hepatology 7:425–515 (1987); insulin gene control region which is active in pancreatic beta cells [Hanahan, Nature 315:115–122 (1985)]; immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58); alpha 1-antitrypsin gene control region which is active in the liver (Kelsey et al, 1987, Genes and Devel. 1:161–171), beta-globin gene control region which is active in myeloid cells (Mogram et al., 1985, Nature 315:338–340; Kollias et al., 1986, Cell 46:89–94); myelin basic protein gene control region which is active in oligodendrocytes in the brain (Readhead et al., 1987, Cell 48:703–712); myosin light chain-2 gene control region which is active in skeletal muscle (Shani, 1985, Nature 314:283–286), and gonadotropic releasing hormone gene control region which is active in the hypothalamus (Mason et al., 1986, Science 234:1372–1378). The invention further encompasses the production of antisense compounds which are capable of specifically hybridizing with a sequence of RNA encoding a modified TIE-2 ligand to modulate its expression. Ecker, U.S. Pat. No. 5,166,195, issued Nov. 24, 1992.

Thus, according to the invention, expression vectors capable of being replicated in a bacterial or eukaryotic host comprising a nucleic acid encoding a modified TIE-2 ligand as described herein, are used to transfect a host and thereby direct expression of such nucleic acid to produce a modified TIE-2 ligand, which may then be recovered in a biologically active form. As used herein, a biologically active form includes a form capable of binding to TIE receptor and causing a biological response such as a differentiated function or influencing the phenotype of the cell expressing the receptor. Such biologically active forms could, for example, induce phosphorylation of the tyrosine kinase domain of TIE receptor. Alternatively, the biological activity may be an effect as an antagonist to the TIE receptor. In alternative embodiments, the active form of a modified TIE-2 ligand is one that can recognize TIE receptor and thereby act as a targeting agent for the receptor for use in both diagnostics and therapeutics. In accordance with such embodiments, the active form need not confer upon any TIE expressing cell any change in phenotype.

Expression vectors containing the gene inserts can be identified by four general approaches: (a) DNA-DNA hybridization, (b) presence or absence of "marker" gene functions, (c) expression of inserted sequences and (d) PCR detection. In the first approach, the presence of a foreign gene inserted in an expression vector can be detected by DNA-DNA hybridization using probes comprising sequences that are homologous to an inserted modified TIE-2 ligand encoding gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if a nucleic acid encoding a modified TIE-2 ligand is inserted within the marker gene sequence of the vector, recombinants containing the insert can be identified by the absence of the marker gene function. In the third approach, recombinant expression vectors can be identified by assaying the foreign gene product expressed by the recombinant. Such assays can be based, for example, on the physical or functional properties of a modified TIE-2 ligand gene product, for example, by binding of the ligand to TIE receptor or a portion thereof which may be tagged with, for example, a detectable antibody or portion thereof or by binding to antibodies produced against the modified TIE-2 ligand protein or a portion thereof. Cells of the present invention may transiently or, preferably, constitutively and permanently express a modified TIE-2 ligand as described herein. In the fourth approach, DNA nucleotide primers can be prepared corresponding to a tie specific DNA sequence. These primers could then be used to PCR a tie gene fragment. (PCR Protocols: A Guide To Methods and Applications, Edited by Michael A. Innis et al., Academic Press (1990)).

The recombinant ligand may be purified by any technique which allows for the subsequent formation of a stable, biologically active protein. Preferably, the ligand is secreted into the culture medium from which it is recovered. Alternatively, the ligand may be recovered from cells either as soluble proteins or as inclusion bodies, from which it may be extracted quantitatively by 8M guanidinium hydrochloride and dialysis in accordance with well known methodology. In order to further purify the ligand, affinity chromatography, conventional ion exchange chromatography, hydrophobic interaction chromatography, reverse phase chromatography or gel filtration may be used.

In additional embodiments of the invention, as described in greater detail in the Examples, a modified TIE-2 ligand encoding gene may be used to inactivate or "knock out" an endogenous gene by homologous recombination, and thereby create a TIE ligand deficient cell, tissue, or animal. For example, and not by way of limitation, the recombinant TIE ligand-4 encoding gene may be engineered to contain an insertional mutation, for example the neo gene, which would inactivate the native TIE ligand-4 encoding gene. Such a construct, under the control of a suitable promoter, may be introduced into a cell, such as an embryonic stem cell, by a technique such as transfection, transduction, or injection. Cells containing the construct may then be selected by G418 resistance. Cells which lack an intact TIE ligand-4 encoding gene may then be identified, e.g. by Southern blotting, PCR detection, Northern blotting or assay of expression. Cells lacking an intact TIE ligand-4 encoding gene may then be fused to early embryo cells to generate transgenic animals deficient in such ligand. Such an animal may be used to define specific in vivo processes, normally dependent upon the ligand.

The present invention also provides for antibodies to a modified TIE-2 ligand described herein which are useful for detection of the ligand in, for example, diagnostic applications. For preparation of monoclonal antibodies directed toward a modified TIE-2 ligand, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in "Monoclonal Antibodies and Cancer Therapy," Alan R. Liss, Inc. pp. 77–96) and the like are within the scope of the present invention.

The monoclonal antibodies may be human monoclonal antibodies or chimeric human-mouse (or other species) monoclonal antibodies. Human monoclonal antibodies may be made by any of numerous techniques known in the art (e.g., Teng et al., 1983, Proc. Natl. Acad. Sci. U.S.A. 80:7308–7312; Kozbor et al., 1983, Immunology Today 4:72–79; Olsson et al., 1982, Meth. Enzymol. 92:3–16). Chimeric antibody molecules may be prepared containing a mouse antigen-binding domain with human constant regions (Morrison et al., 1984, Proc. Natl. Acad. Sci. U.S.A. 81:6851, Takeda et al., 1985, Nature 314:452).

Various procedures known in the art may be used for the production of polyclonal antibodies to epitopes of a modified TIE-2 ligand described herein. For the production of antibody, various host animals, including but not limited to rabbits, mice and rats can be immunized by injection with a modified TIE-2 ligand, or a fragment or derivative thereof. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum.*

A molecular clone of an antibody to a selected a modified TIE-2 ligand epitope can be prepared by known techniques. Recombinant DNA methodology (see e.g., Maniatis et al., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen binding region thereof.

The present invention provides for antibody molecules as well as fragments of such antibody molecules. Antibody fragments which contain the idiotype of the molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent. Antibody molecules may be purified by known techniques, es, immunoabsorption or immunoaffinity chromatography, chromatographic methods such as HPLC (high performance liquid chromatography), or a combination thereof.

The present invention further encompasses an immunoassay for measuring the amount of a modified TIE-2 ligand in a biological sample by a) contacting the biological sample with at least one antibody which specifically binds a modified TIE-2 ligand so that the antibody forms a complex with any modified TIE-2 ligand present in the sample; and b) measuring the amount of the complex and thereby measuring the amount of the modified TIE-2 ligand in the biological sample.

The invention further encompasses an assay for measuring the amount of TIE receptor in a biological sample by a) contacting the biological sample with at least one ligand of the invention so that the ligand forms a complex with the TIE receptor; and b) measuring the amount of the complex and thereby measuring the amount of the TIE receptor in the biological sample.

The present invention also provides for the utilization of a modified TIE-2 ligand which activates the TIE-2 receptor as described herein, to support the survival and/or growth and/or migration and/or differentiation of TIE-2 receptor expressing cells. Thus, the ligand may be used as a supplement to support, for example, endothelial cells in culture.

Further, the creation by applicants of a modified TIE-2 ligand for the TIE-2 receptor enables the utilization of assay systems useful for the identification of agonists or antagonists of the TIE-2 receptor. Such assay systems would be useful in identifying molecules capable of promoting or inhibiting angiogenesis. For example, in one embodiment, antagonists of the TIE-2 receptor may be identified as test molecules that are capable of interfering with the interaction of the TIE-2 receptor with a modified TIE-2 ligand that binds the TIE-2 receptor. Such antagonists are identified by their ability to 1) block the binding of a biologically active modified TIE-2 ligand to the receptor as measured, for example, using BIAcore biosensor technology (BIAcore;

Pharmacia Biosensor, Piscataway, N.J.); or 2) block the ability of a biologically active modified TIE-2 ligand to cause a biological response. Such biological responses include, but are not limited to, phosphorylation of the TIE receptor or downstream components of the TIE signal transduction pathway, or survival, growth or differentiation of TIE receptor bearing cells.

In one embodiment, cells engineered to express the TIE receptor may be dependent for growth on the addition of a modified TIE-2 ligand. Such cells provide useful assay systems for identifying additional agonists of the TIE receptor, or antagonists capable of interfering with the activity of the modified TIE-2 ligand on such cells. Alternatively, autocrine cells, engineered to be capable of co-expressing both a modified TIE-2 ligand and receptor, may provide useful systems for assaying potential agonists or antagonists.

Therefore, the present invention provides for introduction of a TIE-2 receptor into cells that do not normally express this receptor, thus allowing these cells to exhibit profound and easily distinguishable responses to a ligand which binds this receptor. The type of response elicited depends on the cell utilized, and not the specific receptor introduced into the cell. Appropriate cell lines can be chosen to yield a response of the greatest utility for assaying, as well as discovering, molecules that can act on tyrosine kinase receptors. The molecules may be any type of molecule, including but not limited to peptide and non-peptide molecules, that will act in systems to be described in a receptor specific manner.

One of the more useful systems to be exploited involves the introduction of a TIE receptor (or a chimeric receptor comprising the extracellular domain of another receptor tyrosine kinase such as, for example, trkC and the intracellular domain of a TIE receptor) into a fibroblast cell line (e.g., NIH3T3 cells) thus such a receptor which does not normally mediate proliferative or other responses can, following introduction into fibroblasts, nonetheless be assayed by a variety of well established methods to quantitate effects of fibroblast growth factors (e.g. thymidine incorporation or other types of proliferation assays; see van Zoelen, 1990, "The Use of Biological Assays For Detection Of Polypeptide Growth Factors" in Progress Factor Research, Vol. 2, pp. 131–152; Zhan and M. Goldfarb, 1986, Mol. Cell. Biol., Vol. 6, pp. 3541–3544). These assays have the added advantage that any preparation can be assayed both on the cell line having the introduced receptor as well as the parental cell line lacking the receptor; only specific effects on the cell line with the receptor would be judged as being mediated through the introduced receptor. Such cells may be further engineered to express a modified TIE-2 ligand, thus creating an autocrine system useful for assaying for molecules that act as antagonists/agonists of this interaction. Thus, the present invention provides for host cells comprising nucleic acid encoding a modified TIE-2 ligand and nucleic acid encoding TIE receptor.

The TIE receptor/modified TIE-2 ligand interaction also provides a useful system for identifying small molecule agonists or antagonists of the TIE receptor. For example, fragments, mutants or derivatives of a modified TIE-2 ligand may be identified that bind TIE receptor but do not induce any other biological activity. Alternatively, the characterization of a modified TIE-2 ligand enables the further characterization of active portions of the molecule. Further, the identification of a ligand enables the determination of the X-ray crystal structure of the receptor/ligand complex, thus enabling identification of the binding site on the receptor. Knowledge of the binding site will provide useful insight into the rational design of novel agonists and antagonists.

The specific binding of a test molecule to TIE receptor may be measured in a number of ways. For example, the actual binding of test molecule to cells expressing TIE may be detected or measured, by detecting or measuring (i) test molecule bound to the surface of intact cells; (ii) test molecule cross-linked to TIE protein in cell lysates; or (iii) test molecule bound to TIE in vitro. The specific interaction between test molecule and TIE may be evaluated by using reagents that demonstrate the unique properties of that interaction.

As a specific, nonlimiting example, the methods of the invention may be used as follows. Consider a case in which a modified TIE-2 ligand in a sample is to be measured. Varying dilutions of the sample (the test molecule), in parallel with a negative control (NC) containing no modified TIE-2 ligand activity, and a positive control (PC) containing a known amount of a modified TIE-2 ligand, may be exposed to cells that express TIE in the presence of a detectably labeled modified TIE-2 ligand (in this example, radioiodinated ligand). The amount of modified TIE-2 ligand in the test sample may be evaluated by determining the amount of $^{125}$I-labeled modified TIE-2 ligand that binds to the controls and in each of the dilutions, and then comparing the sample values to a standard curve. The more modified TIE-2 ligand in the sample, the less $^{125}$I-ligand that will bind to TIE.

The amount of $^{125}$I-ligand bound may be determined by measuring the amount of radioactivity per cell, or by cross-linking a modified TIE-2 ligand to cell surface proteins using DSS, as described in Meakin and Shooter, 1991, Neuron 6:153–163, and detecting the amount of labeled protein in cell extracts using, for example, SDS polyacrylamide gel electrophoresis, which may reveal a labeled protein having a size corresponding to TIE receptor/modified TIE-2 ligand. The specific test molecule/TIE interaction may further be tested by adding to the assays various dilutions of an unlabeled control ligand that does not bind the TIE receptor and therefore should have no substantial effect on the competition between labeled modified TIE-2 ligand and test molecule for TIE binding. Alternatively, a molecule known to be able to disrupt TIE receptor/modified TIE-2 ligand binding, such as, but not limited to, anti-TIE antibody, or TIE receptorbody as described herein, may be expected to interfere with the competition between $^{125}$I-modified TIE-2 ligand and test molecule for TIE receptor binding.

Detectably labeled modified TIE-2 ligand includes, but is not limited to, a modified TIE-2 ligand linked covalently or noncovalently to a radioactive substance, a fluorescent substance, a substance that has enzymatic activity, a substance that may serve as a substrate for an enzyme (enzymes and substrates associated with colorimetrically detectable reactions are preferred) or to a substance that can be recognized by an antibody molecule that is preferably a detectably labeled antibody molecule.

Alternatively, the specific binding of test molecule to TIE may be measured by evaluating the secondary biological effects of a modified TIE-2 ligand/TIE receptor binding, including, but not limited to, cell growth and/or differentiation or immediate early gene expression or phosphorylation of TIE. For example, the ability of the test molecule to induce differentiation can be tested in cells that lack tie and in comparable cells that express tie; differentiation in tie-expressing cells but not in comparable cells that lack tie would be indicative of a specific test molecule/TIE interaction. A similar analysis could be performed by detecting immediate early gene (e.g. fos and jun) induction in tie-minus and tie-plus cells, or by detecting phosphorylation of TIE using standard phosphorylation assays known in the art. Such analysis might be useful in identifying agonists or antagonists that do not competitively bind to TIE.

Similarly, the present invention provides for a method of identifying a molecule that has the biological activity of a modified TIE-2 ligand comprising (i) exposing a cell that expresses tie to a test molecule and (ii) detecting the specific binding of the test molecule to TIE receptor, in which specific binding to TIE positively correlates with TIE-like activity. Specific binding may be detected by either assaying for direct binding or the secondary biological effects of binding, as discussed supra. Such a method may be particularly useful in identifying new members of the TIE ligand family or, in the pharmaceutical industry, in screening a large array of peptide and non-peptide molecules (e.g., peptidomimetics) for TIE associated biological activity. In a preferred, specific, nonlimiting embodiment of the invention, a large grid of culture wells may be prepared that contain, in alternate rows, PC12 (or fibroblasts, see infra) cells that are either tie-minus or engineered to be tie-plus. A variety of test molecules may then be added such that each column of the grid, or a portion thereof, contains a different test molecule. Each well could then be scored for the presence or absence of growth and/or differentiation. An extremely large number of test molecules could be screened for such activity in this manner.

In additional embodiments, the invention provides for methods of detecting or measuring TIE ligand-like activity or identifying a molecule as having such activity comprising (i) exposing a test molecule to a TIE receptor protein in vitro under conditions that permit binding to occur and (ii) detecting binding of the test molecule to the TIE receptor protein, in which binding of test molecule to TIE receptor correlates with TIE ligand-like activity. According to such methods, the TIE receptor may or may not be substantially purified, may be affixed to a solid support (e.g. as an affinity column or as an ELISA assay), or may be incorporated into an artificial membrane. Binding of test molecule to TIE receptor may be evaluated by any method known in the art. In preferred embodiments, the binding of test molecule may be detected or measured by evaluating its ability to compete with detectably labeled known TIE ligands for TIE receptor binding.

The present invention also provides for a method of detecting the ability of a test molecule to function as an antagonist of TIE ligand-like activity comprising detecting the ability of the molecule to inhibit an effect of TIE ligand binding to TIE receptor on a cell that expresses the receptor. Such an antagonist may or may not interfere with TIE receptor/modified TIE-2 ligand binding. Effects of a modified TIE-2 ligand binding to TIE receptor are preferably biological or biochemical effects, including, but not limited to, cell survival or proliferation, cell transformation, immediate early gene induction, or TIE phosphorylation.

The invention further provides for both a method of identifying antibodies or other molecules capable of neutralizing the ligand or blocking binding to the receptor, as well as the molecules identified by the method. By way of nonlimiting example, the method may be performed via an assay which is conceptually similar to an ELISA assay. For example, TIE receptorbody may be bound to a solid support, such as a plastic multiwell plate. As a control, a known amount of a modified TIE-2 ligand which has been Myc-tagged may then be introduced to the well and any tagged modified TIE-2 ligand which binds the receptorbody may then be identified by means of a reporter antibody directed against the Myc-tag. This assay system may then be used to screen test samples for molecules which are capable of i) binding to the tagged ligand or ii) binding to the receptorbody and thereby blocking binding to the receptorbody by the tagged ligand. For example, a test sample containing a putative molecule of interest together with a known amount of tagged ligand may be introduced to the well and the amount of tagged ligand which binds to the receptorbody may be measured. By comparing the amount of bound tagged ligand in the test sample to the amount in the control, samples containing molecules which are capable of blocking ligand binding to the receptor may be identified. The molecules of interest thus identified may be isolated using methods well known to one of skill in the art.

Once a blocker of ligand binding is found, one of skill in the art would know to perform secondary assays to determine whether the blocker is binding to the receptor or to the ligand, as well as assays to determine if the blocker molecule can neutralize the biological activity of the ligand. For example, by using a binding assay which employs BIAcore biosensor technology (or the equivalent), in which either TIE receptorbody or a modified TIE-2 ligand or ligandbody is covalently attached to a solid support (e.g. carboxymethyl dextran on a gold surface), one of skill in the art would be able to determine if the blocker molecule is binding specifically to the ligand, ligandbody or to the receptorbody. To determine if the blocker molecule can neutralize the biological activity of the ligand, one of skill in the art could perform a phosphorylation assay (see Example 5) or alternatively, a functional bioassay, such as a survival assay, by using primary cultures of, for example, endothelial cells. Alternatively, a blocker molecule which binds to the receptorbody could be an agonist and one of skill in the art would know to how to determine this by performing an appropriate assay for identifying additional agonists of the TIE receptor.

In addition, the invention further contemplates compositions wherein the TIE ligand is the receptor binding domain of a TIE-2 ligand described herein. For example, TIE-2 ligand 1 contains a "coiled coil" domain (beginning at the 5' end and extending to the nucleotide at about position 1160 of FIGS. 4A–4D [SEQ ID NO: 1 and SEQ ID NO: 2] and about position 1157 of FIGS. 5A–5D [SEQ ID NO: 3 and SEQ ID NO: 4]) and a fibrinogen-like domain (which is encoded by the nucleotide sequence of FIGS. 4A–4D [SEQ ID NO: 1 and SEQ ID NO: 2] beginning at about position 1161 and about position 1158 of FIGS. 5A–5D [SEQ ID NO: 3 and SEQ ID NO: 4]). The fibrinogen-like domain of TIE-2 ligand 2 is believed to begin on or around the same amino acid sequence as in ligand 1 (FRDCA) which is encoded by nucleotides beginning around 1197 of FIGS. 6A–6D (SEQ ID NO: 5 and SEQ ID NO: 6). The fibrinogen-like domain of TIE ligand-3 is believed to begin on or around the amino acid sequence which is encoded by nucleotides beginning around position 929 as set forth in FIGS. 21A–21C (SEQ ID NO: 9 and SEQ ID NO: 10). Multimerization of the coiled coil domains during production of the ligand hampers purification. As described in Example 19, Applicants have discovered, however, that the fibrinogen-like domain comprises the TIE-2 receptor binding domain. The monomeric forms of the fibrinogen-like domain do not, however, appear to bind the receptor. Studies utilizing myc-tagged fibrinogen-like domain, which has been "clustered" using anti-myc antibodies, do bind the TIE-2 receptor. [Methods of production of "clustered ligands and ligandbodies are described in Davis, et al. Science 266:816–819 (1994)]. Based on these finding, applicants produced "ligandbodies" which comprise the fibrinogen-like domain of the TIE-2 ligands coupled to the Fc domain of IgG ("fFc's"). These ligandbodies, which form dimers, efficiently bind the TIE-2 receptor. Accordingly, the present invention contemplates the production of modified TIE ligandbodies which may be used as targeting agents, in diagnostics or in therapeutic applications, such as targeting agents for tumors and/or associated vasculature wherein a TIE antagonist is indicated.

The invention herein further provides for the development of the ligand, a fragment or derivative thereof, or another molecule which is a receptor agonist or antagonist, as a therapeutic for the treatment of patients suffering from disorders involving cells, tissues or organs which express the TIE receptor. Such molecules may be used in a method of treatment of the human or animal body, or in a method of diagnosis.

Because TIE receptor has been identified in association with endothelial cells and, as demonstrated herein, blocking of TIE-2 ligand 1 appears to prevent vascularization, applicants expect that a modified TIE-2 ligand described herein may be useful for the induction of vascularization in diseases or disorders where such vascularization is indicated. Such diseases or disorders would include wound healing, ischaemia and diabetes. The ligands may be tested in animal models and used therapeutically as described for other agents, such as vascular endothelial growth factor (VEGF), another endothelial cell-specific factor that is angiogenic. Ferrara, et al. U.S. Pat. No. 5,332,671 issued Jul. 26, 1994. The Ferrara reference, as well as other studies, describe in vitro and in vivo studies that may be used to demonstrate the effect of an angiogenic factor in enhancing blood flow to ischemic myocardium, enhancing wound healing, and in other therapeutic settings wherein neoangiogenesis is desired. [see Sudo, et al. European Patent Application 0 550 296 A2 published Jul. 7, 1993; Banai, et al. Circulation 89:2183–2189 (1994); Unger, et al. Am. J. Physiol. 266:H1588–H1595 (1994); Lazarous, et al. Circulation 91:145–153 (1995)]. According to the invention, a modified TIE-2 ligand may be used alone or in combination with one or more additional pharmaceutically active compounds such as, for example, VEGF or basic fibroblast growth factor (bFGF), as well as cytokines, neurotrophins, etc.

Conversely, antagonists of the TIE receptor, such as modified TIE-2 ligands which bind but do not activate the receptor as described herein, receptorbodies as described herein in Examples 2 and 3, and TIE-2 ligand 2 as described in Example 9, would be useful to prevent or attenuate vascularization, thus preventing or attenuating, for example, tumor growth. These agents may be used alone or in combination with other compositions, such as anti-VEGF antibodies, that have been shown to be useful in treating conditions in which the therapeutic intent is to block angiogenesis. Applicants expect that a modified TIE-2 ligand described herein may also be used in combination with agents, such as cytokine antagonists such as IL-6 antagonists, that are known to block inflammation.

For example, applicants have determined that TIE ligands are expressed in cells within, or closely associated with, tumors. For example, TIE-2 ligand 2 appears to be tightly associated with tumor endothelial cells. Accordingly, it and other TIE antagonists may also be useful in preventing or attenuating, for example, tumor growth. In addition, TIE ligands or ligandbodies may be useful for the delivery of toxins to a receptor bearing cell. Alternatively, other molecules, such as growth factors, cytokines or nutrients, may be delivered to a TIE receptor bearing cell via TIE ligands or ligandbodies. TIE ligands or ligandbodies such as modified TIE-2 ligand described herein may also be used as diagnostic reagents for TIE receptor, to detect the receptor in vivo or in vitro. Where the TIE receptor is associated with a disease state, TIE ligands or ligandbodies such as a modified TIE-2 ligand may be useful as diagnostic reagents for detecting the disease by, for example, tissue staining or whole body imaging. Such reagents include radioisotopes, flurochromes, dyes, enzymes and biotin. Such diagnostics or targeting agents may be prepared as described in Alitalo, et al. WO 95/26364 published Oct. 5, 1995 and Burrows, F. and P. Thorpe, PNAS (USA) 90:8996–9000 (1993) which is incorporated herein in its entirety.

In other embodiments, the TIE ligands, a receptor activating modified TIE-2 ligand described herein are used as hematopoietic factors. A variety of hematopoietic factors and their receptors are involved in the proliferation and/or differentiation and/or migration of the various cells types contained within blood. Because the TIE receptors are expressed in early hematopoietic cells, the TIE ligands are expected to play a comparable role in the proliferation or differentiation or migration of these cells. Thus, for example, TIE containing compositions may be prepared, assayed, examined in in vitro and in vivo biological systems and used therapeutically as described in any of the following: Sousa, U.S. Pat. No. 4,810,643, Lee, et al., Proc. Natl. Acad. Sci. USA 82:4360–4364 (1985) Wong, et al. Science, 228:810–814 (1985); Yokota, et al. Proc. Natl. Acad. Sci (USA) 81:1070 (1984); Bosselman, et al. WO 9105795 published May 2, 1991 entitled "Stem Cell Factor" and Kirkness, et al. WO 95/19985 published Jul. 27, 1995 entitled "Haemopoietic Maturation Factor". Accordingly, receptor activating modified TIE-2 ligand may be used to diagnose or treat conditions in which normal hematopoiesis is suppressed, including, but not limited to anemia, thrombocytopenia, leukopenia and granulocytopenia. In a preferred embodiment, receptor activating modified TIE-2 ligand may be used to stimulate differentiation of blood cell precursors in situations where a patient has a disease, such as acquired immune deficiency syndrome (AIDS) which has caused a reduction in normal blood cell levels, or in clinical settings in which enhancement of hematopoietic populations is desired, such as in conjunction with bone marrow transplant, or in the treatment of aplasia or myelosuppression caused by radiation, chemical treatment or chemotherapy.

The receptor activating modified TIE-2 ligands of the present invention may be used alone, or in combination with another pharmaceutically active agent such as, for example, ctyokines, neurotrophins, interleukins, etc. In a preferred embodiment, the ligands may be used in conjunction with any of a number of the above referenced factors which are known to induce stem cell or other hematopoietic precursor proliferation, or factors acting on later cells in the hematopoietic pathway, including, but not limited to, hemopoietic maturation factor, thrombopoietin, stem cell factor, erythropoietin, G-CSF, GM-CSF, etc.

In an alternative embodiment, TIE receptor antagonists are used to diagnose or treat patients in which the desired result is inhibition of a hematopoietic pathway, such as for the treatment of myeloproliferative or other proliferative disorders of blood forming organs such as thrombocythemias, polycythemias and leukemias. In such embodiments, treatment may comprise use of a therapeutically effective amount of the a modified TIE-2 ligand, TIE antibody, TIE receptorbody, a conjugate of a modified TIE-2 ligand, or a ligandbody or fFC as described herein.

The present invention also provides for pharmaceutical compositions comprising a modified TIE-2 ligand or ligandbodies described herein, peptide fragments thereof, or derivatives in a pharmacologically acceptable vehicle. The modified TIE-2 ligand proteins, peptide fragments, or derivatives may be administered systemically or locally. Any appropriate mode of administration known in the art may be used, including, but not limited to, intravenous, intrathecal, intraarterial, intranasal, oral, subcutaneous, intraperitoneal, or by local injection or surgical implant. Sustained release formulations are also provided for.

The present invention also provides for an antibody which specifically binds such a therapeutic molecule. The antibody may be monoclonal or polyclonal. The invention also provides for a method of using such a monoclonal or polyclonal antibody to measure the amount of the therapeutic molecule in a sample taken from a patient for purposes of monitoring the course of therapy.

The invention further provides for a therapeutic composition comprising a modified TIE-2 ligand or ligandbody and a cytotoxic agent conjugated thereto. In one embodiment, the cytotoxic agent may be a radioisotope or toxin.

The invention also provides for an antibody which specifically binds a modified TIE-2 ligand. The antibody may be monoclonal or polyclonal. The invention further provides for a method of purifying a modified TIE-2 ligand comprising:

a) coupling at least one TIE binding substrate to a solid matrix;
b) incubating the substrate of a) with a cell lysate so that the substrate forms a complex with any modified TIE-2 ligand in the cell lysate;
c) washing the solid matrix; and
d) eluting the modified TIE-2 ligand from the coupled substrate.

The substrate may be any substance that specifically binds the modified TIE-2 ligand. In one embodiment, the substrate is selected from the group consisting of anti-modified TIE-2 ligand antibody, TIE receptor and TIE receptorbody. The invention further provides for a receptorbody which specifically binds a modified TIE-2 ligand, as well as a therapeutic composition comprising the receptorbody in a pharmaceutically acceptable vehicle, and a method of blocking blood vessel growth in a human comprising administering an effective amount of the therapeutic composition.

The invention also provides for a therapeutic composition comprising a receptor activating modified TIE-2 ligand or ligandbody in a pharmaceutically acceptable vehicle, as well as a method of promoting neovascularization in a patient comprising administering to the patient an effective amount of the therapeutic composition.

In addition, the present invention provides for a method for identifying a cell which expresses TIE receptor which comprises contacting a cell with a detectably labeled modified TIE-2 ligand or ligandbody, under conditions permitting binding of the detectably labeled ligand to the TIE receptor and determining whether the detectably labeled ligand is bound to the TIE receptor, thereby identifying the cell as one which expresses TIE receptor. The present invention also provides for a therapeutic composition comprising a modified TIE-2 ligand or ligandbody and a cytotoxic agent conjugated thereto. The cytotoxic agent may be a radioisotope or toxin.

The invention also provides a method of detecting expression of a modified TIE-2 ligand by a cell which comprises obtaining mRNA from the cell, contacting the mRNA so obtained with a labeled nucleic acid molecule encoding a modified TIE-2 ligand, under hybridizing conditions, determining the presence of mRNA hybridized to the labeled molecule, and thereby detecting the expression of a modified TIE-2 ligand in the cell.

The invention further provides a method of detecting expression of a modified TIE-2 ligand in tissue sections which comprises contacting the tissue sections with a labeled nucleic acid molecule encoding a modified TIE-2 ligand, under hybridizing conditions, determining the presence of mRNA hybridized to the labelled molecule, and thereby detecting the expression of a modified TIE-2 ligand in tissue sections.

EXAMPLE 1

Identification of the ABAE Cell Line as Reporter Cells for the TIE-2 Receptor

Adult BAE cells are registered in the European Cell Culture Repository, under ECACC#92010601. (See PNAS 75:2621 (1978)). Northern (RNA) analyses revealed moderate levels of tie-2 transcripts in the ABAE (Adult Bovine Arterial Endothelial) cell line, consistent with in situ hybridization results that demonstrated almost exclusive localization of tie-2 RNAs to vascular endothelial cells. We therefore examined ABAE cell lysates for the presence of TIE-2 protein, as well as the extent to which this TIE-2 protein is tyrosine-phosphorylated under normal versus serum-deprived growth conditions. ABAE cell lysates were harvested and subjected to immunoprecipitation, followed by Western blot analyses of immunoprecipitated proteins with TIE-2 specific and phosphotyrosine-specific antisera. Omission or inclusion of TIE-2 peptides as specific blocking molecules during TIE-2 immunoprecipitation allowed unambiguous identification of TIE-2 as a moderately detectable protein of ~150 kD whose steady-state phosphotyrosine levels diminish to near undetectable levels by prior serum-starvation of the cells.

Culture of ABAE cells and harvest of cell lysates was done as follows. Low-passage-number ABAE cells were plated as a monolayer at a density of $2 \times 10^6$ cells/150 mm plastic petri plate (Falcon) and cultured in Dulbecco's modified Eagle's medium (DMEM) containing 10% bovine calf serum (10% BCS), 2 mM L-glutamine (Q) and 1% each of penicillin and streptomycin (P-S) in an atmosphere of 5% $CO_2$. Prior to harvest of cell lysates, cells were serum-starved for 24 hours in DMEM/Q/P-S, followed by aspiration of the medium and rinsing of the plates with ice-cold phosphate buffered saline (PBS) supplemented with sodium orthovanadate, sodium fluoride and sodium benzamidine. Cells were lysed in a small volume of this rinse buffer that had been supplemented with 1% NP40 detergent and the protease inhibitors PMSF and aprotinin. Insoluble debris was removed from the cell lysates by centrifugation at 14,000×G for 10 minutes, at 4° C. and the supernatants were subjected to immunoprecipitation with antisera specific for TIE-2 receptor, with or without the presence of blocking peptides added to ~20 µg/ml lysate. Immunoprecipitated proteins were resolved by PAGE (7.5% Laemmli gel), and then electro-transferred to PVDF membrane and incubated either with various TIE-2- or phosphotyrosine-specific antisera. TIE-2 protein was visualized by incubation of the membrane with HRP-linked secondary antisera followed by treatment with ECL reagent (Amersham).

EXAMPLE 2

Cloning and Expression of TIE-2 Receptorbody for Affinity-based Study of TIE-2 Ligand Interactions An expression construct was created that would yield a secreted protein consisting of the entire extracellular portion of the rat TIE-2 receptor fused to the human immunoglobulin gamma-1 constant region (IgG1 Fc). This fusion protein is called a TIE-2 "receptorbody" (RB), and would be normally expected to exist as a dimer in solution based on formation of disulfide linkages between individual IgG1 Fc tails. The Fc portion of the TIE-2 RB was prepared as follows. A DNA fragment encoding the Fc portion of human IgG1 that spans from the hinge region to the carboxy-terminus of the protein, was amplified from human placental cDNA by PCR with oligonucleotides corresponding to the published sequence of human IgG1; the resulting DNA fragment was cloned in a plasmid vector. Appropriate DNA restriction fragments from a plasmid encoding the full-length TIE-2 receptor and from the human IgG1 Fc plasmid were ligated on either side of a short PCR-derived fragment that was designed so as to fuse, in-frame, the TIE-2 and human IgG1 Fc protein-coding sequences. Thus, the resulting TIE-2 ectodomain-Fc fusion protein precisely substituted the IgG1 Fc in place of the region spanning the TIE-2 transmembrane and cytoplasmic domains. An alternative method of preparing RBs is described in Goodwin, et. al. Cell 73:447–456 (1993).

Milligram quantities of TIE-2 RB were obtained by cloning the TIE-2 RB DNA fragment into the pVL1393 baculovirus vector and subsequently infecting the *Spodoptera frugiperda* SF-21AE insect cell line. Alternatively, the cell line SF-9 (ATCC Accession No. CRL-1711) or the cell line BTI-TN-5b1–4 may be used. DNA encoding the TIE-2 RB was cloned as an Eco RI-NotI fragment into the baculovirus transfer plasmid pVL1393. Plasmid DNA purified by cesium chloride density gradient centrifugation was recombined into viral DNA by mixing 3 $\mu$g of plasmid DNA with 0.5 $\mu$g of Baculo-Gold DNA (Pharminigen), followed by introduction into liposomes using 30 $\mu$g Lipofectin (GIBCO-BRL). DNA-liposome mixtures were added to SF-21AE cells ($2 \times 10^6$ cells/60 mm dish) in TMN-FH medium (Modified Grace's Insect Cell Medium (GIBCO-BRL) for 5 hours at 27° C., followed by incubation at 27° C. for 5 days in TMN-FH medium supplemented with 5% fetal calf serum. Tissue culture medium was harvested for plaque purification of recombinant viruses, which was carried out using methods previously described (O'Reilly, D. R., L. K. Miller, and V. A. Luckow, *Baculovirus Expression Vectors—A Laboratory Manual*. 1992, New York: W. H. Freeman) except that the agarose overlay contained 125 $\mu$g/mL X-gal (5-bromo-4-chloro-3-indolyl-$\beta$-D-galactopyranoside; GIBCO-BRL). After 5 days of incubation at 27° C., non-recombinant plaques were scored by positive chromogenic reaction to the X-gal substrate, and their positions marked. Recombinant plaques were then visualized by addition of a second overlay containing 100 $\mu$g/mL MTT (3-[4,5-dimethylthiazol-2-yl]2,5,diphenyltetrazolium bromide; Sigma). Putative recombinant virus plaques were picked by plug aspiration, and purified by multiple rounds of plaque isolation to assure homogeneity. Virus stocks were generated by serial, low-multiplicity passage of plaque-purified virus. Low passage stocks of one virus clone (vTIE-2 receptorbody) were produced.

SF-21AE cells were cultured in serum free medium (SF-900 II, Gibco BRL) containing 1× antibiotic/antimycotic solution (Gibco BRL) and 25 mg/L Gentamycin (Gibco BRL). Pluronic F-68 was added as a surfactant to a final concentration of 1 g/L. Cultures (4L) were raised in a bioreactor (Artisan Cell Station System) for at least three days prior to infection. Cells were grown at 27° C., with gassing to 50% dissolved oxygen, at a gas flow rate of 80 mL/min (aeration at a sparge ring). Agitation was by means of a marine impeller at a rate of 100 rpm. Cells were harvested in mid-logarithmic growth phase ($\sim 2 \times 10^6$ cells/mL), concentrated by centrifugation, and infected with 5 plaque forming units of vTIE-2 receptorbody per cell. Cells and inoculum were brought to 400 mL with fresh medium, and virus was adsorbed for 2 hours at 27° C. in a spinner flask. The culture was then resuspended in a final volume of 8L with fresh serum-free medium, and the cells incubated in the bioreactor using the previously described conditions.

Culture medium from vTIE-2 receptorbody-infected SF21AE cells were collected by centrifugation (500×g, 10 minutes) at 72 hours post-infection. Cell supernatants were brought to pH 8 with NaOH. EDTA was added to a final concentration of 10 mM and the supernatant pH was readjusted to 8. Supernatants were filtered (0.45 $\mu$m, Millipore) and loaded on a protein A column (protein A sepharose 4 fast flow or HiTrap protein A, both from Pharmacia). The column was washed with PBS containing 0.5 M NaCl until the absorbance at 280 nm decreased to baseline. The column was washed in PBS and eluted with 0.5 M acetic acid. Column fractions were immediately neutralized by eluting into tubes containing 1 M Tris pH 9. The peak fractions containing the TIE-2 receptorbody were pooled and dialyzed versus PBS.

EXAMPLE 3

Demonstration that TIE-2 has a Critical Role in Development of the Vasculature

Insight into the function of TIE-2 was gained by introduction of "excess" soluble TIE-2 receptorbody (TIE-2 RB) into a developing system. The potential ability of TIE-2 RB to bind, and thereby neutralize, available TIE-2 ligand could result in an observable disruption of normal vascular development and characterization of the ligand. To examine whether TIE-2 RB could be used to disrupt vascular development in early chick embryos, small pieces of a biologically resorbable foam were soaked with TIE-2 RB and inserted immediately beneath the chorioallantoic membrane at positions just lateral to the primitive embryo.

Early chicken embryos develop atop the yolk from a small disk of cells that is covered by the chorioallantoic membrane (CAM). The endothelial cells that will come to line the vasculature in the embryo arise from both extra- and intra-embryonic cell sources. Extra-embryonically-derived endothelial cells, which provide the major source of endothelial cells in the embryo, originate from accretions of mesenchyme that are situated laterally around the embryo-proper, just underneath the CAM. As these mesenchyme cells mature, they give rise to a common progenitor of both the endothelial and hematopoietic cell lineages, termed the hemangioblast. In turn, the hemangioblast gives rise to a mixed population of angioblasts (the endothelial cell progenitor) and hematoblasts (the pluripotential hematopoietic precursor). Formation of rudiments of the circulatory system begins when endothelial cell progeny segregate to form a one-cell-thick vesicle that surrounds the primitive blood cells. Proliferation and migration of these cellular components eventually produces a vast network of blood-filled microvessels under the CAM that will ultimately invade the embryo to join with limited, intra-embryonically-derived vascular elements.

Newly fertilized chicken eggs obtained from Spafas, Inc. (Boston, Mass.) were incubated at 99.5° F., 55% relative humidity. At about 24 hrs. of development, the egg shell was wiped down with 70% ethanol and a dentist's drill was used to make a 1.5 cm. hole in the blunt apex of each egg. The shell membrane was removed to reveal an air space directly above the embryo. Small rectangular pieces of sterile Gelfoam (Upjohn) were cut with a scalpel and soaked in equal concentrations of either TIE-2- or EHK-1 receptorbody. EHK-1 receptorbody was made as set forth in Example 2 using the EHK-1 extracellular domain instead of the TIE-2 extracellular domain (Maisonpierre et al., Oncogene 8:3277–3288 (1993). Each Gelfoam piece absorbed approximately 6 µg of protein in 30 µl. Sterile watchmakers forceps were used to make a small tear in the CAM at a position several millimeters lateral to the primitive embryo. The majority of the piece of RB-soaked Gelfoam was inserted under the CAM and the egg shell was sealed over with a piece of adhesive tape. Other similarly-staged eggs were treated in parallel with RB of the unrelated, neuronally expressed receptor tyrosine kinase, EHK-1 (Maisonpierre et al., Oncogene 8:3277–3288 (1993). Development was allowed to proceed for 4 days and then the embryos were examined by visual inspection. Embryos were removed by carefully breaking the shells in dishes of warmed PBS and carefully cutting away the embryo with surrounding CAM. Of 12 eggs treated with each RB, 6 TIE-2 RB and 5 EHK-1 RB treated embryos had developed beyond the stage observed at the start of the experiment. A dramatic difference was seen between these developed embryos, as shown in FIGS. 1A and 1B. Those treated with EHK-1 RB appeared to have developed relatively normally. Four out of five EHK-1 embryos were viable as judged by the presence of a beating heart. Furthermore, the extra-embryonic vasculature, which is visually obvious due to the presence of red blood cells, was profuse and extended several centimeters laterally under the CAM. By contrast, those treated with TIE-2 RB were severely stunted, ranging from 2–5 mm. in diameter, as compared with more than 10 mm in diameter for the EHK-1 RB embryos. All of the TIE-2 RB treated embryos were dead and their CAMs were devoid of blood vessels. The ability of TIE-2 RB to block vascular development in the chicken demonstrates that TIE-2 ligand is necessary for development of the vasculature.

EXAMPLE 4

Identification of a TIE-2-Specific Binding Activity in Conditioned Medium from the ras Oncogene-Transformed C2C12 Mouse Myoblast Cell Line Screening of ten-fold-concentrated cell-conditioned media (10× CCM) from various cell lines for the presence of soluble, TIE-2-specific binding activity (BIAcore; Pharmacia Biosensor, Piscataway, N.J.) revealed binding activity in serum-free medium from oncogenic-ras-transformed C2C12 cells (C2C12-ras), RAT 2-ras (which is a ras transformed fibroblast cell line), human glioblastoma T98G and the human neuroblastoma cell line known as SHEP-1.

The C2C12-ras 10× CCM originated from a stably transfected line of C2C12 myoblasts that was oncogenically transformed by transfection with the T-24 mutant of H-ras by standard calcium phosphate-based methods. An SV40 based neomycin-resistance expression plasmid was physically linked with the ras expression plasmid in order to permit selection of transfected clones. Resulting G418-resistant ras-C2C12 cells were routinely maintained as a monolayer on plastic dishes in DMEM/glutamine/penicillin-streptomycin supplemented with 10% fetal calf serum (FCS). Serum-free C2C12-ras 10× CCM was made by plating the cells at 60% confluence in a serum free defined media for 12 hours. [Zhan and Goldfarb, Mol. Cell. Biol. 6: 3541–3544 (1986)); Zhan, et al. Oncogene 1: 369–376 (1987)]. The medium was discarded and replaced with fresh DMEM/Q/P-S for 24 hours. This medium was harvested and cells were re-fed fresh DMEM/Q/P-S, which was also harvested after a further 24 hours. These CCM were supplemented with the protease inhibitors PMSF (1 mM) and aprotinin (10 µg/ml), and ten-fold concentrated on sterile size-exclusion membranes (Amicon). TIE-2-binding activity could be neutralized by incubation of the medium with an excess of TIE-2 RB, but not by incubation with EHK-1 RB, prior to BIAcore analysis.

Binding activity of the 10× CCM was measured using biosensor technology (BIAcore; Pharmacia Biosensor, Piscataway, N.J.) which monitors biomolecular interactions in real-time via surface plasmon resonance. Purified TIE-2 RB was covalently coupled through primary amines to the carboxymethyl dextran layer of a CM5 research grade sensor chip (Pharmacia Biosensor; Piscataway, N.J.). The sensor chip surface was activated using a mixture of N-hydroxysuccinimide (NHS) and N-ethyl-N'-(3-dimethylaminopropyl)carbodiimide (EDC), followed by immobilization of TIE-2 RB (25 µg/mL, pH 4.5) and deactivation of unreacted sites with 1.0 M ethanolamine (pH 8.5). A negative control surface of the EHK-1 receptorbody was prepared in a similar manner.

The running buffer used in the system was HBS (10 mM Hepes, 3.4 mM EDTA, 150 mM NaCl, 0.005% P20 surfactant, pH 7.4). The 10× CCM samples were centrifuged for 15 min at 4° C. and further clarified using a sterile, low protein-binding 0.45 µm filter (Millipore; Bedford, Mass.). Dextran (2 mg/ml) and P20 surfactant (0.005%) were added to each CCM sample. Aliquots of 40 µL were injected across the immobilized surface (either TIE-2 or EHK-1) at a flow rate of 5 µL/min and the receptor binding was monitored for 8 min. The binding activity (resonance units, RU) was measured as the difference between a baseline value determined 30 s prior to the sample injection and a measurement taken at 30 s post-injection. Regeneration of the surface was accomplished with one 12-µL pulse of 3 M $MgCl_2$.

The instrument noise level is 20 RU; therefore, any binding activity with a signal above 20 RU may be interpreted as a real interaction with the receptor. For C2C12-ras conditioned media, the binding activities were in the range 60–90 RU for the TIE-2 RB immobilized surface. For the same samples assayed on a EHK-1 RB immobilized surface, the measured activities were less than 35 RU. Specific binding to the TIE-2 receptorbody was evaluated by incubating the samples with an excess of either soluble TIE-2 or EHK-1 RB prior to assaying the binding activity. The addition of soluble EHK-1 RB had no effect on the TIE-2 binding activity of any of the samples, while in the presence of soluble TIE-2 binding to the surface is two-thirds less than that measured in the absence of TIE-2. A repeat assay using >50× concentrated C2C12-ras CCM resulted in a four-fold enhancement over background of the TIE-2 specific binding signal.

EXAMPLE 5

C2C12-ras CCM Contains an Activity that Induces Tyrosine Phosphorylation of TIE-2 Receptor C2C12-ras 10× CCM was examined for its ability to induce tyrosine phosphorylation of TIE-2 in ABAE cells. Serum-starved ABAE cells were briefly incubated with C2C12-ras CCM, lysed and subjected to immunoprecipitation and Western analyses as described above. Stimulation of serum-starved ABAE cells with serum-free C2C12-ras 10× CCM was done as follows. The medium of ABAE cells starved as described above was removed and replaced with either defined medium or 10× CCM that had been pre-warmed to 37° C. After 10 minutes, the media were removed and the cells were twice rinsed on ice with an excess of chilled PBS supplemented with orthovanadate/NaF/benzamidine. Cell lysis and TIE-2-specific immunoprecipitation was done as described above.

ABAE cells incubated for 10 minutes with defined medium showed no induction of TIE-2 tyrosine phosphorylation, whereas incubation with C2C12-ras CCM stimulated at least a 100× increase in TIE-2 phosphorylation. This activity was almost totally depleted by pre-incubation of the C2C12-ras 10× CCM for 90 minutes at room temperature with 13 μg of TIE-2 RB coupled to protein G-Sepharose beads. Medium incubated with protein G Sepharose alone was not depleted of this phosphorylating activity.

EXAMPLE 6

Expression Cloning of TIE-2 Ligand

Figure 2:
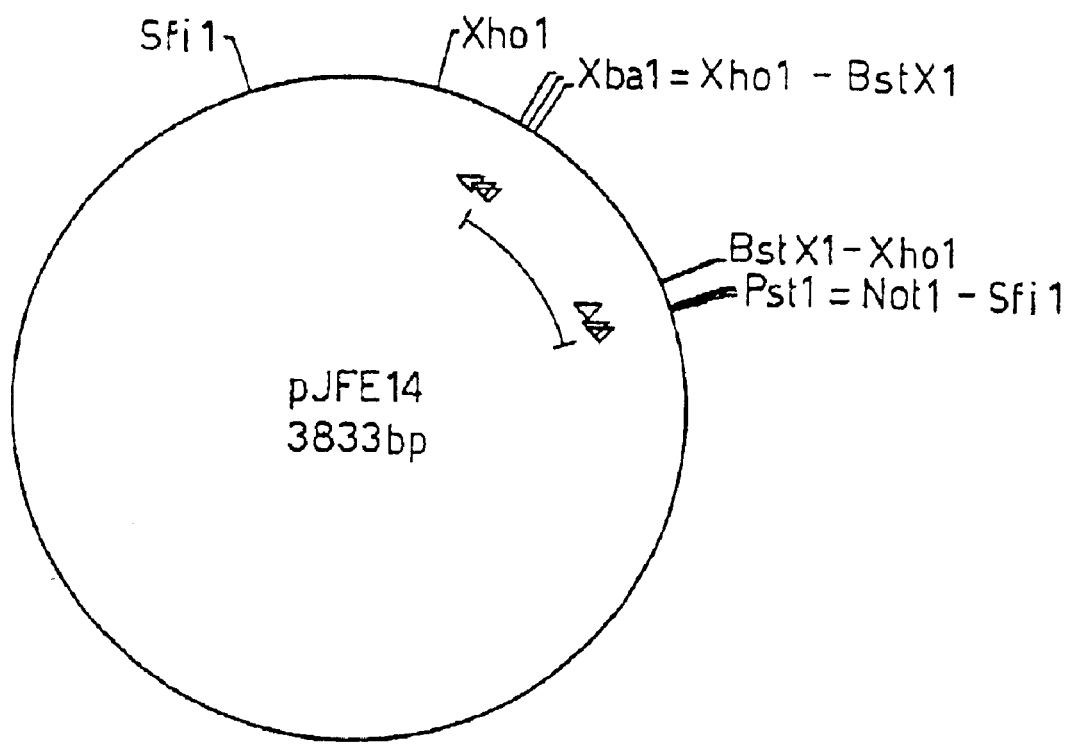
FIG. 2—Vector pJFE14.

COS-7 cells were cultured in Dulbecco's modified Eagle's medium (DMEM) containing 10% fetal bovine serum (FBS), 1% each of penicillin and streptomycin (P/S) and 2 mM glutamine in an atmosphere of 5% $CO_2$. The mouse myoblast C2C12 ras cell line was cultured in Eagle's minimal essential medium (EMEM) with 10% FBS, (P/S) and 2 mM glutamine. Full length mouse TIE-2 ligand cDNA clones were obtained by screening a C2C12 ras cDNA library in the pJFE14 vector expressed in COS cells. This vector, as shown in FIG. 2, is a modified version of the vector $pSR_\alpha$ (Takebe, et al. 1988, Mol. Cell. Biol. 8:466–472). The library was created using the two BSTX1 restriction sites in the pJFE14 vector.

COS-7 cells were transiently transfected with either the pJFE14 library or control vector by the DEAE-dextran transfection protocol. Briefly, COS-7 cells were plated at a density of $1.0\times10^6$ cells/100 mm plate 24 hours prior to transfection. For transfection, the cells were cultured in serum-free DMEM containing 400 μg/ml of DEAE-dextran, 1 μM chloroquine, and 2 mM glutamine, and 1 μg of the appropriate DNA for 3–4 hours at 37° C. in an atmosphere of 5% $CO_2$. The transfection media was aspirated and replaced with PBS with 10% DMSO for 2–3 min. Following this DMSO "shock", the COS-7 cells were placed into DMEM with 10% FBS, 1% each of penicillin and streptomycin, and 2 mM glutamine for 48 hours.

Because the TIE-2 ligand is secreted it was necessary to permeabilize the cells to detect binding of the receptorbody probe to the ligand. Two days after transfection the cells were rinsed with PBS and then incubated with PBS containing 1.8% formaldehyde for 15–30 min. at room temperature. Cells were then washed with PBS and incubated for 15 min. with PBS containing 0.1% Triton X-100 and 10% Bovine Calf Serum to permeabilize the cells and block non-specific binding sites.

The screening was conducted by direct localization of staining using a TIE-2 receptorbody (RB), which consisted of the extracellular domain of TIE-2 fused to the IgG1 constant region. This receptorbody was prepared as set forth in Example 2. A 100 mm dish of transfected, fixed and permeabilized COS cells was probed by incubating them for 30 min with TIE-2 RB. The cells were then washed twice with PBS and incubated for an additional 30 min with PBS/10% Bovine Calf Serum/anti-human IgG-alkaline phosphatase conjugate. After three PBS washes, cells were incubated in alkaline-phosphatase substrate for 30–60 min. The dish was then inspected microscopically for the presence of stained cells. For each stained cell, a small area of cells including the stained cell was scraped from the dish using a plastic pipette tip and plasmid DNA was then rescued and used to electroporate bacterial cells. Single bacterial colonies resulting from the electroporation were picked and plasmid DNA prepared from these colonies was used to transfect COS-7 cells which were probed for TIE-2 ligand expression as evidenced by binding to TIE-2 receptorbodies. This allowed identification of single clones coding for TIE-2 ligand. Confirmation of TIE-2 ligand expression was obtained by phosphorylation of the TIE-2 receptor using the method set forth in Example 5. A plasmid clone encoding the TIE-2 ligand was deposited with the ATCC on Oct. 7, 1994 and designated as "pJFE14 encoding TIE-2 ligand" under ATCC Accession No. 75910.

EXAMPLE 7

Isolation and Sequencing of Full Length cDNA Clone Encoding Human TIE-2 Ligand

Figure 3:
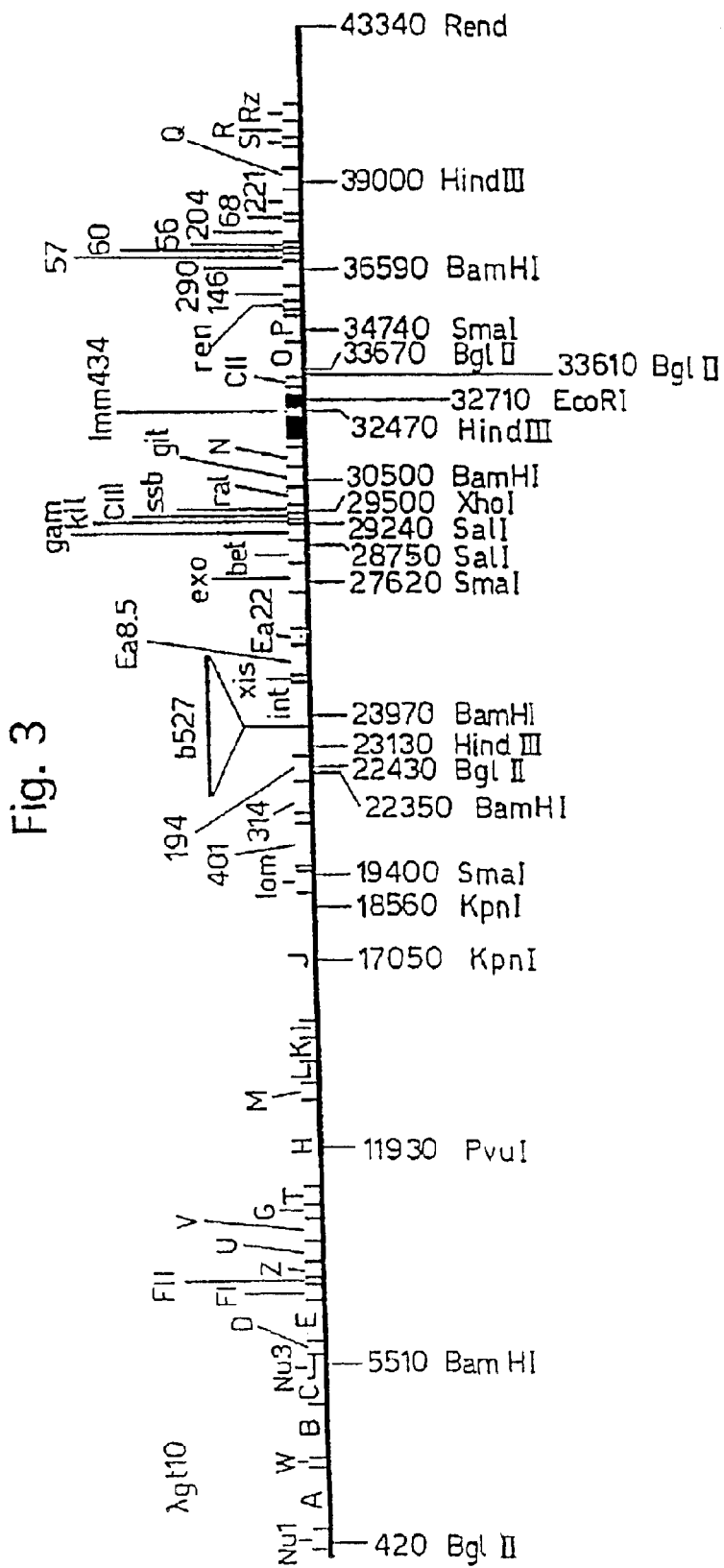
FIG. 3—Restriction map of λgt10.

A human fetal lung cDNA library in lambda gt-10 (see FIG. 3) was obtained from Clontech Laboratories, Inc. (Palo Alto, Calif.). Plaques were plated at a density of $1.25\times10^6$/20×20 cm plate, and replica filters taken following standard procedures (Sambrook, et al., Molecular Cloning: A Laboratory Manual, 2nd Ed., page 8.46, Cold Spring Harbor Laboratory, Cold Spring Harbor, N.Y.).

Isolation of human tie-2 ligand clones was carried out as follows. A 2.2 kb XhoI fragment from the deposited tie-2 ligand clone (ATCC NO. 75910—see Example 6 above) was labeled by random priming to a specific activity of approximately $5\times10^8$ cpm/ng. Hybridization was carried out at 65° C. in hybridization solution containing 0.5 mg/ml salmon sperm DNA. The filters were washed at 65° C. in 2×SSC, 0.1% SDS and exposed to Kodak XAR-5 film overnight at −70° C. Positive phage were plaque purified. High titre phage lysates of pure phage were used for isolation of DNA via a Qiagen column using standard techniques (Qiagen, Inc., Chatsworth, Calif., 1995 catalog, page 36). Phage DNA was digested with EcoRI to release the cloned cDNA fragment for subsequent subcloning. A lambda phage vector containing human tie-2 ligand DNA was deposited with the ATCC on Oct. 26, 1994 under the designation λgt10 encoding htie-2 ligand 1 (ATCC Accession No. 75928). Phage DNA may be subjected directly to DNA sequence analysis by the dideoxy chain termination method (Sanger, et al., 1977, Proc. Natl. Acad. Sci. U.S.A. 74: 5463–5467).

Subcloning of the human tie-2 ligand DNA into a mammalian expression vector may be accomplished as follows. The clone λgt10 encoding htie-2 ligand 1 contains an EcoRI site located 490 base pairs downstream from the start of the coding sequence for the human TIE-2 ligand. The coding region may be excised using unique restriction sites upstream and downstream of the initiator and stop codons respectively. For example, an SpeI site, located 70 bp 5' to the initiator codon, and a Bpu1102i (also known as BlpI) site, located 265 bp 3' to the stop codon, may be used to excise the complete coding region. This may then be subcloned into the pJFE14 cloning vector, using the XbaI (compatible to the SpeI overhang) and the PstI sites (the PstI and Bpu1102i sites are both made blunt ended).

The coding region from the clone λgt10 encoding htie-2 ligand 1 was sequenced using the ABI 373A DNA sequencer and Taq Dideoxy Terminator Cycle Sequencing Kit (Applied Biosystems, Inc., Foster City, Calif.). The nucleotide and deduced amino acid sequence of human TIE-2 ligand from the clone λgt10 encoding htie-2 ligand 1 is shown in FIGS. 4A–4D (SEQ ID NO: 1 and SEQ ID NO: 2).

In addition, full length human tie-2 ligand cDNA clones were obtained by screening a human glioblastoma T98G cDNA library in the pJFE14 vector. Clones encoding human TIE-2 ligand were identified by DNA hybridization using a 2.2 kb XhoI fragment from the deposited tie-2 ligand clone (ATCC NO. 75910) as a probe (see Example 6 above). The coding region was sequenced using the ABI 373A DNA sequencer and Taq Dideoxy Terminator Cycle Sequencing Kit (Applied Biosystems, Inc., Foster City, Calif.). This sequence was nearly identical to that of clone λgt10 encoding htie-2 ligand 1. As shown in FIGS. 4A–4D (SEQ ID NO: 1 and SEQ ID NO: 2), the clone λgt10 encoding htie-2 ligand 1 contains an additional glycine residue which is encoded by nucleotides 1114–1116. The coding sequence of the T98G clone does not contain this glycine residue but otherwise is identical to the coding sequence of the clone λgt10 encoding htie-2 ligand 1. FIGS. 5A–5D (SEQ ID NO: 3 and SEQ ID NO: 4) sets forth the nucleotide and deduced amino acid sequence of human TIE-2 ligand from the T98G clone.

EXAMPLE 8

Isolation and Sequencing of Second Full Length cDNA Clone a Encoding Human TIE-2 Ligand A human fetal lung cDNA library in lambda gt-10 (see FIG. 3) was obtained from Clontech Laboratories, Inc. (Palo Alto, Calif.). Plaques were plated at a density of $1.25 \times 10^6$/20×20 cm plate, and replica filters taken following standard procedures (Sambrook, et al., Molecular Cloning: A Laboratory Manual, 2nd Ed., page 8.46, Cold Spring Harbor Laboratory, Cold Spring Harbor, N.Y.). Duplicate filters were screened at low stringency (2×SSC, 55° C.) with probes made to the human TIE-2 ligand 1 sequence. One of the duplicate filters was probed with a 5' probe, encoding amino acids 25–265 of human TIE-2 ligand 1 as set forth in FIGS. 4A–4D (SEQ ID NO: 1 and SEQ ID NO: 2). The second duplicate filter was probed with a 3' probe, encoding amino acids 282–498 of human TIE-2 ligand 1 sequence (see FIGS. 4A–4D (SEQ ID NO: 1 and SEQ ID NO: 2). Both probes were hybridized at 55° C. in hybridization solution containing 0.5 mg/ml salmon sperm DNA. Filters were washed in 2×SSC at 55° C. and exposed overnight to X-ray film. In addition, duplicate filters were also hybridized at normal stringency (2×SSC, 65° C.) to the full length coding probe of mouse TIE-2 ligand 1 (F3-15, XhoI insert). Three positive clones were picked that fulfilled the following criteria: i. hybridization had not been seen to the full length (mouse) probe at normal stringency, and ii. hybridization was seen at low stringency to both 5' and 3' probes. EcoRI digestion of phage DNA obtained from these clones indicated two independent clones with insert sizes of approximately 2.2 kb and approximately 1.8 kb. The 2.2 kb EcoRI insert was subcloned into the EcoRI sites of both pBluescript KS (Stratagene) and a mammalian expression vector suitable for use in COS cells. Two orientations were identified for the mammalian expression vector. The 2.2 kb insert in pBluescript KS was deposited with the ATCC on Dec. 9, 1994 and designated as pBluescript KS encoding human TIE 2 ligand 2. The start site of the TIE-2 ligand 2 coding sequence is approximately 355 base pairs downstream of the pBluescript EcoRI site.

COS-7 cells were transiently transfected with either the expression vector or control vector by the DEAE-dextran transfection protocol. Briefly, COS-7 cells were plated at a density of $1.0 \times 10^6$ cells/100 mm plate 24 hours prior to transfection. For transfection, the cells were cultured in serum-free DMEM containing 400 μg/ml of DEAE-dextran, 1 μM chloroquine, and 2 mM glutamine, and 1 μg of the appropriate DNA for 3–4 hours at 37° C. in an atmosphere of 5% $CO_2$. The transfection media was aspirated and replaced with phosphate-buffered saline with 10% DMSO for 2–3 min. Following this DMSO "shock", the COS-7 cells were placed into DMEM with 10% FBS, 1% each of penicillin and streptomycin, and 2 mM glutamine for 48 hours.

Because the TIE-2 ligand is secreted it was necessary to permeabilize the cells to detect binding of the receptorbody probe to the ligand. Transfected COS-7 cells were plated at a density of $1.0 \times 10^6$ cells/100 mm plate. The cells were rinsed with PBS and then incubated with PBS containing 1.8% formaldehyde for 15–30 min. at room temperature. Cells were then washed with PBS and incubated for 15 min. with PBS containing 0.1% Triton X-100 and 10% Bovine Calf Serum to permeabilize the cells and block non-specific binding sites. The screening was conducted by direct localization of staining using a TIE-2 receptorbody, which consisted of the extracellular domain of TIE-2 fused to the IgG1 constant region. This receptorbody was prepared as set forth in Example 2. Transfected COS cells were probed by incubating them for 30 min with TIE-2 receptorbody. The cells were then washed twice with PBS, fixed with methanol, and then incubated for an additional 30 min with PBS/10% Bovine Calf Serum/anti-human IgG-alkaline phosphatase conjugate. After three PBS washes, cells were incubated in alkaline-phosphatase substrate for 30–60 min. The dish was then inspected microscopically for the presence of stained cells. Cells expressing one orientation of the clone, but not the other orientation, were seen to bind the TIE-2 receptorbody.

One of skill in the art will readily see that the described methods may be used to further identify other related members of the TIE ligand family.

The coding region from the clone pBluescript KS encoding human TIE-2 ligand 2 was sequenced using the ABI 373A DNA sequencer and Taq Dideoxy Terminator Cycle Sequencing Kit (Applied Biosystems, Inc., Foster City. Calif.). The nucleotide and deduced amino acid sequence of human TIE-2 ligand from the clone pBluescript KS encoding human TIE-2 ligand 2 is shown in FIGS. 6A–6D (SEQ ID NO: 5 and SEQ ID NO: 6).

EXAMPLE 9

TIE-2 Ligand 2 is a Receptor Antagonist

Conditioned media from COS cells expressing either TIE-2 ligand 2 (TL2) or TIE-2 ligand 1 (TL1) were compared for their ability to activate TIE-2 receptors naturally present in human endothelial cell lines.

Lipofectamine reagent (GIBCO-BRL, Inc.) and recommended protocols were used to transfect COS-7 cells with either the pJFE14 expression vector alone, pJFE14 vector containing the human TIE-2 ligand 1 cDNA, or with a pMT21 expression vector (Kaufman, R. J., 1985, Proc. Natl. Acad. Sci. USA 82: 689–693) containing the human TIE-2 ligand 2 cDNA. COS media containing secreted ligands were harvested after three days and concentrated 20-fold by diafiltration (DIAFLO ultrafiltration membranes, Amicon, Inc.). The quantity of active TIE-2 ligand 1 and TIE-2 ligand 2 present in these media was determined and expressed as the amount (in resonance units, R.U.) of TIE-2 receptor specific binding activity measured by a BIAcore binding assay.

Figure 7:
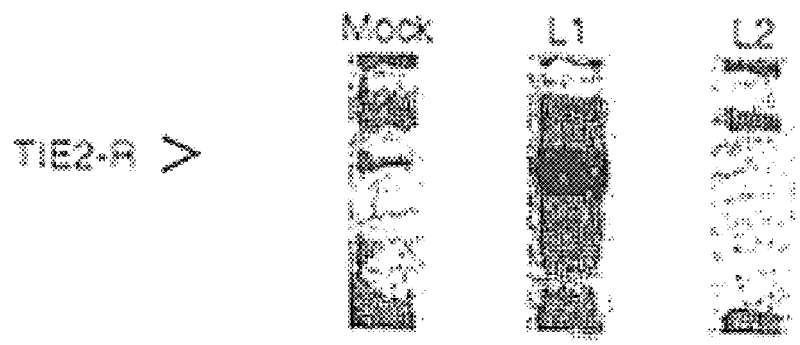
FIG. 7—Western blot showing activation of TIE-2 receptor by TIE-2 ligand 1 (Lane L1) but not by TIE-2 ligand 2 (Lane L2) or control (Mock).

Northern (RNA) analyses revealed significant levels of TIE-2 transcripts in HAEC (Human Aortic Endothelial Cell) human primary endothelial cells (Clonetics, Inc.). Therefore, these cells were used to examine whether TIE-2 receptor is tyrosine-phosphorylated when exposed to COS media containing the TIE-2 ligands. HAEC cells were maintained in a complete endothelial cell growth medium (Clonetics, Inc.) that contained 5% fetal bovine serum, soluble bovine brain extract, 10 ng/ml human EGF, 1 mg/ml hydrocortisone, 50 mg/ml gentamicin and 50 ng/ml amphotericin-B. Assessment of whether TL1 and TL2 could activate TIE-2 receptor in the HAEC cells was done as follows. Semi-confluent HAEC cells were serum-starved for two hours in high-glucose Dulbecco's MEM with added L-glutamine and penicillin-streptomycin at 37° C. followed by replacement of the starvation medium with ligand-containing conditioned COS media for 7 minutes at 37° C. in a 5% CO2 incubator. The cells were subsequently lysed and TIE-2 receptor protein was recovered by immunoprecipitation of the lysates with TIE-2 peptide antiserum, followed by Western blotting with antiphosphotyrosine antiserum, exactly as described in example 1. The results are shown in FIG. 7. Phosphotyrosine levels on the TIE-2 receptor (TIE-2-R) were induced by treatment of HEAC cells with TIE-2 ligand 1 (Lane L1) but not by TIE-2 ligand 2 (Lane L2) conditioned COS media. MOCK is conditioned media from COS transfected with JFE14 empty vector.

Evidence that both TL1 and TL2 specifically bind to the TIE-2 receptor was demonstrated by using a BIAcore to assay the TIE-2 receptor specific binding activities in transfected COS media and by immunostaining of TL1- and TL2-expressing COS cells with TIE-2 receptorbodies.

Because TL2 did not activate the TIE-2 receptor, applicants set out to determine whether TL2 might be capable of serving as an antagonist of TL1 activity. HAEC phosphorylation assays were performed in which cells were first incubated with an "excess" of TL2, followed by addition of dilute TL1. It was reasoned that prior occupancy of TIE-2 receptor due to high levels of TL2 might prevent subsequent stimulation of the receptor following exposure to TL1 present at a limiting concentration.

Figure 8:
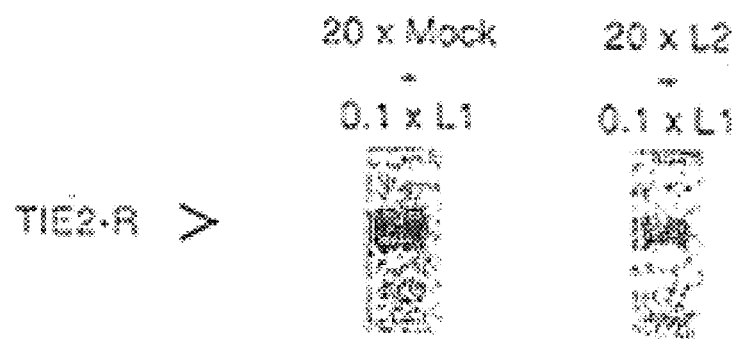
FIG. 8—Western blot showing that prior treatment of HAEC cells with excess TIE-2 ligand 2 (Lane 2) antagonizes the subsequent ability of dilute TIE-2 ligand 1 to activate the TIE-2 receptor (TIE2-R) as compared with prior treatment of HAEC cells with MOCK medium (Lane 1).

Semi-confluent HAEC cells were serum-starved as described above and then incubated for 3 min., at 37° C. with 1–2 ml. of 20× COS/JFE14-TL2 conditioned medium. Control plates were treated with 20× COS/JFE14-only medium (MOCK). The plates were removed from the incubator and various dilutions of COS/JFE14-TL1 medium were then added, followed by further incubation of the plates for 5–7 min. at 37° C. Cells were subsequently rinsed, lysed and TIE-2-specific tyrosine phosphorylation in the lysates was examined by receptor immunoprecipitation and Western blotting, as described above. TL1 dilutions were made using 20× COS/JFE14-TL1 medium diluted to 2×, 0.5×, 0.1×, or 0.02× by addition of 20× COS/JFE14-alone medium. An assay of the initial 20× TL1 and 20× TL2 COS media using BIAcore biosensor technology indicated that they contained similar amounts of TIE-2-specific binding activities, i.e., 445 R.U. and 511 R.U. for TL1 and TL2, respectively. The results of the antiphosphotyrosine Western blot, shown in FIG. 8, indicate that when compared to prior treatment of HAEC cells with MOCK medium (lane 1), prior treatment of HAEC cells with excess TIE-2 ligand 2 (lane 2) antagonizes the subsequent ability of dilute TIE-2 ligand 1 to activate the TIE-2 receptor (TIE-2-R).

Figure 9:
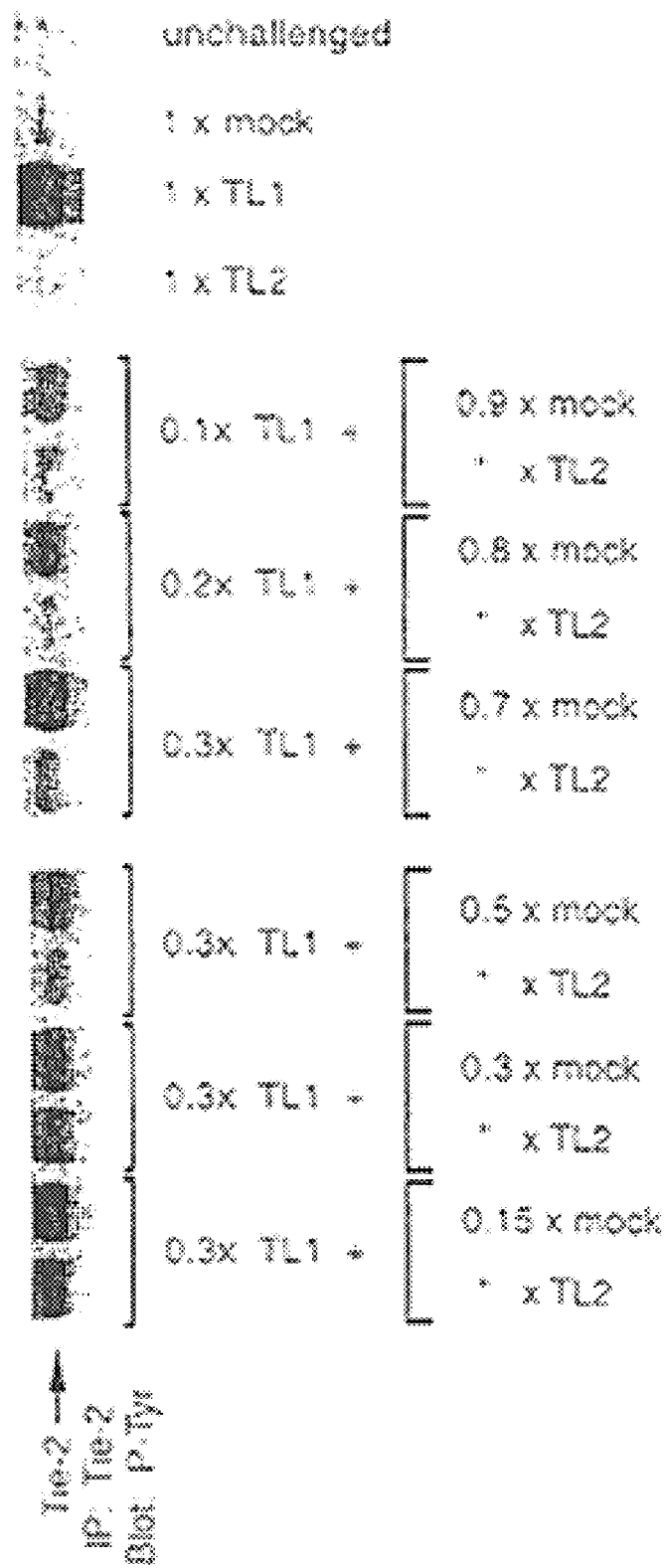
FIG. 9—Western blot demonstrating the ability of TL2 to competitively inhibit TL1 activation of the TIE-2 receptor using the human cell hybrid line, EA.hy926.
Figure 10:
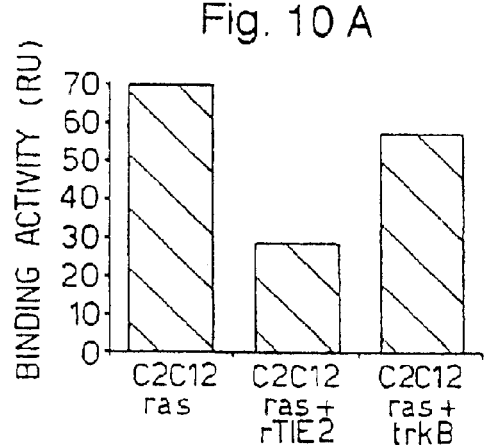
FIGS. 10A–10D—Histogram representation of binding to rat TIE-2 IgG immobilized surface by TIE-2 ligand in C2C12 ras (FIG. 10A), Rat2 ras (FIG. 10B), SHEP (FIG. 10C), and T98G (FIG. 10D) concentrated (10×) conditioned medium. Rat TIE-2 (rTIE2) specific binding is demonstrated by the significant reduction in the binding activity in the presence of 25 μg/ml soluble rat TIE-2 RB as compared to a minor reduction in the presence of soluble trkB RB.
Figure 10:
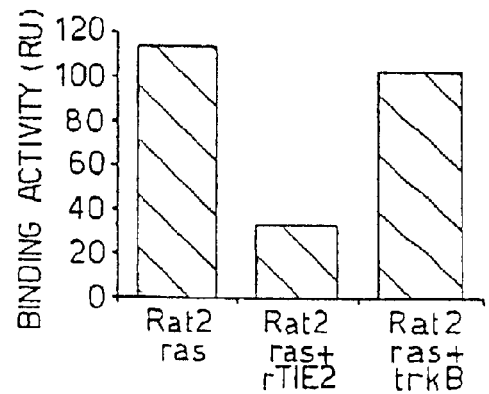
Figure 10:
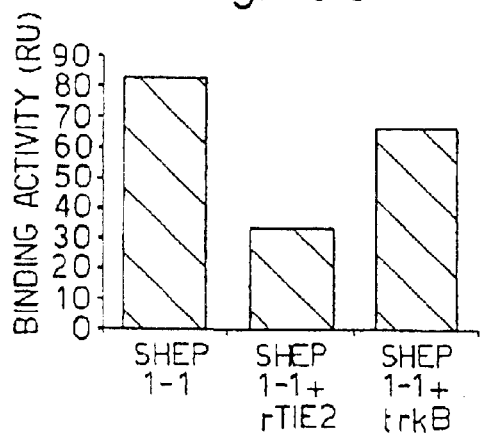
Figure 10:
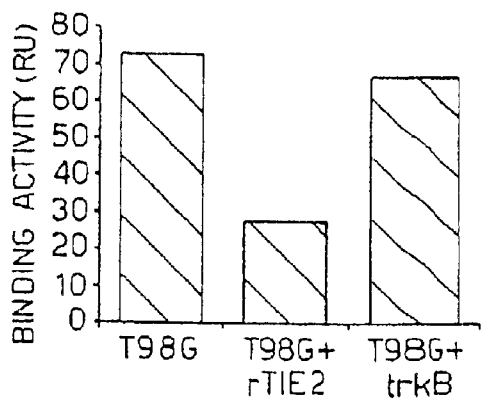
Figure 11:
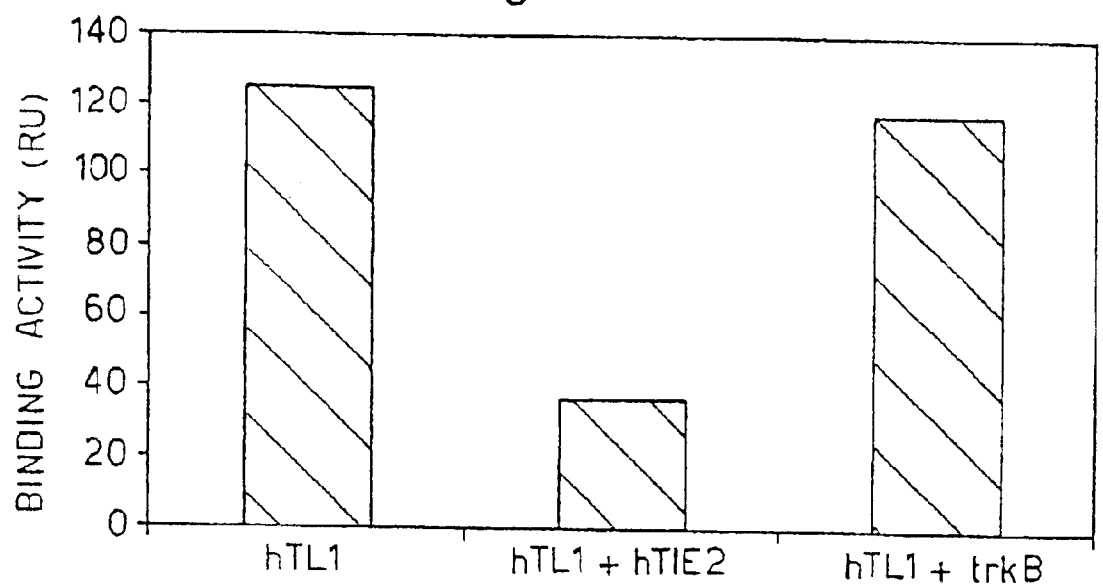
FIGS. 11A–11B—Binding of recombinant human TIE-2 ligand 1 (hTL1) (FIG. 11A) and human TIE-2 ligand 2 (hTL2) (FIG. 11B), in COS cell supernatants, to a human TIE-2 receptorbody (RB) immobilized surface. Human TIE-2-specific binding was determined by incubating the samples with 25 μg/ml of either soluble human TIE-2 RB or trkB RB; significant reduction in the binding activity is observed only for the samples incubated with human TIE-2 RB.
Figure 11:
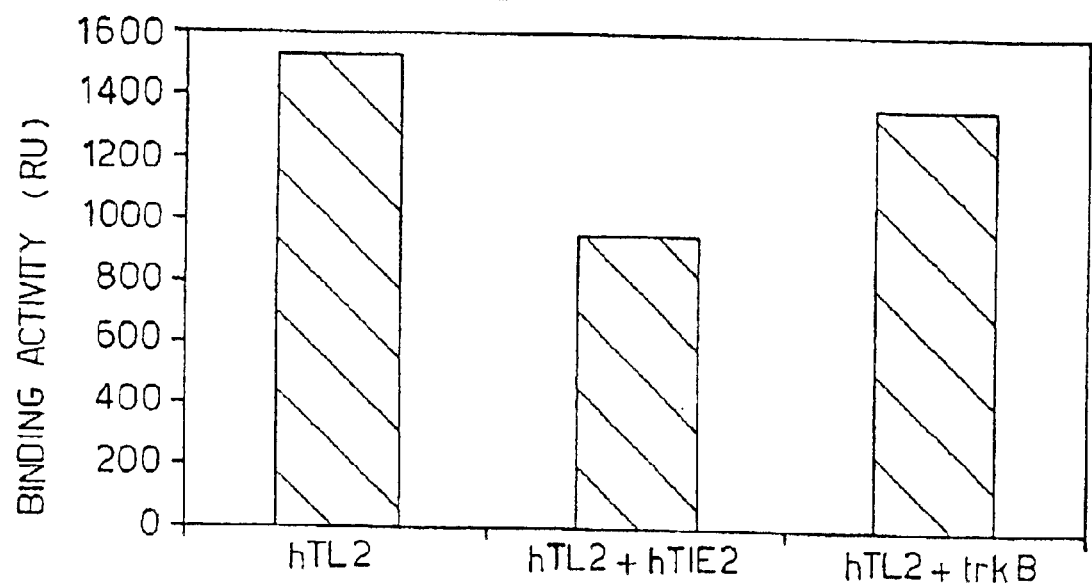

The ability of TL2 to competitively inhibit TL1 activation of the TIE-2-R was further demonstrated using the human cell hybrid line, EA.hy926 (see Example 21 for detailed description of this cell line and its maintenance). Experiments were performed in which unconcentrated COS cell media containing TL1 were mixed at varying dilutions with either MOCK- or TL2-conditioned media and placed on serum-starved EA.hy926 cell monolayers for 5 minutes at 37° C. The media were then removed, the cells were harvested by lysis and TIE-2-specific tyrosine phosphorylation was examined by Western blots, as described above. FIG. 9 shows an experiment which contains three groups of treatments, as viewed from left to right. As shown in the four lanes at the left, treatment of the EA.hy926 cells with 1× COS-TL1 alone robustly activated the endogenous TIE-2-R in these cells, whereas 1× TL2 COS medium was inactive. However, mixture of TL1 with either MOCK or TL2 demonstrated that TL2 can block the activity of TL1 in a dose-dependent fashion. In the central three pairs of lanes the ratio of TL2 (or MOCK) was decreased while the amount of TL1 in the mixture was correspondingly increased from 0.1× to 0.3×. At any of these mixture ratios the TL1:TL2 lanes showed a reduced level of TIE-2-R phosphorylation compared to that of the corresponding TL1:MOCK lanes. When the amount TL1 was held steady and the amount of TL2 (or MOCK) was decreased, however (shown in the three pairs of lanes at the right), a point was reached at which the TL2 in the sample was too dilute to effectively inhibit TL1 activity. The relative amount of each ligand present in these conditioned COS media could be estimated from their binding units as measured by the BIAcore assay and from Western blots of the COS media with ligand-specific antibodies. Consequently, we can infer that only a few-fold molar excess of TL2 is required to effectively block the activity of TL1 in vitro. This is significant because we have observed distinct examples in vivo (see Example 17 and FIG. 16) where TL2 mRNAs achieve considerable abundance relative to those of TL1. Thus, TL2 may be serving an important physiological role in effectively blocking signaling by the TIE-2-R at these sites.

Taken together these data confirm that, unlike TL1, TL2 is unable to stimulate endogenously expressed TIE-2-R on endothelial cells. Furthermore, at a few fold molar excess TL2 can block TL1 stimulation of the TIE-2 receptor, indicating that TL2 is a naturally occurring TIE-2 receptor antagonist.

EXAMPLE 10

Identification of TIE-2-Specific Binding Activity in Conditioned Medium and COS Cell Supernatants Binding activity of 10× CCM from the cell lines C2C12-ras, Rat2 ras, SHEP, and T98G, or COS cell supernatants after transfection with either human TIE-2 ligand 1 (hTL1) or human TIE-2 ligand 2 (hTL2) was measured using biosensor technology (BIAcore; Pharmacia Biosensor, Piscataway, N.J.) which monitors biomolecular interactions in real-time via surface plasmon resonance (SPR). Purified rat or human TIE-2 RB was covalently coupled through primary amines to the carboxymethyl dextran layer of a CM5 research grade sensor chip (Pharmacia Biosensor; Piscataway, N.J.). The sensor chip surface was activated using a mixture of N-hydroxysuccinimide (NHS) and N-ethyl-N'-(3-dimethylaminopropyl)carbodiimide (EDC), followed by immobilization of TIE-2 RB (25 µg/mL, pH 4.5) and deactivation of unreacted sites with 1.0 M ethanolamine (pH 8.5). In general, 9000–10000 RU of each receptorbody was coupled to the sensor chip.

The running buffer used in the system was HBS (10 mM Hepes, 150 mM NaCl, 0.005% P20 surfactant, pH 7.4). The samples were centrifuged for 15 min at 4° C. and further clarified using a sterile, low protein-binding 0.45 μm filter (Millipore; Bedford, Mass.). Dextran (2 mg/ml) and P20 surfactant (0.005%) were added to each sample. Aliquots of 40 μL were injected across the immobilized surface (either rat or human TIE-2) at a flow rate of 5 μL/min and the receptor binding was monitored for 8 min. The binding activity (resonance units, RU) was measured as the difference between a baseline value determined 30 s prior to the sample injection and a measurement taken at 30 s post-injection. Regeneration of the surface was accomplished with one 15-μL pulse of 3 M $MgCl_2$.

The CCM samples (C2C12-ras, Rat2-ras, SHEP, T98G) were tested on the rat TIE-2 RB immobilized surface, while the recombinant hTL1 and hTL2 were tested on the human TIE-2 RB immobilized surface. In each case, specific binding to the TIE-2 receptorbody was evaluated by incubating the samples with 25 μg/ml of either soluble TIE-2 (rat or human) RB or trkB RB prior to assaying the binding activity. As shown in FIGS. 10A–10D and FIGS. 11A–11B, the addition of soluble trkB RB causes a slight decrease in the TIE-2 binding activity, while the addition of soluble TIE-2 RB significantly reduces the binding activity as compared to that measured in the absence of TIE-2 RB.

EXAMPLE 11

TIE-2 RB Specifically Blocks Activation of the TIE-2 Receptor by TIE-2 Ligand 1

The applicants sought to determine whether soluble TIE-2 RB can serve as a competitive inhibitor to block activation of TIE-2 receptor by TIE-2 ligand 1 (TL1). To do this, TL1-containing COS media were preincubated with either TIE-2- or TrkB-RB and then compared for their ability to activate TIE-2 receptors naturally present in a human endothelial cell line.

Conditioned COS media were generated from COS-7 cells transfected with either the pJFE14 expression vector alone (MOCK), or pJFE14 vector containing the human TIE-2 ligand 1 cDNA (TL1) and harvested as described in Example 9 hereinabove, with the exception that the media were sterile filtered but not concentrated. The quantity of TL1 was determined and expressed as the amount (in resonance units, R.U.) of TIE-2 receptor-specific binding activity measured by BIAcore binding assay.

Northern (RNA) analyses revealed significant levels of tie-2 transcripts in HUVEC (Human Umbilical Vein Endothelial Cell) human primary endothelial cells (Clonetics, Inc.). Therefore, these cells were used to examine whether TIE-2 receptor can be tyrosine-phosphorylated when exposed in the presence of TIE-2- or TrkB-RBs to COS media containing TL1. HUVEC cells were maintained at 37° C., 5% $CO_2$ in a complete endothelial cell growth medium (Clonetics, Inc.) that contained 5% fetal bovine serum, soluble bovine brain extract with 10 μg/ml heparin, 10 ng/ml human EGF, 1 ug/ml hydrocortisone, 50 μg/ml gentamicin and 50 ng/ml amphotericin-B. Assessment of whether TL1 could activate the TIE-2 receptor in the HUVEC cells was done as follows. Confluent dishes of HUVEC cells were serum-starved for two-to-four hours in low-glucose Dulbecco's MEM at 37° C., 5% $CO_2$, followed by 10 minute incubation in starvation medium that included 0.1 mM sodium orthovanadate, a potent inhibitor of phosphotyrosine phosphatases. Meanwhile, conditioned COS media were preincubated 30 min. at room temperature with either TIE-2- or TrkB-RB added to 50 μg/ml. The starvation medium was then removed from the HUVEC dishes and incubated with the RB-containing COS media for 7 minutes at 37° C. HUVEC cells were subsequently lysed and TIE-2 receptor protein was recovered by immunoprecipitation with TIE-2 peptide antiserum, followed by Western blotting with an anti-phosphotyrosine antibody, as described in Example 1.

Figure 12:
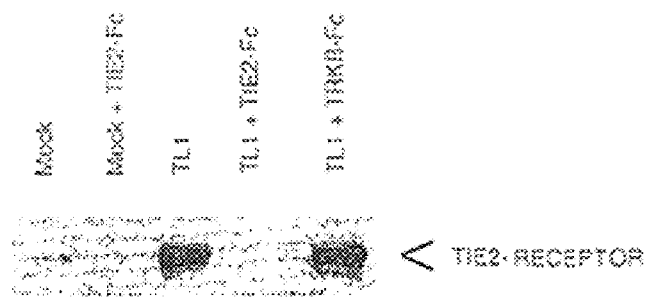
FIG. 12—Western blot showing that TIE-2 receptorbody (denoted TIE-2 RB or, as here, TIE2-Fc) blocks the activation of TIE-2 receptors by TIE-2 ligand 1 (TL1) in HUVEC cells, whereas an unrelated receptorbody (TRKB-Fc) does not block this activation.

The results are shown in FIG. 12. Phosphotyrosine levels on the TIE-2 receptor were induced by treatment of HUVEC cells with TIE-2 ligand 1 (TL1) relative to that seen with control medium (MOCK) and this induction is specifically blocked by prior incubation with TIE-2-RB (TIE-2-Fc) but not by incubation with TrkB-RB (TrkB-Fc). These data indicate that soluble TIE-2 RB can serve as a selective inhibitor to block activation of TIE-2 receptor by TIE-2 ligand 1.

EXAMPLE 12

Construction of TIE-2 Ligandbodies

An expression construct was created that would yield a secreted protein consisting of the entire coding sequence of human TIE-2 ligand 1 (TL1) or TIE-2 ligand 2 (TL2) fused to the human immunoglobulin gamma-1 constant region (IgG1 Fc). These fusion proteins are called TIE-2 "ligandbodies" (TL1-Fc or TL2-Fc). The Fc portion of TL1-Fc and TL2-Fc was prepared as follows. A DNA fragment encoding the Fc portion of human IgG1 that spans from the hinge region to the carboxy-terminus of the protein, was amplified from human placental cDNA by PCR with oligonucleotides corresponding to the published sequence of human IgG1; the resulting DNA fragment was cloned in a plasmid vector. Appropriate DNA restriction fragments from a plasmid encoding full-length TL1 or TL2 and from the human IgG1 Fc plasmid were ligated on either side of a short PCR-derived fragment that was designed so as to fuse, in-frame, TL1 or TL2 with human IgG1 Fc protein-coding sequences.

Milligram quantities of TL2-Fc were obtained by cloning the TL2-Fc DNA fragment into the pVL1393 baculovirus vector and subsequently infecting the Spodoptera frugiperda SF-21AE insect cell line. Alternatively, the cell line SF-9 (ATCC Accession No. CRL-1711) or the cell line BTI-TN-5b1–4 may be used. DNA encoding the TL2-Fc was cloned as an Eco RI-NotI fragment into the baculovirus transfer plasmid pVL1393. Plasmid DNA was recombined into viral DNA by mixing 3 μg of plasmid DNA with 0.5 μg of Baculo-Gold DNA (Pharminigen), followed by introduction into liposomes using 30 μg Lipofectin (GIBCO-BRL). DNA-liposome mixtures were added to SF-21AE cells (2×106 cells/60 mm dish) in TMN-FH medium (Modified Grace's Insect Cell Medium (GIBCO-BRL) for 5 hours at 27° C., followed by incubation at 27° C. for 5 days in TMN-FH medium supplemented with 5% fetal calf serum. Tissue culture medium was harvested for plaque purification of recombinant viruses, which was carried out using methods previously described (O'Reilly, D. R., L. K. Miller, and V. A. Luckow, Baculovirus Expression Vectors—A Laboratory Manual. 1992, New York: W. H. Freeman) except that the agarose overlay contained 125 mg/mL X-gal (5-bromo-4-chloro-3-indolyl-b-D-galactopyranoside; GIBCO-BRL). After 5 days of incubation at 27° C., non-recombinant plaques were scored by positive chromogenic reaction to the X-gal substrate, and their positions marked. Recombinant plaques were then visualized by addition of a second overlay containing 100 mg/mL MTT (3-[4,5-dimethylthiazol-2-yl] 2,5,diphenyltetrazolium bromide; Sigma). Putative recombinant virus plaques were picked by plug aspiration, and purified by multiple rounds of plaque isolation to assure homogeneity. Virus stocks were generated by serial, low-multiplicity passage of plaque-purified virus. Low passage stocks of one virus clone (vTL2-Fc Clone #7) were produced.

SF-21AE cells were cultured in serum-free medium (SF-900 II, Gibco BRL) containing 1× antibiotic/antimycotic solution (Gibco BRL) and 25 mg/L Gentamycin (Gibco BRL). Pluronic F-68 was added as a surfactant to a final concentration of 1 g/L. Cultures (4 L) were raised in a bioreactor (Artisan Cell Station System) for at least three days prior to infection. Cells were grown at 27° C., with gassing to 50% dissolved oxygen, at a gas flow rate of 80 mL/min (aeration at a sparge ring). Agitation was by means of a marine impeller at a rate of 100 rpm. Cells were harvested in mid-logarithmic growth phase (~2×10 6 cells/mL), concentrated by centrifugation, and infected with 5 plaque forming units of vTL2-Fc per cell. Cells and inoculum were brought to 400 mL with fresh medium, and virus was adsorbed for 2 hours at 27° C. in a spinner flask. The culture was then resuspended in a final volume of 8 L with fresh serum-free medium, and the cells incubated in the bioreactor using the previously described conditions.

Culture medium from vTL2-Fc-infected SF21AE cells were collected by centrifugation (500×g, 10 minutes) at 72 hours post-infection. Cell supernatants were brought to pH 8 with NaOH. EDTA was added to a final concentration of 10 mM and the supernatant pH was readjusted to 8. Supernatants were filtered (0.45 µm, Millipore) and loaded on a protein A column (protein A sepharose 4 fast flow or HiTrap protein A, both from Pharmacia). The column was washed with PBS containing 0.5 M NaCl until the absorbance at 280 nm decreased to baseline. The column was washed in PBS and eluted with 0.5 M acetic acid. Column fractions were immediately neutralized by eluting into tubes containing 1 M Tris pH 9. The peak fractions containing the TL2-Fc were pooled and dialyzed versus PBS.

EXAMPLE 13

Expression of TIE-1, TIE-2, TL1, and TL2 in Renal Cell Carcinoma

In situ hybridization experiments were performed on human renal cell carcinoma tumor tissue using TIE-1, TIE-2, TL1, and TL2 cDNA probes. TIE-2, TIE-1, TL1, and TL2 expression were all up-regulated in the tumor vasculature. Ligand expression appeared to be localized to either the vascular endothelial cells (TL2) or very near the vascular endothelial cells in the mesenchyme (TL1). VEGF has been shown to be dramatically up-regulated in this tumor tissue. Brown, et al. Am. J. Pathol. 143:1255–1262 (1993).

EXAMPLE 14

Expression of TIE-1, TIE-2, TL1, and TL2 in Wound Healing

In situ hybridization experiments were performed on cross-sectional tissue slices obtained from a rat cutaneous wound model using TIE-1, TIE-2, TL1, and TL2 cDNA probes. The wound healing model involves pressing a small cork bore against the skin of a rat and removing a small, cylindrical plug of skin. As healing begins at the base of the wound, a vertical slice of tissue is taken and used for in situ hybridization. In the tested tissue sample, TL1 and TL2 appeared to be slightly up-regulated by four days post-injury. In contrast to the slightly up-regulated expression of TL1 and TL2 in this tissue, VEGF expression, which may precede TL1 and TL2 expression, is dramatically up-regulated.

EXAMPLE 15

Expression of TIE Ligands in Fetal Liver and Thymus

Figure 13:
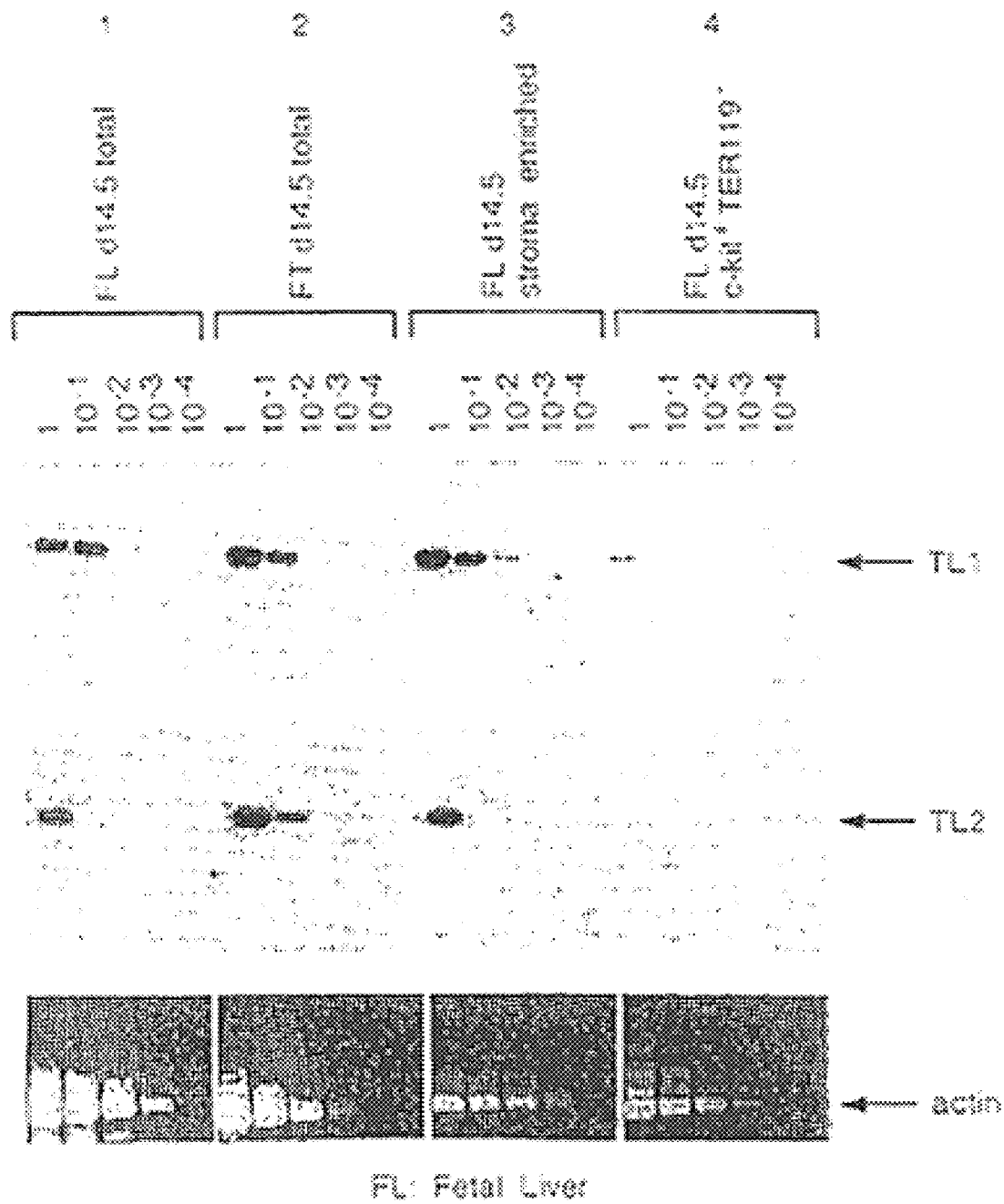
FIG. 13—Agarose gels showing serial dilutions [undiluted (1) to $10^{-4}$] of the TL1 and TL2 RT-PCR products obtained from E14.5 mouse fetal liver (Lanes 1-total, Lanes 3-stromal enriched, and Lanes 4—c-kit$^+$TER119 hematopoietic precursor cells) and E14.5 mouse fetal thymus (Lanes 2-total).
Figure 14:
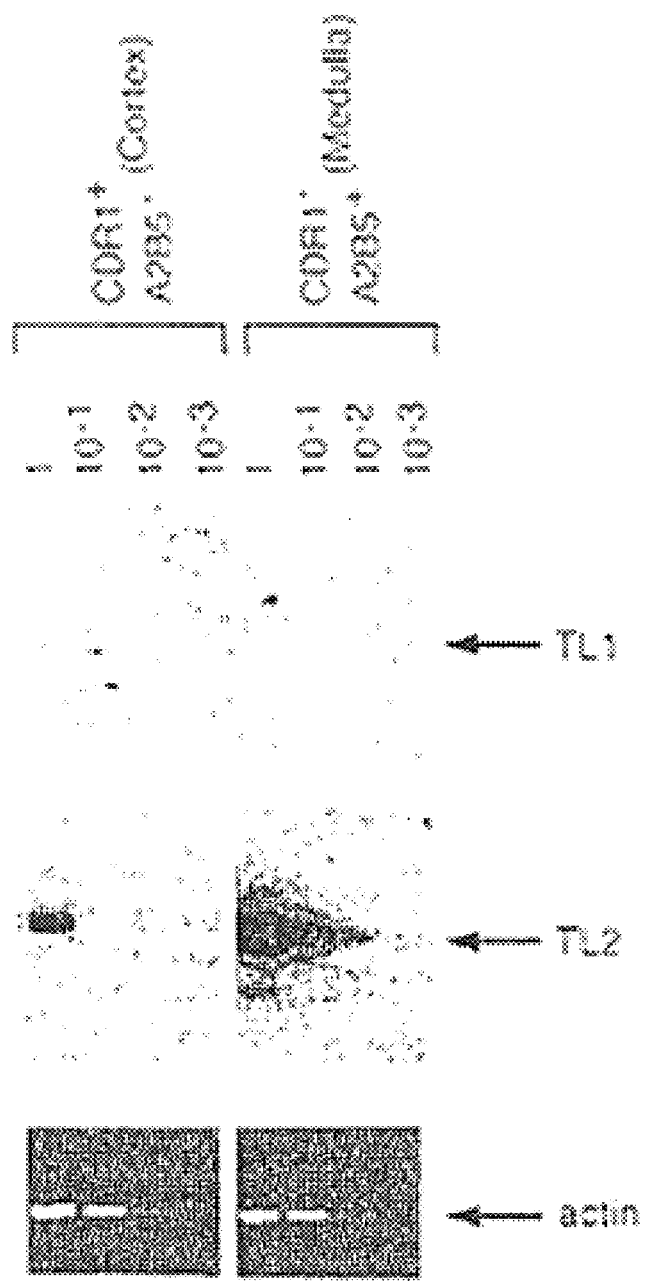
FIG. 14—Agarose gels showing serial dilutions [undiluted (1) to $10^{-3}$] of the TL1 and TL2 RT-PCR products obtained from E17.5 mouse fetal thymus cortical stromal cells (Lanes 1-CDR1+/A2B5−) and medullary stromal cells (Lane CDR1−/A2B5+).

Reverse transcription-PCR (RT-PCR) was performed on mouse E14.5 fetal liver and mouse E17.5 fetal thymus. Agarose gel electrophoresis of the RT-PCR products revealed that in the mouse fetal liver, TIE-2 ligand 1 (TL1) RNA is enriched in the stromal region, but is absent in c-kit$^+$TER119 hematopoietic precursor cells. In this same tissue, TIE-2 ligand 2 (TL2) RNA is enriched in the stromal cells, but absent in the hematopoietic precursor cells (FIG. 13). In the mouse fetal thymus, TL2 is enriched in the stromal cells (FIG. 14).

EXAMPLE 16

The TIE Receptor/Ligand System in Angiogenesis

Although the TIE-2/TIE ligand system appears to play an important role in endothelial cell biology, it has not been shown to play a significant, active role in the early to intermediate stages of vascularization (f angioblast or endothelial cell proliferation and migration, tubule formation, and other early stage events in vascular modeling). In contrast to the receptors and factors known to mediate these aspects of vascular development, the temporally late pattern of expression of TIE-2 and TL1 in the course of vascularization suggests that this system plays a distinct role in the latter stages vascular development, including the structural and functional differentiation and stabilization of new blood vessels. The pattern of expression of TIE-2/TL1 also is consistent with a continuing role in the maintenance of the structural integrity and/or physiological characteristics of an established vasculature.

Figure 15:
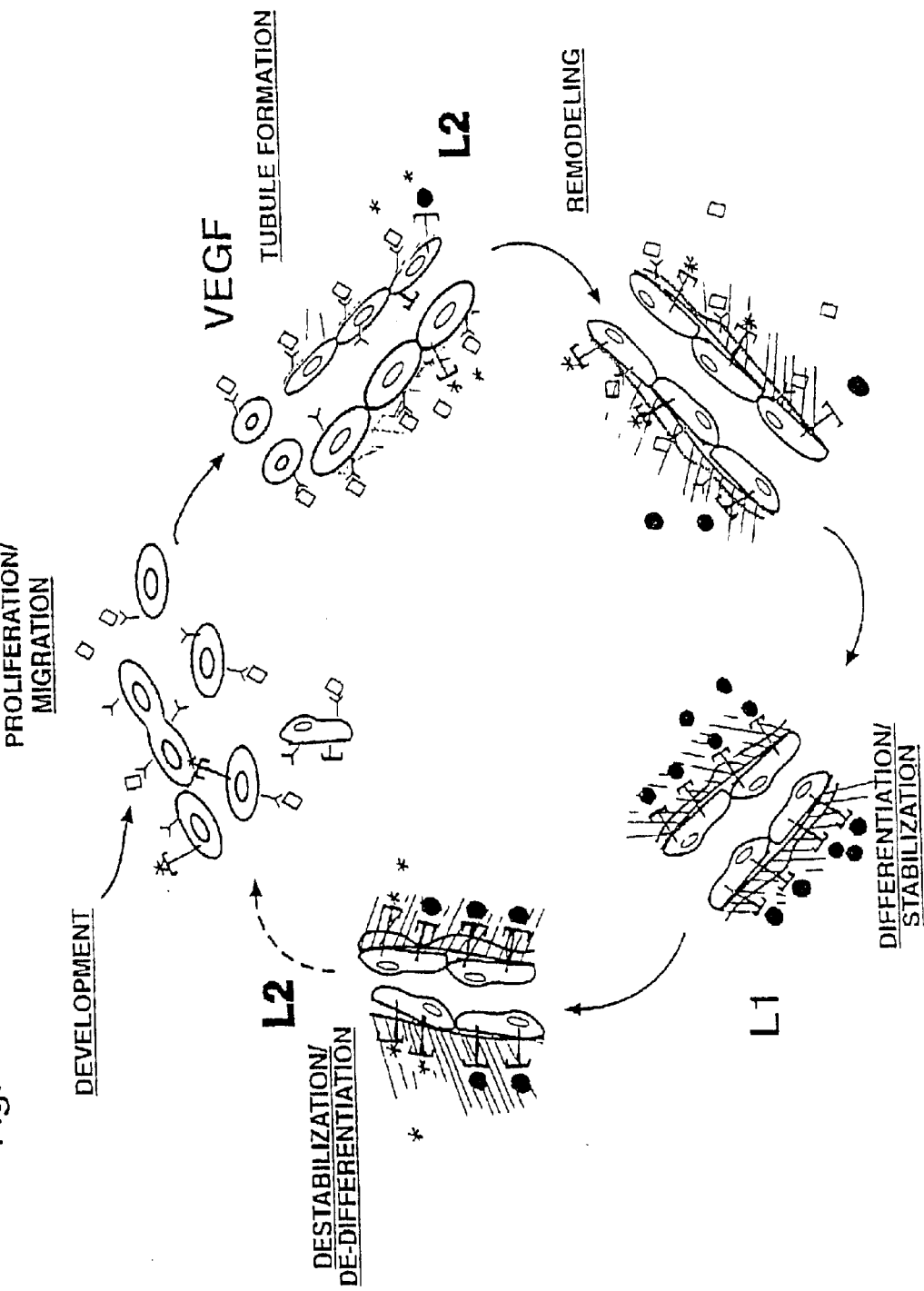
FIG. 15—A schematic representation of the hypothesized role of the TIE-2/TIE ligands in angiogenesis. TL1 is represented by (•), TL2 is represented by (*), TIE-2 is represented by (T), VEGF is represented by ([ ]), and flk-1 (a VEGF receptor) is represented by (Y).

TIE Ligand 2 (TL2) appears to be a competitive inhibitor of TL1. The spatiotemporal characteristics of TL2 expression suggest that this single inhibitory molecule may play multiple, context-dependent roles essential to appropriate vascular development or remodeling (e.g. de-stabilization/de-differentiation of mature endothelial cells allowing the formation of new vessels from existing vasculature, inhibition of inappropriate blood vessel formation, and regression/involution of mature blood vessels). FIG. 15 is a schematic representation of the hypothesized role of the TIE-2/TIE ligands in angiogenesis. In this figure TL1 is represented by (•), TL2 is represented by (*), TIE-2 is represented by (T), VEGF is represented by ([ ]), and flk-1 (a VEGF receptor) is represented by (Y).

EXAMPLE 17

Figure 16:
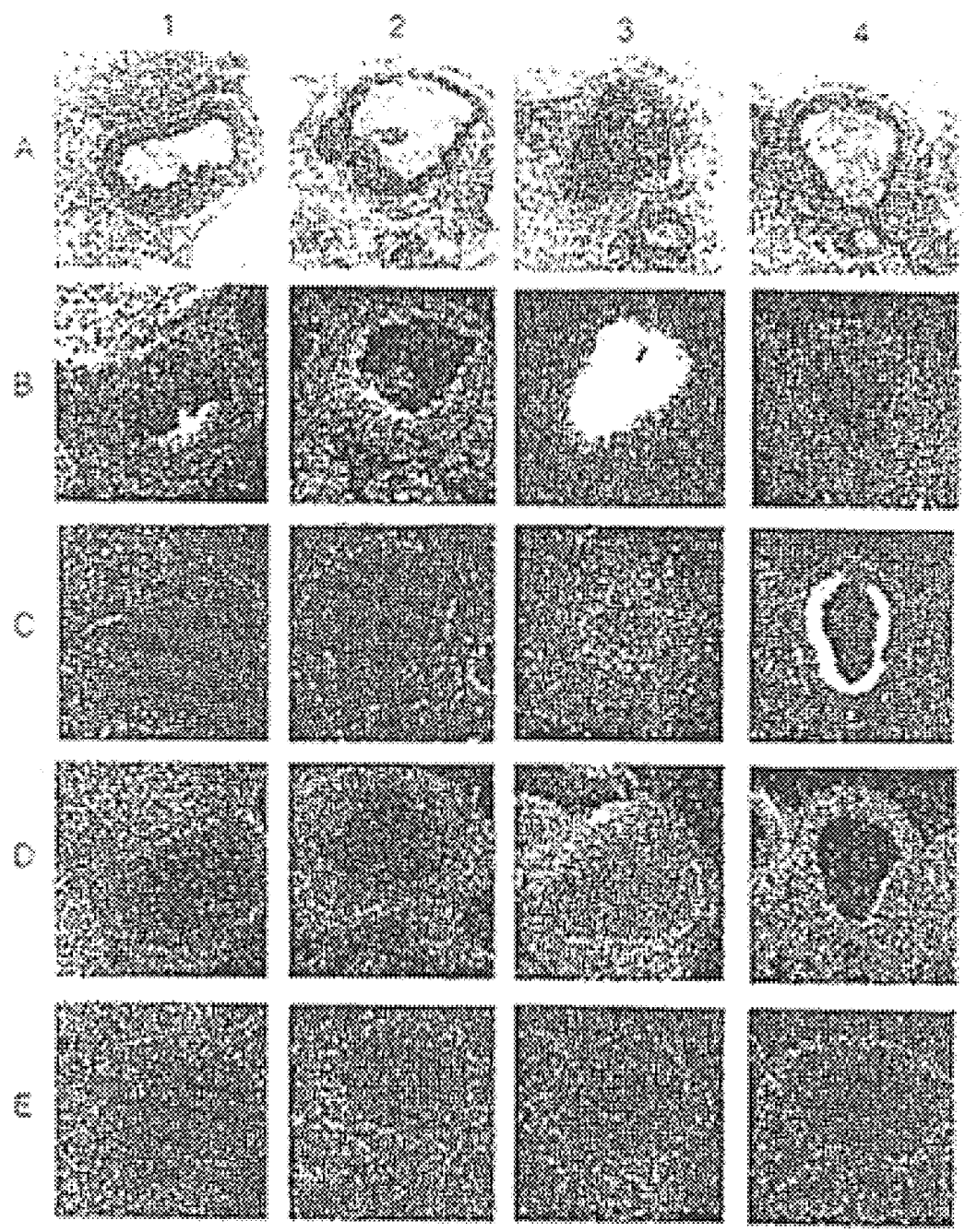
FIG. 16—In situ hybridization slides showing the temporal expression pattern of TIE-2, TL1, TL2, and VEGF during angiogenesis associated with follicular development and corpus luteum formation in the ovary of a rat that was treated with pregnant mare serum. Column 1: Early pre-ovulatory follicle; Column 2: pre-ovulatory follicle; Column 3: early corpus luteum; and Column 4: atretic follicle; Row A: bright field; Row B: VEGF; Row C: TL2; Row D: TL1 and Row E: TIE-2 receptor.

Expression of TIE Ligands in the Female Reproductive System: Expression in the Ovary Preliminary observations made in experiments examining the expression of the TIE receptors and ligands in the female reproductive system are consistent with the hypothesis the TL1 plays a role in neovascularization which temporally follows that of VEGF. The pattern of TL2 expression is also consistent with an antagonism of the action of TL1, and a specific role in vascular regression. To verify this, expression of relevant mRNAs can be examined following experimental induction of follicular and luteal development so that their temporal relation to various aspects of neovascularization/vascular regression can be more clearly defined (e g in conjunction with endothelial cell staining, vascular fills). Angiogenesis associated with follicular development and corpus luteum formation in staged ovaries of mature, female rats or following induced ovulation in pre-pubertal animals was followed using in situ hybridization. FIG. 16 contains photographs of in situ hybridization slides showing the temporal expression pattern of TIE-2, TL1, TL2, and VEGF during the ovarian cycle [Column 1: Early pre-ovulatory follicle; Column 2: pre-ovulatory follicle; Column 3: early corpus luteum; and Column 4: atretic follicle; Row A:bright field; Row B:VEGF; Row C: TL2;

Row D: TL1 and Row E: TIE-2 receptor]. These studies revealed that VEGF, TL1 and TL2 are expressed in a temporally and spatially coordinate fashion with respect to the development and regression of vasculature in the ovary, specifically with respect to the establishment of the vascular system which is generated in the course of the conversion of an ovarian follicle to a corpus luteum (CL).

Briefly, VEGF expression increases in the follicular granule layer prior to its vascularization during the process of luteinization. During the process of CL formation, highest levels of VEGF expression are apparent in the center of the developing CL in the vicinity of luteinizing cells which are not yet vascularized. VEGF levels remain moderately high and are diffusely distributed in the developed CL. In contrast, noticeably enhanced expression of TIE-2 ligand 1 occurs only late in process of CL formation, after a primary vascular plexus has been established. Later, TL1 expression is apparent throughout the CL at which time the definitive capillary network of the CL has been established.

TL2 exhibits a more complex pattern of expression than either VEGF or TL1. In the developing CL, TL2 is expressed at highest levels at the front of the developing capillary plexus between the central avascular region of the CL where VEGF expression is highest, and the most peripheral portion of the CL where TL1 expression is dominant and where the luteinization process is complete and the vascular system is most mature. TL2 also appears to be expressed at high levels in the follicular layer of large follicles which are undergoing atresia. While TL1 is also apparent in atretic follicles, VEGF is not expressed.

The pattern of expression described above is most consistent with a role for VEGF in the initiation of angiogenesis, with TL1 acting late in this process-for example in modeling and/or stabilization of the definitive vascular network. In contrast, TL2 is present both in areas of active expansion of a newly forming vascular network (during CL formation), and in regions which fail to establish a new vasculature and vascular regression is in progress (atretic follicles). This suggests a more dynamic and complex role for TL2, possibly involving destabilization of existing vasculature (necessary for regression) or developing vasculature (necessary for the dynamic modeling of newly forming vessels).

EXAMPLE 18

A Receptorbody Binding Assay and a Ligand Binding and Competition Assay

Figure 19:
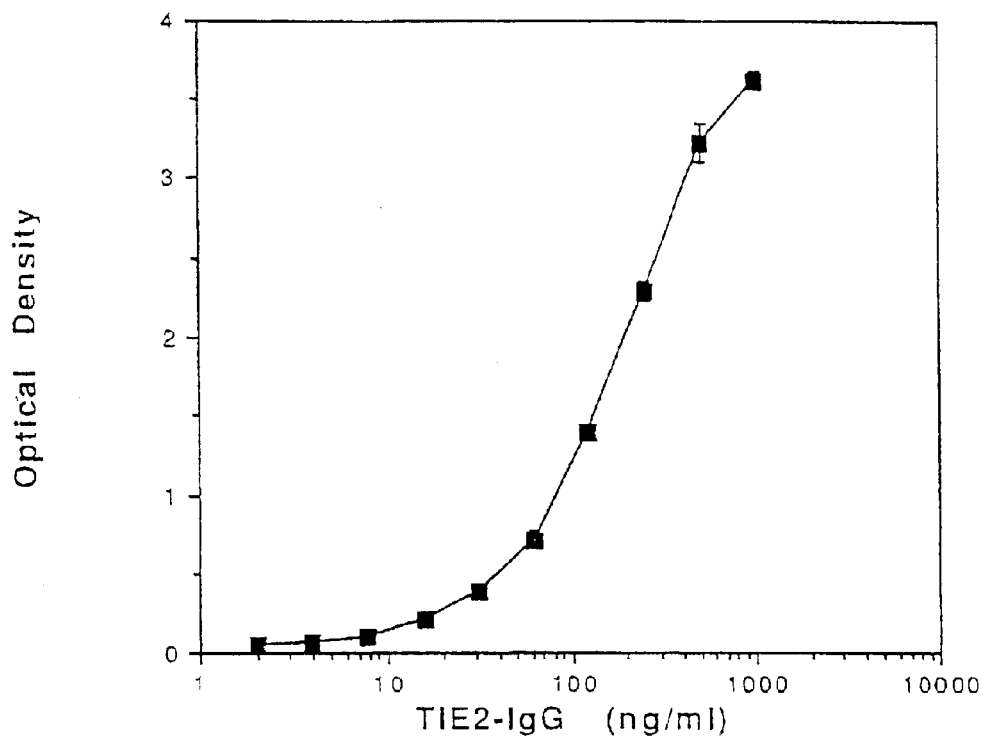
FIG. 19—A typical curve of TIE-2-IgG binding to immobilized TL1 in a quantitative cell-free binding assay.
Figure 20:
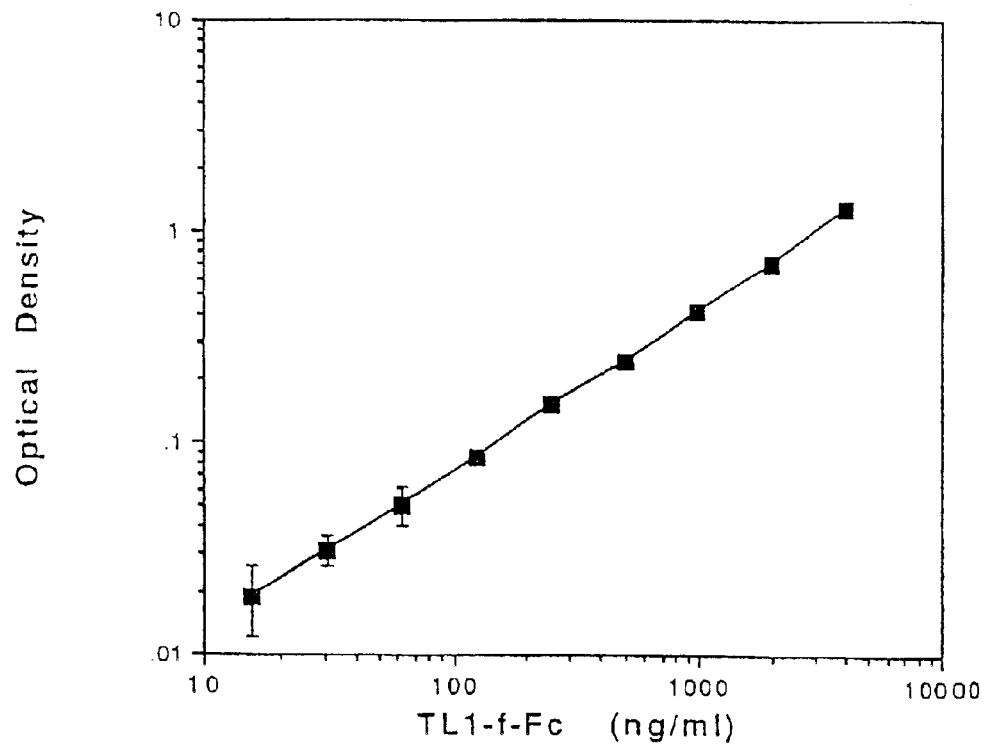
FIG. 20—A typical curve showing TIE-2 ligand 1 ligandbody comprising the fibrinogen-like domain of the ligand bound to the Fc domain of IgG (TL1-fFc) binding to immobilized TIE-2 ectodomain in a quantitative cell-free binding assay.

A quantitative cell-free binding assay with two alternate formats has been developed for detecting either TIE-2 receptorbody binding or ligand binding and competition. In the receptorbody binding version of the assay, TIE-2 ligands (purified or partially purified; either TL1 or TL2) are coated onto an ELISA plate. Receptorbody at varying concentrations is then added, which binds to the immobilized ligand in a dose-dependent manner. At the end of 2 hours, excess receptorbody is washed away, then the amount bound to the plate is reported using a specific anti-human Fc antibody which is alkaline phosphatase tagged. Excess reporter antibody is washed away, then the AP reaction is developed using a colored substrate. The assay is quantitated using a spectrophotometer. FIG. 19 shows a typical TIE-2-IgG binding curve. This assay has been used to evaluate the integrity of TIE-2-IgG after injection into rats and mice. The assay can also be used in this format as a ligand competition assay, in which purified or partially-purified TIE ligands compete with immobilized ligand for receptorbody. In the ligand binding and competition version of the binding assay, TIE-2 ectodomain is coated onto the ELISA plate. The Fc-tagged fibrinogen-like domain fragments of the TIE ligands (TL1-fFc and TL2-fFc) then bind to the ectodomain, and can be detected using the same anti-human Fc antibody as described above. FIG. 20 shows an example of TL1-fFc binding to TIE-2 ectodomain. This version of the assay can also be used to quantitate levels of TL1-fFc in serum or other samples. If untagged ligand (again, either purified or unpurified) is added at the same time as the TL1-fFc, then a competition is set up between tagged ligand fragment and full-length ligand. The full-length ligand can displace the Fc-tagged fragment, and a competition curve is generated.

EXAMPLE 19

EA.hy926 Cell Line can be Used as a Reporter Cell Line for TIE Ligand Activity

EA.hy926 is a cell hybrid line that was established by fusion of HUVEC with the human lung carcinoma-derived line, A549 [Edgell, et al. Proc. Natl. Acad. Sci. (USA) 80, 3734–3737 (1983). EA.hy926 cells have been found to express significant levels of TIE-2 receptor protein with low basal phosphotyrosine levels. The density at which EA.hy926 cells are passaged prior to their use for receptor assays, as well as their degree of confluency at the time of assay, can affect TIE-2 receptor abundance and relative inducibility in response to treatment with ligand. By adopting the following regimen for growing these cells the EA.hy926 cell line can be used as a dependable system for assay of TIE-2 ligand activities.

EA.hy926 cells are seeded at $1.5 \times 10^6$ cells in T-75 flasks (Falconware) and re-fed every other day with high-glucose Dulbecco's MEM, 10% fetal bovine serum, L-glutamine, penicillin-streptomycin, and 1x hypoxanthine-aminopterin-thymidine (HAT, Gibco/BRL). After three to four days of growth, the cells are passaged once again at $1.5 \times 10^6$ cells per T-75 flask and cultured an additional three to four days. For phosphorylation assays, cells prepared as described above were serum-starved by replacement of the culture medium with high-glucose DMEM and incubation for 2–3 hours at 37° C. This medium was aspirated from the flask and samples of conditioned media or purified ligand were added to the flask in a total volume of 1.5 ml followed by incubation at 37° C. for 5 minutes. Flasks were removed from the incubator and placed on a bed of ice. The medium was removed and replaced with 1.25 ml Lysis Buffer containing 1% nonidet P-40, 0.5% sodium deoxycholate, 0.1% SDS in 20 mM Tris, pH 7.6, 150 mM NaCl, 50 mM NaF, 1 mM sodium orthovanadate, 5 mM benzamidine, and 1 mM EDTA containing the protease inhibitors PMSF, aprotinin, and leupeptin. After 10 minutes on ice to allow membrane solubilization, plates were scraped and cell lysates were clarified by microcentrifugation at top speed for 10 minutes at 4° C. TIE-2 receptor was immunoprecipitated from the clarified supernatant by incubation in the cold with an anti-TIE-2 polyclonal antiserum and Protein G-conjugated Sepharose beads. The beads were washed three times with cold cell lysis buffer and boiled 5 minutes in Laemmli sample buffer, which was then loaded on 7.5% SDS-polyacrylamide gels. Resolved proteins were electrotransferred to PVDF (Lamblia-P) membrane and then subjected to Western blot analysis using anti-phosphotyrosine antibody and the ECL reagent. Subsequent comparison of total TIE-2 protein levels on the same blots was done by stripping the anti-phosphotyrosine antibody and reincubating with a polyclonal antiserum specific to the ectodomain of TIE-2.

EXAMPLE 20

Isolation and Sequencing of Full Length cDNA Clone Encoding Mammalian TIE Ligand-3

TIE ligand-3 (TL3) was cloned from a mouse BAC genomic library (Research Genetics) by hybridizing library duplicates, with either mouse TL1 or mouse TL2 probes corresponding to the entire coding sequence of those genes. Each copy of the library was hybridized using phosphate buffer at 55° C. overnight. After hybridization, the filters were washed using 2×SSC, 0.1% SDS at 60° C., followed by exposure of X ray film to the filters. Strong hybridization signals were identified corresponding to mouse TL1 and mouse TL2. In addition, signals were identified which weakly hybridized to both mouse TL1 and mouse TL2. DNA corresponding to these clones was purified, then digested with restriction enzymes, and two fragments which hybridized to the original probes were subcloned into a bacterial plasmid and sequenced. The sequence of the fragments contained two exons with homology to both mouse TL1 and mouse TL2. Primers specific for these sequences were used as PCR primers to identify tissues containing transcripts corresponding to TL3. A PCR band corresponding to TL3 was identified in a mouse uterus cDNA library in lambda gt-11. (Clontech Laboratories, Inc., Palo Alto, Calif.).

Plaques were plated at a density of 1.25×10⁶/20×20 cm plate and replica filters taken following standard procedures (Sambrook, et al., Molecular Cloning: A Laboratory Manual, 2nd Ed., page 8.46, Cold Spring Harbor Laboratory, Cold Spring Harbor, N.Y.). Duplicate filters were screened at "normal" stringency (2×SSC, 65° C.) with a 200 bp PCR radioactive probe made to the mouse TL3 sequence. Hybridization was at 65° C. in a solution containing 0.5 mg/ml salmon sperm DNA. Filters were washed in 2×SSC at 65° C. and exposed for 6 hours to X-ray film. Two positive clones that hybridized in duplicate were picked. EcoRI digestion of phage DNA obtained from these clones indicated two independent clones with insert sizes of approximately 1.2 kb and approximately 2.2 kb. The 2.2 kb EcoRI insert was subcloned into the EcoRI site of pBluescript KS (Stratagene). Sequence analysis showed that the longer clone was lacking an initiator methionine and signal peptide but otherwise encoded a probe homologous to both mouse TL1 and mouse TL2.

Two TL3-specific PCR primers were then synthesised as follows: US2: cctctgggctcgccagtttgttagg (SEQ ID NO: 29) US1: ccagctggcagatatcagg (SEQ ID NO: 30)

The following PCR reactions were performed using expression libraries derived from the mouse cell lines C2C12ras and MG87. In the primary PCR reaction, the specific primer US2 was used in conjunction with vector-specific oligos to allow amplification in either orientation. PCR was in a total volume of 100 ml using 35 cycles of 94° C., 1 mm; 42° C. or 48° C. for 1 mm; 72° C, 1 mm. The secondary PCR reaction included the second specific primer, US1, which is contained within the primary PCR product, in conjunction with the same vector oligos. The secondary reactions were for 30 cycles, using the same temperatures and times as previous. PCR products were gel isolated and submitted for sequence analysis. On the basis of sequences obtained from a total of four independent PCR reactions using two different cDNA libraries, the 5' end of the TL3 sequence was deduced. Northern analysis revealed moderate to low levels of mouse TL3 transcript in mouse placenta. The expression of mouse TL3 consisted of a transcript of approximately 3 kb. The full length TL3 coding sequence is set forth in FIGS. 21A–21C (SEQ ID NO: 9 and SEQ ID NO: 10).

The mouse TL3 sequence may then be used to obtain a human clone containing the coding sequence of human TL3 by hybridizing either a human genomic or cDNA library with a probe corresponding to mouse TL3 as has been described previously, for example, in Example 8 supra.

EXAMPLE 21

Isolation of Full Length Genomic Clone Encoding Human TIE Ligand-4

TIE ligand-4 (TL4) was cloned from a mouse BAC genomic library (BAC HUMAN (II), Genome Systems Inc.) by hybridizing library duplicates, with either a human TL1 radioactive probe corresponding to the entire fibrinogen coding sequence of TL1 (nucleotides 1153 to 1806 of FIGS. 4A–4D [SEQ ID NO: 1 and SEQ ID NO: 2]) or a mouse TL3 radioactive probe corresponding to a segment of 186 nucleotides from the fibrinogen region of mouse TL3 (nucleotides 1307 to 1492 of FIGS. 21A–21C [SEQ ID NO: 9 and SEQ ID NO: 10]). Each probe was labeled by PCR using exact oligonucleotides and standard PCR conditions, except that dCTP was replaced by $P^{32}$dCTP. The PCR mixture was then passed through a gel filtration column to separate the probe from free $P^{32}$ dCTP. Each copy of the library was hybridized using phosphate buffer, and radioactive probe at 55° C. overnight using standard hybridization conditions. After hybridization, the filters were washed using 2×SSC, 0.1% SDS at 55° C., followed by exposure of X ray film. Strong hybridization signals were observed corresponding to human TL1. In addition, signals were identified which weakly hybridized to both human TL1 and mouse TL3. DNA corresponding to these clones was purified using standard procedures, then digested with restriction enzymes, and one fragment which hybridized to the original probes was subcloned into a bacterial plasmid and sequenced. The sequence of the fragments contained one exon with homology to both human TL1 and mouse TL3 and other members of the TIE ligand family. Primers specific for these sequences may be used as PCR primers to identify tissues containing transcripts corresponding to TL4.

The complete sequence of human TL4 may be obtained by sequencing the full BAC clone contained in the deposited bacterial cells. Exons may be identified by homology to known members of the TIE-ligand family such as TL1, TL2 and TL3. The full coding sequence of TL4 may then be determined by splicing together the exons from the TL4 genomic clone which, in turn, may be used to produce the TL4 protein. Alternatively, the exons may be used as probes to obtain a full length cDNA clone, which may then be used to produce the TL4 protein. Exons may also be identified from the BAC clone sequence by homology to protein domains such as fibrinogen domains, coiled coil domains, or protein signals such as signal peptide sequences. Missing exons from the BAC clone m,ay be obtained by identification of contiguous BAC clones, for example, by using the ends of the deposited BAC clone as probes to screen a human genomic library such as the one used herein, by using the exon sequence contained in the BAC clone to screen a cDNA library, or by performing either 5' or 3' RACE procedure using oligonucleotide primers based on the TL4 exon sequences.

Identification of Additional TIE Ligand Family Members

The novel TIE ligand-4 sequence may be used in a rational search for additional members of the TIE ligand family using an approach that takes advantage of the existence of conserved segments of strong homology between the known family members. For example, an alignment of the amino acid sequences of the TIE ligands shows several regions of conserved sequence (see boxed regions of FIGS. 22A–22B (SEQ ID NO: 11, SEQ ID NO: 12, SEQ ID NO: 13, SEQ ID NO: 14, SEQ ID NO: 15, and SEQ ID NO: 16). Degenerate oligonucleotides essentially based on these boxes in combination with either previously known or novel TIE ligand homology segments may be used to identify new TIE ligands.

The highly conserved regions among TL1, TL2 and TL3 may be used in designing degenerate oligonucleotide primers with which to prime PCR reactions using cDNAs. cDNA templates may be generated by reverse transcription of tissue RNAs using oligo d(T) or other appropriate primers. Aliquots of the PCR reactions may then be subjected to electrophoresis on an agarose gel. Resulting amplified DNA fragments may be cloned by insertion into plasmids, sequenced and the DNA sequences compared with those of all known TIE ligands.

Size-selected amplified DNA fragments from these PCR reactions may be cloned into plasmids, introduced into *E. coli* by electroporation, and transformants plated on selective agar. Bacterial colonies from PCR transformation may be analyzed by sequencing of plasmid DNAs that are purified by standard plasmid procedures.

Cloned fragments containing a segment of a novel TIE ligand may be used as hybridization probes to obtain full length cDNA clones from a cDNA library. For example, the human TL4 genomic sequence may be used to obtain a human cDNA clone containing the complete coding sequence of human TL4 by hybridizing a human cDNA library with a probe corresponding to human TL4 as has been described previously.

EXAMPLE 22

Cloning of the Full Coding Sequence of hTL4

Both 5' and 3' coding sequence from the genomic human TL-4 clone encoding human TIE ligand-4 (hTL-4 ATCC Accession No. 98095) was obtained by restriction enzyme digestion, Southern blotting and hybridization of the hTL-4 clone to coding sequences from mouse TL3, followed by subcloning and sequencing the hybridizing fragments. Coding sequences corresponding to the N-terminal and C-terminal amino acids of hTL4 were used to design PCR primers (shown below), which in turn were used for PCR amplification of TL4 from human ovary cDNA. A PCR band was identified as corresponding to human TL4 by DNA sequencing using the ABI 373A DNA sequencer and Taq Dideoxy Terminator Cycle Sequencing Kit (Applied Biosystems, Inc., Foster City, Calif.). The PCR band was then subcloned into vector pCR-script and several plasmid clones were analyzed by sequencing. The complete human TL4 coding sequence was then compiled and is shown in FIGS. 23A–23C (SEQ ID NO: 17 and SEQ ID NO: 18). In another embodiment of the invention, the nucleotide at position 569 is changed from A to G, resulting in an amino acid change from Q to R.

The PCR primers used as described above were designed as follows: hTL4atg 5'-gcatgctatctcgagccaccATGCTCTCCCAGCTAGCCA TGCTGCAG-3'(SEQ ID NO: 27)

hTL4not 5'-gtgtcgacgcggccgctctagatcagacTTAGATGTCCAAA GGCCGTATCATCAT-3'(SEQ ID NO: 28)

Lowercase letters indicate "tail" sequences added to the PCR primers to facilitate cloning of the amplified PCR fragments.

EXAMPLE 23

Construction and Characterization of Modified TIE Ligands

A genetic analysis of TIE-2 ligand-1 and TIE-2 ligand-2 (TL1 and TL2) was undertaken to gain insight into a number of their observed properties. Although TL1 and TL2 share similar structural homology, they exhibit different physical and biological properties. The most prominent feature that distinguishes the two ligands is that although they both bind to the TIE-2 receptor, TL1 is an agonist while TL2 is an antagonist. Under non-reducing electrophoretic conditions both proteins exhibit covalent, multimeric structures. TL1 is produced as a mixture of disulfide cross-linked multimers, primarily trimers and higher order species, without any dimeric species. But TL2 is produced almost exclusively as a dimeric species. Also, while TL2 is produced well in most expression systems, TL1 is expressed poorly and is difficult to produce in large quantities. Finally, production and purification conditions also appear to predispose TL1 to inactivation by proteolytic cleavage at a site near the amino terminus.

To study these differences, several modified ligands were constructed as follows.

Figure 17:
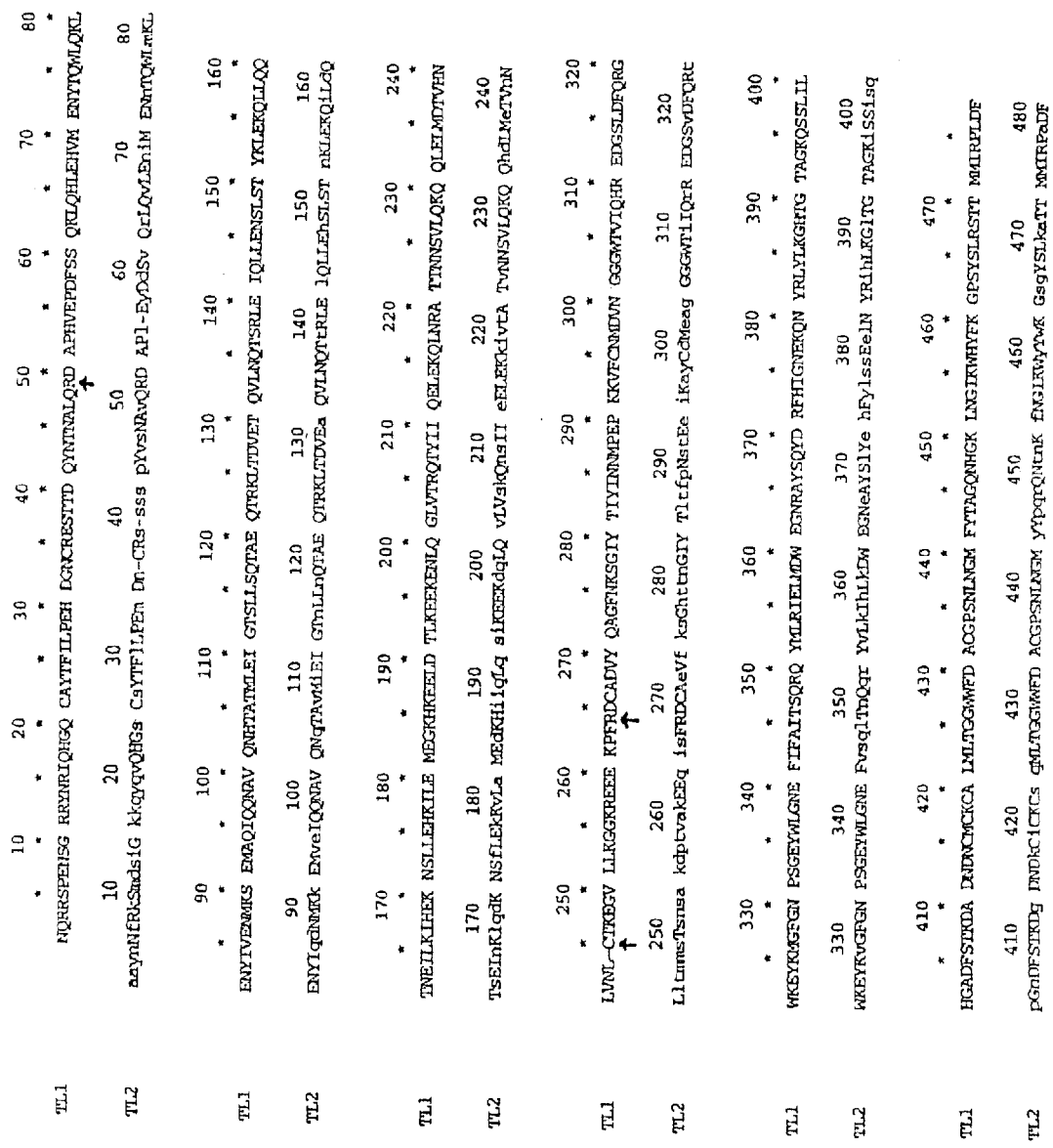
FIG. 17—Comparison of amino acid sequences of mature TL1 protein (SEQ ID NO: 7) and mature TL2 protein (SEQ ID NO: 8). The TL1 sequence is the same as that set forth in FIGS. 4A–4D (SEQ ID NO: 1 AND SEQ ID NO: 2), except that the putative leader sequence has been removed. Similarly, the TL2 sequence is the same as that set forth in FIGS. 6A–6D (SEQ ID NO: 5 and SEQ ID NO: 6), except that the putative leader sequence has been removed. Arrows indicate residues Arg49, Cys245 and Arg264 of TL1, which correspond to the residues at amino acid positions 69, 265 and 284, respectively, of TL1 as set forth in FIGS. 4A–4D (SEQ ID NO: 1 and SEQ ID NO: 2).

23.1. Cysteine substitution—Investigations into what factors might be contributing to the different physical and biological properties of the two molecules revealed the presence in TL1 of a cysteine residue (CYS 265 in FIGS. 4A–4D [SEQ ID NO: 1 and SEQ ID NO: 2]; CYS 245 in FIG. 17 [SEQ ID NO: 7 and SEQ ID NO: 8]) preceding the fibrinogen-like domain in TL1 but absent in TL2—i.e., there was no corresponding cysteine residue in TL2. The CYS265 residue in TL1 is encoded by TGC and is located at about nucleotides 1102–1104 (see FIGS. 4A–4D [SEQ ID NO: 1 and SEQ ID NO: 2]) at the approximate junction between the coiled-coil and fibrinogen-like domains. Because cysteine residues are generally involved in disulfide bond formation, the presence of which can contribute to both the tertiary structure and biological properties of a molecule, it was thought that perhaps the presence of the CYS265 residue in TL1 might be at least partially responsible for the different properties of the two molecules.

To test this hypothesis, an expression plasmid was constructed which contained a mutation in TL1 in which the CYS (residue 265 in FIGS. 4A–4D [SEQ ID NO: 1 and SEQ ID NO: 2]; residue 245 in FIG. 17) was replaced with an amino acid (serine) which does not form disulfide bonds. In addition to this TL1/CYS⁻ mutant, a second expression plasmid was constructed which mutated the approximately corresponding position in TL2 (Met247 in FIG. 17 [SEQ ID NO: 7 and SEQ ID NO: 8]) so that this residue was now a cysteine. Both non-mutated and mutated expression plasmids of TL1 and TL2 were transiently transfected into COS7 cells, cell supernatants containing the recombinant proteins were harvested, and samples were subjected to both reducing and non-reducing SDS/PAGE electrophoresis and subsequent Western blotting.

Figure 18:
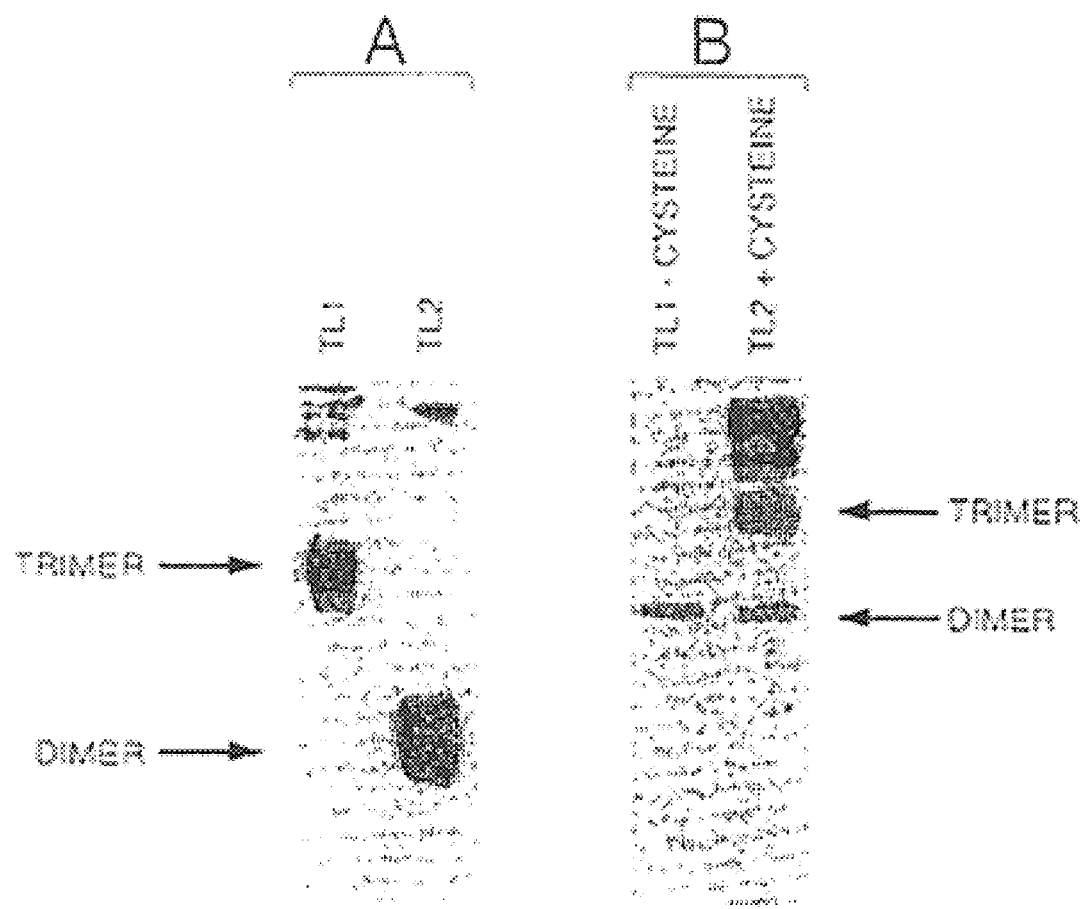
FIG. 18—Western blot of the covalent multimeric structure of TL1 and TL2 (Panel A) and the interconversion of TL1 and TL2 by the mutation of one cysteine (Panel B).

FIG. 18 shows the Western blots under non-reducing conditions of both non-mutated and mutated TL1 and TL2 proteins, revealing that the TL1/CYS⁻ mutant runs as a dimer much like TL2 and that the TL2/CYS+mutant is able to form a trimer, as well as higher-order multimers, more like TL1. When the two mutant proteins were tested for their ability to induce phosphorylation in TIE-2 expressing cells, the TL1/CYS⁻ mutant was able to activate the TIE-2 receptor, whereas the TL2/CYS⁺ mutant was not.

Thus, when the cysteine residue (residue 265 in FIGS. 4A–4D [SEQ ID NO: 1 and SEQ ID NO: 2]; residue 245 in [SEQ ID NO: 7 and SEQ ID NO: 8]) of TL1 was genetically altered to a serine, it was found that the covalent structure of TL1 became similar to that of TL2, i.e., primarily dimeric. The modified TL1 molecule still behaved as an agonist, thus the trimeric and/or higher order multimeric structure was not the determining factor giving TL1 the ability to activate. Although the removal of the cysteine did make a molecule with more desirable properties, it did not improve the production level of TH1.

23.2. Domain deletions—The nucleotide sequences encoding TL1 and TL2 share a genetic structure that can be divided into three domains, based on the amino acid sequences of the mature proteins. The last approximately 215 amino acid residues of each mature protein contains six cysteines and bears strong resemblance to a domain of fibrinogen. This region was thus denoted the "fibrinogen-like" domain or "F-domain." A central region of the mature protein containing approximately 205 residues had a high probability of assuming a "coiled-coil" structure and was denoted the "coiled-coil" domain or "C-domain." The amino-terminal approximately 55 residues of the mature protein contained two cysteines and had a low probability of having a coiled-coil structure. This region was designated the "N-terminal" domain or "N-domain." The modified ligands described herein are designated using a terminology wherein N=N-terminal domain, C=coiled-coil domain, F=fibrinogen-like domain and the numbers 1 and 2 refer to TL1 and TL2 respectively. Thus 1N indicates the N-terminal domain from TL1, 2F indicates the fibrinogen-like domain of TL2, and so forth.

In order to test whether the fibrinogen-like domain (F-domain) of the TIE2 ligands contained TIE-2 activating activity, expression plasmids were constructed which deleted the coiled-coil and N-terminal domains, leaving only that portion of the DNA sequence encoding the F-domain (for TL1, beginning in FIGS. 4A–4D [SEQ ID NO: 1 and SEQ ID NO: 2] at about nucleotide 1159, amino acid residue ARG284; for TL2, corresponding to about nucleotide 1200 in FIGS. 6A–6D [SEQ ID NO: 5 and SEQ ID NO: 6], amino acid residue 282). This mutant construct was then transiently transfected into COS cells. The supernatant containing the recombinant protein was harvested. The TL1/F-domain mutant was tested for its ability to bind the TIE-2 receptor. The results showed that, as a monomer, the TL1/F-domain mutant was not able to bind TIE-2 at a detectable level.

But when the TL1/F-domain monomer was myc-tagged and subsequently clustered with an antibody directed against the myc tag, it exhibited detectable binding to TIE-2. However, the antibody-clustered TL1/F-domain mutant was not able to induce phosphorylation in a TIE-2 expressing cell line.

Thus it was determined that the F-domain of the TIE-2 ligands is involved in binding the receptor but that a truncation consisting of just the F-domain alone is not sufficient for receptor binding. This raised the possibility that the coiled-coil domain was responsible for holding together several fibrinogen-like domains, which might be essential for receptor binding. In an attempt to confirm this hypothesis, the F-domain was fused with the Fc section of human antibody IgG1. Because Fc sections dimerize upon expression by mammalian cells, these recombinant proteins mimicked the theoretical configuration of the F-domains were the native ligands to dimerize. This F-domain-Fc construct bound but failed to activate the receptor. Apparently, multimerization caused by other regions of the ligands is necessary to enable the ligands to bind the TIE receptor. In addition, some other factor outside of the F-domain must contribute to phosphorylation of the receptor.

Mutants were then constructed which were missing the fibrinogen-like domain, and therefore contained only the N-terminal and coiled-coil domains. They were not capable of binding to the receptor. To assess the role of the N-terminal domain in receptor binding and activation, the ligands were truncated to just their C- and F-domains and tagged with a FLAG tag at the N-terminus, creating constructs termed FLAG-1C1F and FLAG-2C2F. Although these molecules stained robustly in COS7 cells transfected transiently to express the TIE receptor, they failed to respond in a phosphorylation assay. Thus the N-domain does contain an essential factor for receptor activation although, as disclosed infra, the ability of chimeric molecule 2N2C1F to activate the receptor shows that even the N-domain of an inactive ligand can fill that role.

The differences in behavior between the myc-tagged F-domain truncation and the Fc-tagged F-domain truncation described previously suggested that the TIE ligands can only bind in dimeric or higher multimeric forms. Indeed, non-reducing SDS-PAGE showed that the TIE ligands exist naturally in dimeric, trimeric, and multimeric forms. That the FLAG-1C1F and FLAG-2C2F truncations can bind to the TIE-2 receptor without dimerization by a synthetic tag (such as Fc), whereas the F truncations cannot, suggests that the C-region is at least partly responsible for the aggregation of the F-domains.

23.3. Swapping Constructs (chimeras)

Applicants had noted that the level of production of TL1 in COS7 cells was approximately tenfold lower than production of TL2. Therefore, chimeras of TL1 and TL2 were constructed in an attempt to explain this difference and also to further characterize the agonist activity of TL1 as compared to the antagonist activity of TL2.

Four chimeras were constructed in which either the N-terminal domain or the fibrinogen domain was exchanged between TL1 and TL2 and were designated using the terminology described previously such that, for example, 1N1C2F refers to a chimera having the N-terminal and coiled-coil domains of TL1, together with the fibrinogen-like domain from TL2.

Figure 25A:
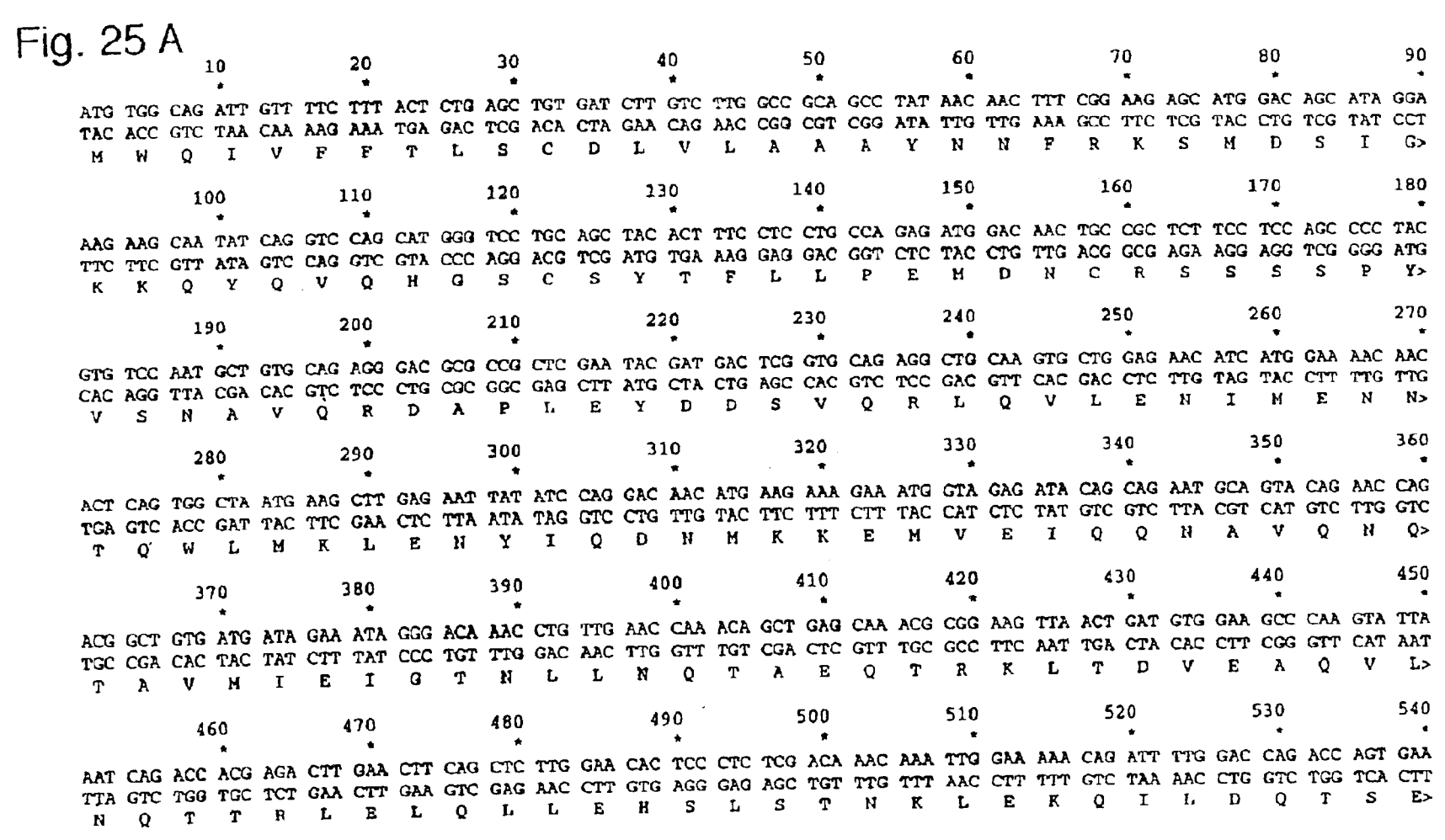
Figure 26A:
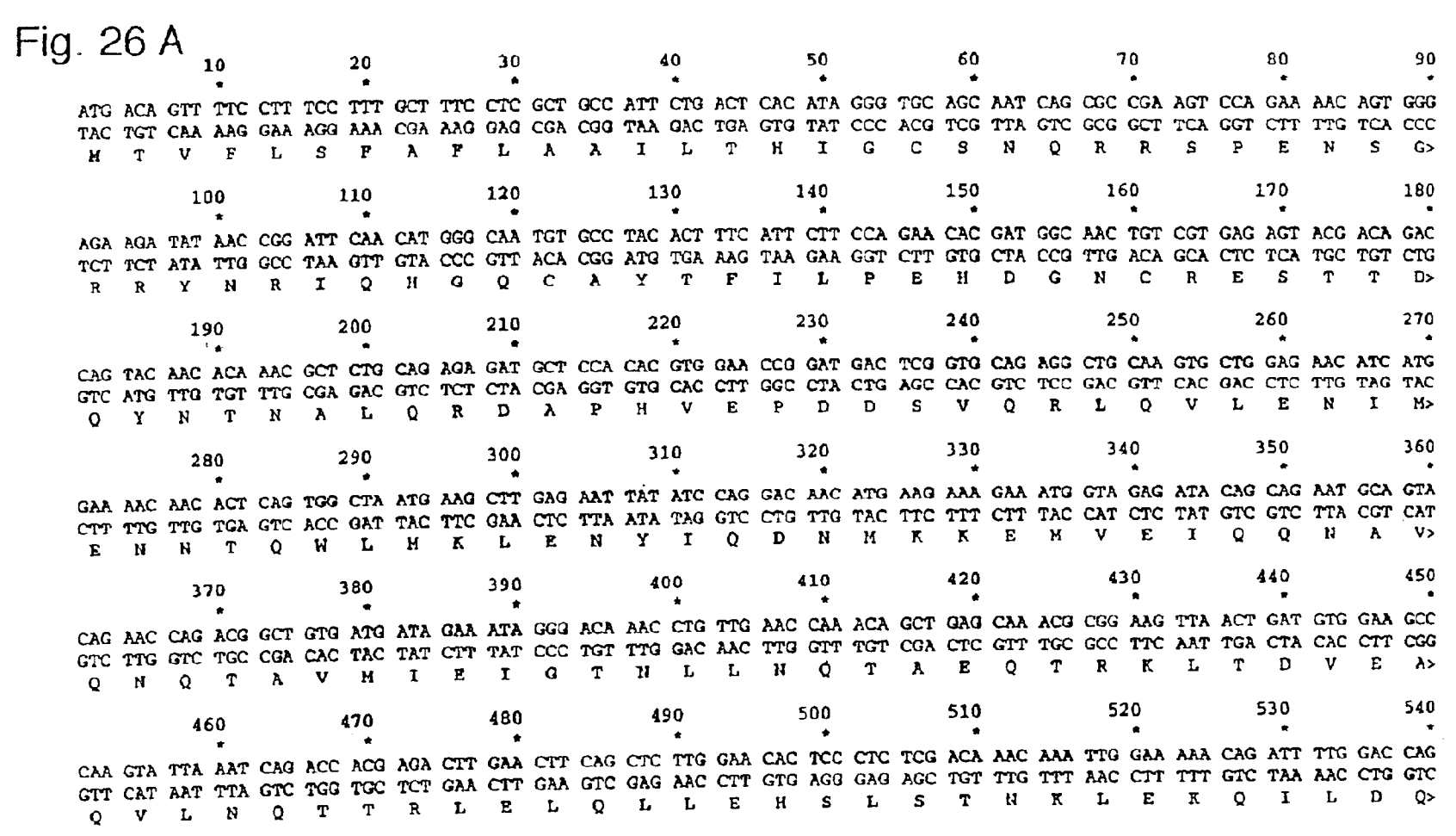
Figure 26C:
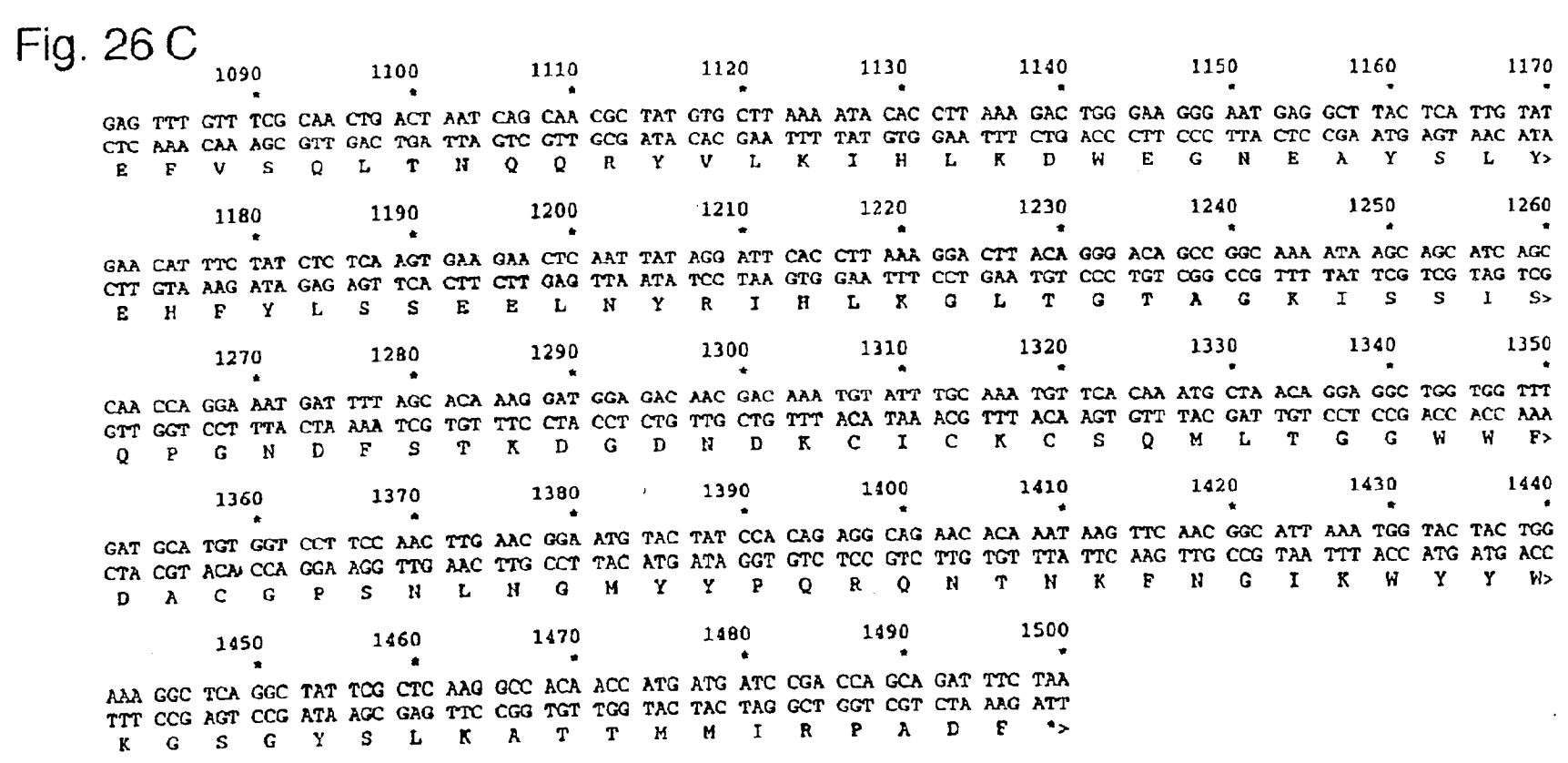

The four chimeras were constructed as follows:
chimera 1—1N1C2F
chimera 2—2N2C1F chimera 3—1N2C2F chimera 4—2N1C1F The nucleotide and amino acid sequences of chimeras 1–4 are shown in FIGS. 24A–24C (SEQ ID NO: 19 and SEQ ID NO: 20), FIGS. 25A–25C (SEQ ID NO: 21 and SEQ ID NO: 22), FIGS. 26A–26C (SEQ ID NO: 23 and SEQ ID NO:24), and FIGS. 27A–27C (SEQ ID NO: 25 and SEQ ID NO: 26) respectively.

Each chimera was inserted into a separate expression vector pJFE14. The chimeras were then transfected into COS7 cells, along with the empty pJFE14 vector, native TL1, and native TL2 as controls, and the culture supernatants were collected.

In order to determine how the swapping affected the level of expression of the ligands, a 1:5 dilution and a 1:50 dilution of the COS7 supernatants were dot-blotted onto nitrocellulose. Three ligands that contained the TL1 N-domain (i.e. native TL1, 1N2C2F and 1N1C2F) were then probed with a rabbit antibody specific to the N-terminus of TL1. Three ligands containing the TL2 N-domain, (i.e. native TL2, 2N1C1F and 2N2C1F) were probed with a rabbit antibody specific for the N-terminus of TL2. The results demonstrated that the COS7 cells were expressing any molecule containing the N-domain of TL2 at roughly ten times the level of any molecule containing the TL1 N-domain, regardless of the makeup of the rest of the protein. The conclusion was that the N-domain must principally control the level of expression of the ligand.

The next question addressed was the chimeras' ability or inability to activate the TIE-2 receptor. EAhy926 cells were challenged with the four chimeras, as well as TL1 as a positive control for phosphorylation and TL2 or an empty pJFE14-transfected COS7 cell supernatant as negative controls for phosphorylation. The cells were lysed, and the TIE-2 receptor was immunoprecipitated out of the cell lysate and run on an SDS-PAGE. The samples were Western blotted and probed with an anti-phosphotyrosine antibody to detect any receptors that had been phosphorylated. Surprisingly, only the constructs containing the TL1 fibrinogen-like domain (2N1C1F and 2N2C1F) could phosphorylate the TIE-2 receptor. Thus, although the N-terminal region of TL1 is essential for activation, it can be replaced by the N-terminal region of TL2, i.e., the information that determines whether the ligand is an agonist or an antagonist is actually contained in the fibrinogen-like domain. Thus it was determined that the F-domain, in addition to binding the TIE-2 receptor, is responsible for the phosphorylation activity of TL1. Further, when TL2, an otherwise inactive molecule, was altered by replacing its F-domain with the TL1 F-domain, the altered TL2 acted as an agonist.

The 2N1C1F construct was somewhat more potent, however. The signal caused by chimera 2N1C1F appeared slightly stronger than that of chimera 2N2C1F, leading to speculation that the C-domain of TL1, though not crucial for phosphorylation, might enhance the potency of TL1. However, since the samples used for the phosphorylation assay were not normalized in terms of the concentration of ligand, it was possible that a stronger phosphorylation signal only indicated the presence of more ligand. The phosphorylation assay was therefore repeated with varying amounts of ligand to determine whether the active chimeras displayed different potencies. The concentration of ligand in the COS7 supernatants of ligand transfections was determined through BIAcore biosenser technology according to methods previously described (Stitt, T. N., et al. (1995) Cell 80: 661–670). BIAcore measured the binding activity of a supernatant to the TIE-2 receptor in arbitrary units called resonance units (RU). Fairly good correlation between RU's and ligand concentration has been generally observed, with 400 RU of activity corresponding to about 1 μg of protein per mL of supernatant. Samples were diluted to concentrations of 100 RU, 20 RU, and 5 RU each and the phosphorylation assay was repeated. The results demonstrated that chimera 2N2C1F was clearly more potent than either the native TL1 or chimera 1N1C2F at the same concentrations.

Another interesting aspect of these exchange constructs is in their levels of expression. Each of the four chimeras was tested for its level of production in COS cells, its ability to bind to TIE2, and its ability to phosphorylate TIE2. The results of these experiments showed that chimeras 1 and 3 were produced at levels comparable to TL1, whereas chimeras 2 and 4 were produced at levels comparable to TL2. Thus a high level of protein production was correlated with the TL2 N-terminal domain. Additionally, when tested on endothelial EAhy926 cells, chimeras 2 and 4 were active, whereas 1 and 3 were not. Thus activity (phosphorylation of the receptor) correlates with the TL1 fibrinogen-like domain. Chimeras 2 and 4 therefore each had the desirable properties of high production levels as well as agonist activity.

23.4. Proteolytic resistant constructs—Based on the observation that a large fraction of TL1 preparations was often proteolytically cleaved near the N-terminus, it was proposed that an arginine residue located at position 49 of the mature protein (see FIG. 17 [SEQ ID NO: 7 and SEQ ID NO: 8]) was a candidate cleavage site that might be involved in the regulation of the protein's activity in vixo, and that replacing the arginine with a serine (R49—>S) might increase the stability of the protein without necessarily affecting its activity. Such a mutant of TL1 was constructed and was found to be about as active as the native TL1 but did not exhibit resistance to proteolytic cleavage.

23.5. Combination mutants—The most potent of the chimeric constructs, 2N1C1F, was additionally altered so that the cysteine encoded by nucleotides 784–786 as shown in FIGS. 27A–27C (SEQ ID NO: 25 and SEQ ID NO: 26) was converted to a serine. This molecule (denoted 2N1C1F (C246S)) was expressed well, potently activated the receptor, was resistant to proteolytic cleavage and was primarily dimeric, rather than higher-order multimeric. Thus the 2N domain appeared to confer protease resistance on the molecule. Finally, this molecule was further altered to eliminate the potentially protease sensitive site encoded by nucleotides 199–201 as shown in FIGS. 27A–27C (SEQ ID NO: 25 and SEQ ID NO: 26), to give a molecule (denoted 2N1C1F (R51->S,C246->S)) which was expected to be activating, well expressed, dimeric, and protease resistant.

Table 1 summarizes the modified TIE-2 ligand constructs that were made and characterizes each of them in terms of ability to bind the TIE-2 receptor, ability to activate the TIE-2 receptor, the type of structure formed (monomer, dimer, etc.) and their relative production levels. Unmodified TL1 (plain) and TL2 (striped) are shown with the three domains as boxes. Thus striped boxes indicate domains from TL2. The cysteine located at position 245 of the mature TL1 protein is indicated by a "C." An "X" through the "C" indicates that that cysteine residue was substituted for by another amino acid as in, for example, the TL1 CYS-mutant. Similarly, an "X" through the "R" in the last construct indicates the substitution for an Arg residue at position 49 of the mature TL1 protein. The "C." is present in one modified TL2 construct showing the TL2 CYS+ mutant. Constructs having Fc tails or flag tagging are also indicated.

Based upon the teachings herein, one of skill in the art can readily see that further constructs may be made in order to create additional modified and chimeric TIE-2 ligands which have altered properties. For example, one may create a construct comprised of the N-terminal domain of TL2 and the F-domain of TL1 fused with the Fc section of human antibody IgG1. This construct would be expected to bind and activate the TIE-2 receptor. Similarly, other constructs may be created using the teachings herein and are therefore considered to be within the scope of this invention.

23.6. Materials and Methods

Construction of Chimeras

Swapping constructs were inserted into a pJFE14 vector in which the XbaI site was changed to an AscI site. This vector was then digested with AscI and NotI yielding an AscI-NotI backbone. DNA fragments for the chimeras were generated by PCR using appropriate oligonucleotides.

The FLAG-1C1F and FLAG-2C2F inserts were subcloned into a pMT21 vector backbone that had been digested with EcoRI and NotI. The "CF" truncations were obtained through PCR, and the FLAG tag and a preceding trypsin signalling sequence were constructed by annealing synthetic oligonucleotides.

Transfections

All constructs were transfected transiently into COS7 cells using either DEAE-Dextran or LipofectAMINE according to standard protocols. Cell cultures were harvested 3 days after the transfection and spun down at 1000 rpm for 1 minute, and the supernatants were transferred to fresh tubes and stored at −20° C.

Staining of FLAG-1C1F-Transfected and FLAG-2C2F-Transfected Cells 6-well dishes of COS7 cells were transfected transiently with the TIE-2 receptor. The COS7 supernatant from various ligand tansfections was incubated on the cells for 30 minutes, followed by two washes with Phosphate Buffered Saline (PBS) without magnesium or calcium. The cells were fixed in −20° C. methanol for 3 minutes, washed once with PBS, and incubated with anti-FLAG M2 antibody (IBI;1:3000 dilution) in PBS/10% Bovine Calf Serum (BCS) for 30 minutes. The cells were washed once with PBS and incubated with goat anti-mouse IgG Alkaline Phosphatase (AP) conjugated antibody (Promega;1:1000) in PBS/10% BCS. The cells were washed twice with PBS and incubated with the phosphate substrate, BCIP/NBT, with 1 mM levamisole.

Phosphorylation Assays

Dilution of COS7 supernatants for the dose response study was done in the supernatants of COS7 cells transfected with the empty vector pJFE14. EA cells that naturally express the TIE-2 receptor were starved for >2 hours in serum-free medium, followed by challenge with the appropriate COS7 supernatant for 10 minutes at 37° C. in an atmosphere of 5% CO2. The cells were then rinsed in ice-cold PBS and lysed with 1% NP40 lysis buffer containing protease inhibitors (10 μg/ml leupeptin, 10 μg/ml aprotinin, 1 mM PMSF) followed by immunoprecipitation with an antibody specific for the TIE-2 receptor. Samples were then subjected to immunoblot analysis, using anti pTyr antibodies.

Dot Blots

Samples were applied to a nitrocellulose membrane, which was blocked and probed with the appropriate antibodies.

TABLE 1

MUTATION ANALYSIS OF TIE LIGANDS

| | N | COILED-COIL | FIBRINOGEN-LIKE | TIE2 Binding | TIE2 Activation | Multimeric Structure | Production Levels |
|---|---|---|---|---|---|---|---|
| TL1 | | c | | + | + | HIGHER ORDER | LOW |
| TL2 | | ▨ | ▨ | + | − | DIMER | HIGH |
| | | | X | + | + | DIMER | LOW |
| | | ▨ | ▨ | + | − | HIGHER ORDER | HIGH |
| | | c | | − | N.D. | N.D. | LOW |
| | | ▨ | | − | N.D. | N.D. | HIGH |
| | | | | − | − | MONOMER | HIGH |
| | | | ▨ | − | − | MONOMER | HIGH |
| | | | Fc | + | − | DIMER | HIGH |
| | | ▨ | Fc | + | − | DIMER | HIGH |
| | | c | Fc | + | + | HIGHER ORDER | LOW |

TABLE 1-continued

MUTATION ANALYSIS OF TIE LIGANDS

| N | COILED-COIL | FIBRINOGEN-LIKE | TIE2 Binding | TIE2 Activation | Multimeric Structure | Production Levels |
|---|---|---|---|---|---|---|
| | [diagram with Fc] | | + | − | HIGHER ORDER | LOW |
| flag- | [diagram c] | | + | + | N.D. | LOW |
| flag- | [diagram] | | + | − | N.D. | HIGH |
| | [diagram c] | | + | − | N.D. | HIGH |
| | | [diagram] | + | − | N.D. | HIGH |
| | [diagram c] | | + | − | N.D. | LOW |
| | [diagram] | | + | + | N.D. | HIGH* |
| | [diagram] | | + | − | N.D. | LOW |
| | [diagram c] | | + | +** | N.D. | HIGH |
| | [diagram X] | | + | +** | DIMER | HIGH |
| | [diagram X c] | | + | + | N.D. | LOW |

*HIGHEST PRODUCTION OF RU
**MOST POTENTLY ACTIVATING
N.D. = NOT DETERMINED

Deposits

The following have been deposited with the American Type Culture Collection, 12301 Parklawn Drive, Rockville, Md. 20852 in accordance with the Budapest Treaty. A plasmid clone encoding a TIE-2 ligand was deposited with the ATCC on Oct. 7, 1994 and designated as "pJFE14 encoding TIE-2 ligand" under ATCC Accession No. 75910. Recombinant *Autographa californica* baculovirus encoding TIE-2 receptorbody was deposited with the ATCC on Oct. 7, 1994 and designated as "vTIE-2 receptorbody" under ATCC Accession No. VR2484. A lambda phage vector containing human tie-2 ligand DNA was deposited with the ATCC on Oct. 26, 1994 and designated as "λgt10 encoding htie-2 ligand 1" under ATCC Accession No. 75928. A plasmid clone encoding a second TIE-2 ligand was deposited with the ATCC on Dec. 9, 1994 and designated as "pBluescript KS encoding human TIE 2 ligand 2" under ATCC Accession No. 75963. *E. coli* strain DH10B containing plasmid pBe-LoBac11 with a human TL-4 gene insert encoding human TIE ligand-4 was deposited with the ATCC on Jul. 2, 1996 and designated as "hTL-4" under ATCC Accession No. 98095.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. An isolated nucleic acid molecule encoding a fusion protein, wherein said fusion protein comprises a modified TIE-2 ligand 2 protein and human immunoglobulin gamma-1 constant region (IgG1 Fc), wherein TIE-2 ligand 2 comprises an N-terminal domain, a coiled-coil domain, and C-terminal fibrinogen-like domain, and the modified TIE-2 ligand protein has the N-terminal and coiled-coil domains deleted and the fibrinogen-like domain comprising amino acids 281–496 of SEQ ID NO: 6.

2. A vector comprising the nucleic acid molecule of claim 1.

3. The vector of claim 2, operatively linked to an expression control sequence capable of directing its expression in a host cell.

4. The vector of claim 3, which is a plasmid.

5. An isolated host-vector system for the production of a modified TIE-2 ligand 2, comprising the vector of claim 2 in a host cell.

6. The isolated host-vector system of claim 5, wherein the host cell is a bacterial, yeast, insect, or mammalian cell.

7. A method for producing a modified TIE-2 ligand 2 protein, comprising growing the isolated host-vector system of claim 6 under conditions permitting production of a modified TIE2-ligand 2 protein, and recovering the polypeptide so produced.

* * * * *

SEQUENCE LISTING

```
<160> NUMBER OF SEQ ID NOS: 30

<210> SEQ ID NO 1
<211> LENGTH: 2149
<212> TYPE: DNA
<213> ORGANISM: Homo sapiens
<220> FEATURE:
<221> NAME/KEY: CDS
```

-continued

<222> LOCATION: (310)..(1803)
<223> OTHER INFORMATION:

<400> SEQUENCE: 1

```
cagctgactc aggcaggctc catgctgaac ggtcacacag agaggaaaca ataaatctca      60
gctactatgc aataaatatc tcaagtttta acgaagaaaa acatcattgc agtgaaataa     120
aaaattttaa aatttagaa caaagctaac aaatggctag ttttctatga ttcttcttca     180
aacgctttct ttgaggggga aagagtcaaa caaacaagca gttttacctg aaataaagaa     240
ctagttttag aggtcagaag aaaggagcaa gttttgcgag aggcacggaa ggagtgtgct     300 ggcagtaca atg aca gtt ttc ctt tcc ttt gct ttc ctc gct gcc att ctg     351
         Met Thr Val Phe Leu Ser Phe Ala Phe Leu Ala Ala Ile Leu
           1               5                  10 act cac ata ggg tgc agc aat cag cgc cga agt cca gaa aac agt ggg       399
Thr His Ile Gly Cys Ser Asn Gln Arg Arg Ser Pro Glu Asn Ser Gly
 15                  20                  25                  30 aga aga tat aac cgg att caa cat ggg caa tgt gcc tac act ttc att       447
Arg Arg Tyr Asn Arg Ile Gln His Gly Gln Cys Ala Tyr Thr Phe Ile
                 35                  40                  45 ctt cca gaa cac gat ggc aac tgt cgt gag agt acg aca gac cag tac       495
Leu Pro Glu His Asp Gly Asn Cys Arg Glu Ser Thr Thr Asp Gln Tyr
         50                  55                  60 aac aca aac gct ctg cag aga gat gct cca cac gtg gaa ccg gat ttc       543
Asn Thr Asn Ala Leu Gln Arg Asp Ala Pro His Val Glu Pro Asp Phe
 65                  70                  75 tct tcc cag aaa ctt caa cat ctg gaa cat gtg atg gaa aat tat act       591
Ser Ser Gln Lys Leu Gln His Leu Glu His Val Met Glu Asn Tyr Thr
             80                  85                  90 cag tgg ctg caa aaa ctt gag aat tac att gtg gaa aac atg aag tcg       639
Gln Trp Leu Gln Lys Leu Glu Asn Tyr Ile Val Glu Asn Met Lys Ser
 95                 100                 105                 110 gag atg gcc cag ata cag cag aat gca gtt cag aac cac acg gct acc       687
Glu Met Ala Gln Ile Gln Gln Asn Ala Val Gln Asn His Thr Ala Thr
                115                 120                 125 atg ctg gag ata gga acc agc ctc ctc tct cag act gca gag cag acc       735
Met Leu Glu Ile Gly Thr Ser Leu Leu Ser Gln Thr Ala Glu Gln Thr
        130                 135                 140 aga aag ctg aca gat gtt gag acc cag gta cta aat caa act tct cga       783
Arg Lys Leu Thr Asp Val Glu Thr Gln Val Leu Asn Gln Thr Ser Arg
            145                 150                 155 ctt gag ata cag ctg ctg gag aat tca tta tcc acc tac aag cta gag       831
Leu Glu Ile Gln Leu Leu Glu Asn Ser Leu Ser Thr Tyr Lys Leu Glu
        160                 165                 170 aag caa ctt ctt caa cag aca aat gaa atc ttg aag atc cat gaa aaa       879
Lys Gln Leu Leu Gln Gln Thr Asn Glu Ile Leu Lys Ile His Glu Lys
175                 180                 185                 190 aac agt tta tta gaa cat aaa atc tta gaa atg gaa gga aaa cac aag       927
Asn Ser Leu Leu Glu His Lys Ile Leu Glu Met Glu Gly Lys His Lys
                195                 200                 205 gaa gag ttg gac acc tta aag gaa gag aaa gag aac ctt caa ggc ttg       975
Glu Glu Leu Asp Thr Leu Lys Glu Glu Lys Glu Asn Leu Gln Gly Leu
        210                 215                 220 gtt act cgt caa aca tat ata atc cag gag ctg gaa aag caa tta aac      1023
Val Thr Arg Gln Thr Tyr Ile Ile Gln Glu Leu Glu Lys Gln Leu Asn
            225                 230                 235 aga gct acc acc aac aac agt gtc ctt cag aag cag caa ctg gag ctg      1071
Arg Ala Thr Thr Asn Asn Ser Val Leu Gln Lys Gln Gln Leu Glu Leu
240                 245                 250
```

-continued

```
atg gac aca gtc cac aac ctt gtc aat ctt tgc act aaa gaa ggt gtt     1119
Met Asp Thr Val His Asn Leu Val Asn Leu Cys Thr Lys Glu Gly Val
255                 260                 265                 270 tta cta aag gga gga aaa aga gag gaa gag aaa cca ttt aga gac tgt     1167
Leu Leu Lys Gly Gly Lys Arg Glu Glu Glu Lys Pro Phe Arg Asp Cys
            275                 280                 285 gca gat gta tat caa gct ggt ttt aat aaa agt gga atc tac act att     1215
Ala Asp Val Tyr Gln Ala Gly Phe Asn Lys Ser Gly Ile Tyr Thr Ile
        290                 295                 300 tat att aat aat atg cca gaa ccc aaa aag gtg ttt tgc aat atg gat     1263
Tyr Ile Asn Asn Met Pro Glu Pro Lys Lys Val Phe Cys Asn Met Asp
    305                 310                 315 gtc aat ggg gga ggt tgg act gta ata caa cat cgt gaa gat gga agt     1311
Val Asn Gly Gly Gly Trp Thr Val Ile Gln His Arg Glu Asp Gly Ser
320                 325                 330 cta gat ttc caa aga ggc tgg aag gaa tat aaa atg ggt ttt gga aat     1359
Leu Asp Phe Gln Arg Gly Trp Lys Glu Tyr Lys Met Gly Phe Gly Asn
335                 340                 345                 350 ccc tcc ggt gaa tat tgg ctg ggg aat gag ttt att ttt gcc att acc     1407
Pro Ser Gly Glu Tyr Trp Leu Gly Asn Glu Phe Ile Phe Ala Ile Thr
            355                 360                 365 agt cag agg cag tac atg cta aga att gag tta atg gac tgg gaa ggg     1455
Ser Gln Arg Gln Tyr Met Leu Arg Ile Glu Leu Met Asp Trp Glu Gly
        370                 375                 380 aac cga gcc tat tca cag tat gac aga ttc cac ata gga aat gaa aag     1503
Asn Arg Ala Tyr Ser Gln Tyr Asp Arg Phe His Ile Gly Asn Glu Lys
    385                 390                 395 caa aac tat agg ttg tat tta aaa ggt cac act ggg aca gca gga aaa     1551
Gln Asn Tyr Arg Leu Tyr Leu Lys Gly His Thr Gly Thr Ala Gly Lys
400                 405                 410 cag agc agc ctg atc tta cac ggt gct gat ttc agc act aaa gat gct     1599
Gln Ser Ser Leu Ile Leu His Gly Ala Asp Phe Ser Thr Lys Asp Ala
415                 420                 425                 430 gat aat gac aac tgt atg tgc aaa tgt gcc ctc atg tta aca gga gga     1647
Asp Asn Asp Asn Cys Met Cys Lys Cys Ala Leu Met Leu Thr Gly Gly
            435                 440                 445 tgg tgg ttt gat gct tgt ggc ccc tcc aat cta aat gga atg ttc tat     1695
Trp Trp Phe Asp Ala Cys Gly Pro Ser Asn Leu Asn Gly Met Phe Tyr
        450                 455                 460 act gcg gga caa aac cat gga aaa ctg aat ggg ata aag tgg cac tac     1743
Thr Ala Gly Gln Asn His Gly Lys Leu Asn Gly Ile Lys Trp His Tyr
    465                 470                 475 ttc aaa ggg ccc agt tac tcc tta cgt tcc aca act atg atg att cga     1791
Phe Lys Gly Pro Ser Tyr Ser Leu Arg Ser Thr Thr Met Met Ile Arg
480                 485                 490 cct tta gat ttt tgaaagcgca atgtcagaag cgattatgaa agcaacaaag        1843
Pro Leu Asp Phe
495 aaatccggag aagctgccag gtgagaaact gtttgaaaac ttcagaagca acaatattg    1903 tctcccttcc agcaataagt ggtagttatg tgaagtcacc aaggttcttg accgtgaatc   1963 tggagccgtt tgagttcaca agagtctcta cttggggtga cagtgctcac gtggctcgac   2023 tatagaaaac tccactgact gtcgggcttt aaaaagggaa gaaactgctg agcttgctgt   2083 gcttcaaact actactggac cttatttggg aactatggta gccagatgat aaatatggtt   2143 aatttc                                                              2149
```

<210> SEQ ID NO 2
<211> LENGTH: 498

<212> TYPE: PRT
<213> ORGANISM: Homo sapiens

<400> SEQUENCE: 2

```
Met Thr Val Phe Leu Ser Phe Ala Phe Leu Ala Ala Ile Leu Thr His
 1               5                  10                  15

Ile Gly Cys Ser Asn Gln Arg Arg Ser Pro Glu Asn Ser Gly Arg Arg
                20                  25                  30

Tyr Asn Arg Ile Gln His Gly Gln Cys Ala Tyr Thr Phe Ile Leu Pro
            35                  40                  45

Glu His Asp Gly Asn Cys Arg Glu Ser Thr Thr Asp Gln Tyr Asn Thr
        50                  55                  60

Asn Ala Leu Gln Arg Asp Ala Pro His Val Glu Pro Asp Phe Ser Ser
65                  70                  75                  80

Gln Lys Leu Gln His Leu Glu His Val Met Glu Asn Tyr Thr Gln Trp
                85                  90                  95

Leu Gln Lys Leu Glu Asn Tyr Ile Val Glu Asn Met Lys Ser Glu Met
            100                 105                 110

Ala Gln Ile Gln Gln Asn Ala Val Gln Asn His Thr Ala Thr Met Leu
        115                 120                 125

Glu Ile Gly Thr Ser Leu Leu Ser Gln Thr Ala Glu Gln Thr Arg Lys
    130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
                165                 170                 175

Leu Leu Gln Gln Thr Asn Glu Ile Leu Lys Ile His Glu Lys Asn Ser
            180                 185                 190

Leu Leu Glu His Lys Ile Leu Glu Met Glu Gly Lys His Lys Glu Glu
        195                 200                 205

Leu Asp Thr Leu Lys Glu Glu Lys Glu Asn Leu Gln Gly Leu Val Thr
    210                 215                 220

Arg Gln Thr Tyr Ile Ile Gln Glu Leu Glu Lys Gln Leu Asn Arg Ala
225                 230                 235                 240

Thr Thr Asn Asn Ser Val Leu Gln Lys Gln Gln Leu Glu Leu Met Asp
                245                 250                 255

Thr Val His Asn Leu Val Asn Leu Cys Thr Lys Glu Gly Val Leu Leu
            260                 265                 270

Lys Gly Gly Lys Arg Glu Glu Lys Pro Phe Arg Asp Cys Ala Asp
        275                 280                 285

Val Tyr Gln Ala Gly Phe Asn Lys Ser Gly Ile Tyr Thr Ile Tyr Ile
    290                 295                 300

Asn Asn Met Pro Glu Pro Lys Lys Val Phe Cys Asn Met Asp Val Asn
305                 310                 315                 320

Gly Gly Gly Trp Thr Val Ile Gln His Arg Glu Asp Gly Ser Leu Asp
                325                 330                 335

Phe Gln Arg Gly Trp Lys Glu Tyr Lys Met Gly Phe Gly Asn Pro Ser
            340                 345                 350

Gly Glu Tyr Trp Leu Gly Asn Glu Phe Ile Phe Ala Ile Thr Ser Gln
        355                 360                 365

Arg Gln Tyr Met Leu Arg Ile Glu Leu Met Asp Trp Glu Gly Asn Arg
    370                 375                 380

Ala Tyr Ser Gln Tyr Asp Arg Phe His Ile Gly Asn Glu Lys Gln Asn
385                 390                 395                 400
```

```
Tyr Arg Leu Tyr Leu Lys Gly His Thr Gly Thr Ala Gly Lys Gln Ser
            405                 410                 415

Ser Leu Ile Leu His Gly Ala Asp Phe Ser Thr Lys Asp Ala Asp Asn
            420                 425                 430

Asp Asn Cys Met Cys Lys Cys Ala Leu Met Leu Thr Gly Gly Trp Trp
            435                 440                 445

Phe Asp Ala Cys Gly Pro Ser Asn Leu Asn Gly Met Phe Tyr Thr Ala
    450                 455                 460

Gly Gln Asn His Gly Lys Leu Asn Gly Ile Lys Trp His Tyr Phe Lys
465                 470                 475                 480

Gly Pro Ser Tyr Ser Leu Arg Ser Thr Thr Met Met Ile Arg Pro Leu
                485                 490                 495

Asp Phe

<210> SEQ ID NO 3
<211> LENGTH: 2146
<212> TYPE: DNA
<213> ORGANISM: Homo sapiens
<220> FEATURE:
<221> NAME/KEY: CDS
<222> LOCATION: (310)..(1803)
<223> OTHER INFORMATION:

<400> SEQUENCE: 3
cagctgactc aggcaggctc catgctgaac ggtcacacag agaggaaaca ataaatctca      60
gctactatgc aataaatatc tcaagtttta acgaagaaaa acatcattgc agtgaaataa     120
aaaattttaa aattttagaa caaagctaac aaatggctag ttttctatga ttcttcttca     180
aacgctttct tgaggggga aagagtcaaa caaacaagca gttttacctg aaataaagaa      240
ctagttttag aggtcagaag aaaggagcaa gttttgcgag aggcacggaa ggagtgtgct     300 ggcagtaca atg aca gtt ttc ctt tcc ttt gct ttc ctc gct gcc att ctg    351
          Met Thr Val Phe Leu Ser Phe Ala Phe Leu Ala Ala Ile Leu
            1               5                  10 act cac ata ggg tgc agc aat cag cgc cga agt cca gaa aac agt ggg       399
Thr His Ile Gly Cys Ser Asn Gln Arg Arg Ser Pro Glu Asn Ser Gly
 15                  20                  25                  30 aga aga tat aac cgg att caa cat ggg caa tgt gcc tac act ttc att       447
Arg Arg Tyr Asn Arg Ile Gln His Gly Gln Cys Ala Tyr Thr Phe Ile
                 35                  40                  45 ctt cca gaa cac gat ggc aac tgt cgt gag agt acg aca gac cag tac       495
Leu Pro Glu His Asp Gly Asn Cys Arg Glu Ser Thr Thr Asp Gln Tyr
             50                  55                  60 aac aca aac gct ctg cag aga gat gct cca cac gtg gaa ccg gat ttc       543
Asn Thr Asn Ala Leu Gln Arg Asp Ala Pro His Val Glu Pro Asp Phe
         65                  70                  75 tct tcc cag aaa ctt caa cat ctg gaa cat gtg atg gaa aat tat act       591
Ser Ser Gln Lys Leu Gln His Leu Glu His Val Met Glu Asn Tyr Thr
     80                  85                  90 cag tgg ctg caa aaa ctt gag aat tac att gtg gaa aac atg aag tcg       639
Gln Trp Leu Gln Lys Leu Glu Asn Tyr Ile Val Glu Asn Met Lys Ser
 95                 100                 105                 110 gag atg gcc cag ata cag cag aat gca gtt cag aac cac acg gct acc       687
Glu Met Ala Gln Ile Gln Gln Asn Ala Val Gln Asn His Thr Ala Thr
                115                 120                 125 atg ctg gag ata gga acc agc ctc ctc tct cag act gca gag cag acc       735
Met Leu Glu Ile Gly Thr Ser Leu Leu Ser Gln Thr Ala Glu Gln Thr
            130                 135                 140
```

-continued

| | | |
|---|---|---|
| aga aag ctg aca gat gtt gag acc cag gta cta aat caa act tct cga<br>Arg Lys Leu Thr Asp Val Glu Thr Gln Val Leu Asn Gln Thr Ser Arg<br>          145                        150                        155 | 783 |
| ctt gag ata cag ctg ctg gag aat tca tta tcc acc tac aag cta gag<br>Leu Glu Ile Gln Leu Leu Glu Asn Ser Leu Ser Thr Tyr Lys Leu Glu<br>   160                        165                     170 | 831 |
| aag caa ctt ctt caa cag aca aat gaa atc ttg aag atc cat gaa aaa<br>Lys Gln Leu Leu Gln Gln Thr Asn Glu Ile Leu Lys Ile His Glu Lys<br>175                    180                     185                    190 | 879 |
| aac agt tta tta gaa cat aaa atc tta gaa atg gaa gga aaa cac aag<br>Asn Ser Leu Leu Glu His Lys Ile Leu Glu Met Glu Gly Lys His Lys<br>                   195                     200                    205 | 927 |
| gaa gag ttg gac acc tta aag gaa gag aaa gag aac ctt caa ggc ttg<br>Glu Glu Leu Asp Thr Leu Lys Glu Glu Lys Glu Asn Leu Gln Gly Leu<br>              210                     215                    220 | 975 |
| gtt act cgt caa aca tat ata atc cag gag ctg gaa aag caa tta aac<br>Val Thr Arg Gln Thr Tyr Ile Ile Gln Glu Leu Glu Lys Gln Leu Asn<br>          225                     230                    235 | 1023 |
| aga gct acc acc aac aac agt gtc ctt cag aag cag caa ctg gag ctg<br>Arg Ala Thr Thr Asn Asn Ser Val Leu Gln Lys Gln Gln Leu Glu Leu<br>240                    245                     250 | 1071 |
| atg gac aca gtc cac aac ctt gtc aat ctt tgc act aaa gaa gtt tta<br>Met Asp Thr Val His Asn Leu Val Asn Leu Cys Thr Lys Glu Val Leu<br>255                    260                     265                    270 | 1119 |
| cta aag gga gga aaa aga gag gaa gag aaa cca ttt aga gac tgt gca<br>Leu Lys Gly Gly Lys Arg Glu Glu Glu Lys Pro Phe Arg Asp Cys Ala<br>                   275                     280                    285 | 1167 |
| gat gta tat caa gct ggt ttt aat aaa agt gga atc tac act att tat<br>Asp Val Tyr Gln Ala Gly Phe Asn Lys Ser Gly Ile Tyr Thr Ile Tyr<br>              290                     295                    300 | 1215 |
| att aat aat atg cca gaa ccc aaa aag gtg ttt tgc aat atg gat gtc<br>Ile Asn Asn Met Pro Glu Pro Lys Lys Val Phe Cys Asn Met Asp Val<br>          305                     310                    315 | 1263 |
| aat ggg gga ggt tgg act gta ata caa cat cgt gaa gat gga agt cta<br>Asn Gly Gly Gly Trp Thr Val Ile Gln His Arg Glu Asp Gly Ser Leu<br>320                    325                     330 | 1311 |
| gat ttc caa aga ggc tgg aag gaa tat aaa atg ggt ttt gga aat ccc<br>Asp Phe Gln Arg Gly Trp Lys Glu Tyr Lys Met Gly Phe Gly Asn Pro<br>335                    340                     345                    350 | 1359 |
| tcc ggt gaa tat tgg ctg ggg aat gag ttt att ttt gcc att acc agt<br>Ser Gly Glu Tyr Trp Leu Gly Asn Glu Phe Ile Phe Ala Ile Thr Ser<br>                   355                     360                    365 | 1407 |
| cag agg cag tac atg cta aga att gag tta atg gac tgg gaa ggg aac<br>Gln Arg Gln Tyr Met Leu Arg Ile Glu Leu Met Asp Trp Glu Gly Asn<br>              370                     375                    380 | 1455 |
| cga gcc tat tca cag tat gac aga ttc cac ata gga aat gaa aag caa<br>Arg Ala Tyr Ser Gln Tyr Asp Arg Phe His Ile Gly Asn Glu Lys Gln<br>          385                     390                    395 | 1503 |
| aac tat agg ttg tat tta aaa ggt cac act ggg aca gca gga aaa cag<br>Asn Tyr Arg Leu Tyr Leu Lys Gly His Thr Gly Thr Ala Gly Lys Gln<br>400                    405                     410 | 1551 |
| agc agc ctg atc tta cac ggt gct gat ttc agc act aaa gat gct gat<br>Ser Ser Leu Ile Leu His Gly Ala Asp Phe Ser Thr Lys Asp Ala Asp<br>415                    420                     425                    430 | 1599 |
| aat gac aac tgt atg tgc aaa tgt gcc ctc atg tta aca gga gga tgg<br>Asn Asp Asn Cys Met Cys Lys Cys Ala Leu Met Leu Thr Gly Gly Trp<br>                   435                     440                    445 | 1647 |
| tgg ttt gat gct tgt ggc ccc tcc aat cta aat gga atg ttc tat act<br>Trp Phe Asp Ala Cys Gly Pro Ser Asn Leu Asn Gly Met Phe Tyr Thr<br>              450                     455                    460 | 1695 |

```
gcg gga caa aac cat cga aaa ctg aat ggg ata aag tgg cac tac ttc    1743
Ala Gly Gln Asn His Arg Lys Leu Asn Gly Ile Lys Trp His Tyr Phe
            465                 470                 475 aaa ggg ccc agt tac tcc tta cgt tcc aca act atg atg att cga cct    1791
Lys Gly Pro Ser Tyr Ser Leu Arg Ser Thr Thr Met Met Ile Arg Pro
        480                 485                 490 tta gat ttt tga aagcgcaatg tcagaagcga ttatgaaagc aacaaagaaa        1843
Leu Asp Phe
495 tccggagaag ctgccaggtg agaaactgtt tgaaaacttc agaagcaaac aatattgtct  1903 cccttccacc aataagtggt agttatgtga agtcaccaag gttcttgacc gtgaatctgg  1963 agccgtttga gttcacaaga gtctctactt ggggtgacag tgctcacgtg gctcgactat  2023 agaaaactcc actgactgtc gggctttaaa aagggaagaa actgctgagc ttgctgtgct  2083 tcaaactact actggacctt attttggaac tatggtagcc agatgataaa tatggttaat  2143 ttc                                                                2146

<210> SEQ ID NO 4
<211> LENGTH: 497
<212> TYPE: PRT
<213> ORGANISM: Homo sapiens

<400> SEQUENCE: 4

Met Thr Val Phe Leu Ser Phe Ala Phe Leu Ala Ala Ile Leu Thr His
1               5                   10                  15

Ile Gly Cys Ser Asn Gln Arg Arg Ser Pro Glu Asn Ser Gly Arg Arg
            20                  25                  30

Tyr Asn Arg Ile Gln His Gly Gln Cys Ala Tyr Thr Phe Ile Leu Pro
        35                  40                  45

Glu His Asp Gly Asn Cys Arg Glu Ser Thr Thr Asp Gln Tyr Asn Thr
    50                  55                  60

Asn Ala Leu Gln Arg Asp Ala Pro His Val Glu Pro Asp Phe Ser Ser
65                  70                  75                  80

Gln Lys Leu Gln His Leu Glu His Val Met Glu Asn Tyr Thr Gln Trp
                85                  90                  95

Leu Gln Lys Leu Glu Asn Tyr Ile Val Glu Asn Met Lys Ser Glu Met
            100                 105                 110

Ala Gln Ile Gln Gln Asn Ala Val Gln Asn His Thr Ala Thr Met Leu
        115                 120                 125

Glu Ile Gly Thr Ser Leu Leu Ser Gln Thr Ala Glu Gln Thr Arg Lys
    130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
                165                 170                 175

Leu Leu Gln Gln Thr Asn Glu Ile Leu Lys Ile His Glu Lys Asn Ser
            180                 185                 190

Leu Leu Glu His Lys Ile Leu Glu Met Glu Gly Lys His Lys Glu Glu
        195                 200                 205

Leu Asp Thr Leu Lys Glu Glu Lys Glu Asn Leu Gln Gly Leu Val Thr
    210                 215                 220

Arg Gln Thr Tyr Ile Ile Gln Glu Leu Glu Lys Gln Leu Asn Arg Ala
225                 230                 235                 240

Thr Thr Asn Asn Ser Val Leu Gln Lys Gln Gln Leu Glu Leu Met Asp
```

```
                  245                 250                 255
Thr Val His Asn Leu Val Asn Leu Cys Thr Lys Glu Val Leu Lys
                260                 265                 270
Gly Gly Lys Arg Glu Glu Lys Pro Phe Arg Asp Cys Ala Asp Val
            275                 280                 285
Tyr Gln Ala Gly Phe Asn Lys Ser Gly Ile Tyr Thr Ile Tyr Ile Asn
        290                 295                 300
Asn Met Pro Glu Pro Lys Lys Val Phe Cys Asn Met Asp Val Asn Gly
305                 310                 315                 320
Gly Gly Trp Thr Val Ile Gln His Arg Glu Asp Gly Ser Leu Asp Phe
                325                 330                 335
Gln Arg Gly Trp Lys Glu Tyr Lys Met Gly Phe Gly Asn Pro Ser Gly
                340                 345                 350
Glu Tyr Trp Leu Gly Asn Glu Phe Ile Phe Ala Ile Thr Ser Gln Arg
            355                 360                 365
Gln Tyr Met Leu Arg Ile Glu Leu Met Asp Trp Glu Gly Asn Arg Ala
        370                 375                 380
Tyr Ser Gln Tyr Asp Arg Phe His Ile Gly Asn Glu Lys Gln Asn Tyr
385                 390                 395                 400
Arg Leu Tyr Leu Lys Gly His Thr Gly Thr Ala Gly Lys Gln Ser Ser
                405                 410                 415
Leu Ile Leu His Gly Ala Asp Phe Ser Thr Lys Asp Ala Asp Asn Asp
                420                 425                 430
Asn Cys Met Cys Lys Cys Ala Leu Met Leu Thr Gly Gly Trp Trp Phe
            435                 440                 445
Asp Ala Cys Gly Pro Ser Asn Leu Asn Gly Met Phe Tyr Thr Ala Gly
        450                 455                 460
Gln Asn His Arg Lys Leu Asn Gly Ile Lys Trp His Tyr Phe Lys Gly
465                 470                 475                 480
Pro Ser Tyr Ser Leu Arg Ser Thr Thr Met Met Ile Arg Pro Leu Asp
                485                 490                 495
Phe

<210> SEQ ID NO 5
<211> LENGTH: 2282
<212> TYPE: DNA
<213> ORGANISM: Homo sapiens
<220> FEATURE:
<221> NAME/KEY: CDS
<222> LOCATION: (357)..(1844)
<223> OTHER INFORMATION:

<400> SEQUENCE: 5
gaattcctgg gttggtgttt atctcctccc agccttgagg gagggaacaa cactgtagga      60
tctggggaga gaggaacaaa ggaccgtgaa agctgctctg taaaagctga cacagccctc     120
ccaagtgagc aggactgttc ttcccactgc aatctgacag tttactgcat gcctggagag     180
aacacagcag taaaaccag gtttgctact ggaaaaagag gaaagagaag actttcattg      240
acggacccag ccatggcagc gtagcagccc tgcgtttcag acggcagcag ctcgggactc     300
tggacgtgtg tttgccctca gtttgctaa gctgctggtt tattactgaa gaaaga atg      359
                                                                  Met
                                                                   1 tgg cag att gtt ttc ttt act ctg agc tgt gat ctt gtc ttg gcc gca      407
Trp Gln Ile Val Phe Phe Thr Leu Ser Cys Asp Leu Val Leu Ala Ala
         5                   10                  15
```

-continued

| | | | | | | | | | | | | | | | |
|---|---|---|---|---|---|---|---|---|---|---|---|---|---|---|---|
| gcc | tat | aac | aac | ttt | cgg | aag | agc | atg | gac | agc | ata | gga | aag | aag | caa | 455 |
| Ala | Tyr | Asn | Asn | Phe | Arg | Lys | Ser | Met | Asp | Ser | Ile | Gly | Lys | Lys | Gln | |
| | | 20 | | | | 25 | | | | 30 | | | | | | |

| tat | cag | gtc | cag | cat | ggg | tcc | tgc | agc | tac | act | ttc | ctc | ctg | cca | gag | 503 |
| Tyr | Gln | Val | Gln | His | Gly | Ser | Cys | Ser | Tyr | Thr | Phe | Leu | Leu | Pro | Glu | |
| 35 | | | | | 40 | | | | | 45 | | | | | | |

| atg | gac | aac | tgc | cgc | tct | tcc | tcc | agc | ccc | tac | gtg | tcc | aat | gct | gtg | 551 |
| Met | Asp | Asn | Cys | Arg | Ser | Ser | Ser | Ser | Pro | Tyr | Val | Ser | Asn | Ala | Val | |
| 50 | | | | | 55 | | | | | 60 | | | | | 65 | |

| cag | agg | gac | gcg | ccg | ctc | gaa | tac | gat | gac | tcg | gtg | cag | agg | ctg | caa | 599 |
| Gln | Arg | Asp | Ala | Pro | Leu | Glu | Tyr | Asp | Asp | Ser | Val | Gln | Arg | Leu | Gln | |
| | | | | 70 | | | | | 75 | | | | | 80 | | |

| gtg | ctg | gag | aac | atc | atg | gaa | aac | aac | act | cag | tgg | cta | atg | aag | ctt | 647 |
| Val | Leu | Glu | Asn | Ile | Met | Glu | Asn | Asn | Thr | Gln | Trp | Leu | Met | Lys | Leu | |
| | | | 85 | | | | | 90 | | | | | 95 | | | |

| gag | aat | tat | atc | cag | gac | aac | atg | aag | aaa | gaa | atg | gta | gag | ata | cag | 695 |
| Glu | Asn | Tyr | Ile | Gln | Asp | Asn | Met | Lys | Lys | Glu | Met | Val | Glu | Ile | Gln | |
| | | 100 | | | | | 105 | | | | | 110 | | | | |

| cag | aat | gca | gta | cag | aac | cag | acg | gct | gtg | atg | ata | gaa | ata | ggg | aca | 743 |
| Gln | Asn | Ala | Val | Gln | Asn | Gln | Thr | Ala | Val | Met | Ile | Glu | Ile | Gly | Thr | |
| | 115 | | | | | 120 | | | | | 125 | | | | | |

| aac | ctg | ttg | aac | caa | aca | gct | gag | caa | acg | cgg | aag | tta | act | gat | gtg | 791 |
| Asn | Leu | Leu | Asn | Gln | Thr | Ala | Glu | Gln | Thr | Arg | Lys | Leu | Thr | Asp | Val | |
| 130 | | | | | 135 | | | | | 140 | | | | | 145 | |

| gaa | gcc | caa | gta | tta | aat | cag | acc | acg | aga | ctt | gaa | ctt | cag | ctc | ttg | 839 |
| Glu | Ala | Gln | Val | Leu | Asn | Gln | Thr | Thr | Arg | Leu | Glu | Leu | Gln | Leu | Leu | |
| | | | | 150 | | | | | 155 | | | | | 160 | | |

| gaa | cac | tcc | ctc | tcg | aca | aac | aaa | ttg | gaa | aaa | cag | att | ttg | gac | cag | 887 |
| Glu | His | Ser | Leu | Ser | Thr | Asn | Lys | Leu | Glu | Lys | Gln | Ile | Leu | Asp | Gln | |
| | | | 165 | | | | | 170 | | | | | 175 | | | |

| acc | agt | gaa | ata | aac | aaa | ttg | caa | gat | aag | aac | agt | ttc | cta | gaa | aag | 935 |
| Thr | Ser | Glu | Ile | Asn | Lys | Leu | Gln | Asp | Lys | Asn | Ser | Phe | Leu | Glu | Lys | |
| | | 180 | | | | | 185 | | | | | 190 | | | | |

| aag | gtg | cta | gct | atg | gaa | gac | aag | cac | atc | atc | caa | cta | cag | tca | ata | 983 |
| Lys | Val | Leu | Ala | Met | Glu | Asp | Lys | His | Ile | Ile | Gln | Leu | Gln | Ser | Ile | |
| | 195 | | | | | 200 | | | | | 205 | | | | | |

| aaa | gaa | gag | aaa | gat | cag | cta | cag | gtg | tta | gta | tcc | aag | caa | aat | tcc | 1031 |
| Lys | Glu | Glu | Lys | Asp | Gln | Leu | Gln | Val | Leu | Val | Ser | Lys | Gln | Asn | Ser | |
| 210 | | | | | 215 | | | | | 220 | | | | | 225 | |

| atc | att | gaa | gaa | cta | gaa | aaa | aaa | ata | gtg | act | gcc | acg | gtg | aat | aat | 1079 |
| Ile | Ile | Glu | Glu | Leu | Glu | Lys | Lys | Ile | Val | Thr | Ala | Thr | Val | Asn | Asn | |
| | | | | 230 | | | | | 235 | | | | | 240 | | |

| tca | gtt | ctt | caa | aag | cag | caa | cat | gat | ctc | atg | gag | aca | gtt | aat | aac | 1127 |
| Ser | Val | Leu | Gln | Lys | Gln | Gln | His | Asp | Leu | Met | Glu | Thr | Val | Asn | Asn | |
| | | | 245 | | | | | 250 | | | | | 255 | | | |

| tta | ctg | act | atg | atg | tcc | aca | tca | aac | tca | gct | aag | gac | ccc | act | gtt | 1175 |
| Leu | Leu | Thr | Met | Met | Ser | Thr | Ser | Asn | Ser | Ala | Lys | Asp | Pro | Thr | Val | |
| | | 260 | | | | | 265 | | | | | 270 | | | | |

| gct | aaa | gaa | gaa | caa | atc | agc | ttc | aga | gac | tgt | gct | gaa | gta | ttc | aaa | 1223 |
| Ala | Lys | Glu | Glu | Gln | Ile | Ser | Phe | Arg | Asp | Cys | Ala | Glu | Val | Phe | Lys | |
| | 275 | | | | | 280 | | | | | 285 | | | | | |

| tca | gga | cac | acc | aca | aat | ggc | atc | tac | acg | tta | aca | ttc | cct | aat | tct | 1271 |
| Ser | Gly | His | Thr | Thr | Asn | Gly | Ile | Tyr | Thr | Leu | Thr | Phe | Pro | Asn | Ser | |
| 290 | | | | | 295 | | | | | 300 | | | | | 305 | |

| aca | gaa | gag | atc | aag | gcc | tac | tgt | gac | atg | gaa | gct | gga | gga | ggc | ggg | 1319 |
| Thr | Glu | Glu | Ile | Lys | Ala | Tyr | Cys | Asp | Met | Glu | Ala | Gly | Gly | Gly | Gly | |
| | | | | 310 | | | | | 315 | | | | | 320 | | |

| tgg | aca | att | att | cag | cga | cgt | gag | gat | ggc | agc | gtt | gat | ttt | cag | agg | 1367 |
| Trp | Thr | Ile | Ile | Gln | Arg | Arg | Glu | Asp | Gly | Ser | Val | Asp | Phe | Gln | Arg | |
| | | | 325 | | | | | 330 | | | | | 335 | | | |

```
act tgg aaa gaa tat aaa gtg gga ttt ggt aac cct tca gga gaa tat    1415
Thr Trp Lys Glu Tyr Lys Val Gly Phe Gly Asn Pro Ser Gly Glu Tyr
            340                 345                 350 tgg ctg gga aat gag ttt gtt tcg caa ctg act aat cag caa cgc tat    1463
Trp Leu Gly Asn Glu Phe Val Ser Gln Leu Thr Asn Gln Gln Arg Tyr
        355                 360                 365 gtg ctt aaa ata cac ctt aaa gac tgg gaa ggg aat gag gct tac tca    1511
Val Leu Lys Ile His Leu Lys Asp Trp Glu Gly Asn Glu Ala Tyr Ser
370                 375                 380                 385 ttg tat gaa cat ttc tat ctc tca agt gaa gaa ctc aat tat agg att    1559
Leu Tyr Glu His Phe Tyr Leu Ser Ser Glu Glu Leu Asn Tyr Arg Ile
                390                 395                 400 cac ctt aaa gga ctt aca ggg aca gcc ggc aaa ata agc agc atc agc    1607
His Leu Lys Gly Leu Thr Gly Thr Ala Gly Lys Ile Ser Ser Ile Ser
            405                 410                 415 caa cca gga aat gat ttt agc aca aag gat gga gac aac gac aaa tgt    1655
Gln Pro Gly Asn Asp Phe Ser Thr Lys Asp Gly Asp Asn Asp Lys Cys
        420                 425                 430 att tgc aaa tgt tca caa atg cta aca gga ggc tgg tgg ttt gat gca    1703
Ile Cys Lys Cys Ser Gln Met Leu Thr Gly Gly Trp Trp Phe Asp Ala
435                 440                 445 tgt ggt cct tcc aac ttg aac gga atg tac tat cca cag agg cag aac    1751
Cys Gly Pro Ser Asn Leu Asn Gly Met Tyr Tyr Pro Gln Arg Gln Asn
450                 455                 460                 465 aca aat aag ttc aac ggc att aaa tgg tac tac tgg aaa ggc tca ggc    1799
Thr Asn Lys Phe Asn Gly Ile Lys Trp Tyr Tyr Trp Lys Gly Ser Gly
                470                 475                 480 tat tcg ctc aag gcc aca acc atg atg atc cga cca gca gat ttc       1844
Tyr Ser Leu Lys Ala Thr Thr Met Met Ile Arg Pro Ala Asp Phe
            485                 490                 495 taaacatccc agtccacctg aggaactgtc tcgaactatt ttcaaagact taagcccagt   1904
gcactgaaag tcacggctgc gcactgtgtc ctcttccacc acagagggcg tgtgctcggt   1964
gctgacggga cccacatgct ccagattaga gcctgtaaac tttatcactt aaacttgcat   2024
cacttaacgg accaaagcaa gaccctaaac atccataatt gtgattagac agaacaccta   2084
tgcaaagatg aacccgaggc tgagaatcag actgacagtt tacagacgct gctgtcacaa   2144
ccaagaatgt tatgtgcaag tttatcagta aataactgga aaacagaaca cttatgttat   2204
acaatacaga tcatcttgga actgcattct tctgagcact gtttatacac tgtgtaaata   2264
cccatatgtc ctgaattc                                                 2282

<210> SEQ ID NO 6
<211> LENGTH: 496
<212> TYPE: PRT
<213> ORGANISM: Homo sapiens

<400> SEQUENCE: 6

Met Trp Gln Ile Val Phe Phe Thr Leu Ser Cys Asp Leu Val Leu Ala
1               5                   10                  15

Ala Ala Tyr Asn Asn Phe Arg Lys Ser Met Asp Ser Ile Gly Lys Lys
            20                  25                  30

Gln Tyr Gln Val Gln His Gly Ser Cys Ser Tyr Thr Phe Leu Leu Pro
        35                  40                  45

Glu Met Asp Asn Cys Arg Ser Ser Ser Ser Pro Tyr Val Ser Asn Ala
    50                  55                  60

Val Gln Arg Asp Ala Pro Leu Glu Tyr Asp Asp Ser Val Gln Arg Leu
65                  70                  75                  80
```

```
Gln Val Leu Glu Asn Ile Met Glu Asn Thr Gln Trp Leu Met Lys
                 85                  90                  95

Leu Glu Asn Tyr Ile Gln Asp Asn Met Lys Lys Glu Met Val Glu Ile
                100                 105                 110

Gln Gln Asn Ala Val Gln Asn Thr Ala Val Met Ile Glu Ile Gly
            115                 120                 125

Thr Asn Leu Leu Asn Gln Thr Ala Glu Gln Thr Arg Lys Leu Thr Asp
    130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
                180                 185                 190

Lys Lys Val Leu Ala Met Glu Asp Lys His Ile Ile Gln Leu Gln Ser
                195                 200                 205

Ile Lys Glu Glu Lys Asp Gln Leu Gln Val Leu Val Ser Lys Gln Asn
    210                 215                 220

Ser Ile Ile Glu Glu Leu Glu Lys Lys Ile Val Thr Ala Thr Val Asn
225                 230                 235                 240

Asn Ser Val Leu Gln Lys Gln Gln His Asp Leu Met Glu Thr Val Asn
                245                 250                 255

Asn Leu Leu Thr Met Met Ser Thr Ser Asn Ser Ala Lys Asp Pro Thr
                260                 265                 270

Val Ala Lys Glu Glu Gln Ile Ser Phe Arg Asp Cys Ala Glu Val Phe
                275                 280                 285

Lys Ser Gly His Thr Thr Asn Gly Ile Tyr Thr Leu Thr Phe Pro Asn
                290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
                325                 330                 335

Arg Thr Trp Lys Glu Tyr Lys Val Gly Phe Gly Asn Pro Ser Gly Glu
                340                 345                 350

Tyr Trp Leu Gly Asn Glu Phe Val Ser Gln Leu Thr Asn Gln Gln Arg
                355                 360                 365

Tyr Val Leu Lys Ile His Leu Lys Asp Trp Glu Gly Asn Glu Ala Tyr
    370                 375                 380

Ser Leu Tyr Glu His Phe Tyr Leu Ser Ser Glu Glu Leu Asn Tyr Arg
385                 390                 395                 400

Ile His Leu Lys Gly Leu Thr Gly Thr Ala Gly Lys Ile Ser Ser Ile
                405                 410                 415

Ser Gln Pro Gly Asn Asp Phe Ser Thr Lys Asp Gly Asp Asn Asp Lys
                420                 425                 430

Cys Ile Cys Lys Cys Ser Gln Met Leu Thr Gly Gly Trp Trp Phe Asp
                435                 440                 445

Ala Cys Gly Pro Ser Asn Leu Asn Gly Met Tyr Tyr Pro Gln Arg Gln
    450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
                485                 490                 495
```

```
<210> SEQ ID NO 7
<211> LENGTH: 478
<212> TYPE: PRT
<213> ORGANISM: Homo sapiens

<400> SEQUENCE: 7
```

| | | | | | | | | | | | | | | | |
|---|---|---|---|---|---|---|---|---|---|---|---|---|---|---|---|
|Asn|Gln|Arg|Arg|Ser|Pro|Glu|Asn|Ser|Gly|Arg|Arg|Tyr|Asn|Arg|Ile|
|1| | | |5| | | |10| | | | |15| | |
|Gln|His|Gly|Gln|Cys|Ala|Tyr|Thr|Phe|Ile|Leu|Pro|Glu|His|Asp|Gly|
| | | |20| | | | |25| | | | |30| | |
|Asn|Cys|Arg|Glu|Ser|Thr|Thr|Asp|Gln|Tyr|Asn|Thr|Asn|Ala|Leu|Gln|
| | |35| | | | |40| | | | |45| | | |
|Arg|Asp|Ala|Pro|His|Val|Glu|Pro|Asp|Phe|Ser|Ser|Gln|Lys|Leu|Gln|
| |50| | | | |55| | | | |60| | | | |
|His|Leu|Glu|His|Val|Met|Glu|Asn|Tyr|Thr|Gln|Trp|Leu|Gln|Lys|Leu|
|65| | | | |70| | | | |75| | | | |80|
|Glu|Asn|Tyr|Ile|Val|Glu|Asn|Met|Lys|Ser|Glu|Met|Ala|Gln|Ile|Gln|
| | | | |85| | | | |90| | | | |95| |
|Gln|Asn|Ala|Val|Gln|Asn|His|Thr|Ala|Thr|Met|Leu|Glu|Ile|Gly|Thr|
| | | |100| | | | |105| | | | |110| | |
|Ser|Leu|Leu|Ser|Gln|Thr|Ala|Glu|Gln|Thr|Arg|Lys|Leu|Thr|Asp|Val|
| | | |115| | | | |120| | | | |125| | |
|Glu|Thr|Gln|Val|Leu|Asn|Gln|Thr|Ser|Arg|Leu|Glu|Ile|Gln|Leu|Leu|
| |130| | | | |135| | | | |140| | | | |
|Glu|Asn|Ser|Leu|Ser|Thr|Tyr|Lys|Leu|Glu|Lys|Gln|Leu|Leu|Gln|Gln|
|145| | | | |150| | | | |155| | | | |160|
|Thr|Asn|Glu|Ile|Leu|Lys|Ile|His|Glu|Lys|Asn|Ser|Leu|Leu|Glu|His|
| | | | |165| | | | |170| | | | |175| |
|Lys|Ile|Leu|Glu|Met|Glu|Gly|Lys|His|Lys|Glu|Glu|Leu|Asp|Thr|Leu|
| | | |180| | | | |185| | | | |190| | |
|Lys|Glu|Glu|Lys|Glu|Asn|Leu|Gln|Gly|Leu|Val|Thr|Arg|Gln|Thr|Tyr|
| | |195| | | | |200| | | | |205| | | |
|Ile|Ile|Gln|Glu|Leu|Glu|Lys|Gln|Leu|Asn|Arg|Ala|Thr|Thr|Asn|Asn|
| |210| | | | |215| | | | |220| | | | |
|Ser|Val|Leu|Gln|Lys|Gln|Gln|Leu|Glu|Leu|Met|Asp|Thr|Val|His|Asn|
|225| | | | |230| | | | |235| | | | |240|
|Leu|Val|Asn|Leu|Cys|Thr|Lys|Glu|Gly|Val|Leu|Leu|Lys|Gly|Gly|Lys|
| | | | |245| | | | |250| | | | |255| |
|Arg|Glu|Glu|Glu|Lys|Pro|Phe|Arg|Asp|Cys|Ala|Asp|Val|Tyr|Gln|Ala|
| | | |260| | | | |265| | | | |270| | |
|Gly|Phe|Asn|Lys|Ser|Gly|Ile|Tyr|Thr|Ile|Tyr|Ile|Asn|Asn|Met|Pro|
| | | |275| | | | |280| | | | |285| | |
|Glu|Pro|Lys|Lys|Val|Phe|Cys|Asn|Met|Asp|Val|Asn|Gly|Gly|Gly|Trp|
| |290| | | | |295| | | | |300| | | | |
|Thr|Val|Ile|Gln|His|Arg|Glu|Asp|Gly|Ser|Leu|Asp|Phe|Gln|Arg|Gly|
|305| | | | |310| | | | |315| | | | |320|
|Trp|Lys|Glu|Tyr|Lys|Met|Gly|Phe|Gly|Asn|Pro|Ser|Gly|Glu|Tyr|Trp|
| | | | |325| | | | |330| | | | |335| |
|Leu|Gly|Asn|Glu|Phe|Ile|Phe|Ala|Ile|Thr|Ser|Gln|Arg|Gln|Tyr|Met|
| | | |340| | | | |345| | | | |350| | |
|Leu|Arg|Ile|Glu|Leu|Met|Asp|Trp|Glu|Gly|Asn|Arg|Ala|Tyr|Ser|Gln|
| | |355| | | | |360| | | | |365| | | |
|Tyr|Asp|Arg|Phe|His|Ile|Gly|Asn|Glu|Lys|Gln|Asn|Tyr|Arg|Leu|Tyr|
| |370| | | | |375| | | | |380| | | | |

-continued

```
Leu Lys Gly His Thr Gly Thr Ala Gly Lys Gln Ser Ser Leu Ile Leu
385                 390                 395                 400

His Gly Ala Asp Phe Ser Thr Lys Asp Ala Asp Asn Asp Asn Cys Met
                405                 410                 415

Cys Lys Cys Ala Leu Met Leu Thr Gly Gly Trp Trp Phe Asp Ala Cys
                420                 425                 430

Gly Pro Ser Asn Leu Asn Gly Met Phe Tyr Thr Ala Gly Gln Asn His
                435                 440                 445

Gly Lys Leu Asn Gly Ile Lys Trp His Tyr Phe Lys Gly Pro Ser Tyr
        450                 455                 460

Ser Leu Arg Ser Thr Thr Met Met Ile Arg Pro Leu Asp Phe
465                 470                 475

<210> SEQ ID NO 8
<211> LENGTH: 480
<212> TYPE: PRT
<213> ORGANISM: Homo sapiens

<400> SEQUENCE: 8

Ala Ala Tyr Asn Asn Phe Arg Lys Ser Met Asp Ser Ile Gly Lys Lys
1               5                   10                  15

Gln Tyr Gln Val Gln His Gly Ser Cys Ser Tyr Thr Phe Leu Leu Pro
                20                  25                  30

Glu Met Asp Asn Cys Arg Ser Ser Ser Pro Tyr Val Ser Asn Ala
            35                  40                  45

Val Gln Arg Asp Ala Pro Leu Glu Tyr Asp Asp Ser Val Gln Arg Leu
    50                  55                  60

Gln Val Leu Glu Asn Ile Met Glu Asn Asn Thr Gln Trp Leu Met Lys
65                  70                  75                  80

Leu Glu Asn Tyr Ile Gln Asp Asn Met Lys Lys Glu Met Val Glu Ile
                85                  90                  95

Gln Gln Asn Ala Val Gln Asn Gln Thr Ala Val Met Ile Glu Ile Gly
                100                 105                 110

Thr Asn Leu Leu Asn Gln Thr Ala Glu Gln Thr Arg Lys Leu Thr Asp
            115                 120                 125

Val Glu Ala Gln Val Leu Asn Gln Thr Thr Arg Leu Glu Leu Gln Leu
    130                 135                 140

Leu Glu His Ser Leu Ser Thr Asn Lys Leu Glu Lys Gln Ile Leu Asp
145                 150                 155                 160

Gln Thr Ser Glu Ile Asn Lys Leu Gln Asp Lys Asn Ser Phe Leu Glu
                165                 170                 175

Lys Lys Val Leu Ala Met Glu Asp Lys His Ile Ile Gln Leu Gln Ser
            180                 185                 190

Ile Lys Glu Glu Lys Asp Gln Leu Gln Val Leu Val Ser Lys Gln Asn
    195                 200                 205

Ser Ile Ile Glu Glu Leu Glu Lys Lys Ile Val Thr Ala Thr Val Asn
210                 215                 220

Asn Ser Val Leu Gln Lys Gln Gln His Asp Leu Met Glu Thr Val Asn
225                 230                 235                 240

Asn Leu Leu Thr Met Met Ser Thr Ser Asn Ser Ala Lys Asp Pro Thr
                245                 250                 255

Val Ala Lys Glu Glu Gln Ile Ser Phe Arg Asp Cys Ala Glu Val Phe
            260                 265                 270

Lys Ser Gly His Thr Thr Asn Gly Ile Tyr Thr Leu Thr Phe Pro Asn
```

-continued

```
                275                 280                 285
Ser Thr Glu Glu Ile Lys Ala Tyr Cys Asp Met Glu Ala Gly Gly Gly
    290                 295                 300

Gly Trp Thr Ile Ile Gln Arg Arg Glu Asp Gly Ser Val Asp Phe Gln
305                 310                 315                 320

Arg Thr Trp Lys Glu Tyr Lys Val Gly Phe Gly Asn Pro Ser Gly Glu
                325                 330                 335

Tyr Trp Leu Gly Asn Glu Phe Val Ser Gln Leu Thr Asn Gln Gln Arg
            340                 345                 350

Tyr Val Leu Lys Ile His Leu Lys Asp Trp Glu Gly Asn Glu Ala Tyr
        355                 360                 365

Ser Leu Tyr Glu His Phe Tyr Leu Ser Ser Glu Glu Leu Asn Tyr Arg
    370                 375                 380

Ile His Leu Lys Gly Leu Thr Gly Thr Ala Gly Lys Ile Ser Ser Ile
385                 390                 395                 400

Ser Gln Pro Gly Asn Asp Phe Ser Thr Lys Asp Gly Asp Asn Asp Lys
                405                 410                 415

Cys Ile Cys Lys Cys Ser Gln Met Leu Thr Gly Gly Trp Trp Phe Asp
            420                 425                 430

Ala Cys Gly Pro Ser Asn Leu Asn Gly Met Tyr Tyr Pro Gln Arg Gln
        435                 440                 445

Asn Thr Asn Lys Phe Asn Gly Ile Lys Trp Tyr Tyr Trp Lys Gly Ser
    450                 455                 460

Gly Tyr Ser Leu Lys Ala Thr Thr Met Met Ile Arg Pro Ala Asp Phe
465                 470                 475                 480

<210> SEQ ID NO 9
<211> LENGTH: 1849
<212> TYPE: DNA
<213> ORGANISM: Homo sapiens
<220> FEATURE:
<221> NAME/KEY: CDS
<222> LOCATION: (47)..(1573)
<223> OTHER INFORMATION: The fibrinogen-like domain starts at position
      929.

<400> SEQUENCE: 9
ctgtcctggt acctgacaag accacctcac caccacttgg tctcag atg ctc tgc        55
                                                  Met Leu Cys
                                                    1 cag cca gct atg cta cta gat ggc ctc ctc ctg ctg gcc acc atg gct      103
Gln Pro Ala Met Leu Leu Asp Gly Leu Leu Leu Leu Ala Thr Met Ala
  5                  10                  15 gca gcc cag cac aga ggg cca gaa gcc ggt ggg cac cgc cag att cac      151
Ala Ala Gln His Arg Gly Pro Glu Ala Gly Gly His Arg Gln Ile His
 20                  25                  30                  35 cag gtc cgg cgt ggc cag tgc agc tac acc ttt gtg gtg ccg gag cct      199
Gln Val Arg Arg Gly Gln Cys Ser Tyr Thr Phe Val Val Pro Glu Pro
                 40                  45                  50 gat atc tgc cag ctg gcg ccg aca gcg gcg cct gag gct ttg ggg ggc      247
Asp Ile Cys Gln Leu Ala Pro Thr Ala Ala Pro Glu Ala Leu Gly Gly
             55                  60                  65 tcc aat agc ctc cag agg gac ttg cct gcc tcg agg ctg cac cta aca      295
Ser Asn Ser Leu Gln Arg Asp Leu Pro Ala Ser Arg Leu His Leu Thr
         70                  75                  80 gac tgg cga gcc cag agg gcc cag cgg gcc cag cgt gtg agc cag ctg      343
Asp Trp Arg Ala Gln Arg Ala Gln Arg Ala Gln Arg Val Ser Gln Leu
     85                  90                  95
```

-continued

| | |
|---|---|
| gag aag ata cta gag aat aac act cag tgg ctg ctg aag ctg gag cag<br>Glu Lys Ile Leu Glu Asn Asn Thr Gln Trp Leu Leu Lys Leu Glu Gln<br>100             105                 110                 115 | 391 |
| tcc atc aag gtg aac ttg agg tca cac ctg gtg cag gcc cag cag gac<br>Ser Ile Lys Val Asn Leu Arg Ser His Leu Val Gln Ala Gln Gln Asp<br>                120                 125                 130 | 439 |
| aca atc cag aac cag aca act acc atg ctg gca ctg ggt gcc aac ctc<br>Thr Ile Gln Asn Gln Thr Thr Thr Met Leu Ala Leu Gly Ala Asn Leu<br>        135                 140                 145 | 487 |
| atg aac cag acc aaa gct cag acc cac aag ctg act gct gtg gag gca<br>Met Asn Gln Thr Lys Ala Gln Thr His Lys Leu Thr Ala Val Glu Ala<br>            150                 155                 160 | 535 |
| cag gtc cta aac cag aca ttg cac atg aag acc caa atg ctg gag aac<br>Gln Val Leu Asn Gln Thr Leu His Met Lys Thr Gln Met Leu Glu Asn<br>165                 170                 175 | 583 |
| tca ctg tcc acc aac aag ctg gag cgg cag atg ctg atg cag agc cga<br>Ser Leu Ser Thr Asn Lys Leu Glu Arg Gln Met Leu Met Gln Ser Arg<br>180                 185                 190                 195 | 631 |
| gag ctg cag cgg ctg cag ggt cgc aac agg gcc ctg gag acc agg ctg<br>Glu Leu Gln Arg Leu Gln Gly Arg Asn Arg Ala Leu Glu Thr Arg Leu<br>                200                 205                 210 | 679 |
| cag gca ctg gaa gca caa cat cag gcc cag ctt aac agc ctc caa gag<br>Gln Ala Leu Glu Ala Gln His Gln Ala Gln Leu Asn Ser Leu Gln Glu<br>        215                 220                 225 | 727 |
| aag agg gaa caa ctg cac agt ctc ctg ggc cat cag acc ggg acc ctg<br>Lys Arg Glu Gln Leu His Ser Leu Leu Gly His Gln Thr Gly Thr Leu<br>            230                 235                 240 | 775 |
| gct aac ctg aag cac aat ctg cac gct ctc agc agc aat tcc agc tcc<br>Ala Asn Leu Lys His Asn Leu His Ala Leu Ser Ser Asn Ser Ser Ser<br>245                 250                 255 | 823 |
| ctg cag cag cag cag cag caa ctg acg gag ttt gta cag cgc ctg gta<br>Leu Gln Gln Gln Gln Gln Gln Leu Thr Glu Phe Val Gln Arg Leu Val<br>260                 265                 270                 275 | 871 |
| cgg att gta gcc cag gac cag cat ccg gtt tcc tta aag aca cct aag<br>Arg Ile Val Ala Gln Asp Gln His Pro Val Ser Leu Lys Thr Pro Lys<br>                280                 285                 290 | 919 |
| cca gtg ttc cag gac tgt gca gag atc aag cgc tcc ggg gtt aat acc<br>Pro Val Phe Gln Asp Cys Ala Glu Ile Lys Arg Ser Gly Val Asn Thr<br>        295                 300                 305 | 967 |
| agc ggt gtc tat acc atc tat gag acc aac atg aca aag cct ctc aag<br>Ser Gly Val Tyr Thr Ile Tyr Glu Thr Asn Met Thr Lys Pro Leu Lys<br>            310                 315                 320 | 1015 |
| gtg ttc tgt gac atg gag act gat gga ggt ggc tgg acc ctc atc cag<br>Val Phe Cys Asp Met Glu Thr Asp Gly Gly Gly Trp Thr Leu Ile Gln<br>325                 330                 335 | 1063 |
| cac cgg gag gat gga agc gta aat ttc cag agg acc tgg gaa gaa tac<br>His Arg Glu Asp Gly Ser Val Asn Phe Gln Arg Thr Trp Glu Glu Tyr<br>340                 345                 350                 355 | 1111 |
| aaa gag ggt ttt ggt aat gtg gcc aga gag cac tgg ctg ggc aat gag<br>Lys Glu Gly Phe Gly Asn Val Ala Arg Glu His Trp Leu Gly Asn Glu<br>                360                 365                 370 | 1159 |
| gct gtg cac cgc ctc acc agc aga acg gcc tac ttg cta cgc gtg gaa<br>Ala Val His Arg Leu Thr Ser Arg Thr Ala Tyr Leu Leu Arg Val Glu<br>        375                 380                 385 | 1207 |
| ctg cat gac tgg gaa ggc cgc cag acc tcc atc cag tat gag aac ttc<br>Leu His Asp Trp Glu Gly Arg Gln Thr Ser Ile Gln Tyr Glu Asn Phe<br>            390                 395                 400 | 1255 |
| cag ctg ggc agc gag agg cag cgg tac agc ctc tct gtg aat gac agc<br>Gln Leu Gly Ser Glu Arg Gln Arg Tyr Ser Leu Ser Val Asn Asp Ser<br>405                 410                 415 | 1303 |

-continued

```
agc agt tca gca ggg cgc aag aac agc ctg gct cct cag ggc acc aag       1351
Ser Ser Ser Ala Gly Arg Lys Asn Ser Leu Ala Pro Gln Gly Thr Lys
420                 425                 430                 435 ttc agc acc aaa gac atg gac aat gat aac tgc atg tgt aaa tgt gct       1399
Phe Ser Thr Lys Asp Met Asp Asn Asp Asn Cys Met Cys Lys Cys Ala
                440                 445                 450 cag atg ctg tct gga ggg tgg tgg ttt gat gcc tgt ggc ctc tcc aac       1447
Gln Met Leu Ser Gly Gly Trp Trp Phe Asp Ala Cys Gly Leu Ser Asn
            455                 460                 465 ctc aat ggc atc tac tat tca gtt cat cag cac ttg cac aag atc aat       1495
Leu Asn Gly Ile Tyr Tyr Ser Val His Gln His Leu His Lys Ile Asn
        470                 475                 480 ggc atc cgc tgg cac tac ttc cga ggc ccc agc tac tca ctg cac ggc       1543
Gly Ile Arg Trp His Tyr Phe Arg Gly Pro Ser Tyr Ser Leu His Gly
    485                 490                 495 aca cgc atg atg ctg agg cca atg ggt gcc tgacacacag ccctgcagag         1593
Thr Arg Met Met Leu Arg Pro Met Gly Ala
500                 505 actgatgccg taggaggatt ctcaacccag gtgactctgt gcacgctggg ccctgcccag     1653
aaatcagtgc ccagggctca tcttgacatt ctggaacatc ggaaccagct taccttgccc    1713
ctgaattaca agaattcacc tgcctccctg ttgccctcta attgtgaaat tgctgggtgc     1773
ttgaaggcac ctgcctctgt tggaaccata ctctttcccc ctcctgctgc atgcccggga   1833
atccctgcca tgaact                                                     1849

<210> SEQ ID NO 10
<211> LENGTH: 509
<212> TYPE: PRT
<213> ORGANISM: Homo sapiens

<400> SEQUENCE: 10

Met Leu Cys Gln Pro Ala Met Leu Leu Asp Gly Leu Leu Leu Leu Ala
1               5                   10                  15

Thr Met Ala Ala Ala Gln His Arg Gly Pro Glu Ala Gly Gly His Arg
            20                  25                  30

Gln Ile His Gln Val Arg Arg Gly Gln Cys Ser Tyr Thr Phe Val Val
        35                  40                  45

Pro Glu Pro Asp Ile Cys Gln Leu Ala Pro Thr Ala Ala Pro Glu Ala
    50                  55                  60

Leu Gly Gly Ser Asn Ser Leu Gln Arg Asp Leu Pro Ala Ser Arg Leu
65                  70                  75                  80

His Leu Thr Asp Trp Arg Ala Gln Arg Ala Gln Arg Ala Gln Arg Val
                85                  90                  95

Ser Gln Leu Glu Lys Ile Leu Glu Asn Asn Thr Gln Trp Leu Leu Lys
            100                 105                 110

Leu Glu Gln Ser Ile Lys Val Asn Leu Arg Ser His Leu Val Gln Ala
        115                 120                 125

Gln Gln Asp Thr Ile Gln Asn Gln Thr Thr Thr Met Leu Ala Leu Gly
    130                 135                 140

Ala Asn Leu Met Asn Gln Thr Lys Ala Gln Thr His Lys Leu Thr Ala
145                 150                 155                 160

Val Glu Ala Gln Val Leu Asn Gln Thr Leu His Met Lys Thr Gln Met
                165                 170                 175

Leu Glu Asn Ser Leu Ser Thr Asn Lys Leu Glu Arg Gln Met Leu Met
            180                 185                 190
```

```
Gln Ser Arg Glu Leu Gln Arg Leu Gln Gly Arg Asn Arg Ala Leu Glu
            195                 200                 205

Thr Arg Leu Gln Ala Leu Glu Ala Gln His Gln Ala Gln Leu Asn Ser
        210                 215                 220

Leu Gln Glu Lys Arg Glu Gln Leu His Ser Leu Leu Gly His Gln Thr
225                 230                 235                 240

Gly Thr Leu Ala Asn Leu Lys His Asn Leu His Ala Leu Ser Ser Asn
                245                 250                 255

Ser Ser Ser Leu Gln Gln Gln Gln Gln Leu Thr Glu Phe Val Gln
            260                 265                 270

Arg Leu Val Arg Ile Val Ala Gln Asp Gln His Pro Val Ser Leu Lys
        275                 280                 285

Thr Pro Lys Pro Val Phe Gln Asp Cys Ala Glu Ile Lys Arg Ser Gly
290                 295                 300

Val Asn Thr Ser Gly Val Tyr Thr Ile Tyr Glu Thr Asn Met Thr Lys
305                 310                 315                 320

Pro Leu Lys Val Phe Cys Asp Met Glu Thr Asp Gly Gly Gly Trp Thr
                325                 330                 335

Leu Ile Gln His Arg Glu Asp Gly Ser Val Asn Phe Gln Arg Thr Trp
            340                 345                 350

Glu Glu Tyr Lys Glu Gly Phe Gly Asn Val Ala Arg Glu His Trp Leu
        355                 360                 365

Gly Asn Glu Ala Val His Arg Leu Thr Ser Arg Thr Ala Tyr Leu Leu
    370                 375                 380

Arg Val Glu Leu His Asp Trp Glu Gly Arg Gln Thr Ser Ile Gln Tyr
385                 390                 395                 400

Glu Asn Phe Gln Leu Gly Ser Glu Arg Gln Arg Tyr Ser Leu Ser Val
                405                 410                 415

Asn Asp Ser Ser Ser Ala Gly Arg Lys Asn Ser Leu Ala Pro Gln
            420                 425                 430

Gly Thr Lys Phe Ser Thr Lys Asp Met Asp Asn Asp Asn Cys Met Cys
        435                 440                 445

Lys Cys Ala Gln Met Leu Ser Gly Gly Trp Trp Phe Asp Ala Cys Gly
    450                 455                 460

Leu Ser Asn Leu Asn Gly Ile Tyr Tyr Ser Val His Gln His Leu His
465                 470                 475                 480

Lys Ile Asn Gly Ile Arg Trp His Tyr Phe Arg Gly Pro Ser Tyr Ser
                485                 490                 495

Leu His Gly Thr Arg Met Met Leu Arg Pro Met Gly Ala
            500                 505

<210> SEQ ID NO 11
<211> LENGTH: 503
<212> TYPE: PRT
<213> ORGANISM: Homo sapiens

<400> SEQUENCE: 11

Met Leu Leu Asp Gly Leu Leu Leu Ala Thr Met Ala Ala Ala Gln
1               5                   10                  15

His Arg Gly Pro Glu Ala Gly Gly His Arg Gln Ile His Gln Val Arg
            20                  25                  30

Arg Gly Gln Cys Ser Tyr Thr Phe Val Val Pro Glu Pro Asp Ile Cys
        35                  40                  45

Gln Leu Ala Pro Thr Ala Ala Pro Glu Ala Leu Gly Gly Ser Asn Ser
    50                  55                  60
```

-continued

```
Leu Gln Arg Asp Leu Pro Ala Ser Arg Leu His Leu Thr Asp Trp Arg
 65                  70                  75                  80

Ala Gln Arg Ala Gln Arg Ala Gln Arg Val Ser Gln Leu Glu Lys Ile
                 85                  90                  95

Leu Glu Asn Asn Thr Gln Trp Leu Leu Lys Leu Glu Gln Ser Ile Lys
            100                 105                 110

Val Asn Leu Arg Ser His Leu Val Gln Ala Gln Gln Asp Thr Ile Gln
        115                 120                 125

Asn Gln Thr Thr Thr Met Leu Ala Leu Gly Ala Asn Leu Met Asn Gln
130                 135                 140

Thr Lys Ala Gln Thr His Lys Leu Thr Ala Val Glu Ala Gln Val Leu
145                 150                 155                 160

Asn Gln Thr Leu His Met Lys Thr Gln Met Leu Glu Asn Ser Leu Ser
                165                 170                 175

Thr Asn Lys Leu Glu Arg Gln Met Leu Met Gln Ser Arg Glu Leu Gln
            180                 185                 190

Arg Leu Gln Gly Arg Asn Arg Ala Leu Glu Thr Arg Leu Gln Ala Leu
        195                 200                 205

Glu Ala Gln His Gln Ala Gln Leu Asn Ser Leu Gln Glu Lys Arg Glu
    210                 215                 220

Gln Leu His Ser Leu Leu Gly His Gln Thr Gly Thr Leu Ala Asn Leu
225                 230                 235                 240

Lys His Asn Leu His Ala Leu Ser Ser Asn Ser Ser Ser Leu Gln Gln
                245                 250                 255

Gln Gln Gln Gln Leu Thr Glu Phe Val Gln Arg Leu Val Arg Ile Val
            260                 265                 270

Ala Gln Asp Gln His Pro Val Ser Leu Lys Thr Pro Lys Pro Val Phe
        275                 280                 285

Gln Asp Cys Ala Glu Ile Lys Arg Ser Gly Val Asn Thr Ser Gly Val
    290                 295                 300

Tyr Thr Ile Tyr Glu Thr Asn Met Thr Lys Pro Leu Lys Val Phe Cys
305                 310                 315                 320

Asp Met Glu Thr Asp Gly Gly Gly Trp Thr Leu Ile Gln His Arg Glu
                325                 330                 335

Asp Gly Ser Val Asn Phe Gln Arg Thr Trp Glu Glu Tyr Lys Glu Gly
            340                 345                 350

Phe Gly Asn Val Ala Arg Glu His Trp Leu Gly Asn Glu Ala Val His
        355                 360                 365

Arg Leu Thr Ser Arg Thr Ala Tyr Leu Leu Arg Val Glu Leu His Asp
    370                 375                 380

Trp Glu Gly Arg Gln Thr Ser Ile Gln Tyr Glu Asn Phe Gln Leu Gly
385                 390                 395                 400

Ser Glu Arg Gln Arg Tyr Ser Leu Ser Val Asn Asp Ser Ser Ser Ser
                405                 410                 415

Ala Gly Arg Lys Asn Ser Leu Ala Pro Gln Gly Thr Lys Phe Ser Thr
            420                 425                 430

Lys Asp Met Asp Asn Asp Asn Cys Met Cys Lys Cys Ala Gln Met Leu
        435                 440                 445

Ser Gly Gly Trp Trp Phe Asp Ala Cys Gly Leu Ser Asn Leu Asn Gly
    450                 455                 460

Ile Tyr Tyr Ser Val His Gln His Leu His Lys Ile Asn Gly Ile Arg
465                 470                 475                 480
```

```
Trp His Tyr Phe Arg Gly Pro Ser Tyr Ser Ile His Gly Thr Arg Met
                485                 490                 495
Met Leu Arg Pro Met Gly Ala
            500

<210> SEQ ID NO 12
<211> LENGTH: 490
<212> TYPE: PRT
<213> ORGANISM: Homo sapiens

<400> SEQUENCE: 12

Ala Phe Leu Ala Ala Ile Leu Thr His Ile Gly Cys Ser Asn Gln Arg
1               5                   10                  15

Arg Ser Pro Glu Asn Ser Gly Arg Arg Tyr Asn Arg Ile Gln His Gly
            20                  25                  30

Gln Cys Ala Tyr Thr Phe Ile Leu Pro Glu His Asp Gly Asn Cys Arg
        35                  40                  45

Glu Ser Thr Thr Asp Gln Tyr Asn Thr Asn Ala Leu Gln Arg Asp Ala
    50                  55                  60

Pro His Val Glu Pro Asp Phe Ser Ser Gln Lys Leu Gln His Leu Glu
65                  70                  75                  80

His Val Met Glu Asn Tyr Thr Gln Trp Leu Gln Lys Leu Glu Asn Tyr
                85                  90                  95

Ile Val Glu Asn Met Lys Ser Glu Met Ala Gln Ile Gln Gln Asn Ala
            100                 105                 110

Val Gln Asn His Thr Ala Thr Met Leu Glu Ile Gly Thr Ser Leu Leu
        115                 120                 125

Ser Gln Thr Ala Glu Gln Thr Arg Lys Leu Thr Asp Val Glu Thr Gln
    130                 135                 140

Val Leu Asn Gln Thr Ser Arg Leu Glu Ile Gln Leu Leu Glu Asn Ser
145                 150                 155                 160

Leu Ser Thr Tyr Lys Leu Glu Lys Gln Leu Gln Gln Thr Asn Glu
                165                 170                 175

Ile Leu Lys Ile His Glu Lys Asn Ser Leu Leu Glu His Lys Ile Leu
            180                 185                 190

Glu Met Glu Gly Lys His Lys Glu Glu Leu Asp Thr Leu Lys Glu Glu
        195                 200                 205

Lys Glu Asn Leu Gln Gly Leu Val Thr Arg Gln Thr Tyr Ile Ile Gln
    210                 215                 220

Glu Leu Glu Lys Gln Leu Asn Arg Ala Thr Thr Asn Asn Ser Val Leu
225                 230                 235                 240

Gln Lys Gln Gln Leu Glu Leu Met Asp Thr Val His Asn Leu Val Asn
                245                 250                 255

Leu Cys Thr Lys Glu Val Leu Leu Lys Gly Gly Lys Arg Glu Glu Glu
            260                 265                 270

Lys Pro Phe Arg Asp Cys Ala Asp Val Tyr Gln Ala Gly Phe Asn Lys
        275                 280                 285

Ser Gly Ile Tyr Thr Ile Tyr Ile Asn Asn Met Pro Glu Pro Lys Lys
    290                 295                 300

Val Phe Cys Asn Met Asp Val Asn Gly Gly Gly Trp Thr Val Ile Gln
305                 310                 315                 320

His Arg Glu Asp Gly Ser Leu Asp Phe Gln Arg Gly Trp Lys Glu Tyr
                325                 330                 335

Lys Met Gly Phe Gly Asn Pro Ser Gly Glu Tyr Trp Leu Gly Asn Glu
            340                 345                 350
```

```
Phe Ile Phe Ala Ile Thr Ser Gln Arg Gln Tyr Met Leu Arg Ile Glu
            355                 360                 365
Leu Met Asp Trp Glu Gly Asn Arg Ala Tyr Ser Gln Tyr Asp Arg Phe
        370                 375                 380
His Ile Gly Asn Glu Lys Gln Asn Tyr Arg Leu Tyr Leu Lys Gly His
385                 390                 395                 400
Thr Gly Thr Ala Gly Lys Gln Ser Ser Leu Ile Leu His Gly Ala Asp
                405                 410                 415
Phe Ser Thr Lys Asp Ala Asp Asn Asp Asn Cys Met Cys Lys Cys Ala
                420                 425                 430
Leu Met Leu Thr Gly Gly Trp Trp Phe Asp Ala Cys Gly Pro Ser Asn
            435                 440                 445
Leu Asn Gly Met Phe Tyr Thr Ala Gly Gln Asn His Gly Lys Leu Asn
        450                 455                 460
Gly Ile Lys Trp His Tyr Phe Lys Gly Pro Ser Tyr Ser Ile Arg Ser
465                 470                 475                 480
Thr Thr Met Met Ile Arg Pro Leu Asp Phe
                485                 490

<210> SEQ ID NO 13
<211> LENGTH: 491
<212> TYPE: PRT
<213> ORGANISM: Homo sapiens

<400> SEQUENCE: 13

Ala Phe Leu Ala Ala Ile Leu Ala His Ile Gly Cys Thr Thr Gln Arg
1               5                   10                  15
Arg Ser Pro Glu Asn Ser Gly Arg Arg Phe Asn Arg Ile Gln His Gly
            20                  25                  30
Gln Cys Thr Tyr Thr Phe Ile Leu Pro Glu Gln Asp Gly Asn Cys Arg
        35                  40                  45
Glu Ser Thr Thr Asp Gln Tyr Asn Thr Asn Ala Leu Gln Arg Asp Ala
    50                  55                  60
Pro His Val Glu Gln Asp Phe Ser Phe Gln Lys Leu Gln His Leu Glu
65                  70                  75                  80
His Val Met Glu Asn Tyr Thr Gln Trp Leu Gln Lys Leu Glu Ser Tyr
                85                  90                  95
Ile Val Glu Asn Met Lys Ser Glu Met Ala Gln Leu Gln Gln Asn Ala
            100                 105                 110
Val Gln Asn His Thr Ala Thr Met Leu Glu Ile Gly Thr Ser Leu Leu
        115                 120                 125
Ser Gln Thr Ala Glu Gln Thr Arg Lys Leu Thr Asp Val Glu Thr Gln
    130                 135                 140
Val Leu Asn Gln Thr Ser Arg Leu Glu Ile Gln Leu Leu Glu Asn Ser
145                 150                 155                 160
Leu Ser Thr Tyr Lys Leu Glu Lys Gln Leu Leu Gln Gln Thr Asn Glu
                165                 170                 175
Ile Leu Lys Ile His Glu Lys Asn Ser Leu Leu Glu His Lys Ile Leu
            180                 185                 190
Glu Met Glu Glu Arg His Lys Glu Glu Met Asp Thr Leu Lys Glu Glu
        195                 200                 205
Lys Glu Asn Leu Gln Gly Leu Val Thr Arg Gln Ser Tyr Ile Ile Gln
    210                 215                 220
Glu Leu Glu Lys Gln Leu Asn Lys Ala Thr Thr Asn Asn Ser Val Leu
```

```
                225                 230                 235                 240
Gln Lys Gln Gln Leu Glu Leu Met Asp Thr Val His Thr Leu Ile Thr
                245                 250                 255
Leu Cys Ser Lys Glu Gly Val Leu Leu Lys Asn Ala Lys Arg Glu Glu
                260                 265                 270
Glu Lys Pro Phe Arg Asp Cys Ala Asp Val Tyr Gln Ala Gly Phe Asn
                275                 280                 285
Lys Ser Gly Ile Tyr Thr Ile Tyr Ile Asn Asn Val Ser Asp Pro Lys
                290                 295                 300
Lys Val Phe Cys Asn Met Asp Val Asn Gly Gly Gly Trp Thr Val Ile
305                 310                 315                 320
Gln His Arg Glu Asp Gly Ser Leu Asp Phe Gln Lys Gly Trp Lys Glu
                325                 330                 335
Tyr Lys Met Gly Phe Gly Ser Pro Ser Gly Glu Tyr Trp Leu Gly Asn
                340                 345                 350
Glu Phe Ile Phe Ala Ile Thr Ser Gln Arg Gln Tyr Ser Leu Arg Ile
                355                 360                 365
Glu Leu Met Asp Trp Glu Gly Asn Arg Ala Tyr Ser Gln Tyr Asp Arg
                370                 375                 380
Phe His Ile Gly Asn Glu Lys Gln Asn Tyr Arg Leu Tyr Leu Lys Gly
385                 390                 395                 400
His Ser Gly Thr Ala Gly Lys Gln Ser Ser Leu Ile Leu His Gly Ala
                405                 410                 415
Glu Phe Ser Thr Lys Asp Ala Asp Asn Asp Asn Cys Met Cys Lys Cys
                420                 425                 430
Ala Leu Met Leu Thr Gly Gly Trp Trp Phe Asp Ala Cys Gly Pro Ser
                435                 440                 445
Asn Leu Asn Gly Met Phe Tyr Thr Ala Gly Gln Asn His Gly Lys Leu
                450                 455                 460
Asn Gly Ile Lys Trp His Tyr Phe Lys Gly Pro Arg Tyr Ser Ile Arg
465                 470                 475                 480
Ser Thr Thr Met Met Ile Arg Pro Leu Asp Phe
                485                 490

<210> SEQ ID NO 14
<211> LENGTH: 497
<212> TYPE: PRT
<213> ORGANISM: Mus sp.

<400> SEQUENCE: 14

Met Thr Val Phe Leu Ser Phe Ala Phe Phe Ala Ala Ile Leu Thr His
1               5                   10                  15
Ile Gly Cys Ser Asn Gln Arg Arg Asn Pro Glu Asn Ser Gly Arg Arg
                20                  25                  30
Tyr Asn Arg Ile Gln His Gly Gln Cys Ala Tyr Thr Phe Ile Leu Pro
            35                  40                  45
Glu His Asp Gly Asn Cys Arg Glu Ser Thr Thr Asp Gln Tyr Asn Thr
        50                  55                  60
Asn Ala Leu Gln Arg Asp Ala Pro His Val Glu Pro Asp Phe Ser Ser
65                  70                  75                  80
Gln Lys Leu Gln His Leu Glu His Val Met Glu Asn Tyr Thr Gln Trp
                85                  90                  95
Leu Gln Lys Leu Glu Asn Tyr Ile Val Glu Asn Met Lys Ser Glu Met
            100                 105                 110
```

```
Ala Gln Ile Gln Gln Asn Ala Val Gln Asn His Thr Ala Thr Met Leu
        115                 120                 125

Glu Ile Gly Thr Ser Leu Leu Ser Gln Thr Ala Glu Gln Thr Arg Lys
        130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
                165                 170                 175

Leu Leu Gln Thr Asn Glu Ile Leu Lys Ile His Glu Lys Asn Ser Leu
                180                 185                 190

Leu Glu His Lys Ile Leu Glu Met Glu Gly Lys His Lys Glu Glu Met
            195                 200                 205

Asp Thr Leu Lys Glu Glu Lys Glu Asn Leu Gln Gly Leu Val Ser Arg
        210                 215                 220

Gln Ser Phe Ile Ile Gln Glu Leu Glu Lys Gln Leu Ser Arg Ala Thr
225                 230                 235                 240

Asn Asn Asn Ser Ile Leu Gln Lys Gln Gln Leu Glu Leu Met Asp Thr
                245                 250                 255

Val His Asn Leu Ile Ser Leu Cys Thr Lys Glu Gly Val Leu Leu Lys
                260                 265                 270

Gly Gly Lys Arg Glu Glu Lys Pro Phe Arg Asp Cys Ala Asp Val
        275                 280                 285

Tyr Gln Ala Gly Phe Asn Lys Ser Gly Ile Tyr Thr Ile Tyr Phe Asn
        290                 295                 300

Asn Val Pro Glu Pro Lys Lys Val Phe Cys Asn Met Asp Val Asn Gly
305                 310                 315                 320

Gly Gly Trp Thr Val Ile Gln His Arg Glu Asp Gly Ser Leu Asp Phe
                325                 330                 335

Gln Lys Gly Trp Lys Glu Tyr Lys Met Gly Phe Gly Ser Pro Ser Gly
                340                 345                 350

Glu Tyr Trp Leu Gly Asn Glu Phe Ile Phe Ala Ile Thr Ser Gln Arg
            355                 360                 365

Gln Tyr Met Leu Arg Ile Glu Leu Met Asp Trp Glu Gly Asn Arg Ala
        370                 375                 380

Tyr Ser Gln Tyr Asp Arg Phe His Ile Gly Asn Glu Lys Gln Asn Tyr
385                 390                 395                 400

Arg Leu Tyr Leu Lys Gly His Thr Gly Thr Ala Gly Lys Gln Ser Ser
                405                 410                 415

Leu Ile Leu His Gly Ala Asp Phe Ser Thr Lys Asp Ala Asp Asn Asp
                420                 425                 430

Asn Cys Met Cys Lys Cys Ala Leu Met Leu Thr Gly Gly Trp Trp Phe
            435                 440                 445

Asp Ala Cys Gly Pro Ser Asn Leu Asn Gly Met Phe Tyr Thr Ala Gly
        450                 455                 460

Gln Asn His Gly Lys Leu Asn Gly Ile Lys Trp His Tyr Phe Lys Gly
465                 470                 475                 480

Pro Arg Tyr Ser Ile Arg Ser Thr Thr Met Met Ile Arg Pro Leu Asp
                485                 490                 495

Phe

<210> SEQ ID NO 15
<211> LENGTH: 496
<212> TYPE: PRT
<213> ORGANISM: Mus sp.
```

<400> SEQUENCE: 15

Met Trp Gln Ile Ile Phe Leu Thr Phe Gly Trp Asp Ala Val Leu Thr
1               5                   10                  15

Ser Ala Tyr Ser Asn Phe Arg Lys Ser Val Asp Ser Thr Gly Arg Arg
            20                  25                  30

Arg Tyr Arg Ile Gln Asn Gly Pro Cys Ala Tyr Thr Phe Leu Leu Pro
            35                  40                  45

Glu Thr Asp Ser Gly Arg Ser Ser Ser Thr Tyr Met Thr Asn Ala
50                      55                  60

Val Gln Arg Asp Ala Pro Pro Asp Tyr Glu Asp Ser Val Gln Ser Leu
65                  70                  75                  80

Gln Leu Leu Glu Asn Val Met Glu Asn Tyr Thr Gln Trp Leu Met Lys
                85                  90                  95

Leu Glu Asn Tyr Ile Gln Asp Asn Met Lys Lys Glu Met Ala Glu Ile
            100                 105                 110

Gln Gln Asn Val Val Gln Asn His Thr Ala Val Met Ile Glu Ile Gly
            115                 120                 125

Thr Ser Leu Leu Ser Gln Thr Ala Glu Gln Thr Arg Lys Leu Thr Asp
            130                 135                 140

Val Glu Thr Gln Val Leu Asn Gln Thr Thr Arg Leu Glu Leu Gln Leu
145                 150                 155                 160

Leu Gln His Ser Ile Ser Thr Tyr Lys Leu Glu Lys Gln Ile Leu Asp
                165                 170                 175

Gln Thr Ser Glu Ile Asn Lys Ile His Asn Lys Asn Ser Phe Leu Glu
            180                 185                 190

Gln Lys Val Leu Asp Met Glu Gly Lys His Ser Glu Glu Met Gln Thr
            195                 200                 205

Met Lys Glu Gln Lys Asp Glu Leu Gln Val Leu Val Ser Lys Gln Ser
210                 215                 220

Ser Val Ile Asp Glu Leu Glu Lys Lys Leu Val Thr Ala Thr Val Asn
225                 230                 235                 240

Asn Ser Leu Leu Gln Lys Gln Gln His Asp Leu Met Asp Thr Val Asn
                245                 250                 255

Ser Leu Leu Thr Met Met Ser Ser Pro Asn Ser Lys Ser Ser Leu Ala
            260                 265                 270

Ile Arg Arg Glu Glu Gln Thr Thr Phe Arg Asp Cys Ala Asp Val Phe
            275                 280                 285

Lys Ala Gly Leu Thr Lys Ser Gly Ile Tyr Thr Leu Thr Phe Pro Asn
            290                 295                 300

Ser Pro Glu Glu Ile Lys Ala Tyr Cys Asn Met Asp Val Gly Gly Gly
305                 310                 315                 320

Gly Trp Thr Val Ile Gln His Arg Glu Asp Gly Ser Leu Asp Phe Gln
                325                 330                 335

Lys Gly Trp Lys Glu Tyr Lys Met Gly Phe Gly Asn Pro Leu Gly Glu
            340                 345                 350

Tyr Trp Leu Gly Asn Glu Phe Ile Ser Gln Ile Thr Gly Gln His Arg
            355                 360                 365

Tyr Val Leu Lys Ile Gln Leu Lys Asp Trp Glu Gly Asn Glu Ala His
            370                 375                 380

Ser Leu Tyr Asp His Phe Tyr Ile Ala Gly Glu Glu Ser Asn Tyr Arg
385                 390                 395                 400

Ile His Leu Thr Gly Leu Thr Gly Thr Ala Ala Lys Ile Ser Ser Ile

```
                        405                 410                 415
Ser Gln Pro Gly Ser Asp Phe Ser Thr Lys Asp Ser Asp Asn Asp Lys
            420                 425                 430

Cys Ile Cys Lys Cys Ser Leu Met Leu Thr Gly Gly Trp Trp Phe Asp
        435                 440                 445

Ala Cys Gly Pro Ser Asn Leu Asn Gly Gln Phe Tyr Pro Gln Lys Gln
    450                 455                 460

Asn Thr Asn Lys Phe Asn Gly Ile Lys Trp Tyr Tyr Trp Lys Gly Ser
465                 470                 475                 480

Gly Tyr Ser Ile Lys Ala Thr Thr Met Met Ile Arg Pro Ala Asp Phe
                485                 490                 495

<210> SEQ ID NO 16
<211> LENGTH: 496
<212> TYPE: PRT
<213> ORGANISM: Homo sapiens

<400> SEQUENCE: 16

Met Trp Gln Ile Val Phe Phe Thr Leu Ser Cys Asp Ala Val Leu Thr
1               5                   10                  15

Ala Ala Tyr Asn Asn Phe Arg Lys Ser Met Asp Ser Ile Gly Lys Lys
            20                  25                  30

Arg Tyr Arg Ile Gln His Gly Ser Cys Ala Tyr Thr Phe Leu Leu Pro
        35                  40                  45

Glu Met Asp Asn Gly Arg Ser Ser Ser Thr Tyr Val Thr Asn Ala
    50                  55                  60

Val Gln Arg Asp Ala Pro Pro Glu Tyr Glu Asp Ser Val Gln Ser Leu
65                  70                  75                  80

Gln Leu Leu Glu Asn Val Met Glu Asn Tyr Thr Gln Trp Leu Met Lys
                85                  90                  95

Leu Glu Asn Tyr Ile Gln Asp Asn Met Lys Lys Glu Met Ala Glu Ile
            100                 105                 110

Gln Gln Asn Ala Val Gln Asn His Thr Ala Val Met Ile Glu Ile Gly
        115                 120                 125

Thr Ser Leu Leu Ser Gln Thr Ala Glu Gln Thr Arg Lys Leu Thr Asp
130                 135                 140

Val Glu Thr Gln Val Leu Asn Gln Thr Thr Arg Leu Glu Leu Gln Leu
145                 150                 155                 160

Leu Gln His Ser Ile Ser Thr Tyr Lys Leu Glu Lys Gln Ile Leu Asp
                165                 170                 175

Gln Thr Ser Glu Ile Asn Lys Ile His Asp Lys Asn Ser Phe Leu Glu
            180                 185                 190

Lys Lys Val Leu Asp Met Glu Asp Lys His Ile Ile Glu Met Gln Thr
        195                 200                 205

Ile Lys Glu Glu Lys Asp Glu Leu Gln Val Leu Val Ser Lys Gln Asn
    210                 215                 220

Ser Ile Ile Glu Glu Leu Glu Lys Lys Ile Val Thr Ala Thr Val Asn
225                 230                 235                 240

Asn Ser Val Leu Gln Lys Gln Gln His Asp Leu Met Asp Thr Val Asn
                245                 250                 255

Asn Leu Leu Thr Met Met Ser Thr Ser Asn Ser Ala Lys Asp Ser Thr
            260                 265                 270

Val Ala Arg Glu Glu Gln Ile Ser Phe Arg Asp Cys Ala Asp Val Phe
        275                 280                 285
```

-continued

```
Lys Ala Gly His Thr Lys Asn Gly Ile Tyr Thr Leu Thr Phe Pro Asn
290                 295                 300

Ser Pro Glu Glu Ile Lys Ala Tyr Cys Asn Met Asp Ala Gly Gly Gly
305                 310                 315                 320

Gly Trp Thr Ile Ile Gln Arg Arg Glu Asp Gly Ser Leu Asp Phe Gln
                325                 330                 335

Lys Gly Trp Lys Glu Tyr Lys Val Gly Phe Gly Ser Pro Ser Gly Glu
            340                 345                 350

Tyr Trp Leu Gly Asn Glu Phe Ile Ser Gln Ile Thr Asn Gln Gln Arg
        355                 360                 365

Tyr Val Leu Lys Ile His Leu Lys Asp Trp Glu Gly Asn Glu Ala Tyr
370                 375                 380

Ser Leu Tyr Asp His Phe Tyr Ile Ser Gly Glu Glu Leu Asn Tyr Arg
385                 390                 395                 400

Ile His Leu Lys Gly Leu Thr Gly Thr Ala Ala Lys Ile Ser Ser Ile
                405                 410                 415

Ser Gln Pro Gly Asn Asp Phe Ser Thr Lys Asp Gly Asp Asn Asp Lys
            420                 425                 430

Cys Ile Cys Lys Cys Ser Leu Met Leu Thr Gly Gly Trp Trp Phe Asp
        435                 440                 445

Ala Cys Gly Pro Ser Asn Leu Asn Gly Met Phe Tyr Pro Gln Arg Gln
450                 455                 460

Asn Thr Asn Lys Phe Asn Gly Ile Lys Trp Tyr Tyr Trp Lys Gly Ser
465                 470                 475                 480

Gly Tyr Ser Ile Lys Ala Thr Thr Met Met Ile Arg Pro Ala Asp Phe
                485                 490                 495
```

<210> SEQ ID NO 17
<211> LENGTH: 1512
<212> TYPE: DNA
<213> ORGANISM: Homo sapiens
<220> FEATURE:
<221> NAME/KEY: CDS
<222> LOCATION: (1)..(1512)
<223> OTHER INFORMATION:

<400> SEQUENCE: 17

```
atg ctc tcc cag cta gcc atg ctg cag ggc agc ctc ctc ctt gtg gtt      48
Met Leu Ser Gln Leu Ala Met Leu Gln Gly Ser Leu Leu Leu Val Val
1               5                  10                  15 gcc acc atg tct gtg gct caa cag aca agg cag gag gcg gat agg ggc      96
Ala Thr Met Ser Val Ala Gln Gln Thr Arg Gln Glu Ala Asp Arg Gly
            20                  25                  30 tgc gag aca ctt gta gtc cag cac ggc cac tgt agc tac acc ttc ttg     144
Cys Glu Thr Leu Val Val Gln His Gly His Cys Ser Tyr Thr Phe Leu
        35                  40                  45 ctg ccc aag tct gag ccc tgc cct ccg ggg cct gag gtc tcc agg gac     192
Leu Pro Lys Ser Glu Pro Cys Pro Pro Gly Pro Glu Val Ser Arg Asp
    50                  55                  60 tcc aac acc ctc cag aga gaa tca ctg gcc aac cca ctg cac ctg ggg     240
Ser Asn Thr Leu Gln Arg Glu Ser Leu Ala Asn Pro Leu His Leu Gly
65                  70                  75                  80 aag ttg ccc acc cag cag gtg aaa cag ctg gag cag gca ctg cag aac     288
Lys Leu Pro Thr Gln Gln Val Lys Gln Leu Glu Gln Ala Leu Gln Asn
                85                  90                  95 aac acg cag tgg ctg aag aag cta gag agg gcc atc aag acg atc ttg     336
Asn Thr Gln Trp Leu Lys Lys Leu Glu Arg Ala Ile Lys Thr Ile Leu
            100                 105                 110
```

-continued

| | |
|---|---|
| agg tcg aag ctg gag cag gtc cag cag caa atg gcc cag aat cag acg<br>Arg Ser Lys Leu Glu Gln Val Gln Gln Gln Met Ala Gln Asn Gln Thr<br>    115                    120                  125 | 384 |
| gcc ccc atg cta gag ctg ggc acc agc ctc ctg aac cag acc act gcc<br>Ala Pro Met Leu Glu Leu Gly Thr Ser Leu Leu Asn Gln Thr Thr Ala<br>130                    135                  140 | 432 |
| cag atc cgc aag ctg acc gac atg gag gct cag ctc ctg aac cag aca<br>Gln Ile Arg Lys Leu Thr Asp Met Glu Ala Gln Leu Leu Asn Gln Thr<br>145                  150                  155                  160 | 480 |
| tca aga atg gat gcc cag atg cca gag acc ttt ctg tcc acc aac aag<br>Ser Arg Met Asp Ala Gln Met Pro Glu Thr Phe Leu Ser Thr Asn Lys<br>                165                  170                  175 | 528 |
| ctg gag aac cag ctg ctg cta cag agg cag aag ctc cag cag ctt cag<br>Leu Glu Asn Gln Leu Leu Leu Gln Arg Gln Lys Leu Gln Gln Leu Gln<br>            180                  185                  190 | 576 |
| ggc caa aac agc gcg ctc gag aag cgg ttg cag gcc ctg gag acc aag<br>Gly Gln Asn Ser Ala Leu Glu Lys Arg Leu Gln Ala Leu Glu Thr Lys<br>            195                  200                  205 | 624 |
| cag cag gag gag ctg gcc agc atc ctc agc aag aag gcg aag ctg ctg<br>Gln Gln Glu Glu Leu Ala Ser Ile Leu Ser Lys Lys Ala Lys Leu Leu<br>210                    215                  220 | 672 |
| aac acg ctg agc cgc cag agc gcc gcc ctc acc aac atc gag cgc ggc<br>Asn Thr Leu Ser Arg Gln Ser Ala Ala Leu Thr Asn Ile Glu Arg Gly<br>225                    230                  235                  240 | 720 |
| ctg cgc ggt gtc agg cac aac tcc agc ctc ctg cag gac cag cag cac<br>Leu Arg Gly Val Arg His Asn Ser Ser Leu Leu Gln Asp Gln Gln His<br>                245                  250                  255 | 768 |
| agc ctg cgc cag ctg ctg gtg ttg ttg cgg cac ctg gtg caa gaa agg<br>Ser Leu Arg Gln Leu Leu Val Leu Leu Arg His Leu Val Gln Glu Arg<br>            260                  265                  270 | 816 |
| gct aac gcc tcg gcc ccg gcc ttc ata atg gca ggt gag cag gtg ttc<br>Ala Asn Ala Ser Ala Pro Ala Phe Ile Met Ala Gly Glu Gln Val Phe<br>275                    280                  285 | 864 |
| cag gac tgt gca gag atc cag cgc tct ggg gcc agt gcc agt ggt gtc<br>Gln Asp Cys Ala Glu Ile Gln Arg Ser Gly Ala Ser Ala Ser Gly Val<br>            290                  295                  300 | 912 |
| tac acc atc cag gtg tcc aat gca acg aag ccc agg aag gtg ttc tgt<br>Tyr Thr Ile Gln Val Ser Asn Ala Thr Lys Pro Arg Lys Val Phe Cys<br>305                    310                  315                  320 | 960 |
| gac ctg cag agc agt gga ggc agg tgg acc ctc atc cag cgc cgt gag<br>Asp Leu Gln Ser Ser Gly Gly Arg Trp Thr Leu Ile Gln Arg Arg Glu<br>            325                  330                  335 | 1008 |
| aat ggc acc gtg aat ttt cag cgg aac tgg aag gat tac aaa cag ggc<br>Asn Gly Thr Val Asn Phe Gln Arg Asn Trp Lys Asp Tyr Lys Gln Gly<br>                340                  345                  350 | 1056 |
| ttc gga gac cca gct ggg gag cac tgg ctg ggc aat gaa gtg gtg cac<br>Phe Gly Asp Pro Ala Gly Glu His Trp Leu Gly Asn Glu Val Val His<br>            355                  360                  365 | 1104 |
| cag ctc acc aga agg gca gcc tac tct ctg cgt gtg gag ctg caa gac<br>Gln Leu Thr Arg Arg Ala Ala Tyr Ser Leu Arg Val Glu Leu Gln Asp<br>            370                  375                  380 | 1152 |
| tgg gaa ggc cac gag gcc tat gcc cag tac gaa cat ttc cac ctg ggc<br>Trp Glu Gly His Glu Ala Tyr Ala Gln Tyr Glu His Phe His Leu Gly<br>385                    390                  395                  400 | 1200 |
| agt gag aac cag cta tac agg ctt tct gtg gtc ggg tac agc ggc tca<br>Ser Glu Asn Gln Leu Tyr Arg Leu Ser Val Val Gly Tyr Ser Gly Ser<br>                405                  410                  415 | 1248 |
| gca ggg cgc cag agc agc ctg gtc ctg cag aac acc agc ttt agc acc<br>Ala Gly Arg Gln Ser Ser Leu Val Leu Gln Asn Thr Ser Phe Ser Thr<br>            420                  425                  430 | 1296 |

-continued

```
ctt gac tca gac aac gac cac tgt ctc tgc aag tgt gcc cag gtg atg      1344
Leu Asp Ser Asp Asn Asp His Cys Leu Cys Lys Cys Ala Gln Val Met
        435                 440                 445 tct gga ggg tgg tgg ttt gac gcc tgt ggc ctg tca aac ctc aac ggc      1392
Ser Gly Gly Trp Trp Phe Asp Ala Cys Gly Leu Ser Asn Leu Asn Gly
450                 455                 460 gtc tac tac cac gct ccc gac aac aag tac aag atg gac ggc atc cgc      1440
Val Tyr Tyr His Ala Pro Asp Asn Lys Tyr Lys Met Asp Gly Ile Arg
465                 470                 475                 480 tgg cac tac ttc aag ggc ccc agc tac tca ctg cgt gcc tct cgc atg      1488
Trp His Tyr Phe Lys Gly Pro Ser Tyr Ser Leu Arg Ala Ser Arg Met
                485                 490                 495 atg ata cgg cct ttg gac atc taa                                      1512
Met Ile Arg Pro Leu Asp Ile
            500

<210> SEQ ID NO 18
<211> LENGTH: 503
<212> TYPE: PRT
<213> ORGANISM: Homo sapiens

<400> SEQUENCE: 18

Met Leu Ser Gln Leu Ala Met Leu Gln Gly Ser Leu Leu Val Val
1               5                   10                  15

Ala Thr Met Ser Val Ala Gln Gln Thr Arg Gln Glu Ala Asp Arg Gly
                20                  25                  30

Cys Glu Thr Leu Val Val Gln His Gly His Cys Ser Tyr Thr Phe Leu
            35                  40                  45

Leu Pro Lys Ser Glu Pro Cys Pro Pro Gly Pro Glu Val Ser Arg Asp
        50                  55                  60

Ser Asn Thr Leu Gln Arg Glu Ser Leu Ala Asn Pro Leu His Leu Gly
65                  70                  75                  80

Lys Leu Pro Thr Gln Gln Val Lys Gln Leu Glu Gln Ala Leu Gln Asn
                85                  90                  95

Asn Thr Gln Trp Leu Lys Lys Leu Glu Arg Ala Ile Lys Thr Ile Leu
            100                 105                 110

Arg Ser Lys Leu Glu Gln Val Gln Gln Met Ala Gln Asn Gln Thr
        115                 120                 125

Ala Pro Met Leu Glu Leu Gly Thr Ser Leu Leu Asn Gln Thr Thr Ala
130                 135                 140

Gln Ile Arg Lys Leu Thr Asp Met Glu Ala Gln Leu Leu Asn Gln Thr
145                 150                 155                 160

Ser Arg Met Asp Ala Gln Met Pro Glu Thr Phe Leu Ser Thr Asn Lys
                165                 170                 175

Leu Glu Asn Gln Leu Leu Leu Gln Arg Gln Lys Leu Gln Gln Leu Gln
            180                 185                 190

Gly Gln Asn Ser Ala Leu Glu Lys Arg Leu Gln Ala Leu Glu Thr Lys
        195                 200                 205

Gln Gln Glu Glu Leu Ala Ser Ile Leu Ser Lys Ala Lys Leu Leu
210                 215                 220

Asn Thr Leu Ser Arg Gln Ser Ala Ala Leu Thr Asn Ile Glu Arg Gly
225                 230                 235                 240

Leu Arg Gly Val Arg His Asn Ser Ser Leu Leu Gln Asp Gln His
                245                 250                 255

Ser Leu Arg Gln Leu Leu Val Leu Leu Arg His Leu Val Gln Glu Arg
            260                 265                 270
```

```
        Ala Asn Ala Ser Ala Pro Ala Phe Ile Met Ala Gly Glu Gln Val Phe
                    275                 280                 285

Gln Asp Cys Ala Glu Ile Gln Arg Ser Gly Ala Ser Ala Ser Gly Val
                    290                 295                 300

Tyr Thr Ile Gln Val Ser Asn Ala Thr Lys Pro Arg Lys Val Phe Cys
        305                 310                 315                 320

Asp Leu Gln Ser Ser Gly Gly Arg Trp Thr Leu Ile Gln Arg Arg Glu
                    325                 330                 335

Asn Gly Thr Val Asn Phe Gln Arg Asn Trp Lys Asp Tyr Lys Gln Gly
                    340                 345                 350

Phe Gly Asp Pro Ala Gly Glu His Trp Leu Gly Asn Glu Val Val His
                    355                 360                 365

Gln Leu Thr Arg Arg Ala Ala Tyr Ser Leu Arg Val Glu Leu Gln Asp
                    370                 375                 380

Trp Glu Gly His Glu Ala Tyr Ala Gln Tyr Glu His Phe His Leu Gly
        385                 390                 395                 400

Ser Glu Asn Gln Leu Tyr Arg Leu Ser Val Val Gly Tyr Ser Gly Ser
                    405                 410                 415

Ala Gly Arg Gln Ser Ser Leu Val Leu Gln Asn Thr Ser Phe Ser Thr
                    420                 425                 430

Leu Asp Ser Asp Asn Asp His Cys Leu Cys Lys Cys Ala Gln Val Met
                    435                 440                 445

Ser Gly Gly Trp Trp Phe Asp Ala Cys Gly Leu Ser Asn Leu Asn Gly
                    450                 455                 460

Val Tyr Tyr His Ala Pro Asp Asn Lys Tyr Lys Met Asp Gly Ile Arg
        465                 470                 475                 480

Trp His Tyr Phe Lys Gly Pro Ser Tyr Ser Leu Arg Ala Ser Arg Met
                    485                 490                 495

Met Ile Arg Pro Leu Asp Ile
                    500

<210> SEQ ID NO 19
<211> LENGTH: 1497
<212> TYPE: DNA
<213> ORGANISM: Artificial Sequence
<220> FEATURE:
<223> OTHER INFORMATION: Description of Artificial Sequence: Chimeric
<221> NAME/KEY: CDS
<222> LOCATION: (1)..(1494)
<223> OTHER INFORMATION: 1N1C2F (chimera 1)
<220> FEATURE:
<223> OTHER INFORMATION: Putative leader sequence is encoded by
      nucleotides 1-60

<400> SEQUENCE: 19 atg aca gtt ttc ctt tcc ttt gct ttc ctc gct gcc att ctg act cac        48
Met Thr Val Phe Leu Ser Phe Ala Phe Leu Ala Ala Ile Leu Thr His
1               5                   10                  15 ata ggg tgc agc aat cag cgc cga agt cca gaa aac agt ggg aga aga        96
Ile Gly Cys Ser Asn Gln Arg Arg Ser Pro Glu Asn Ser Gly Arg Arg
            20                  25                  30 tat aac cgg att caa cat ggg caa tgt gcc tac act ttc att ctt cca       144
Tyr Asn Arg Ile Gln His Gly Gln Cys Ala Tyr Thr Phe Ile Leu Pro
        35                  40                  45 gaa cac gat ggc aac tgt cgt gag agt acg aca gac cag tac aac aca       192
Glu His Asp Gly Asn Cys Arg Glu Ser Thr Thr Asp Gln Tyr Asn Thr
    50                  55                  60 aac gct ctg cag aga gat gct cca cac gtg gaa ccg gat ttc tct tcc       240
```

```
                                                          -continued

Asn Ala Leu Gln Arg Asp Ala Pro His Val Glu Pro Asp Phe Ser Ser
65              70                  75                  80 cag aaa ctt caa cat ctg gaa cat gtg atg gaa aat tat act cag tgg        288
Gln Lys Leu Gln His Leu Glu His Val Met Glu Asn Tyr Thr Gln Trp
                85                  90                  95 ctg caa aaa ctt gag aat tac att gtg gaa aac atg aag tcg gag atg        336
Leu Gln Lys Leu Glu Asn Tyr Ile Val Glu Asn Met Lys Ser Glu Met
                100                 105                 110 gcc cag ata cag cag aat gca gtt cag aac cac acg gct acc atg ctg        384
Ala Gln Ile Gln Gln Asn Ala Val Gln Asn His Thr Ala Thr Met Leu
                115                 120                 125 gag ata gga acc agc ctc ctc tct cag act gca gag cag acc aga aag        432
Glu Ile Gly Thr Ser Leu Leu Ser Gln Thr Ala Glu Gln Thr Arg Lys
            130                 135                 140 ctg aca gat gtt gag acc cag gta cta aat caa act tct cga ctt gag        480
Leu Thr Asp Val Glu Thr Gln Val Leu Asn Gln Thr Ser Arg Leu Glu
145                 150                 155                 160 ata cag ctg ctg gag aat tca tta tcc acc tac aag cta gag aag caa        528
Ile Gln Leu Leu Glu Asn Ser Leu Ser Thr Tyr Lys Leu Glu Lys Gln
                165                 170                 175 ctt ctt caa cag aca aat gaa atc ttg aag atc cat gaa aaa aac agt        576
Leu Leu Gln Gln Thr Asn Glu Ile Leu Lys Ile His Glu Lys Asn Ser
                180                 185                 190 tta tta gaa cat aaa atc tta gaa atg gaa gga aaa cac aag gaa gag        624
Leu Leu Glu His Lys Ile Leu Glu Met Glu Gly Lys His Lys Glu Glu
                195                 200                 205 ttg gac acc tta aag gaa gag aaa gag aac ctt caa ggc ttg gtt act        672
Leu Asp Thr Leu Lys Glu Glu Lys Glu Asn Leu Gln Gly Leu Val Thr
210                 215                 220 cgt caa aca tat ata atc cag gag ctg gaa aag caa tta aac aga gct        720
Arg Gln Thr Tyr Ile Ile Gln Glu Leu Glu Lys Gln Leu Asn Arg Ala
225                 230                 235                 240 acc acc aac aac agt gtc ctt cag aag cag caa ctg gag ctg atg gac        768
Thr Thr Asn Asn Ser Val Leu Gln Lys Gln Gln Leu Glu Leu Met Asp
                245                 250                 255 aca gtc cac aac ctt gtc aat ctt tgc act aaa gaa ggt gtt tta cta        816
Thr Val His Asn Leu Val Asn Leu Cys Thr Lys Glu Gly Val Leu Leu
                260                 265                 270 aag gga gga aaa aga gag gaa gag aaa cca ttt aga gac tgt gct gaa        864
Lys Gly Gly Lys Arg Glu Glu Glu Lys Pro Phe Arg Asp Cys Ala Glu
                275                 280                 285 gta ttc aaa tca gga cac acc aca aat ggc atc tac acg tta aca ttc        912
Val Phe Lys Ser Gly His Thr Thr Asn Gly Ile Tyr Thr Leu Thr Phe
                290                 295                 300 cct aat tct aca gaa gag atc aag gcc tac tgt gac atg gaa gct gga        960
Pro Asn Ser Thr Glu Glu Ile Lys Ala Tyr Cys Asp Met Glu Ala Gly
305                 310                 315                 320 gga ggc ggg tgg aca att att cag cga cgt gag gat ggc agc gtt gat       1008
Gly Gly Gly Trp Thr Ile Ile Gln Arg Arg Glu Asp Gly Ser Val Asp
                325                 330                 335 ttt cag agg act tgg aaa gaa tat aaa gtg gga ttt ggt aac cct tca       1056
Phe Gln Arg Thr Trp Lys Glu Tyr Lys Val Gly Phe Gly Asn Pro Ser
                340                 345                 350 gga gaa tat tgg ctg gga aat gag ttt gtt tcg caa ctg act aat cag       1104
Gly Glu Tyr Trp Leu Gly Asn Glu Phe Val Ser Gln Leu Thr Asn Gln
                355                 360                 365 caa cgc tat gtg ctt aaa ata cac ctt aaa gac tgg gaa ggg aat gag       1152
Gln Arg Tyr Val Leu Lys Ile His Leu Lys Asp Trp Glu Gly Asn Glu
                370                 375                 380
```

```
gct tac tca ttg tat gaa cat ttc tat ctc tca agt gaa gaa ctc aat    1200
Ala Tyr Ser Leu Tyr Glu His Phe Tyr Leu Ser Ser Glu Glu Leu Asn
385                 390                 395                 400 tat agg att cac ctt aaa gga ctt aca ggg aca gcc ggc aaa ata agc    1248
Tyr Arg Ile His Leu Lys Gly Leu Thr Gly Thr Ala Gly Lys Ile Ser
            405                 410                 415 agc atc agc caa cca gga aat gat ttt agc aca aag gat gga gac aac    1296
Ser Ile Ser Gln Pro Gly Asn Asp Phe Ser Thr Lys Asp Gly Asp Asn
420                 425                 430 gac aaa tgt att tgc aaa tgt tca caa atg cta aca gga ggc tgg tgg    1344
Asp Lys Cys Ile Cys Lys Cys Ser Gln Met Leu Thr Gly Gly Trp Trp
        435                 440                 445 ttt gat gca tgt ggt cct tcc aac ttg aac gga atg tac tat cca cag    1392
Phe Asp Ala Cys Gly Pro Ser Asn Leu Asn Gly Met Tyr Tyr Pro Gln
450                 455                 460 agg cag aac aca aat aag ttc aac ggc att aaa tgg tac tac tgg aaa    1440
Arg Gln Asn Thr Asn Lys Phe Asn Gly Ile Lys Trp Tyr Tyr Trp Lys
465                 470                 475                 480 ggc tca ggc tat tcg ctc aag gcc aca acc atg atg atc cga cca gca    1488
Gly Ser Gly Tyr Ser Leu Lys Ala Thr Thr Met Met Ile Arg Pro Ala
            485                 490                 495 gat ttc taa                                                        1497
Asp Phe

<210> SEQ ID NO 20
<211> LENGTH: 498
<212> TYPE: PRT
<213> ORGANISM: Artificial Sequence
<220> FEATURE:
<223> OTHER INFORMATION: Description of Artificial Sequence: Chimeric
<220> FEATURE:
<223> OTHER INFORMATION: 1N1C2F (chimera 1)

<400> SEQUENCE: 20

Met Thr Val Phe Leu Ser Phe Ala Phe Leu Ala Ala Ile Leu Thr His
1               5                   10                  15

Ile Gly Cys Ser Asn Gln Arg Arg Ser Pro Glu Asn Ser Gly Arg Arg
            20                  25                  30

Tyr Asn Arg Ile Gln His Gly Gln Cys Ala Tyr Thr Phe Ile Leu Pro
        35                  40                  45

Glu His Asp Gly Asn Cys Arg Glu Ser Thr Thr Asp Gln Tyr Asn Thr
    50                  55                  60

Asn Ala Leu Gln Arg Asp Ala Pro His Val Glu Pro Asp Phe Ser Ser
65                  70                  75                  80

Gln Lys Leu Gln His Leu Glu His Val Met Glu Asn Tyr Thr Gln Trp
                85                  90                  95

Leu Gln Lys Leu Glu Asn Tyr Ile Val Glu Asn Met Lys Ser Glu Met
            100                 105                 110

Ala Gln Ile Gln Gln Asn Ala Val Gln Asn His Thr Ala Thr Met Leu
        115                 120                 125

Glu Ile Gly Thr Ser Leu Leu Ser Gln Thr Ala Glu Gln Thr Arg Lys
    130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
                165                 170                 175

Leu Leu Gln Gln Thr Asn Glu Ile Leu Lys Ile His Glu Lys Asn Ser
            180                 185                 190
```

-continued

```
Leu Leu Glu His Lys Ile Leu Glu Met Glu Gly Lys His Lys Glu Glu
        195                 200                 205
Leu Asp Thr Leu Lys Glu Glu Lys Glu Asn Leu Gln Gly Leu Val Thr
    210                 215                 220
Arg Gln Thr Tyr Ile Ile Gln Glu Leu Glu Lys Gln Leu Asn Arg Ala
225                 230                 235                 240
Thr Thr Asn Asn Ser Val Leu Gln Lys Gln Gln Leu Glu Leu Met Asp
                245                 250                 255
Thr Val His Asn Leu Val Asn Leu Cys Thr Lys Glu Gly Val Leu Leu
            260                 265                 270
Lys Gly Gly Lys Arg Glu Glu Lys Pro Phe Arg Asp Cys Ala Glu
        275                 280                 285
Val Phe Lys Ser Gly His Thr Thr Asn Gly Ile Tyr Thr Leu Thr Phe
    290                 295                 300
Pro Asn Ser Thr Glu Glu Ile Lys Ala Tyr Cys Asp Met Glu Ala Gly
305                 310                 315                 320
Gly Gly Gly Trp Thr Ile Ile Gln Arg Arg Glu Asp Gly Ser Val Asp
                325                 330                 335
Phe Gln Arg Thr Trp Lys Glu Tyr Lys Val Gly Phe Gly Asn Pro Ser
            340                 345                 350
Gly Glu Tyr Trp Leu Gly Asn Glu Phe Val Ser Gln Leu Thr Asn Gln
        355                 360                 365
Gln Arg Tyr Val Leu Lys Ile His Leu Lys Asp Trp Glu Gly Asn Glu
    370                 375                 380
Ala Tyr Ser Leu Tyr Glu His Phe Tyr Leu Ser Ser Glu Glu Leu Asn
385                 390                 395                 400
Tyr Arg Ile His Leu Lys Gly Leu Thr Gly Thr Ala Gly Lys Ile Ser
                405                 410                 415
Ser Ile Ser Gln Pro Gly Asn Asp Phe Ser Thr Lys Asp Gly Asp Asn
            420                 425                 430
Asp Lys Cys Ile Cys Lys Cys Ser Gln Met Leu Thr Gly Gly Trp Trp
        435                 440                 445
Phe Asp Ala Cys Gly Pro Ser Asn Leu Asn Gly Met Tyr Tyr Pro Gln
    450                 455                 460
Arg Gln Asn Thr Asn Lys Phe Asn Gly Ile Lys Trp Tyr Tyr Trp Lys
465                 470                 475                 480
Gly Ser Gly Tyr Ser Leu Lys Ala Thr Thr Met Met Ile Arg Pro Ala
                485                 490                 495
Asp Phe

<210> SEQ ID NO 21
<211> LENGTH: 1491
<212> TYPE: DNA
<213> ORGANISM: Artificial Sequence
<220> FEATURE:
<223> OTHER INFORMATION: Description of Artificial Sequence: Chimeric
<221> NAME/KEY: CDS
<222> LOCATION: (1)..(1491)
<223> OTHER INFORMATION: 2N2C1F (chimera 2)
<220> FEATURE:
<223> OTHER INFORMATION: Putative leader sequence is encoded by
      nucleotides 1-48

<400> SEQUENCE: 21 atg tgg cag att gtt ttc ttt act ctg agc tgt gat ctt gtc ttg gcc      48
Met Trp Gln Ile Val Phe Phe Thr Leu Ser Cys Asp Leu Val Leu Ala
1               5                   10                  15
```

```
                                                        -continued gca gcc tat aac aac ttt cgg aag agc atg gac agc ata gga aag aag        96
Ala Ala Tyr Asn Asn Phe Arg Lys Ser Met Asp Ser Ile Gly Lys Lys
             20                  25                  30 caa tat cag gtc cag cat ggg tcc tgc agc tac act ttc ctc ctg cca       144
Gln Tyr Gln Val Gln His Gly Ser Cys Ser Tyr Thr Phe Leu Leu Pro
 35                  40                  45 gag atg gac aac tgc cgc tct tcc tcc agc ccc tac gtg tcc aat gct       192
Glu Met Asp Asn Cys Arg Ser Ser Ser Ser Pro Tyr Val Ser Asn Ala
 50                  55                  60 gtg cag agg gac gcg ccg ctc gaa tac gat gac tcg gtg cag agg ctg       240
Val Gln Arg Asp Ala Pro Leu Glu Tyr Asp Asp Ser Val Gln Arg Leu
 65                  70                  75                  80 caa gtg ctg gag aac atc atg gaa aac aac act cag tgg cta atg aag       288
Gln Val Leu Glu Asn Ile Met Glu Asn Asn Thr Gln Trp Leu Met Lys
                 85                  90                  95 ctt gag aat tat atc cag gac aac atg aag aaa gaa atg gta gag ata       336
Leu Glu Asn Tyr Ile Gln Asp Asn Met Lys Lys Glu Met Val Glu Ile
            100                 105                 110 cag cag aat gca gta cag aac cag acg gct gtg atg ata gaa ata ggg       384
Gln Gln Asn Ala Val Gln Asn Gln Thr Ala Val Met Ile Glu Ile Gly
        115                 120                 125 aca aac ctg ttg aac caa aca gct gag caa acg cgg aag tta act gat       432
Thr Asn Leu Leu Asn Gln Thr Ala Glu Gln Thr Arg Lys Leu Thr Asp
130                 135                 140 gtg gaa gcc caa gta tta aat cag acc acg aga ctt gaa ctt cag ctc       480
Val Glu Ala Gln Val Leu Asn Gln Thr Thr Arg Leu Glu Leu Gln Leu
145                 150                 155                 160 ttg gaa cac tcc ctc tcg aca aac aaa ttg gaa aaa cag att ttg gac       528
Leu Glu His Ser Leu Ser Thr Asn Lys Leu Glu Lys Gln Ile Leu Asp
                165                 170                 175 cag acc agt gaa ata aac aaa ttg caa gat aag aac agt ttc cta gaa       576
Gln Thr Ser Glu Ile Asn Lys Leu Gln Asp Lys Asn Ser Phe Leu Glu
            180                 185                 190 aag aag gtg cta gct atg gaa gac aag cac atc atc caa cta cag tca       624
Lys Lys Val Leu Ala Met Glu Asp Lys His Ile Ile Gln Leu Gln Ser
        195                 200                 205 ata aaa gaa gag aaa gat cag cta cag gtg tta gta tcc aag caa aat       672
Ile Lys Glu Glu Lys Asp Gln Leu Gln Val Leu Val Ser Lys Gln Asn
210                 215                 220 tcc atc att gaa gaa cta gaa aaa aaa ata gtg act gcc acg gtg aat       720
Ser Ile Ile Glu Glu Leu Glu Lys Lys Ile Val Thr Ala Thr Val Asn
225                 230                 235                 240 aat tca gtt ctt caa aag cag caa cat gat ctc atg gag aca gtt aat       768
Asn Ser Val Leu Gln Lys Gln Gln His Asp Leu Met Glu Thr Val Asn
                245                 250                 255 aac tta ctg act atg atg tcc aca tca aac tca gct aag gac ccc act       816
Asn Leu Leu Thr Met Met Ser Thr Ser Asn Ser Ala Lys Asp Pro Thr
            260                 265                 270 gtt gct aaa gaa gaa caa atc agc ttc aga gac tgt gca gat gta tat       864
Val Ala Lys Glu Glu Gln Ile Ser Phe Arg Asp Cys Ala Asp Val Tyr
        275                 280                 285 caa gct ggt ttt aat aaa agt gga atc tac act att tat att aat aat       912
Gln Ala Gly Phe Asn Lys Ser Gly Ile Tyr Thr Ile Tyr Ile Asn Asn
290                 295                 300 atg cca gaa ccc aaa aag gtg ttt tgc aat atg gat gtc aat ggg gga       960
Met Pro Glu Pro Lys Lys Val Phe Cys Asn Met Asp Val Asn Gly Gly
305                 310                 315                 320 ggt tgg act gta ata caa cat cgt gaa gat gga agt cta gat ttc caa      1008
Gly Trp Thr Val Ile Gln His Arg Glu Asp Gly Ser Leu Asp Phe Gln
                325                 330                 335
```

```
aga ggc tgg aag gaa tat aaa atg ggt ttt gga aat ccc tcc ggt gaa      1056
Arg Gly Trp Lys Glu Tyr Lys Met Gly Phe Gly Asn Pro Ser Gly Glu
        340                 345                 350 tat tgg ctg ggg aat gag ttt att ttt gcc att acc agt cag agg cag      1104
Tyr Trp Leu Gly Asn Glu Phe Ile Phe Ala Ile Thr Ser Gln Arg Gln
355                 360                 365 tac atg cta aga att gag tta atg gac tgg gaa ggg aac cga gcc tat      1152
Tyr Met Leu Arg Ile Glu Leu Met Asp Trp Glu Gly Asn Arg Ala Tyr
    370                 375                 380 tca cag tat gac aga ttc cac ata gga aat gaa aag caa aac tat agg      1200
Ser Gln Tyr Asp Arg Phe His Ile Gly Asn Glu Lys Gln Asn Tyr Arg
385                 390                 395                 400 ttg tat tta aaa ggt cac act ggg aca gca gga aaa cag agc agc ctg      1248
Leu Tyr Leu Lys Gly His Thr Gly Thr Ala Gly Lys Gln Ser Ser Leu
                405                 410                 415 atc tta cac ggt gct gat ttc agc act aaa gat gct gat aat gac aac      1296
Ile Leu His Gly Ala Asp Phe Ser Thr Lys Asp Ala Asp Asn Asp Asn
            420                 425                 430 tgt atg tgc aaa tgt gcc ctc atg tta aca gga gga tgg tgg ttt gat      1344
Cys Met Cys Lys Cys Ala Leu Met Leu Thr Gly Gly Trp Trp Phe Asp
        435                 440                 445 gct tgt ggc ccc tcc aat cta aat gga atg ttc tat act gcg gga caa      1392
Ala Cys Gly Pro Ser Asn Leu Asn Gly Met Phe Tyr Thr Ala Gly Gln
    450                 455                 460 aac cat gga aaa ctg aat ggg ata aag tgg cac tac ttc aaa ggg ccc      1440
Asn His Gly Lys Leu Asn Gly Ile Lys Trp His Tyr Phe Lys Gly Pro
465                 470                 475                 480 agt tac tcc tta cgt tcc aca act atg atg att cga cct tta gat ttt      1488
Ser Tyr Ser Leu Arg Ser Thr Thr Met Met Ile Arg Pro Leu Asp Phe
                485                 490                 495 tga                                                                  1491

<210> SEQ ID NO 22
<211> LENGTH: 496
<212> TYPE: PRT
<213> ORGANISM: Artificial Sequence
<220> FEATURE:
<223> OTHER INFORMATION: Description of Artificial Sequence: Chimeric
<220> FEATURE:
<223> OTHER INFORMATION: 2N2C1F (chimera 2)

<400> SEQUENCE: 22

Met Trp Gln Ile Val Phe Phe Thr Leu Ser Cys Asp Leu Val Leu Ala
1               5                   10                  15

Ala Ala Tyr Asn Asn Phe Arg Lys Ser Met Asp Ser Ile Gly Lys Lys
            20                  25                  30

Gln Tyr Gln Val Gln His Gly Ser Cys Ser Tyr Thr Phe Leu Leu Pro
        35                  40                  45

Glu Met Asp Asn Cys Arg Ser Ser Ser Pro Tyr Val Ser Asn Ala
    50                  55                  60

Val Gln Arg Asp Ala Pro Leu Glu Tyr Asp Asp Ser Val Gln Arg Leu
65                  70                  75                  80

Gln Val Leu Glu Asn Ile Met Glu Asn Asn Thr Gln Trp Leu Met Lys
                85                  90                  95

Leu Glu Asn Tyr Ile Gln Asp Asn Met Lys Lys Glu Met Val Glu Ile
            100                 105                 110

Gln Gln Asn Ala Val Gln Asn Gln Thr Ala Val Met Ile Glu Ile Gly
        115                 120                 125
```

```
        Thr Asn Leu Leu Asn Gln Thr Ala Glu Gln Thr Arg Lys Leu Thr Asp
            130                 135                 140

Val Glu Ala Gln Val Leu Asn Gln Thr Thr Arg Leu Glu Leu Gln Leu
        145                 150                 155                 160

Leu Glu His Ser Leu Ser Thr Asn Lys Leu Glu Lys Gln Ile Leu Asp
                        165                 170                 175

Gln Thr Ser Glu Ile Asn Lys Leu Gln Asp Lys Asn Ser Phe Leu Glu
                    180                 185                 190

Lys Lys Val Leu Ala Met Glu Asp Lys His Ile Ile Gln Leu Gln Ser
                195                 200                 205

Ile Lys Glu Glu Lys Asp Gln Leu Gln Val Leu Val Ser Lys Gln Asn
            210                 215                 220

Ser Ile Ile Glu Leu Glu Lys Lys Ile Val Thr Ala Thr Val Asn
        225                 230                 235                 240

Asn Ser Val Leu Gln Lys Gln Gln His Asp Leu Met Glu Thr Val Asn
                        245                 250                 255

Asn Leu Leu Thr Met Met Ser Thr Ser Asn Ser Ala Lys Asp Pro Thr
                    260                 265                 270

Val Ala Lys Glu Glu Gln Ile Ser Phe Arg Asp Cys Ala Asp Val Tyr
                275                 280                 285

Gln Ala Gly Phe Asn Lys Ser Gly Ile Tyr Thr Ile Tyr Ile Asn Asn
            290                 295                 300

Met Pro Glu Pro Lys Lys Val Phe Cys Asn Met Asp Val Asn Gly Gly
        305                 310                 315                 320

Gly Trp Thr Val Ile Gln His Arg Glu Asp Gly Ser Leu Asp Phe Gln
                        325                 330                 335

Arg Gly Trp Lys Glu Tyr Lys Met Gly Phe Gly Asn Pro Ser Gly Glu
                    340                 345                 350

Tyr Trp Leu Gly Asn Glu Phe Ile Phe Ala Ile Thr Ser Gln Arg Gln
                355                 360                 365

Tyr Met Leu Arg Ile Glu Leu Met Asp Trp Glu Gly Asn Arg Ala Tyr
            370                 375                 380

Ser Gln Tyr Asp Arg Phe His Ile Gly Asn Glu Lys Gln Asn Tyr Arg
        385                 390                 395                 400

Leu Tyr Leu Lys Gly His Thr Gly Thr Ala Gly Lys Gln Ser Ser Leu
                        405                 410                 415

Ile Leu His Gly Ala Asp Phe Ser Thr Lys Asp Ala Asp Asn Asp Asn
                    420                 425                 430

Cys Met Cys Lys Cys Ala Leu Met Leu Thr Gly Gly Trp Trp Phe Asp
                435                 440                 445

Ala Cys Gly Pro Ser Asn Leu Asn Gly Met Phe Tyr Thr Ala Gly Gln
            450                 455                 460

Asn His Gly Lys Leu Asn Gly Ile Lys Trp His Tyr Phe Lys Gly Pro
        465                 470                 475                 480

Ser Tyr Ser Leu Arg Ser Thr Thr Met Met Ile Arg Pro Leu Asp Phe
                        485                 490                 495

<210> SEQ ID NO 23
<211> LENGTH: 1500
<212> TYPE: DNA
<213> ORGANISM: Artificial Sequence
<220> FEATURE:
<223> OTHER INFORMATION: Description of Artificial Sequence: Chimeric
<221> NAME/KEY: CDS
<222> LOCATION: (1)..(1497)
<223> OTHER INFORMATION: 1N2C2F (chimera 3)
```

<220> FEATURE:
<223> OTHER INFORMATION: Putative leader sequence is encoded by nucleotides 1-60

<400> SEQUENCE: 23

| | | | | | | | | | | | | | | | | |
|---|---|---|---|---|---|---|---|---|---|---|---|---|---|---|---|---|
| atg | aca | gtt | ttc | ctt | tcc | ttt | gct | ttc | ctc | gct | gcc | att | ctg | act | cac | 48 |
| Met | Thr | Val | Phe | Leu | Ser | Phe | Ala | Phe | Leu | Ala | Ala | Ile | Leu | Thr | His | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ata | ggg | tgc | agc | aat | cag | cgc | cga | agt | cca | gaa | aac | agt | ggg | aga | aga | 96 |
| Ile | Gly | Cys | Ser | Asn | Gln | Arg | Arg | Ser | Pro | Glu | Asn | Ser | Gly | Arg | Arg | |
| | | | 20 | | | | | 25 | | | | | 30 | | | |

| | | | | | | | | | | | | | | | | |
|---|---|---|---|---|---|---|---|---|---|---|---|---|---|---|---|---|
| tat | aac | cgg | att | caa | cat | ggg | caa | tgt | gcc | tac | act | ttc | att | ctt | cca | 144 |
| Tyr | Asn | Arg | Ile | Gln | His | Gly | Gln | Cys | Ala | Tyr | Thr | Phe | Ile | Leu | Pro | |
| | | 35 | | | | | 40 | | | | | 45 | | | | |

| | | | | | | | | | | | | | | | | |
|---|---|---|---|---|---|---|---|---|---|---|---|---|---|---|---|---|
| gaa | cac | gat | ggc | aac | tgt | cgt | gag | agt | acg | aca | gac | cag | tac | aac | aca | 192 |
| Glu | His | Asp | Gly | Asn | Cys | Arg | Glu | Ser | Thr | Thr | Asp | Gln | Tyr | Asn | Thr | |
| | 50 | | | | | 55 | | | | | 60 | | | | | |

| | | | | | | | | | | | | | | | | |
|---|---|---|---|---|---|---|---|---|---|---|---|---|---|---|---|---|
| aac | gct | ctg | cag | aga | gat | gct | cca | cac | gtg | gaa | ccg | gat | gac | tcg | gtg | 240 |
| Asn | Ala | Leu | Gln | Arg | Asp | Ala | Pro | His | Val | Glu | Pro | Asp | Asp | Ser | Val | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| cag | agg | ctg | caa | gtg | ctg | gag | aac | atc | atg | gaa | aac | aac | act | cag | tgg | 288 |
| Gln | Arg | Leu | Gln | Val | Leu | Glu | Asn | Ile | Met | Glu | Asn | Asn | Thr | Gln | Trp | |
| | | | | 85 | | | | | 90 | | | | | 95 | | |

| | | | | | | | | | | | | | | | | |
|---|---|---|---|---|---|---|---|---|---|---|---|---|---|---|---|---|
| cta | atg | aag | ctt | gag | aat | tat | atc | cag | gac | aac | atg | aag | aaa | gaa | atg | 336 |
| Leu | Met | Lys | Leu | Glu | Asn | Tyr | Ile | Gln | Asp | Asn | Met | Lys | Lys | Glu | Met | |
| | | | 100 | | | | | 105 | | | | | 110 | | | |

| | | | | | | | | | | | | | | | | |
|---|---|---|---|---|---|---|---|---|---|---|---|---|---|---|---|---|
| gta | gag | ata | cag | cag | aat | gca | gta | cag | aac | cag | acg | gct | gtg | atg | ata | 384 |
| Val | Glu | Ile | Gln | Gln | Asn | Ala | Val | Gln | Asn | Gln | Thr | Ala | Val | Met | Ile | |
| | | 115 | | | | | 120 | | | | | 125 | | | | |

| | | | | | | | | | | | | | | | | |
|---|---|---|---|---|---|---|---|---|---|---|---|---|---|---|---|---|
| gaa | ata | ggg | aca | aac | ctg | ttg | aac | caa | aca | gct | gag | caa | acg | cgg | aag | 432 |
| Glu | Ile | Gly | Thr | Asn | Leu | Leu | Asn | Gln | Thr | Ala | Glu | Gln | Thr | Arg | Lys | |
| | 130 | | | | | 135 | | | | | 140 | | | | | |

| | | | | | | | | | | | | | | | | |
|---|---|---|---|---|---|---|---|---|---|---|---|---|---|---|---|---|
| tta | act | gat | gtg | gaa | gcc | caa | gta | tta | aat | cag | acc | acg | aga | ctt | gaa | 480 |
| Leu | Thr | Asp | Val | Glu | Ala | Gln | Val | Leu | Asn | Gln | Thr | Thr | Arg | Leu | Glu | |
| 145 | | | | 150 | | | | | 155 | | | | | 160 | | |

| | | | | | | | | | | | | | | | | |
|---|---|---|---|---|---|---|---|---|---|---|---|---|---|---|---|---|
| ctt | cag | ctc | ttg | gaa | cac | tcc | ctc | tcg | aca | aac | aaa | ttg | gaa | aaa | cag | 528 |
| Leu | Gln | Leu | Leu | Glu | His | Ser | Leu | Ser | Thr | Asn | Lys | Leu | Glu | Lys | Gln | |
| | | | | 165 | | | | | 170 | | | | | 175 | | |

| | | | | | | | | | | | | | | | | |
|---|---|---|---|---|---|---|---|---|---|---|---|---|---|---|---|---|
| att | ttg | gac | cag | acc | agt | gaa | ata | aac | aaa | ttg | caa | gat | aag | aac | agt | 576 |
| Ile | Leu | Asp | Gln | Thr | Ser | Glu | Ile | Asn | Lys | Leu | Gln | Asp | Lys | Asn | Ser | |
| | | | 180 | | | | | 185 | | | | | 190 | | | |

| | | | | | | | | | | | | | | | | |
|---|---|---|---|---|---|---|---|---|---|---|---|---|---|---|---|---|
| ttc | cta | gaa | aag | aag | gtg | cta | gct | atg | gaa | gac | aag | cac | atc | atc | caa | 624 |
| Phe | Leu | Glu | Lys | Lys | Val | Leu | Ala | Met | Glu | Asp | Lys | His | Ile | Ile | Gln | |
| | | 195 | | | | | 200 | | | | | 205 | | | | |

| | | | | | | | | | | | | | | | | |
|---|---|---|---|---|---|---|---|---|---|---|---|---|---|---|---|---|
| cta | cag | tca | ata | aaa | gaa | gag | aaa | gat | cag | cta | cag | gtg | tta | gta | tcc | 672 |
| Leu | Gln | Ser | Ile | Lys | Glu | Glu | Lys | Asp | Gln | Leu | Gln | Val | Leu | Val | Ser | |
| | 210 | | | | | 215 | | | | | 220 | | | | | |

| | | | | | | | | | | | | | | | | |
|---|---|---|---|---|---|---|---|---|---|---|---|---|---|---|---|---|
| aag | caa | aat | tcc | atc | att | gaa | gaa | cta | gaa | aaa | aaa | ata | gtg | act | gcc | 720 |
| Lys | Gln | Asn | Ser | Ile | Ile | Glu | Glu | Leu | Glu | Lys | Lys | Ile | Val | Thr | Ala | |
| 225 | | | | 230 | | | | | 235 | | | | | 240 | | |

| | | | | | | | | | | | | | | | | |
|---|---|---|---|---|---|---|---|---|---|---|---|---|---|---|---|---|
| acg | gtg | aat | aat | tca | gtt | ctt | caa | aag | cag | caa | cat | gat | ctc | atg | gag | 768 |
| Thr | Val | Asn | Asn | Ser | Val | Leu | Gln | Lys | Gln | Gln | His | Asp | Leu | Met | Glu | |
| | | | | 245 | | | | | 250 | | | | | 255 | | |

| | | | | | | | | | | | | | | | | |
|---|---|---|---|---|---|---|---|---|---|---|---|---|---|---|---|---|
| aca | gtt | aat | aac | tta | ctg | act | atg | atg | tcc | aca | tca | aac | tca | gct | aag | 816 |
| Thr | Val | Asn | Asn | Leu | Leu | Thr | Met | Met | Ser | Thr | Ser | Asn | Ser | Ala | Lys | |
| | | | 260 | | | | | 265 | | | | | 270 | | | |

| | | | | | | | | | | | | | | | | |
|---|---|---|---|---|---|---|---|---|---|---|---|---|---|---|---|---|
| gac | ccc | act | gtt | gct | aaa | gaa | gaa | caa | atc | agc | ttc | aga | gac | tgt | gct | 864 |
| Asp | Pro | Thr | Val | Ala | Lys | Glu | Glu | Gln | Ile | Ser | Phe | Arg | Asp | Cys | Ala | |
| | | 275 | | | | | 280 | | | | | 285 | | | | |

| | | | | | | | | | | | | | | | | |
|---|---|---|---|---|---|---|---|---|---|---|---|---|---|---|---|---|
| gaa | gta | ttc | aaa | tca | gga | cac | acc | aca | aat | ggc | atc | tac | acg | tta | aca | 912 |

```
                Glu Val Phe Lys Ser Gly His Thr Thr Asn Gly Ile Tyr Thr Leu Thr
                    290                 295                 300 ttc cct aat tct aca gaa gag atc aag gcc tac tgt gac atg gaa gct       960
Phe Pro Asn Ser Thr Glu Glu Ile Lys Ala Tyr Cys Asp Met Glu Ala
305                 310                 315                 320 gga gga ggc ggg tgg aca att att cag cga cgt gag gat ggc agc gtt      1008
Gly Gly Gly Gly Trp Thr Ile Ile Gln Arg Arg Glu Asp Gly Ser Val
                325                 330                 335 gat ttt cag agg act tgg aaa gaa tat aaa gtg gga ttt ggt aac cct      1056
Asp Phe Gln Arg Thr Trp Lys Glu Tyr Lys Val Gly Phe Gly Asn Pro
                340                 345                 350 tca gga gaa tat tgg ctg gga aat gag ttt gtt tcg caa ctg act aat      1104
Ser Gly Glu Tyr Trp Leu Gly Asn Glu Phe Val Ser Gln Leu Thr Asn
                355                 360                 365 cag caa cgc tat gtg ctt aaa ata cac ctt aaa gac tgg gaa ggg aat      1152
Gln Gln Arg Tyr Val Leu Lys Ile His Leu Lys Asp Trp Glu Gly Asn
370                 375                 380 gag gct tac tca ttg tat gaa cat ttc tat ctc tca agt gaa gaa ctc      1200
Glu Ala Tyr Ser Leu Tyr Glu His Phe Tyr Leu Ser Ser Glu Glu Leu
385                 390                 395                 400 aat tat agg att cac ctt aaa gga ctt aca ggg aca gcc ggc aaa ata      1248
Asn Tyr Arg Ile His Leu Lys Gly Leu Thr Gly Thr Ala Gly Lys Ile
                405                 410                 415 agc agc atc agc caa cca gga aat gat ttt agc aca aag gat gga gac      1296
Ser Ser Ile Ser Gln Pro Gly Asn Asp Phe Ser Thr Lys Asp Gly Asp
                420                 425                 430 aac gac aaa tgt att tgc aaa tgt tca caa atg cta aca gga ggc tgg      1344
Asn Asp Lys Cys Ile Cys Lys Cys Ser Gln Met Leu Thr Gly Gly Trp
                435                 440                 445 tgg ttt gat gca tgt ggt cct tcc aac ttg aac gga atg tac tat cca      1392
Trp Phe Asp Ala Cys Gly Pro Ser Asn Leu Asn Gly Met Tyr Tyr Pro
                450                 455                 460 cag agg cag aac aca aat aag ttc aac ggc att aaa tgg tac tac tgg      1440
Gln Arg Gln Asn Thr Asn Lys Phe Asn Gly Ile Lys Trp Tyr Tyr Trp
465                 470                 475                 480 aaa ggc tca ggc tat tcg ctc aag gcc aca acc atg atg atc cga cca      1488
Lys Gly Ser Gly Tyr Ser Leu Lys Ala Thr Thr Met Met Ile Arg Pro
                485                 490                 495 gca gat ttc taa                                                      1500
Ala Asp Phe <210> SEQ ID NO 24
<211> LENGTH: 499
<212> TYPE: PRT
<213> ORGANISM: Artificial Sequence
<220> FEATURE:
<223> OTHER INFORMATION: Description of Artificial Sequence: Chimeric
<220> FEATURE:
<223> OTHER INFORMATION: 1N2C2F (chimera 3)

<400> SEQUENCE: 24

Met Thr Val Phe Leu Ser Phe Ala Phe Leu Ala Ala Ile Leu Thr His
1               5                   10                  15

Ile Gly Cys Ser Asn Gln Arg Arg Ser Pro Glu Asn Ser Gly Arg Arg
                20                  25                  30

Tyr Asn Arg Ile Gln His Gly Gln Cys Ala Tyr Thr Phe Ile Leu Pro
                35                  40                  45

Glu His Asp Gly Asn Cys Arg Glu Ser Thr Thr Asp Gln Tyr Asn Thr
                50                  55                  60

Asn Ala Leu Gln Arg Asp Ala Pro His Val Glu Pro Asp Asp Ser Val
```

-continued

```
                65                  70                  75                  80
            Gln Arg Leu Gln Val Leu Glu Asn Ile Met Glu Asn Asn Thr Gln Trp
                            85                  90                  95
            Leu Met Lys Leu Glu Asn Tyr Ile Gln Asp Asn Met Lys Lys Glu Met
                        100                 105                 110
            Val Glu Ile Gln Gln Asn Ala Val Gln Asn Gln Thr Ala Val Met Ile
                    115                 120                 125
            Glu Ile Gly Thr Asn Leu Leu Asn Gln Thr Ala Glu Gln Thr Arg Lys
                130                 135                 140
            Leu Thr Asp Val Glu Ala Gln Val Leu Asn Gln Thr Thr Arg Leu Glu
            145                 150                 155                 160
            Leu Gln Leu Leu Glu His Ser Leu Ser Thr Asn Lys Leu Glu Lys Gln
                            165                 170                 175
            Ile Leu Asp Gln Thr Ser Glu Ile Asn Lys Leu Gln Asp Lys Asn Ser
                        180                 185                 190
            Phe Leu Glu Lys Lys Val Leu Ala Met Glu Asp Lys His Ile Ile Gln
                    195                 200                 205
            Leu Gln Ser Ile Lys Glu Glu Lys Asp Gln Leu Gln Val Leu Val Ser
                210                 215                 220
            Lys Gln Asn Ser Ile Ile Glu Glu Leu Glu Lys Lys Ile Val Thr Ala
            225                 230                 235                 240
            Thr Val Asn Asn Ser Val Leu Gln Lys Gln Gln His Asp Leu Met Glu
                            245                 250                 255
            Thr Val Asn Asn Leu Leu Thr Met Met Ser Thr Ser Asn Ser Ala Lys
                        260                 265                 270
            Asp Pro Thr Val Ala Lys Glu Glu Gln Ile Ser Phe Arg Asp Cys Ala
                    275                 280                 285
            Glu Val Phe Lys Ser Gly His Thr Thr Asn Gly Ile Tyr Thr Leu Thr
                290                 295                 300
            Phe Pro Asn Ser Thr Glu Glu Ile Lys Ala Tyr Cys Asp Met Glu Ala
            305                 310                 315                 320
            Gly Gly Gly Gly Trp Thr Ile Ile Gln Arg Arg Glu Asp Gly Ser Val
                            325                 330                 335
            Asp Phe Gln Arg Thr Trp Lys Glu Tyr Lys Val Gly Phe Gly Asn Pro
                        340                 345                 350
            Ser Gly Glu Tyr Trp Leu Gly Asn Glu Phe Val Ser Gln Leu Thr Asn
                    355                 360                 365
            Gln Gln Arg Tyr Val Leu Lys Ile His Leu Lys Asp Trp Glu Gly Asn
                370                 375                 380
            Glu Ala Tyr Ser Leu Tyr Glu His Phe Tyr Leu Ser Ser Glu Glu Leu
            385                 390                 395                 400
            Asn Tyr Arg Ile His Leu Lys Gly Leu Thr Gly Thr Ala Gly Lys Ile
                            405                 410                 415
            Ser Ser Ile Ser Gln Pro Gly Asn Asp Phe Ser Thr Lys Asp Gly Asp
                        420                 425                 430
            Asn Asp Lys Cys Ile Cys Lys Cys Ser Gln Met Leu Thr Gly Gly Trp
                    435                 440                 445
            Trp Phe Asp Ala Cys Gly Pro Ser Asn Leu Asn Gly Met Tyr Tyr Pro
                450                 455                 460
            Gln Arg Gln Asn Thr Asn Lys Phe Asn Gly Ile Lys Trp Tyr Tyr Trp
            465                 470                 475                 480
            Lys Gly Ser Gly Tyr Ser Leu Lys Ala Thr Thr Met Met Ile Arg Pro
                            485                 490                 495
```

Ala Asp Phe

<210> SEQ ID NO 25
<211> LENGTH: 1488
<212> TYPE: DNA
<213> ORGANISM: Artificial Sequence
<220> FEATURE:
<223> OTHER INFORMATION: Description of Artificial Sequence: Chimeric
<221> NAME/KEY: CDS
<222> LOCATION: (1)..(1485)
<223> OTHER INFORMATION: 2N1C1F (chimera 4)
<220> FEATURE:
<223> OTHER INFORMATION: Putative leader sequence is encoded by
      nucleotides 1-48

<400> SEQUENCE: 25

```
atg tgg cag att gtt ttc ttt act ctg agc tgt gat ctt gtc ttg gcc      48
Met Trp Gln Ile Val Phe Phe Thr Leu Ser Cys Asp Leu Val Leu Ala
1               5                   10                  15 gca gcc tat aac aac ttt cgg aag agc atg gac agc ata gga aag aag      96
Ala Ala Tyr Asn Asn Phe Arg Lys Ser Met Asp Ser Ile Gly Lys Lys
            20                  25                  30 caa tat cag gtc cag cat ggg tcc tgc agc tac act ttc ctc ctg cca     144
Gln Tyr Gln Val Gln His Gly Ser Cys Ser Tyr Thr Phe Leu Leu Pro
        35                  40                  45 gag atg gac aac tgc cgc tct tcc tcc agc ccc tac gtg tcc aat gct     192
Glu Met Asp Asn Cys Arg Ser Ser Ser Ser Pro Tyr Val Ser Asn Ala
    50                  55                  60 gtg cag agg gac gcg ccg ctc gaa tac gat ttc tct tcc cag aaa ctt     240
Val Gln Arg Asp Ala Pro Leu Glu Tyr Asp Phe Ser Ser Gln Lys Leu
65                  70                  75                  80 caa cat ctg gaa cat gtg atg gaa aat tat act cag tgg ctg caa aaa     288
Gln His Leu Glu His Val Met Glu Asn Tyr Thr Gln Trp Leu Gln Lys
                85                  90                  95 ctt gag aat tac att gtg gaa aac atg aag tcg gag atg gcc cag ata     336
Leu Glu Asn Tyr Ile Val Glu Asn Met Lys Ser Glu Met Ala Gln Ile
            100                 105                 110 cag cag aat gca gtt cag aac cac acg gct acc atg ctg gag ata gga     384
Gln Gln Asn Ala Val Gln Asn His Thr Ala Thr Met Leu Glu Ile Gly
        115                 120                 125 acc agc ctc ctc tct cag act gca gag cag acc aga aag ctg aca gat     432
Thr Ser Leu Leu Ser Gln Thr Ala Glu Gln Thr Arg Lys Leu Thr Asp
    130                 135                 140 gtt gag acc cag gta cta aat caa act tct cga ctt gag ata cag ctg     480
Val Glu Thr Gln Val Leu Asn Gln Thr Ser Arg Leu Glu Ile Gln Leu
145                 150                 155                 160 ctg gag aat tca tta tcc acc tac aag cta gag aag caa ctt ctt caa     528
Leu Glu Asn Ser Leu Ser Thr Tyr Lys Leu Glu Lys Gln Leu Leu Gln
                165                 170                 175 cag aca aat gaa atc ttg aag atc cat gaa aaa aac agt tta tta gaa     576
Gln Thr Asn Glu Ile Leu Lys Ile His Glu Lys Asn Ser Leu Leu Glu
            180                 185                 190 cat aaa atc tta gaa atg gaa gga aaa cac aag gaa gag ttg gac acc     624
His Lys Ile Leu Glu Met Glu Gly Lys His Lys Glu Glu Leu Asp Thr
        195                 200                 205 tta aag gaa gag aaa gag aac ctt caa ggc ttg gtt act cgt caa aca     672
Leu Lys Glu Glu Lys Glu Asn Leu Gln Gly Leu Val Thr Arg Gln Thr
    210                 215                 220 tat ata atc cag gag ctg gaa aag caa tta aac aga gct acc acc aac     720
Tyr Ile Ile Gln Glu Leu Glu Lys Gln Leu Asn Arg Ala Thr Thr Asn
225                 230                 235                 240
```

```
aac agt gtc ctt cag aag cag caa ctg gag ctg atg gac aca gtc cac      768
Asn Ser Val Leu Gln Lys Gln Gln Leu Glu Leu Met Asp Thr Val His
            245                 250                 255 aac ctt gtc aat ctt tgc act aaa gaa ggt gtt tta cta aag gga gga      816
Asn Leu Val Asn Leu Cys Thr Lys Glu Gly Val Leu Leu Lys Gly Gly
        260                 265                 270 aaa aga gag gaa gag aaa cca ttt aga gac tgt gca gat gta tat caa      864
Lys Arg Glu Glu Glu Lys Pro Phe Arg Asp Cys Ala Asp Val Tyr Gln
    275                 280                 285 gct ggt ttt aat aaa agt gga atc tac act att tat att aat aat atg      912
Ala Gly Phe Asn Lys Ser Gly Ile Tyr Thr Ile Tyr Ile Asn Asn Met
290                 295                 300 cca gaa ccc aaa aag gtg ttt tgc aat atg gat gtc aat ggg gga ggt      960
Pro Glu Pro Lys Lys Val Phe Cys Asn Met Asp Val Asn Gly Gly Gly
305                 310                 315                 320 tgg act gta ata caa cat cgt gaa gat gga agt cta gat ttc caa aga     1008
Trp Thr Val Ile Gln His Arg Glu Asp Gly Ser Leu Asp Phe Gln Arg
            325                 330                 335 ggc tgg aag gaa tat aaa atg ggt ttt gga aat ccc tcc ggt gaa tat     1056
Gly Trp Lys Glu Tyr Lys Met Gly Phe Gly Asn Pro Ser Gly Glu Tyr
        340                 345                 350 tgg ctg ggg aat gag ttt att ttt gcc att acc agt cag agg cag tac     1104
Trp Leu Gly Asn Glu Phe Ile Phe Ala Ile Thr Ser Gln Arg Gln Tyr
    355                 360                 365 atg cta aga att gag tta atg gac tgg gaa ggg aac cga gcc tat tca     1152
Met Leu Arg Ile Glu Leu Met Asp Trp Glu Gly Asn Arg Ala Tyr Ser
370                 375                 380 cag tat gac aga ttc cac ata gga aat gaa aag caa aac tat agg ttg     1200
Gln Tyr Asp Arg Phe His Ile Gly Asn Glu Lys Gln Asn Tyr Arg Leu
385                 390                 395                 400 tat tta aaa ggt cac act ggg aca gca gga aaa cag agc agc ctg atc     1248
Tyr Leu Lys Gly His Thr Gly Thr Ala Gly Lys Gln Ser Ser Leu Ile
            405                 410                 415 tta cac ggt gct gat ttc agc act aaa gat gct gat aat gac aac tgt     1296
Leu His Gly Ala Asp Phe Ser Thr Lys Asp Ala Asp Asn Asp Asn Cys
        420                 425                 430 atg tgc aaa tgt gcc ctc atg tta aca gga gga tgg tgg ttt gat gct     1344
Met Cys Lys Cys Ala Leu Met Leu Thr Gly Gly Trp Trp Phe Asp Ala
    435                 440                 445 tgt ggc ccc tcc aat cta aat gga atg ttc tat act gcg gga caa aac     1392
Cys Gly Pro Ser Asn Leu Asn Gly Met Phe Tyr Thr Ala Gly Gln Asn
450                 455                 460 cat gga aaa ctg aat ggg ata aag tgg cac tac ttc aaa ggg ccc agt     1440
His Gly Lys Leu Asn Gly Ile Lys Trp His Tyr Phe Lys Gly Pro Ser
465                 470                 475                 480 tac tcc tta cgt tcc aca act atg atg att cga cct tta gat ttt tga    1488
Tyr Ser Leu Arg Ser Thr Thr Met Met Ile Arg Pro Leu Asp Phe
            485                 490                 495

<210> SEQ ID NO 26
<211> LENGTH: 495
<212> TYPE: PRT
<213> ORGANISM: Artificial Sequence
<220> FEATURE:
<223> OTHER INFORMATION: Description of Artificial Sequence: Chimeric
<220> FEATURE:
<223> OTHER INFORMATION: 2N1C1F (chimera 4)

<400> SEQUENCE: 26

Met Trp Gln Ile Val Phe Phe Thr Leu Ser Cys Asp Leu Val Leu Ala
1               5                   10                  15
```

```
Ala Ala Tyr Asn Asn Phe Arg Lys Ser Met Asp Ser Ile Gly Lys Lys
        20                  25                  30

Gln Tyr Gln Val Gln His Gly Ser Cys Ser Tyr Thr Phe Leu Leu Pro
        35                  40                  45

Glu Met Asp Asn Cys Arg Ser Ser Ser Pro Tyr Val Ser Asn Ala
 50                  55                  60

Val Gln Arg Asp Ala Pro Leu Glu Tyr Asp Phe Ser Ser Gln Lys Leu
 65              70                  75                      80

Gln His Leu Glu His Val Met Glu Asn Tyr Thr Gln Trp Leu Gln Lys
            85                  90                  95

Leu Glu Asn Tyr Ile Val Glu Asn Met Lys Ser Glu Met Ala Gln Ile
            100                 105                 110

Gln Gln Asn Ala Val Gln Asn His Thr Ala Thr Met Leu Glu Ile Gly
        115                 120                 125

Thr Ser Leu Leu Ser Gln Thr Ala Glu Gln Thr Arg Lys Leu Thr Asp
 130                 135                 140

Val Glu Thr Gln Val Leu Asn Gln Thr Ser Arg Leu Glu Ile Gln Leu
145                 150                 155                 160

Leu Glu Asn Ser Leu Ser Thr Tyr Lys Leu Glu Lys Gln Leu Leu Gln
                165                 170                 175

Gln Thr Asn Glu Ile Leu Lys Ile His Glu Lys Asn Ser Leu Leu Glu
            180                 185                 190

His Lys Ile Leu Glu Met Glu Gly Lys His Lys Glu Glu Leu Asp Thr
            195                 200                 205

Leu Lys Glu Glu Lys Glu Asn Leu Gln Gly Leu Val Thr Arg Gln Thr
 210                 215                 220

Tyr Ile Ile Gln Glu Leu Glu Lys Gln Leu Asn Arg Ala Thr Thr Asn
225                 230                 235                 240

Asn Ser Val Leu Gln Lys Gln Gln Leu Glu Leu Met Asp Thr Val His
                245                 250                 255

Asn Leu Val Asn Leu Cys Thr Lys Glu Gly Val Leu Leu Lys Gly Gly
            260                 265                 270

Lys Arg Glu Glu Lys Pro Phe Arg Asp Cys Ala Asp Val Tyr Gln
            275                 280                 285

Ala Gly Phe Asn Lys Ser Gly Ile Tyr Thr Ile Tyr Ile Asn Asn Met
 290                 295                 300

Pro Glu Pro Lys Lys Val Phe Cys Asn Met Asp Val Asn Gly Gly Gly
305                 310                 315                 320

Trp Thr Val Ile Gln His Arg Glu Asp Gly Ser Leu Asp Phe Gln Arg
                325                 330                 335

Gly Trp Lys Glu Tyr Lys Met Gly Phe Gly Asn Pro Ser Gly Glu Tyr
            340                 345                 350

Trp Leu Gly Asn Glu Phe Ile Phe Ala Ile Thr Ser Gln Arg Gln Tyr
            355                 360                 365

Met Leu Arg Ile Glu Leu Met Asp Trp Glu Gly Asn Arg Ala Tyr Ser
 370                 375                 380

Gln Tyr Asp Arg Phe His Ile Gly Asn Glu Lys Gln Asn Tyr Arg Leu
385                 390                 395                 400

Tyr Leu Lys Gly His Thr Gly Thr Ala Gly Lys Gln Ser Ser Leu Ile
                405                 410                 415

Leu His Gly Ala Asp Phe Ser Thr Lys Asp Ala Asp Asn Asp Asn Cys
            420                 425                 430

Met Cys Lys Cys Ala Leu Met Leu Thr Gly Gly Trp Trp Phe Asp Ala
```

```
                    435                 440                 445
Cys Gly Pro Ser Asn Leu Asn Gly Met Phe Tyr Thr Ala Gly Gln Asn
    450                 455                 460

His Gly Lys Leu Asn Gly Ile Lys Trp His Tyr Phe Lys Gly Pro Ser
465                 470                 475                 480

Tyr Ser Leu Arg Ser Thr Thr Met Met Ile Arg Pro Leu Asp Phe
                485                 490                 495

<210> SEQ ID NO 27
<211> LENGTH: 47
<212> TYPE: DNA
<213> ORGANISM: Artificial Sequence
<220> FEATURE:
<223> OTHER INFORMATION: Description of Artificial Sequence: PCR Primer

<400> SEQUENCE: 27
gcatgctatc tcgagccacc atgctctccc agctagccat gctgcag            47

<210> SEQ ID NO 28
<211> LENGTH: 55
<212> TYPE: DNA
<213> ORGANISM: Artificial Sequence
<220> FEATURE:
<223> OTHER INFORMATION: Description of Artificial Sequence: PCR Primer

<400> SEQUENCE: 28
gtgtcgacgc ggccgctcta gatcagactt agatgtccaa aggccgtatc atcat   55

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: PCR Primer

<400> SEQUENCE: 29 cctctgggctcgccagtttgttagg                                       25

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: PCR Primer

<400> SEQUENCE: 30 ccagctggcagatatcagg                                             19
```